(12) United States Patent
Swayze et al.

(10) Patent No.: US 11,633,483 B2
(45) Date of Patent: *Apr. 25, 2023

(54) MODULATORS OF PCSK9 EXPRESSION

(71) Applicant: Ionis Pharmaceuticals, Inc., Carlsbad, CA (US)

(72) Inventors: Eric E. Swayze, Encinitas, CA (US); Susan M. Freier, San Diego, CA (US); Huynh-Hoa Bui, San Diego, CA (US)

(73) Assignee: IONIS PHARMACEUTICALS, INC., Carlsbad, CA (US)

( * ) Notice: Subject to any disclaimer, the term of this patent is extended or adjusted under 35 U.S.C. 154(b) by 129 days.

This patent is subject to a terminal disclaimer.

(21) Appl. No.: 16/953,704

(22) Filed: Nov. 20, 2020

(65) Prior Publication Data

US 2021/0077630 A1   Mar. 18, 2021

Related U.S. Application Data

(60) Continuation of application No. 16/671,630, filed on Nov. 1, 2019, now Pat. No. 11,000,595, which is a division of application No. 15/933,739, filed on Mar. 23, 2018, now Pat. No. 10,517,953.

(60) Provisional application No. 62/476,051, filed on Mar. 24, 2017.

(51) Int. Cl.
| | | |
|---|---|---|
| C07H 21/02 | (2006.01) |
| C07H 21/04 | (2006.01) |
| A61K 47/54 | (2017.01) |
| A61K 31/7125 | (2006.01) |
| A61K 31/712 | (2006.01) |
| A61K 9/00 | (2006.01) |
| A61K 47/68 | (2017.01) |
| A61P 3/06 | (2006.01) |
| A61K 31/7115 | (2006.01) |
| C12N 15/113 | (2010.01) |

(52) U.S. Cl.
CPC .......... *A61K 47/549* (2017.08); *A61K 9/0019* (2013.01); *A61K 31/712* (2013.01); *A61K 31/7115* (2013.01); *A61K 31/7125* (2013.01); *A61K 47/6807* (2017.08); *A61P 3/06* (2018.01); *C12N 15/1137* (2013.01); *C12N 2310/11* (2013.01); *C12N 2310/315* (2013.01); *C12N 2310/3231* (2013.01); *C12N 2310/3341* (2013.01); *C12N 2310/341* (2013.01); *C12Y 304/21061* (2013.01)

(58) Field of Classification Search
CPC .......... C12N 15/113; C12N 2310/11
See application file for complete search history.

(56) References Cited

U.S. PATENT DOCUMENTS

| | | |
|---|---|---|
| 8,106,022 B2 | 1/2012 | Manoharan et al. |
| 8,450,467 B2 | 5/2013 | Manoharan et al. |
| 8,828,956 B2 | 9/2014 | Manoharan et al. |
| 9,370,581 B2 | 6/2016 | Manoharan et al. |
| 9,370,582 B2 | 6/2016 | Manoharan et al. |
| 9,450,467 B2 | 9/2016 | Intelisano |
| 9,867,882 B2 | 1/2018 | Manoharan et al. |
| 2007/0173473 A1 | 7/2007 | McSwiaaen |
| 2016/0017323 A1 | 1/2016 | Prakash et al. |
| 2016/0289677 A1 | 10/2016 | Albaek |
| 2019/0184018 A1 | 6/2019 | Manoharan et al. |

FOREIGN PATENT DOCUMENTS

| | | |
|---|---|---|
| EP | 3633036 A1 | 4/2020 |
| WO | 2007/131237 A2 | 11/2007 |
| WO | 2007/143315 A2 | 12/2007 |
| WO | 2007/146511 A2 | 12/2007 |
| WO | 2008/066776 A2 | 6/2008 |
| WO | 2008/109472 A2 | 9/2008 |
| WO | 2009/114475 A2 | 9/2009 |
| WO | 2009/148605 A2 | 12/2009 |
| WO | 2014/089313 A1 | 6/2014 |
| WO | 2014179620 A1 | 11/2014 |
| WO | 2014/207232 A1 | 12/2014 |
| WO | 2015/188194 A1 | 12/2015 |
| WO | 2017/191503 A1 | 11/2017 |
| WO | 2018/089912 A2 | 5/2018 |
| WO | 2018/154380 A1 | 8/2018 |
| WO | 2018/223056 A1 | 12/2018 |

OTHER PUBLICATIONS

Tsuyoshi Yamamoto et al: "Cholesterol-lowering Action of BNA-based Antisense Oligonucleotides Targeting PCSK9 in Atherogenic Diet-induced Hypercholesterolemic Mice", Molecular Therapy—Nucleic Acids, vol. 1, No. 1, 2012, p. e22.
Richard G. Lee et al: "Antisense Technology: An Emerging Platform for Cardiovascular Disease Therapeutics", Journal of Cardiovascular Translational Research, vol. 6, No. 6, Jul. 16, 2013 (Jul. 16, 2013), pp. 969-980.
M. E. Visser et al: "Antisense oligonucleotides for the treatment of dyslipidaemia", European Heart Journal, vol. 33, No. 12, May 24, 2012 (May 24, 2012), pp. 1451-1458.
Supplemental European Search Report for EP 18772304 dated Dec. 2, 2020.
Bertrand, et al., "Comparison of antisense oligonucleotides and siRNAs in cell culture and in vivo", Comparative Study, Biochem Biophys Res Commun. Aug. 3, 20020;296(4).
International Search Report for International Application No. PCT/US2018/023936, dated Aug. 23, 2018.
Shemesh et al., Molecular Therapy-Nucleic Acids, 2015, 5, e319, pp. 1-16.

*Primary Examiner* — Amy H Bowman

(57) ABSTRACT

The present embodiments provide methods, compounds, and compositions useful for inhibiting PCSK9 expression, which may be useful for treating, preventing, or ameliorating a disease associated with PCSK9.

15 Claims, No Drawings

Specification includes a Sequence Listing.

MODULATORS OF PCSK9 EXPRESSION

SEQUENCE LISTING

The present application is being filed along with a Sequence Listing in electronic format. The Sequence Listing is provided as a file entitled 200615-US-NP-Sequence-Listing_ST25.txt created Mar. 22, 2018, which is 431 kb in size. The information in the electronic format of the sequence listing is incorporated herein by reference in its entirety.

FIELD

The present embodiments provide methods, compounds, and compositions useful for inhibiting proprotein convertase subtilisin/kexin type 9 (PCSK9) expression, and in certain instances, reducing the amount of PCSK9 protein in a cell or animal, which can be useful for treating, preventing, or ameliorating a disease associated with PCSK9.

BACKGROUND

Proprotein convertase subtilisin/kexin type 9 (PCSK9) is an enzyme with an important role in lipoprotein metabolism. Rare gain-of-function mutations in PCSK9 lead to a high LDL-C level and premature coronary heart disease, whereas loss-of-function variants lead to a low LDL-C level and a reduced incidence of coronary heart disease (Zhao et al., Am. J. Hum. Genet. 2006, 79: 514-523; Horton et al., J. Lipid Res. 2009, 50: Suppl: S172-S177). Therefore, PCSK9 is a well-validated target for LDL-cholesterol-lowering therapy (Hooper et al., Expert Opin. Biol. Ther. 2013, 13: 429-435).

Antibodies for blocking PCSK9, Alirocumab and Evolocumab, have been demonstrated to reduce circulating PCSK9 levels and lower LDL-cholesterol levels but have a short duration of action, necessitating frequent subcutaneous injections (Zhang et al., BMC Med. 2015, 13: 123; Navarese et al., Ann. Intern. Med. 2015, 163: 40-51).

It is an object herein to provide compounds, methods, and pharmaceutical compositions for the improved treatment of diseases such as cardiovascular diseases, dyslipidemias, mixed dyslipidemias, and hypercholesterolemia.

SUMMARY

Provided herein are compounds and methods for reducing the amount or activity of PCSK9 mRNA, and in certain embodiments, reducing the amount of PCSK9 protein in a cell or animal. In certain embodiments, the animal has a cardiovascular disease. In certain embodiments, the disease is dyslipidemia. In certain embodiments, the disease is mixed dyslipidemia. In certain embodiments, the disease is hypercholesterolemia. Certain compounds provided herein are directed to compounds and compositions that reduce LDL-cholesterol in an animal.

Certain embodiments provided herein are directed to potent and tolerable compounds and compositions useful for inhibiting PCSK9 expression, which can be useful for treating, preventing, ameliorating, or slowing progression of a cardiovascular disease. Certain embodiments provided herein are directed to compounds and compositions that are more potent or have greater therapeutic value than compounds publicly disclosed.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ISIS number indicate a combination of nucleobase sequence, chemical modification, and motif.

Definitions

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'O(CH$_2$)$_2$—OCH$_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of PCSK9", it is implied that PCSK9 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a bicyclic furanosyl sugar moiety comprising a bridge connecting the 4'-carbon and the 2'-carbon, wherein the bridge has the formula: 4'-CH(CH$_3$)—O-2'.

"cEt nucleoside" means a nucleoside comprising a cEt modified sugar moiety.

"Chemical modification" in a compound describes the substitutions or changes through chemical reaction, of any of the units in the compound relative to the original state of such unit. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Differently modified" means chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Double-stranded antisense compound" means an antisense compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to, the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound. Linker-nucleosides are not considered part of the oligonucleotide portion of a compound even if they are contiguous with the oligonucleotide.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating PCSK9 RNA can mean to increase or decrease the level of PCSK9 RNA and/or PCSK9 protein in a cell, tissue, organ or organism. A "modulator" effects the change in the cell, tissue, organ or organism. For example, a PCSK9 compound can be a modulator that decreases the amount of PCSK9 RNA and/or PCSK9 protein in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an individual. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites" are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" with reference to a target nucleic acid means to reduce or block expression of the target nucleic acid while exhibiting fewer, minimal, or no effects on non-target nucleic acids. Reduction does not necessarily indicate a total elimination of the target nucleic acid's expression.

"Standard cell assay" means assay(s) described in the Examples and reasonable variations thereof.

"Standard in vivo experiment" means the procedure(s) described in the Example(s) and reasonable variations thereof.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary compounds or nucleic acids.

"PCSK9" means any nucleic acid or protein of PCSK9. "PCSK9 nucleic acid" means any nucleic acid encoding PCSK9. For example, in certain embodiments, a PCSK9 nucleic acid includes a DNA sequence encoding PCSK9, an RNA sequence transcribed from DNA encoding PCSK9 (including genomic DNA comprising introns and exons) and an mRNA sequence encoding PCSK9. "PCSK9 mRNA" means an mRNA encoding a PCSK9 protein. The target may be referred to in either upper or lower case.

"PCSK9 specific inhibitor" refers to any agent capable of specifically inhibiting PCSK9 RNA and/or PCSK9 protein expression or activity at the molecular level. For example, PCSK9 specific inhibitors include nucleic acids (including antisense compounds), peptides, antibodies, small molecules, and other agents capable of inhibiting the expression of PCSK9 RNA and/or PCSK9 protein.

"Target gene" refers to a gene encoding a target.

"Targeting" means the specific hybridization of a compound to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

Certain Embodiments

Certain embodiments provide methods, compounds and compositions for inhibiting PCSK9 expression.

Certain embodiments provide compounds targeted to a PCSK9 nucleic acid. In certain embodiments, the PCSK9 nucleic acid has the sequence set forth in RefSeq or GENBANK Accession No. NM_174936.3 and GENBANK Accession No. NC_000001.11 truncated from nucleotides 55036001 to 55068000 (incorporated by reference, disclosed herein as SEQ ID NO: 1 and SEQ ID NO: 2, respectively). In certain embodiments, the compound is an antisense compound or oligomeric compound. In certain embodiments, the compound is single-stranded. In certain embodiments, the compound is double-stranded.

Certain embodiments provide a compound comprising a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 9 to 80 linked nucleosides in length and having a nucleobase sequence comprising at least 9 contiguous nucleobases of any of the nucleobase sequences of SEQ ID NOs: 3-1540. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 10 to 80 linked nucleosides in length and having a nucleobase sequence comprising at least 10 contiguous nucleobases of any of the nucleobase sequences of SEQ ID NOs: 3-1540. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 11 to 80 linked nucleosides in length and having a nucleobase sequence comprising at least 11 contiguous nucleobases of any of the nucleobase sequences of SEQ ID NOs: 3-1540. In certain embodiments, the compound is an antisense compound or oligomeric compound. In certain embodiments, the compound is single-stranded. In certain embodiments, the compound is double-stranded. In certain embodiments, the modified oligonucleotide is 11 to 30 linked nucleosides in length.

Certain embodiments provide a compound comprising a modified oligonucleotide 12 to 80 linked nucleosides in length and having a nucleobase sequence comprising at least 12 contiguous nucleobases of any of the nucleobase sequences of SEQ ID NOs: 3-1540. In certain embodiments, the compound is an antisense compound or oligomeric compound. In certain embodiments, the compound is single-stranded. In certain embodiments, the compound is double-stranded. In certain embodiments, the modified oligonucleotide is 12 to 30 linked nucleosides in length.

In certain embodiments, the compound comprises a modified oligonucleotide 30 linked nucleosides in length. In certain embodiments, the compound is an antisense compound or oligomeric compound.

Certain embodiments provide a compound comprising a modified oligonucleotide 14 to 80 linked nucleosides in length and having a nucleobase sequence comprising the nucleobase sequence of any one of SEQ ID NOs: 3-1540. In certain embodiments, the compound is an antisense compound or oligomeric compound. In certain embodiments, the compound is single-stranded. In certain embodiments, the compound is double-stranded. In certain embodiments, the modified oligonucleotide is 14 to 30 linked nucleosides in length.

Certain embodiments provide a compound comprising a modified oligonucleotide consisting of the nucleobase sequence of any one of SEQ ID NOs: 3-1540. In certain embodiments, the compound is an antisense compound or oligomeric compound. In certain embodiments, the compound is single-stranded. In certain embodiments, the compound is double-stranded.

Certain embodiments provide a compound comprising a modified oligonucleotide 8 to 80 linked nucleosides in length and complementary within nucleobases 6356-6371, 12843-12947, 12905-12948, 17681-17700, 19653-19673, 27626-27669, 27895-27949, and 28105-28136 of SEQ ID NO: 2, wherein said modified oligonucleotide is at least 85%, at least 90%, at least 95%, or 100% complementary to SEQ ID NO: 2. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 8 to 80 linked nucleosides in length and having a nucleobase sequence comprising a portion of at least 8 contiguous nucleobases complementary to an equal length portion of nucleobases 6356-6371, 12843-12947, 12905-12948, 17681-17700, 19653-19673, 27626-27669, 27895-27949, and 28105-28136 of SEQ ID NO: 2, wherein said modified oligonucleotide is at least 85%, at least 90%, at least 95%, or 100% complementary to SEQ ID NO: 2. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

In certain embodiments, compounds target a region of a PCSK9 nucleic acid. In certain embodiments, such compounds targeted to a region of a PCSK9 nucleic acid have a contiguous nucleobase portion that is complementary to an equal length nucleobase portion of the region. For example, the portion can be at least an 8, 9, 10, 11, 12, 13, 14, 15, 16, 17, 18, 19, or 20 contiguous nucleobase portion complementary to an equal length portion of a region recited herein. In certain embodiments, such compounds target the following nucleotide regions of SEQ ID NO: 2: 6356-6371, 12843-12947, 12905-12948, 17681-17700, 19653-19673, 27626-27669, 27895-27949, and 28105-28136. In certain embodiments, these compounds are antisense compounds, oligomeric compounds, or oligonucleotides.

In certain embodiments, a compound comprises a modified oligonucleotide 8 to 80 linked nucleosides in length and having at least an 8, 9, 10, 11, 12, 13, 14, 15, or 16 contiguous nucleobase portion complementary to an equal length portion within nucleotides 6356-6371, 12909-12924, 17685-17700, 19658-19673, 27643-27658, 27906-27921, 27916-27931, 27917-27932, and 28107-28122 of SEQ ID NO: 2. In certain embodiments, the modified oligonucleotide is 10 to 30 linked nucleosides in length.

In certain embodiments, a compound comprises a modified oligonucleotide 8 to 80 linked nucleosides in length and complementary within nucleotides 6356-6371, 12909-12924, 17685-17700, 19658-19673, 27643-27658, 27906-27921, 27916-27931, 27917-27932, and 28107-28122 of SEQ ID NO: 2. In certain embodiments, the modified oligonucleotide is 10 to 30 linked nucleosides in length.

In certain embodiments, a compound comprises a modified oligonucleotide 8 to 80 linked nucleosides in length and having a nucleobase sequence comprising at least an 8, 9, 10, 11, 12, 13, 14, 15, or 16 contiguous nucleobase portion any one of SEQ ID NOs: 1016, 1528, 763, 1071, 1147, 1149, 1016, 955, 1195, and 353. In certain embodiments, the modified oligonucleotide is 10 to 30 linked nucleosides in length.

In certain embodiments, a compound comprises a modified oligonucleotide 8 to 80 linked nucleosides in length and having a nucleobase sequence comprising any one of SEQ ID NOs: 1016, 1528, 763, 1071, 1147, 1149, 1016, 955, 1195, and 353. In certain embodiments, the modified oligonucleotide is 10 to 30 linked nucleosides in length.

In certain embodiments, a compound comprises a modified oligonucleotide having a nucleobase sequence consisting of any one of SEQ ID NOs: 1016, 1528, 763, 1071, 1147, 1149, 1016, 955, 1195, and 353.

In certain embodiments, compounds targeted to PCSK9 are ISIS 863568, ISIS 863579, ISIS 863581, ISIS 863582, ISIS 863587, ISIS 863633, ISIS 863655, ISIS 863670, and ISIS 863681. Out of over 1540 compounds that were screened as described in the Examples section below, ISIS 863568, ISIS 863579, ISIS 863581, ISIS 863582, ISIS 863587, ISIS 863633, ISIS 863655, ISIS 863670, and ISIS 863681 emerged as the top lead compounds. In particular, ISIS 863633 exhibited the best combination of properties in terms of potency and tolerability out of over 1540 compounds.

In certain embodiments, any of the foregoing modified oligonucleotides comprises at least one modified internucleoside linkage, at least one modified sugar, and/or at least one modified nucleobase.

In certain embodiments, any of the foregoing modified oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH3)-O-2' group, a 4'-CH2-O-2' group, or a 4'-(CH2)2-O-2' group.

In certain embodiments, the modified oligonucleotide comprises at least one modified internucleoside linkage, such as a phosphorothioate internucleoside linkage.

In certain embodiments, any of the foregoing modified oligonucleotides comprises at least one modified nucleobase, such as 5-methylcytosine.

In certain embodiments, any of the foregoing modified oligonucleotides comprises:
  a gap segment consisting of linked deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar. In certain embodiments, the modified oligonucleotide is 14 to 80 linked nucleosides in length having a nucleobase sequence comprising the sequence recited in any one of SEQ ID NOs: 1016, 1528, 763, 1071, 1147, 1149, 1016, 955, 1195, and 353. In certain embodiments, the modified oligo nucleotide is 10 to 30 linked nucleosides in length having a nucleobase sequence comprising the sequence recited in any one of SEQ ID NOs: 1016, 1528, 763, 1071, 1147, 1149, 1016, 955, 1195, and 353. In certain embodiments, the modified oligonucleotide is 14 linked nucleosides in length having a nucleobase sequence consisting of the sequence recited in any one of SEQ ID NOs: 1016, 1528, 763, 1071, 1147, 1149, 1016, 955, 1195, and 353.

In certain embodiments, a compound comprises or consists of a modified oligonucleotide 16-80 linked nucleobases in length having a nucleobase sequence comprising the sequence recited in any one of SEQ ID NOs: 1016, 1528, 763, 1071, 1147, 1149, 1016, 955, 1195, and 353, wherein the modified oligonucleotide comprises a gap segment consisting of ten linked deoxynucleosides;
a 5' wing segment consisting of three linked nucleosides; and
a 3' wing segment consisting of three linked nucleosides;
wherein the gap segment is positioned between the 5' wing segment and the 3' wing segment, wherein each nucleoside of each wing segment comprises a cEt sugar; wherein each internucleoside linkage is a phosphorothioate linkage and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound comprises or consists of ISIS 863633 or salt thereof, having the following chemical structure:

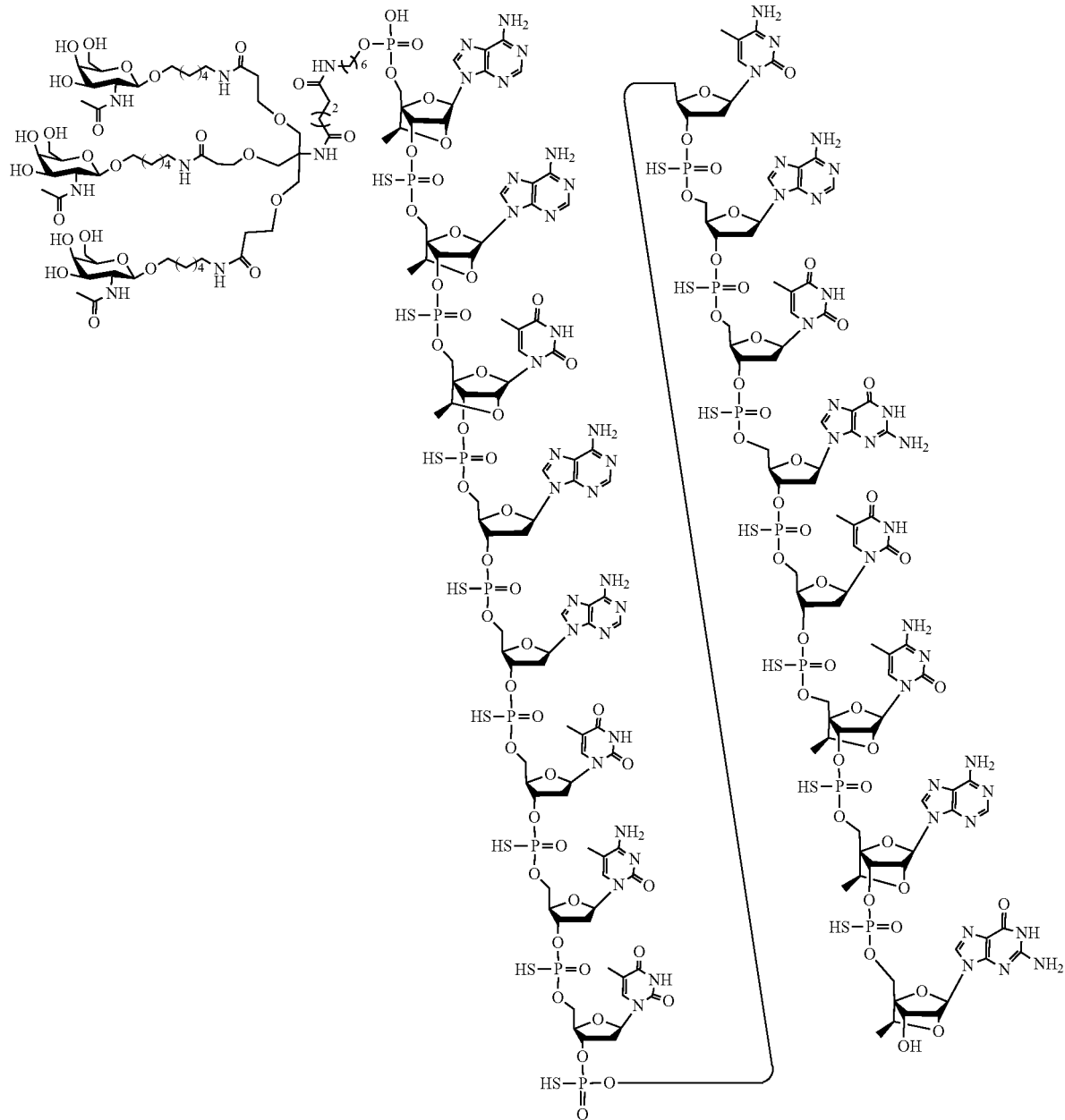

In certain embodiments, a compound comprises or consists of ISIS 863633 or salt thereof, having the following chemical structure:
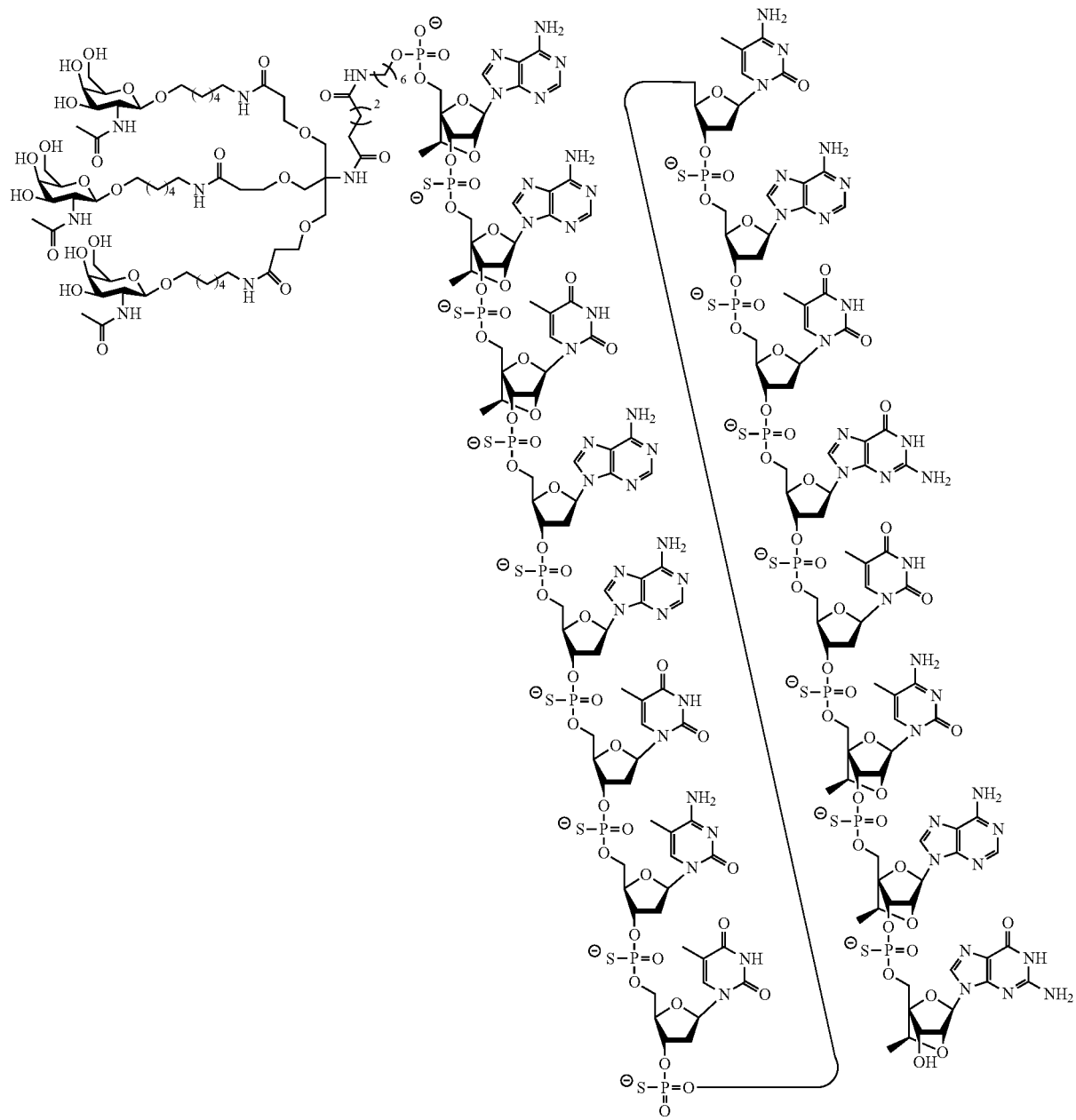

In certain embodiments, a compound comprises or consists of the sodium salt of ISIS 863633, having the following chemical structure:

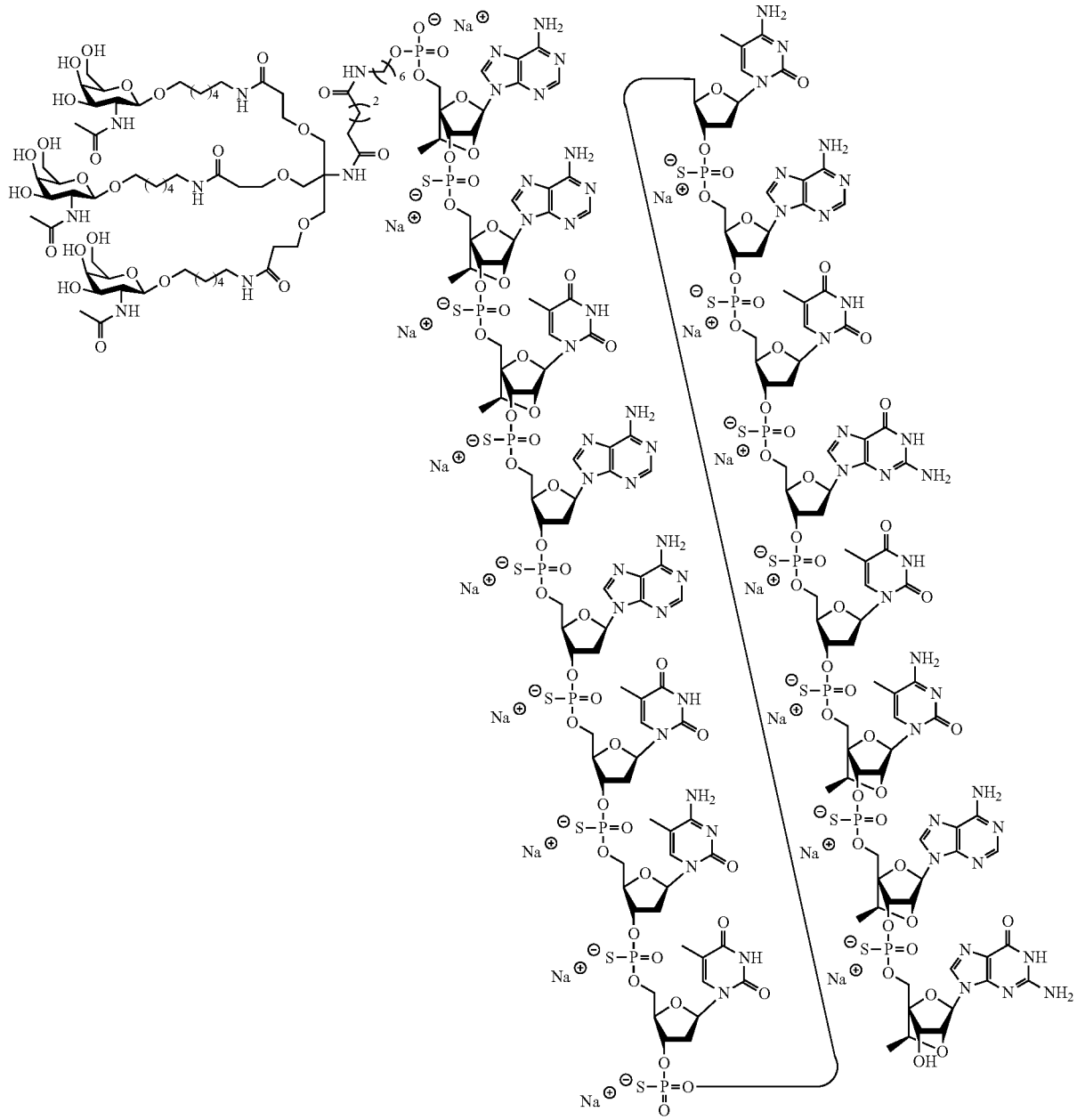

In any of the foregoing embodiments, the compound or oligonucleotide can be at least 85%, at least 90%, at least 95%, at least 98%, at least 99%, or 100% complementary to a nucleic acid encoding PCSK9.

In any of the foregoing embodiments, the compound can be single-stranded. In certain embodiments, the compound comprises deoxyribonucleotides. In certain embodiments, the compound is double-stranded. In certain embodiments, the compound is double-stranded and comprises ribonucleotides. In any of the foregoing embodiments, the compound can be an antisense compound or oligomeric compound.

In any of the foregoing embodiments, the compound can be 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides in length. In certain embodiments, the compound comprises or consists of an oligonucleotide.

In certain embodiments, a compound comprises a modified oligonucleotide described herein and a conjugate group. In certain embodiments, the conjugate group is linked to the modified oligonucleotide at the 5' end of the modified oligonucleotide. In certain embodiments, the conjugate group is linked to the modified oligonucleotide at the 3' end of the modified oligonucleotide. In certain embodiments, the conjugate group comprises at least one N-Acetylgalactosamine (GalNAc), at least two N-Acetylgalactosamines (GalNAcs), or at least three N-Acetylgalactosamines (GalNAcs).

In certain embodiments, compounds or compositions provided herein comprise a pharmaceutically acceptable salt of the modified oligonucleotide. In certain embodiments, the salt is a sodium salt. In certain embodiments, the salt is a potassium salt.

In certain embodiments, the compounds or compositions as described herein are active by virtue of having at least one of an in vitro $IC_{50}$ of less than 5 µM, less than 4.5 µM, less than 4 µM, less than 3.5 µM, less than 3 µM, less than 2.5 µM, less than 2 µM, less than 1.5 µM, less than 1 µM, less than 0.9 µM, less than 0.8 µM, less than 0.7 µM, less than 0.6 µM, less than 0.5 µM, less than 0.4 µM, less than 0.3 µM, less than 0.2 µM, or less than 0.1 µM.

In certain embodiments, the compounds or compositions as described herein are highly tolerable as demonstrated by having at least one of an increase an alanine transaminase (ALT) or aspartate transaminase (AST) value of no more than 4 fold, 3 fold, or 2 fold over saline treated animals or an increase in liver, spleen, or kidney weight of no more than 30%, 20%, 15%, 12%, 10%, 5%, or 2% compared to control treated animals. In certain embodiments, the compounds or compositions as described herein are highly tolerable as demonstrated by having no increase of ALT or AST over control treated animals. In certain embodiments, the compounds or compositions as described herein are highly tolerable as demonstrated by having no increase in liver, spleen, or kidney weight over control animals.

Certain embodiments provide a composition comprising the compound of any of the aforementioned embodiments or any pharmaceutically acceptable salt thereof and at least one of a pharmaceutically acceptable carrier or diluent. In certain embodiments, the composition has a viscosity less than about 40 centipoise (cP), less than about 30 centipose (cP), less than about 20 centipose (cP), less than about 15 centipose (cP), or less than about 10 centipose (cP). In certain embodiments, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain embodiments, the composition having any of the aforementioned viscosities and/or compound concentrations has a temperature of room temperature or about 20° C., about 21° C., about 22° C., about 23° C., about 24° C., about 25° C., about 26° C., about 27° C., about 28° C., about 29° C., or about 30° C.

Certain Indications

Certain embodiments provided herein relate to methods of inhibiting PCSK9 expression, which can be useful for treating, preventing, or ameliorating a disease associated with PCSK9 in an individual, by administration of a compound that targets PCSK9. In certain embodiments, the compound can be a PCSK9 specific inhibitor. In certain embodiments, the compound can be an antisense compound, oligomeric compound, or oligonucleotide targeted to PCSK9.

Examples of diseases associated with PCSK9 treatable, preventable, and/or ameliorable with the methods provided herein include a cardiovascular disease, dyslipidemia, mixed dyslipidemia, hypercholesterolemia, a reduction in LDL cholesterol, and reduction in atherogenic apolipoprotein (a) [Lp(a)].

In certain embodiments, a method of treating, preventing, or ameliorating a disease associated with PCSK9 in an individual comprises administering to the individual a compound comprising a PCSK9 specific inhibitor, thereby treating, preventing, or ameliorating the disease. In certain embodiments, the individual is identified as having or at risk of having a disease associated with PCSK9. In certain embodiments, the disease is a cardiovascular disease. In certain embodiments, the compound comprises an antisense compound targeted to PCSK9. In certain embodiments, the compound comprises an oligonucleotide targeted to PCSK9. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, a compound comprises a modified oligonucleotide 14 to 80 linked nucleosides in length and having a nucleobase sequence comprising the nucleobase sequence of any one of SEQ ID NOs: 3-1540. In certain embodiments, a compound comprises a modified oligonucleotide consisting of the nucleobase sequence of any one of SEQ ID NOs: 3-1540. In certain embodiments, a compound comprises a modified oligonucleotide 14 to 80 linked nucleosides in length having a nucleobase sequence comprising any one of SEQ ID NOs: 1016, 1528, 763, 1071, 1147, 1149, 1016, 955, 1195, and 353. In certain embodiments, a compound comprises a modified oligonucleotide having a nucleobase sequence consisting of any one of SEQ ID NOs: 1016, 1528, 763, 1071, 1147, 1149, 1016, 955, 1195, and 353. In any of the foregoing embodiments, the modified oligonucleotide can be 10 to 30 linked nucleosides in length. In certain embodiments, the compound is ISIS 863568, ISIS 863579, ISIS 863581, ISIS 863582, ISIS 863587, ISIS 863633, ISIS 863655, ISIS 863670, and ISIS 863681. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound reduces LDL-cholesterol levels, reduces Lp(a) levels, induces LDL receptor (LDL-R) activity, and regulates LDL receptor-LDL-cholesterol homeostasis.

In certain embodiments, a method of treating, preventing, or ameliorating a cardiovascular disease comprises administering to the individual a compound comprising a PCSK9 specific inhibitor, thereby treating, preventing, or ameliorating the cardiovascular disease. In certain embodiments, the cardiovascular disease is dyslipidemia or hypercholesterolemia. In certain embodiments, the compound comprises an antisense compound targeted to PCSK9. In certain embodiments, the compound comprises an oligonucleotide targeted to PCSK9. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, a compound comprises a modified oligonucleotide 14 to 80 linked nucleosides in length and having a nucleobase sequence comprising the nucleobase sequence of any one of SEQ ID NOs: 3-1540. In certain embodiments, a compound comprises a modified oligonucleotide consisting of the nucleobase sequence of any one of SEQ ID NOs: 3-1540. In certain embodiments, a compound comprises a modified oligonucleotide 14 to 80 linked nucleosides in length having a nucleobase sequence comprising any one of SEQ ID NOs: 1016, 1528, 763, 1071, 1147, 1149, 1016, 955, 1195, and 353. In certain embodiments, a compound comprises a modified oligonucleotide having a nucleobase sequence consisting of any one of SEQ ID NOs: 1016, 1528, 763, 1071, 1147, 1149, 1016, 955, 1195, and 353. In any of the foregoing embodiments, the modified oligonucleotide can be 10 to 30 linked nucleosides in length. In certain embodiments, the compound is ISIS 863568, ISIS 863579, ISIS 863581, ISIS 863582, ISIS 863587, ISIS 863633, ISIS 863655, ISIS 863670, and ISIS 863681. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound reduces LDL-cholesterol levels. In certain embodiments, administering the compound reduces Lp(a) levels. In certain embodiments, administering the compound induces LDL receptor (LDL-R) activity. In certain embodiments, administering the compound regulates LDL receptor-LDL-cholesterol homeostasis.

In certain embodiments, a method of inhibiting expression of PCSK9 in an individual having, or at risk of having, a disease associated with PCSK9 comprises administering to the individual a compound comprising a PCSK9 specific inhibitor, thereby inhibiting expression of PCSK9 in the individual. In certain embodiments, administering the compound inhibits expression of PCSK9 in the liver. In certain embodiments, the disease is a cardiovascular disease. In certain embodiments, the individual has, or is at risk of having dyslipidemia. In certain embodiments, the individual has, or is at risk of having hypercholesterolemia. In certain embodiments, the individual has, or is at risk of having mixed dyslipidemia. In certain embodiments, the compound comprises an antisense compound targeted to PCSK9. In certain embodiments, the compound comprises an oligonucleotide targeted to PCSK9. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, a compound comprises a modified oligonucleotide 14 to 80 linked nucleosides in length and having a nucleobase sequence comprising the nucleobase sequence of any one of SEQ ID NOs: 3-1540. In certain embodiments, a compound comprises a modified oligonucleotide consisting of the nucleobase sequence of any one of SEQ ID NOs: 3-1540. In certain embodiments, a compound comprises a modified oligonucleotide 14 to 80 linked nucleosides in length having a nucleobase sequence comprising any one of SEQ ID NOs: 1016, 1528, 763, 1071, 1147, 1149, 1016, 955, 1195, and 353. In certain embodiments, a compound comprises a modified oligonucleotide having a nucleobase sequence consisting of any one of SEQ ID NOs: 1016, 1528, 763, 1071, 1147, 1149, 1016, 955, 1195, and 353. In any of the foregoing embodiments, the modified oligonucleotide can be 10 to 30 linked nucleosides in length. In certain embodiments, the compound is ISIS 863568, ISIS 863579, ISIS 863581, ISIS 863582, ISIS 863587, ISIS 863633, ISIS 863655, ISIS 863670, and ISIS 863681. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound reduces LDL-cholesterol levels. In certain embodiments, administering the compound reduces Lp(a) levels. In certain embodiments, administering the compound induces LDL receptor (LDL-R) activity. In certain embodiments, administering the compound regulates LDL receptor-LDL-cholesterol homeostasis.

In certain embodiments, a method of inhibiting expression of PCSK9 in a cell comprises contacting the cell with a compound comprising a PCSK9 specific inhibitor, thereby inhibiting expression of PCSK9 in the cell. In certain embodiments, the cell is a hepatocyte. In certain embodiments, the cell is in the liver. In certain embodiments, the cell is in the liver of an individual who has, or is at risk of having a cardiovascular disease. In certain embodiments, the cell is in the liver of an individual who has, or is at risk of having dyslipidemia. In certain embodiments, the cell is in the liver of an individual who has, or is at risk of having mixed dyslipidemia. In certain embodiments, the cell is in the liver of an individual who has, or is at risk of having hypercholesterolemia. In certain embodiments, administering the compound inhibits expression of PCSK9 in the liver. In certain embodiments, the individual has, or is at risk of having, a cardiovascular disease. In certain embodiments, the individual has, or is at risk of having dyslipidemia. In certain embodiments, the individual has, or is at risk of having mixed dyslipidemia. In certain embodiments, the individual has, or is at risk of having hypercholesterolemia. In certain embodiments, the compound comprises an antisense compound targeted to PCSK9. In certain embodiments, the compound comprises an oligonucleotide targeted to PCSK9. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, a compound comprises a modified oligonucleotide 14 to 80 linked nucleosides in length and having a nucleobase sequence comprising the nucleobase sequence of any one of SEQ ID NOs: 3-1540. In certain embodiments, a compound comprises a modified oligonucleotide consisting of the nucleobase sequence of any one of SEQ ID NOs: 3-1540. In certain embodiments, a compound comprises a modified oligonucleotide 14 to 80 linked nucleosides in length having a nucleobase sequence comprising any one of SEQ ID NOs: 1016, 1528, 763, 1071, 1147, 1149, 1016, 955, 1195, and 353. In certain embodiments, a compound comprises a modified oligonucleotide having a nucleobase sequence consisting of any one of SEQ ID NOs: 1016, 1528, 763, 1071, 1147, 1149, 1016, 955, 1195, and 353. In any of the foregoing embodiments, the modified oligonucleotide can be 10 to 30 linked nucleosides in length. In certain embodiments, the compound is ISIS 863568, ISIS 863579, ISIS 863581, ISIS 863582, ISIS 863587, ISIS 863633, ISIS 863655, ISIS 863670, and ISIS 863681. In any of the foregoing embodiments, the compound can be single-stranded or double-stranded. In any of the foregoing embodiments, the compound can be an antisense compound or oligomeric compound.

In certain embodiments, a method of reducing or inhibiting LDL-cholesterol levels, reducing or inhibiting Lp(a) levels, inducing LDL receptor (LDL-R) activity, or regulating LDL receptor-LDL-cholesterol homeostasis in the liver of an individual having, or at risk of having, a disease associated with PCSK9 comprises administering to the individual a compound comprising a PCSK9 specific inhibitor, thereby reducing or inhibiting LDL-cholesterol and Lp(a) levels, inducing LDL receptor (LDL-R) activity, and regulating LDL receptor-LDL-cholesterol homeostasis in the liver of the individual. In certain embodiments, the individual has, or is at risk of having, a cardiovascular disease. In certain embodiments, the individual has, or is at risk of having, dyslipidemia. In certain embodiments, the individual has, or is at risk of having, mixed dyslipidemia. In certain embodiments, the individual has, or is at risk of having, hypercholesterolemia. In certain embodiments, the compound comprises an antisense compound targeted to PCSK9. In certain embodiments, the compound comprises an oligonucleotide targeted to PCSK9. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, a compound comprises a modified oligonucleotide 14 to 80 linked nucleosides in length and having a nucleobase sequence comprising the nucleobase sequence of any one of SEQ ID NOs: 3-1540. In certain embodiments, a compound comprises a modified oligonucleotide consisting of the nucleobase sequence of any one of SEQ ID NOs: 3-1540. In certain embodiments, a compound comprises a modified oligonucleotide 14 to 80 linked nucleosides in length having a nucleobase sequence comprising any one of SEQ ID NOs: 1016, 1528, 763, 1071, 1147, 1149, 1016, 955, 1195, and 353. In certain embodiments, a compound comprises a modified oligonucleotide having a nucleobase sequence consisting of any one of SEQ ID NOs: 1016, 1528, 763, 1071, 1147, 1149, 1016, 955, 1195, and 353. In any of the foregoing embodiments, the modified oligonucleotide can be 10 to 30 linked nucleosides in length. In certain embodiments, the compound is ISIS 863568, ISIS 863579, ISIS 863581, ISIS 863582, ISIS 863587, ISIS 863633, ISIS 863655, ISIS 863670, and ISIS 863681. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, the individual is identified as having or at risk of having a disease associated with PCSK9.

Certain embodiments are drawn to a compound comprising a PCSK9 specific inhibitor for use in treating a disease associated with PCSK9. In certain embodiments, the disease is a cardiovascular disease. In certain embodiments, the disease is dyslipidemia. In certain embodiments, the disease is mixed dyslipidemia. In certain embodiments, the disease is hypercholesterolemia In certain embodiments, the compound comprises an antisense compound targeted to PCSK9. In certain embodiments, the compound comprises an oligonucleotide targeted to PCSK9. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, a compound comprises a modified oligonucleotide 14 to 80 linked nucleosides in length and having a nucleobase sequence comprising the nucleobase sequence of any one of SEQ ID NOs: 3-1540. In certain embodiments, a compound comprises a modified oligonucleotide consisting of the nucleobase sequence of any one of SEQ ID NOs: 3-1540. In certain embodiments, a compound comprises a modified oligonucleotide 14 to 80 linked nucleosides in length having a nucleobase sequence comprising any one of SEQ ID NOs: 1016, 1528, 763, 1071, 1147, 1149, 1016, 955, 1195, and 353. In certain embodiments, a compound comprises a modified oligonucleotide having a nucleobase sequence consisting of any one of SEQ ID NOs: 1016, 1528, 763, 1071, 1147, 1149, 1016, 955, 1195, and 353. In any of the foregoing embodiments, the modified oligonucleotide can be 10 to 30 linked nucleosides in length. In certain embodiments, the compound is ISIS 863568, ISIS 863579, ISIS 863581, ISIS 863582, ISIS 863587, ISIS 863633, ISIS 863655, ISIS 863670, and ISIS 863681. In any of the foregoing embodiments, the compound can be single-stranded or double-stranded. In any of the foregoing embodiments, the compound can be an antisense compound or oligomeric compound. In certain embodiments, the compound is administered to the individual parenterally.

Certain embodiments are drawn to a compound comprising a PCSK9 specific inhibitor for use in reducing or inhibiting LDL-cholesterol, reducing or inhibiting Lp(a) levels, inducing LDL receptor (LDL-R) activity, and regulating LDL receptor-LDL-cholesterol homeostasis of an individual having or at risk of having a cardiovascular disease. In certain embodiments, the cardiovascular disease is dyslipidemia or hypercholesterolemia. In certain embodiments, the compound comprises an antisense compound targeted to PCSK9. In certain embodiments, the compound comprises an oligonucleotide targeted to PCSK9. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, a compound comprises a modified oligonucleotide 14 to 80 linked nucleosides in length and having a nucleobase sequence comprising the nucleobase sequence of any one of SEQ ID NOs: 3-1540. In certain embodiments, a compound comprises a modified oligonucleotide consisting of the nucleobase sequence of any one of SEQ ID NOs: 3-1540. In certain embodiments, a compound comprises a modified oligonucleotide 14 to 80 linked nucleosides in length having a nucleobase sequence comprising any one of SEQ ID NOs: 1016, 1528, 763, 1071, 1147, 1149, 1016, 955, 1195, and 353. In certain embodiments, a compound comprises a modified oligonucleotide having a nucleobase sequence consisting of any one of SEQ ID NOs: 1016, 1528, 763, 1071, 1147, 1149, 1016, 955, 1195, and 353. In any of the foregoing embodiments, the modified oligonucleotide can be 10 to 30 linked nucleosides in length. In certain embodiments, the compound is ISIS 863568, ISIS 863579, ISIS 863581, ISIS 863582, ISIS 863587, ISIS 863633, ISIS 863655, ISIS 863670, and ISIS 863681. In any of the foregoing embodiments, the compound can be single-stranded or double-stranded. In any of the foregoing embodiments, the compound can be an antisense compound or oligomeric compound.

Certain embodiments are drawn to use of a compound comprising a PCSK9 specific inhibitor for the manufacture or preparation of a medicament for treating a disease associated with PCSK9. Certain embodiments are drawn to use of a compound comprising a PCSK9 specific inhibitor for the preparation of a medicament for treating a disease associated with PCSK9. In certain embodiments, the disease is a cardiovascular disease. In certain embodiments, the disease is dyslipidemia. In certain embodiments, the disease is mixed dyslipidemia. In certain embodiments, the disease is hypercholesterolemia. In certain embodiments, the compound comprises an antisense compound targeted to PCSK9. In certain embodiments, the compound comprises an oligonucleotide targeted to PCSK9. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, a compound comprises a modified oligonucleotide 14 to 80 linked nucleosides in length and having a nucleobase sequence comprising the nucleobase sequence of any one of SEQ ID NOs: 3-1540. In certain embodiments, a compound comprises a modified oligonucleotide consisting of the nucleobase sequence of any one of SEQ ID NOs: 3-1540. In certain embodiments, a compound comprises a modified oligonucleotide 14 to 80 linked nucleosides in length having a nucleobase sequence comprising any one of SEQ ID NOs: 1016, 1528, 763, 1071, 1147, 1149, 1016, 955, 1195, and 353. In certain embodiments, a compound comprises a modified oligonucleotide having a nucleobase sequence consisting of any one of SEQ ID NOs: 1016, 1528, 763, 1071, 1147, 1149, 1016, 955, 1195, and 353. In any of the foregoing embodiments, the modified oligonucleotide can be 10 to 30 linked nucleosides in length. In certain embodiments, the compound is ISIS 863568, ISIS 863579, ISIS 863581, ISIS 863582, ISIS 863587, ISIS 863633, ISIS 863655, ISIS 863670, and ISIS 863681. In any of the foregoing embodiments, the compound can be single-stranded or double-stranded. In any of the foregoing embodiments, the compound can be an antisense compound or oligomeric compound.

Certain embodiments are drawn to use of a compound comprising a PCSK9 specific inhibitor for the manufacture or preparation of a medicament for reducing or inhibiting LDL-cholesterol levels, reducing or inhibiting Lp(a) levels, inducing LDL receptor (LDL-R) activity, and regulating LDL receptor-LDL-cholesterol homeostasis of an individual having or at risk of having a cardiovascular disease. In certain embodiments, the cardiovascular disease is dyslipidemia or hypercholesterolemia. Certain embodiments are drawn to use of a compound comprising a PCSK9 specific inhibitor for the preparation of a medicament for reducing or inhibiting LDL-cholesterol levels, reducing or inhibiting Lp(a) levels, inducing LDL receptor (LDL-R) activity, and regulating LDL receptor-LDL-cholesterol homeostasis of an individual having or at risk of having a cardiovascular disease. In certain embodiments, the cardiovascular disease is dyslipidemia or hypercholesterolemia. In certain embodiments, the compound comprises an antisense compound targeted to PCSK9. In certain embodiments, the compound comprises an oligonucleotide targeted to PCSK9. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-1540. In certain embodiments, a compound comprises a modified oligonucleotide 14 to 80 linked nucleosides in length and having a nucleobase sequence comprising the nucleobase sequence of any one of SEQ ID NOs: 3-1540. In certain embodiments, a compound comprises a modified oligonucleotide consisting of the nucleobase sequence of any one of SEQ ID NOs: 3-1540. In certain embodiments, a compound comprises a modified oligonucleotide 14 to 80 linked nucleosides in length having a nucleobase sequence comprising any one of SEQ ID NOs: 1016, 1528, 763, 1071, 1147, 1149, 1016, 955, 1195, and 353. In certain embodiments, a compound comprises a modified oligonucleotide having a nucleobase sequence consisting of any one of SEQ ID NOs: 1016, 1528, 763, 1071, 1147, 1149, 1016, 955, 1195, and 353. In any of the foregoing embodiments, the modified oligonucleotide can be 10 to 30 linked nucleosides in length. In certain embodiments, the compound is ISIS 863568, ISIS 863579, ISIS 863581, ISIS 863582, ISIS 863587, ISIS 863633, ISIS 863655, ISIS 863670, and ISIS 863681. In any of the foregoing embodiments, the compound can be single-stranded or double-stranded. In any of the foregoing embodiments, the compound can be an antisense compound or oligomeric compound.

In any of the foregoing methods or uses, the compound can be targeted to PCSK9. In certain embodiments, the compound comprises or consists of a modified oligonucleotide, for example a modified oligonucleotide 8 to 80 linked nucleosides in length, 10 to 30 linked nucleosides in length, 12 to 30 linked nucleosides in length, or 20 linked nucleosides in length. In certain embodiments, the modified oligonucleotide is at least 80%, 85%, 90%, 95% or 100% complementary to any of the nucleobase sequences recited in SEQ ID NOs: 1, 2, 1545-1550. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing embodiments, the modified oligonucleotide is 12 to 30, 15 to 30, 15 to 25, 15 to 24, 16 to 24, 17 to 24, 18 to 24, 19 to 24, 20 to 24, 19 to 22, 20 to 22, 16 to 20, or 17 or 20 linked nucleosides in length. In certain embodiments, the modified oligonucleotide is at least 80%, 85%, 90%, 95% or 100% complementary to any of the nucleobase sequences recited in SEQ ID NOs: 1, 2, 1545-1550. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing methods or uses, the compound comprises or consists of a modified oligonucleotide 14 to 30 linked nucleosides in length and having a nucleobase sequence comprising any one of SEQ ID NOs: 3-1540, wherein the modified oligonucleotide comprises:

a gap segment consisting of linked 2'-deoxynucleosides;
a 5' wing segment consisting of linked nucleosides; and
a 3' wing segment consisting of linked nucleosides;

wherein the gap segment is positioned between the 5' wing segment and the 3' wing segment and wherein each nucleoside of each wing segment comprises a modified sugar.

In any of the foregoing methods or uses, the compound comprises or consists a modified oligonucleotide 16 to 80 linked nucleobases in length having a nucleobase sequence comprising or consisting of the sequence recited in any one of SEQ ID NOs: 1016, 1528, 763, 1071, 1147, 1149, 1016, 955, 1195, and 353, wherein the modified oligonucleotide comprises
a gap segment consisting of ten linked deoxynucleosides;
a 5' wing segment consisting of three linked nucleosides; and
a 3' wing segment consisting of three linked nucleosides;
wherein the gap segment is positioned between the 5' wing segment and the 3' wing segment, wherein each nucleoside of each wing segment comprises a cEt sugar; wherein each internucleoside linkage is a phosphorothioate linkage; wherein each cytosine is a 5-methylcytosine. In certain embodiments, the modified oligonucleotide is 16-80 linked nucleosides in length. In certain embodiments, the modified oligonucleotide is 16-30 linked nucleosides in length.

In any of the foregoing methods or uses, the compound comprises or consists of ISIS 863633 or salt thereof, having the following chemical structure:

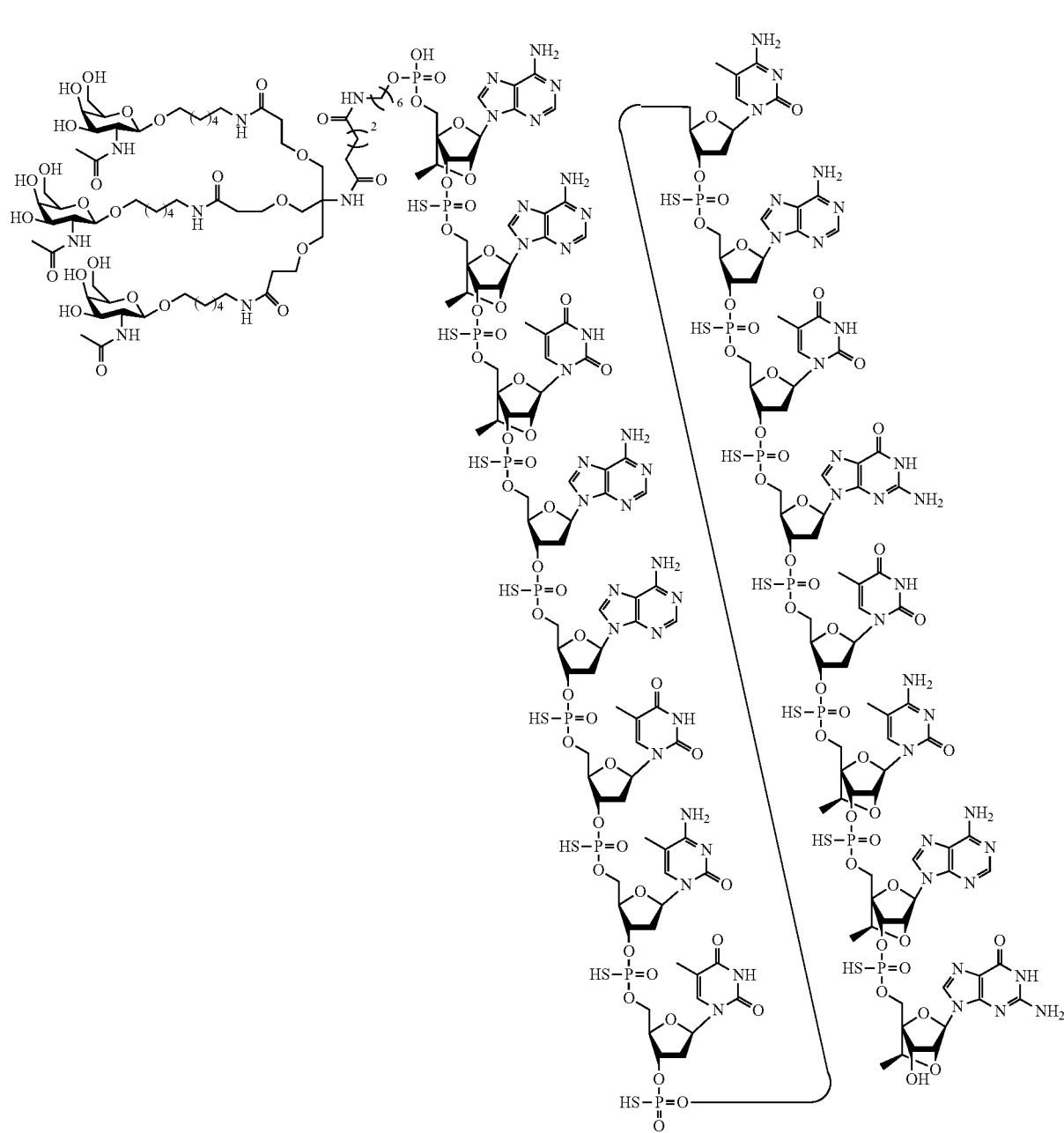

In any of the foregoing methods or uses, the compound comprises or consists of ISIS 863633 or salt thereof, having the following chemical structure:
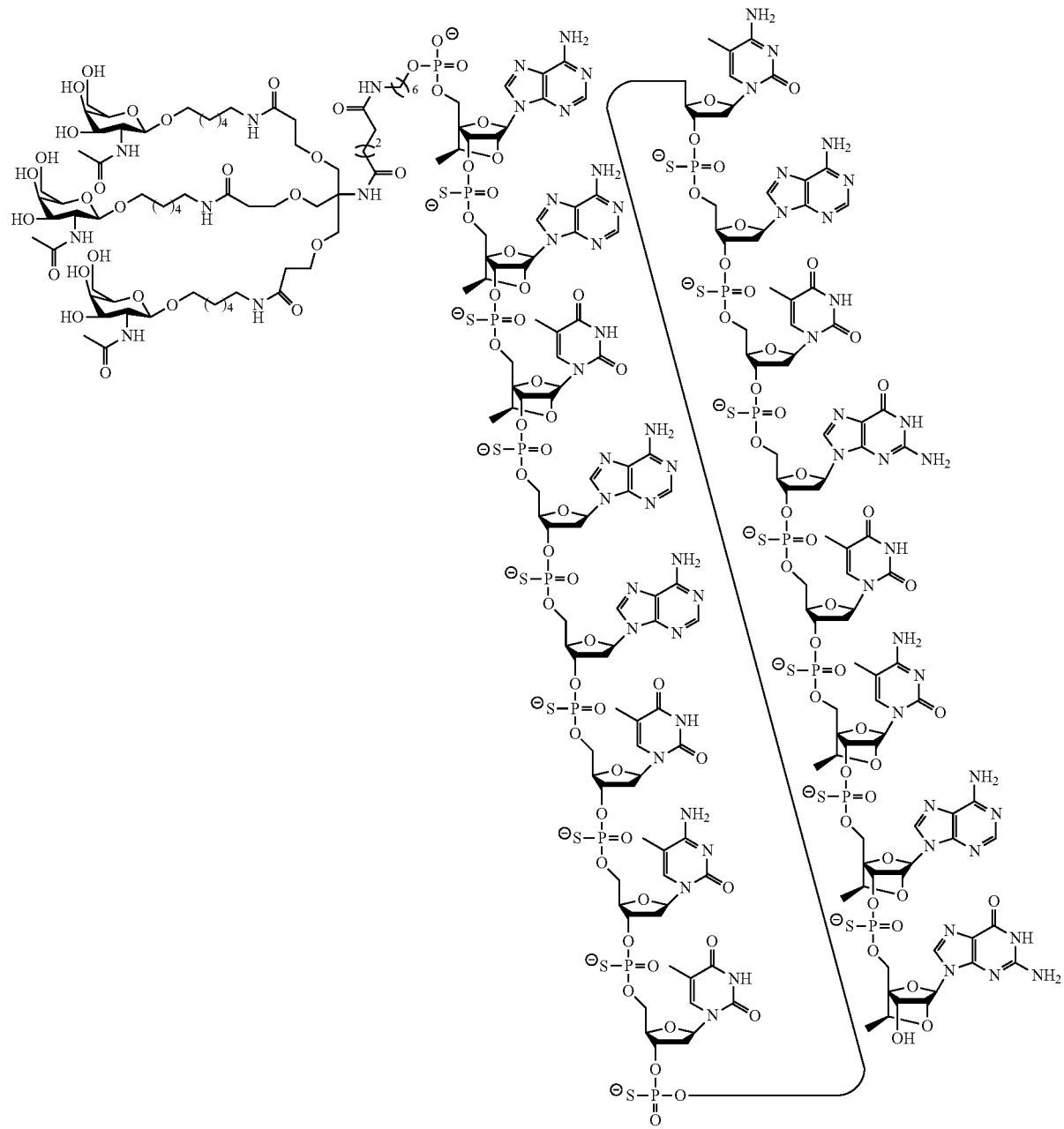

In any of the foregoing methods or uses, the compound comprises or consists of the sodium salt of ISIS 863633, having the following chemical structure:

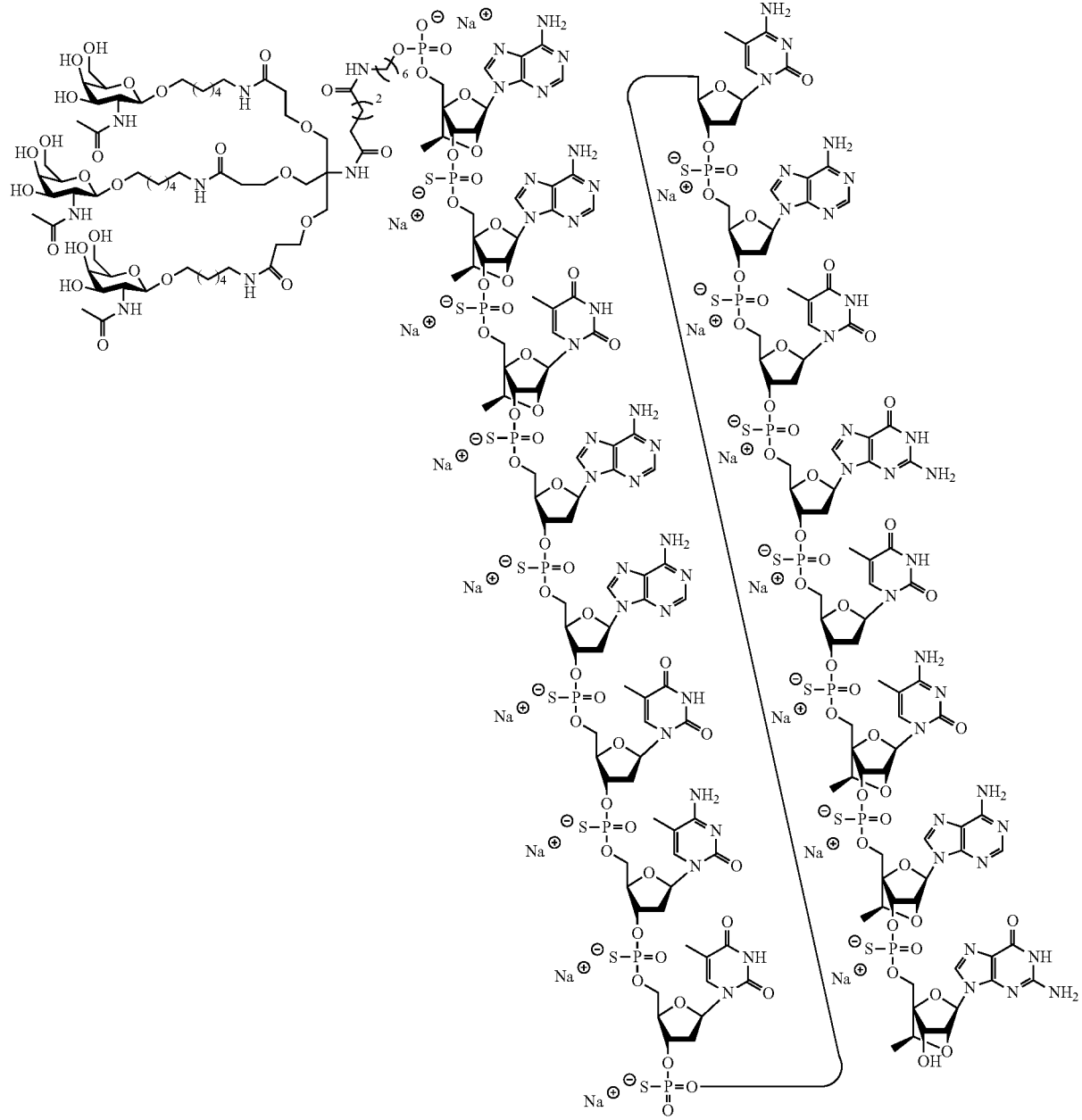

In any of the foregoing methods or uses, the compound can be administered parenterally. For example, in certain embodiments the compound can be administered through injection or infusion. Parenteral administration includes subcutaneous administration, intravenous administration, intramuscular administration, intraarterial administration, intraperitoneal administration, or intracranial administration, e.g. intrathecal or intracerebroventricular administration.

Certain Compounds

In certain embodiments, compounds described herein can be antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, the first modified oligonucleotide is 12-30 linked nucleosides in length and the second modified oligonucleotide is 12-30 linked nucleosides in length. In certain embodiments, one of the modified oligonucleotides has a nucleobase sequence comprising at least 8 contiguous nucleobases of any of SEQ ID NOs: 3-1540.

In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, a compound described herein comprises an oligonucleotide 12 to 30 linked subunits in length. In certain embodiments, a compound described herein comprises an oligonucleotide 12 to 22 linked subunits in length. In certain embodiments, compound described herein comprises an oligonucleotide 14 to 30 linked subunits in length. In certain embodiments, compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 21 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits in length, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to a PCSK9 nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. *Proc. Natl. Acad. Sci. USA* 1992, 89:7305-7309; Gautschi et al. *J. Natl. Cancer Inst.* March 2001, 93:463-471; Maher and Dolnick *Nuc. Acid. Res.* 1998, 16:3341-3358). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to be equivalent to other terms used to describe sequence specific RNA interference, such as post transcriptional gene silencing, translational inhibition, or epigenetics.

In certain embodiments, a compound described herein can comprise any of the oligonucleotide sequences targeted to PCSK9 described herein. In certain embodiments, the compound can be double-stranded. In certain embodiments, the compound comprises a first strand comprising at least an 8, 9, 10, 11, 12, 13, 14, 15, 16, 17, 18, 19, or 20 contiguous nucleobase portion of any one of SEQ ID NOs: 3-1540 and a second strand. In certain embodiments, the compound comprises a first strand comprising the nucleobase sequence of any one of SEQ ID NOs: 3-1540 and a second strand. In certain embodiments, the compound comprises ribonucleotides in which the first strand has uracil (U) in place of thymine (T) in any one of SEQ ID NOs: 3-1540. In certain embodiments, the compound comprises (i) a first strand comprising a nucleobase sequence complementary to the site on PCSK9 to which any of SEQ ID NOs: 3-1540 is targeted, and (ii) a second strand. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains one or two capped strands, as disclosed, for example, by WO 00/63364, filed Apr. 19, 2000.

In certain embodiments, the first strand of the compound is an siRNA guide strand and the second strand of the compound is an siRNA passenger strand. In certain embodiments, the second strand of the compound is complementary to the first strand. In certain embodiments, each strand of the compound is 16, 17, 18, 19, 20, 21, 22, or 23 linked nucleosides in length. In certain embodiments, the first or second strand of the compound can comprise a conjugate group.

In certain embodiments, a compound described herein can comprise any of the oligonucleotide sequences targeted to PCSK9 described herein. In certain embodiments, the compound is single stranded. In certain embodiments, such a compound is a single-stranded RNAi (ssRNAi) compound. In certain embodiments, the compound comprises at least an 8, 9, 10, 11, 12, 13, 14, 15, 16, 17, 18, 19, or 20 contiguous nucleobase portion of any one of SEQ ID NOs: 3-1540. In certain embodiments, the compound comprises the nucleobase sequence of any one of SEQ ID NOs: 3-1540 In certain embodiments, the compound comprises ribonucleotides in which uracil (U) is in place of thymine (T) in any one of SEQ ID NOs: 3-1540. In certain embodiments, the compound comprises a nucleobase sequence complementary to the site on PCSK9 to which any of SEQ ID NOs: 3-1540 is targeted. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains a capped strand, as disclosed, for example, by WO 00/63364, filed Apr. 19, 2000. In certain embodiments, the compound consists of 16, 17, 18, 19, 20, 21, 22, or 23 linked nucleosides. In certain embodiments, the compound can comprise a conjugate group.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the compound that are beneficial for use as a therapeutic or research tool. In certain embodiments, radioactive isotopic substitutions may make the compound suitable for research or diagnostic purposes, such as an imaging assay.

Certain Mechanisms

In certain embodiments, compounds described herein comprise or consist of modified oligonucleotides. In certain embodiments, compounds described herein are antisense compounds. In certain embodiments, compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Nucleotide sequences that encode PCSK9 include, without limitation, the following: RefSEQ No. GENBANK Accession No. NM_174936.3 (SEQ ID NO: 1), GENBANK Accession No. NC_000001.11 truncated from nucleotides 55036001 to 55068000 (SEQ ID NO: 2), GENBANK Accession No. AK124635.1 (SEQ ID NO: 1545), GENBANK Accession No. NT_032977.8 truncated from nucleotides 25475000 to 25504000 (SEQ ID NO: 1546), GENBANK Accession No. DA092236.1 (SEQ ID NO: 1547), GENBANK Accession No. DA803830.1 (SEQ ID NO: 1548), GENBANK Accession No. DC352135.1 (SEQ ID NO: 1549), and GENBANK Accession No. NR_110451.1 (SEQ ID NO: 1550).

Hybridization

In some embodiments, hybridization occurs between a compound disclosed herein and a PCSK9 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a PCSK9 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine (mC) and guanine (G)

unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a PCSK9 nucleic acid may be tolerated provided that the compound remains able to specifically hybridize to a target nucleic acid. Moreover, a compound may hybridize over one or more segments of a PCSK9 nucleic acid such that intervening or adjacent segments are not involved in the hybridization event (e.g., a loop structure, mismatch or hairpin structure).

In certain embodiments, the compounds provided herein, or a specified portion thereof, are, are at least, or are up to 70%, 80%, 85%, 86%, 87%, 88%, 89%, 90%, 91%, 92%, 93%, 94%, 95%, 96%, 97%, 98%, 99%, or 100% complementary to a PCSK9 nucleic acid, a target region, target segment, or specified portion thereof. In certain embodiments, the compounds provided herein, or a specified portion thereof, are 70% to 75%, 75% to 80%, 80% to 85%, 85% to 90%, 90% to 95%, 95% to 100%, or any number in between these ranges, complementary to a PCSK9 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid. Percent complementarity of a compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a PCSK9 nucleic acid, or a target region, or a target segment or target sequence thereof. As used herein, "fully complementary" means each nucleobase of a compound is complementary to the corresponding nucleobase of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a PCSK9 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a PCSK9 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific ION number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific ION number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

In certain embodiments, compounds described herein comprise or consist of antisense compounds. In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein comprise or consist of oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearly non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., US2010/190837 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a linear 2'-substituent group selected from: F, OCH$_3$, and OCH$_2$CH$_2$OCH$_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; Allerson et al., US2008/0039618; and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

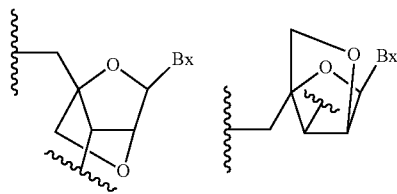

LNA (β-D-configuration) α-L-LNA (α-L-configuration)
bridge=4'-CH$_2$—O-2' bridge=4'-CH$_2$—O-2'
α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. *Bioorg. & Med. Chem.* 2002, 10, 841-854), fluoro HNA:

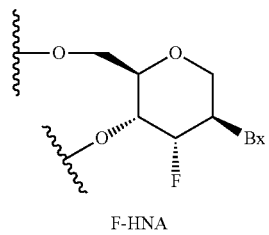

F-HNA ("F-HNA", see e.g., Swayze et al., U.S. Pat. No. 8,088,904; Swayze et al., U.S. Pat. No. 8,440,803; and Swayze et al., U.S. Pat. No. 9,005,906, F-HNA can also be referred to as a F-THP or 3'-fluoro tetrahydropyran), and nucleosides comprising additional modified THP compounds having the formula:

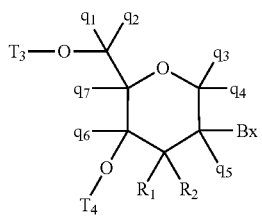

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

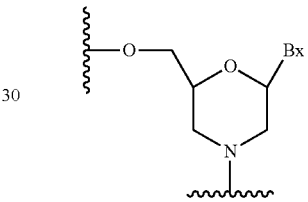

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.,* 2013, 11, 5853-5865), and nucleosides and oligonucleotides described in Manoharan et al., US2013/130378.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a PCSK9 nucleic acid comprise one or more modified nucleobases. In certain embodiments, the modified nucleobase is 5-methylcytosine. In certain embodiments, each cytosine is a 5-methylcytosine.

3. Modified Internucleoside Linkages

The naturally occurring internucleoside linkage of RNA and DNA is a 3' to 5' phosphodiester linkage In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

In certain embodiments, compounds targeted to a PCSK9 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH2-N(CH3)-O—CH2-), thiodiester, thionocarbamate (—O—C(=O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(=O)—N(H)-5'), amide-4 (3'-CH2-N(H)—C(=O)-5'), formacetal (3'-O—CH2-O-5'), methoxypropyl, and thioformacetal (3'-S—CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

4. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

a. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

In certain embodiments, a modified oligonucleotide can comprise a sugar motif described in Swayze et al., US2010/0197762; Freier et al., US2014/0107330; Freier et al., US2015/0184153; and Seth et al., US2015/0267195, each of which is incorporated by reference in its entirety herein.

b. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

c. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

5. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide is modified. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a sense transcript.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Mano-haran et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi:10.1038/mtna. 2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds, a conjugate group is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

3. Certain Cell-Targeting Conjugate Moieties

In certain embodiments, a conjugate group comprises a cell-targeting conjugate moiety. In certain embodiments, a conjugate group has the general formula:

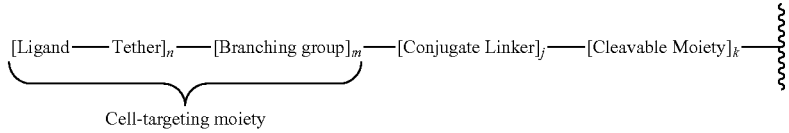

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate. In certain embodiments, each ligand is, independently selected from galactose, N-acetyl galactoseamine (GalNAc), mannose, glucose, glucosamine and fucose. In certain embodiments, each ligand is N-acetyl galactoseamine (GalNAc). In certain embodiments, the cell-targeting moiety comprises 3 GalNAc ligands. In certain embodiments, the cell-targeting moiety comprises 2 GalNAc ligands. In certain embodiments, the cell-targeting moiety comprises 1 GalNAc ligand.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry*, 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, conjugate groups comprise a cell-targeting moiety having the formula:

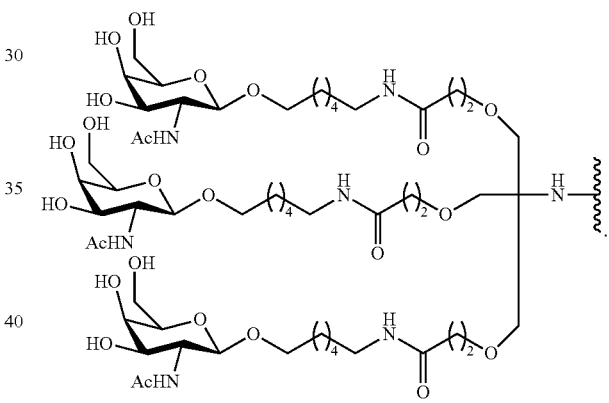

In certain embodiments, conjugate groups comprise a cell-targeting moiety having the formula:

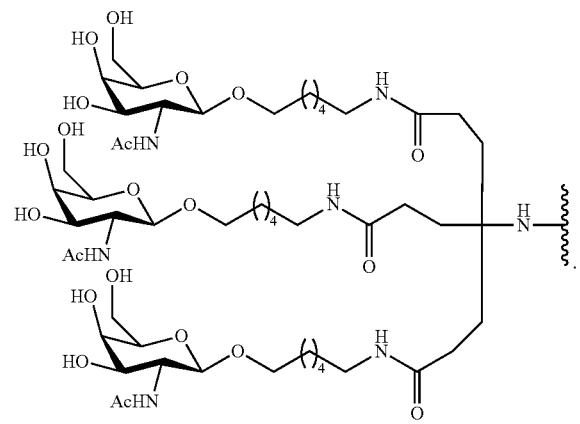

In certain embodiments, conjugate groups comprise a cell-targeting moiety having the formula:
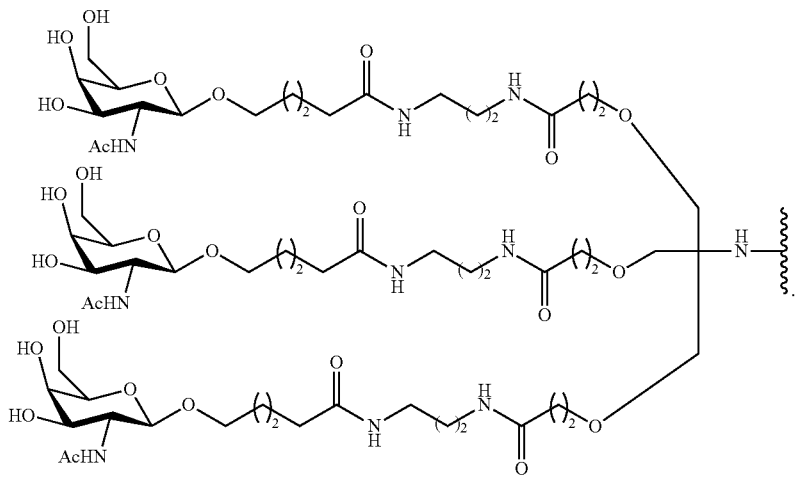
In certain embodiments, compounds described herein comprise a conjugate group described herein as "LICA-1". LICA-1 is shown below without the optional cleavable moiety at the end of the conjugate linker:
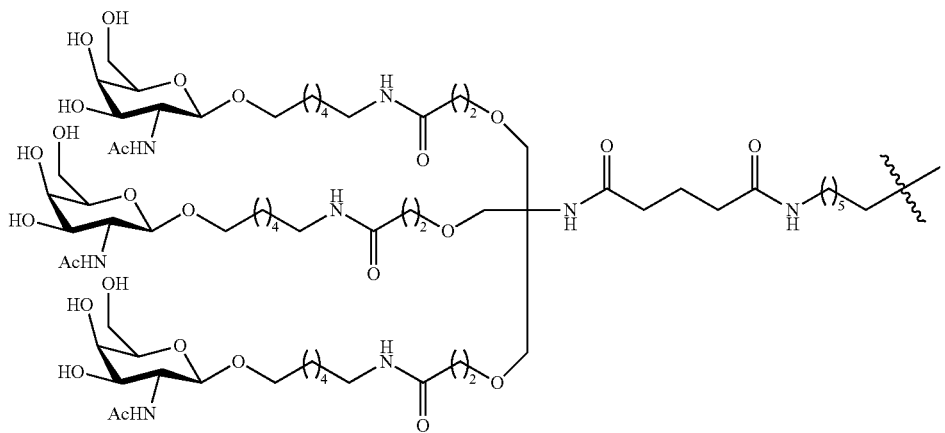

In certain embodiments, compounds described herein comprise LICA-1 and a cleavable moiety within the conjugate linker have the formula:

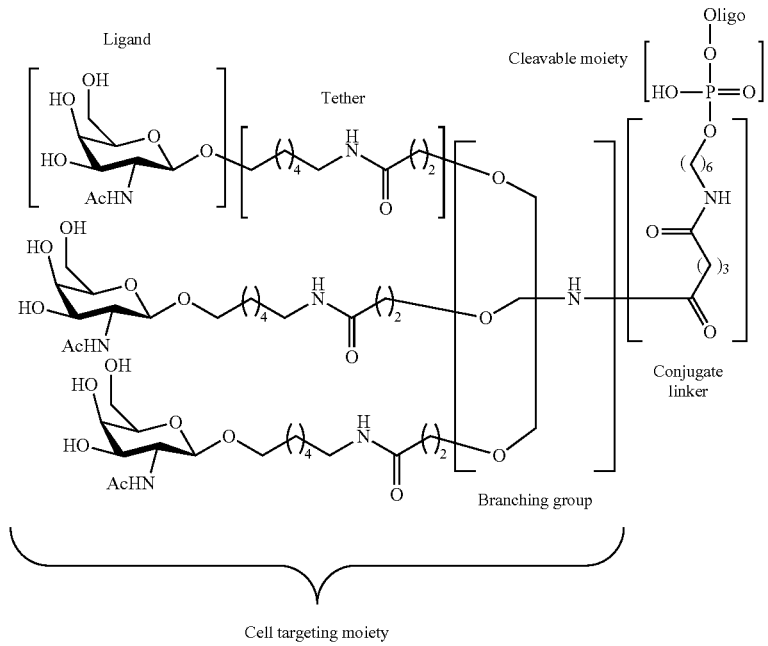

wherein oligo is an oligonucleotide.

Representative publications that teach the preparation of certain of the above noted conjugate groups and compounds comprising conjugate groups, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, 9,127,276, US 2006/0148740, US 2011/0123520, WO 2013/033230 and WO 2012/037254, Biessen et al., *J. Med. Chem.* 1995, 38, 1846-1852, Lee et al., *Bioorganic & Medicinal Chemistry* 2011, 19, 2494-2500, Rensen et al., *J. Biol. Chem.* 2001, 276, 37577-37584, Rensen et al., *J. Med. Chem.* 2004, 47, 5798-5808, Sliedregt et al., *J. Med. Chem.* 1999, 42, 609-618, and Valentijn et al., *Tetrahedron*, 1997, 53, 759-770, each of which is incorporated by reference herein in its entirety.

In certain embodiments, compounds described herein comprise modified oligonucleotides comprising a gapmer or fully modified motif and a conjugate group comprising at least one, two, or three GalNAc ligands. In certain embodiments compounds described herein comprise a conjugate group found in any of the following references: Lee, *Carbohydr Res*, 1978, 67, 509-514; Connolly et al., *J Biol Chem*, 1982, 257, 939-945; Pavia et al., *Int J Pep Protein Res*, 1983, 22, 539-548; Lee et al., Biochem, 1984, 23, 4255-4261; Lee et al., *Glycoconjugate J*, 1987, 4, 317-328; Toyokuni et al., *Tetrahedron Lett*, 1990, 31, 2673-2676; Biessen et al., *J Med Chem*, 1995, 38, 1538-1546; Valentijn et al., *Tetrahedron*, 1997, 53, 759-770; Kim et al., *Tetrahedron Lett*, 1997, 38, 3487-3490; Lee et al., *Bioconjug Chem*, 1997, 8, 762-765; Kato et al., *Glycobiol*, 2001, 11, 821-829; Rensen et al., *J Biol Chem*, 2001, 276, 37577-37584; Lee et al., *Methods Enzymol*, 2003, 362, 38-43; Westerlind et al., *Glycoconj J*, 2004, 21, 227-241; Lee et al., *Bioorg Med Chem Lett*, 2006, 16(19), 5132-5135; Maierhofer et al., *Bioorg Med Chem*, 2007, 15, 7661-7676; Khorev et al., *Bioorg Med Chem*, 2008, 16, 5216-5231; Lee et al., *Bioorg Med Chem*, 2011, 19, 2494-2500; Kornilova et al., Analyt Biochem, 2012, 425, 43-46; Pujol et al., *Angew Chemie Int Ed Engl*, 2012, 51, 7445-7448; Biessen et al., *J Med Chem*, 1995, 38, 1846-1852; Sliedregt et al., *J Med Chem*, 1999, 42, 609-618; Rensen et al., *J Med Chem*, 2004, 47, 5798-5808; Rensen et al., *Arterioscler Thromb Vasc Biol*, 2006, 26, 169-175; van Rossenberg et al., *Gene Ther*, 2004, 11, 457-464; Sato et al., *J Am Chem Soc*, 2004, 126, 14013-14022; Lee et al., *J Org Chem*, 2012, 77, 7564-7571; Biessen et al., FASEB J, 2000, 14, 1784-1792; Rajur et al., *Bioconjug Chem*, 1997, 8, 935-940; Duff et al., *Methods Enzymol*, 2000, 313, 297-321; Maier et al., *Bioconjug Chem*, 2003, 14, 18-29; Jayaprakash et al., *Org Lett*, 2010, 12, 5410-5413; Manoharan, *Antisense Nucleic Acid Drug Dev*, 2002, 12, 103-128; Merwin et al., *Bioconjug Chem*, 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/

0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, or extent of disease.

Certain embodiments provide pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, or extent of disease.

A compound described herein targeted to PCSK9 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection.

Accordingly, in one embodiment, employed in the methods described herein is a pharmaceutical composition comprising a compound targeted to PCSK9 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

Certain Selected Compounds

Approximately 1540 newly designed compounds and a few previously disclosed compounds of various lengths, chemistries, and motifs were tested for their effect on human PCSK9 mRNA in vitro in several cell types (Example 1-2). Of 1540 compounds tested for potency at a single dose in vitro, 183 selected compounds were tested for dose dependent inhibition in HepG2 cells (Example 2). Of the 183 compounds tested by dose response assays, 134 oligonucleotides were selected for single dose in vivo tolerability in rodents. These 134 oligonucleotides were conjugated at the 3'-end with THA-$C_6$-GalNAc3-(3R,5S)-5-(hydroxymethyl) pyrrolidin-3-ol phosphate endcap (henceforth referred to as 3'-THA).

In the single dose rodent tolerability model, BALB/c mice are dosed with a high concentration of 3'-THA oligonucleotide and liver function markers, such as alanine transaminase and aspartate transaminase, are measured (Example 3). ISIS 863413 (SEQ ID NO: 1096), ISIS 863419 (SEQ ID NO: 1419), ISIS 863424 (SEQ ID NO: 1297), ISIS 863425 (SEQ ID NO: 1528), ISIS 863427 (SEQ ID NO: 1145), ISIS 863433 (SEQ ID NO: 1223), ISIS 863434 (SEQ ID NO: 377), ISIS 863436 (SEQ ID NO: 763), ISIS 863437 (SEQ ID NO: 994), ISIS 863438 (SEQ ID NO: 1071), ISIS 863439 (SEQ ID NO: 1147), ISIS 863441 (SEQ ID NO: 1302), ISIS 863444 (SEQ ID NO: 1149), ISIS 863445 (SEQ ID NO: 455), ISIS 863448 (SEQ ID NO: 1380), ISIS 863452 (SEQ ID NO: 691), ISIS 863472 (SEQ ID NO: 926), ISIS 863473 (SEQ ID NO: 1233), ISIS 863474 (SEQ ID NO: 619), ISIS 863475 (SEQ ID NO: 388), ISIS 863477 (SEQ ID NO: 1542), ISIS 863479 (SEQ ID NO: 1158), ISIS 863480 (SEQ ID NO: 1235), ISIS 863481 (SEQ ID NO: 389), ISIS 863482 (SEQ ID NO: 1312), ISIS 863483 (SEQ ID NO: 1240), ISIS 863484 (SEQ ID NO: 549), ISIS 863485 (SEQ ID NO: 550), ISIS 863486 (SEQ ID NO: 781), ISIS 863489 (SEQ ID NO: 939), ISIS 863490 (SEQ ID NO: 1016), ISIS 863491 (SEQ ID NO: 1243), ISIS 863493 (SEQ ID NO: 629), ISIS 863494 (SEQ ID NO: 1017), ISIS 863495 (SEQ ID NO: 1092), ISIS 863496 (SEQ ID NO: 1244), ISIS 863497 (SEQ ID NO: 554), ISIS 863498 (SEQ ID NO: 478), ISIS 863499 (SEQ ID NO: 1094), ISIS 863502 (SEQ ID NO: 563), ISIS 863506 (SEQ ID NO: 410), ISIS 863507 (SEQ ID NO: 1411), ISIS 863509 (SEQ ID NO: 721), ISIS 863510 (SEQ ID NO: 1258), ISIS 863511 (SEQ ID NO: 645), ISIS 863512 (SEQ ID NO: 955), ISIS 863514 (SEQ ID NO: 1413), ISIS 863516 (SEQ ID NO: 881), ISIS 863517 (SEQ ID NO: 648), ISIS 863518 (SEQ ID NO: 725), ISIS 863520 (SEQ ID NO: 1111), ISIS 863522 (SEQ ID NO: 1188), ISIS 863524 (SEQ ID NO: 885), ISIS 863525 (SEQ ID NO: 504), ISIS 863526 (SEQ ID NO: 1043), ISIS 863527 (SEQ ID NO: 1195), ISIS 863531 (SEQ ID NO: 426), ISIS 863533 (SEQ ID NO: 427), ISIS 863536 (SEQ ID NO: 585), ISIS 863537 (SEQ ID NO: 1047), ISIS 863538 (SEQ ID NO: 353), ISIS 863539 (SEQ ID NO: 1352), ISIS 863541 (SEQ ID NO: 1203), ISIS 863545 (SEQ ID NO: 1516), ISIS 863547 (SEQ ID NO: 1213), ISIS 863548 (SEQ ID NO: 367), ISIS 863549 (SEQ ID NO: 1061), ISIS 863550 (SEQ ID NO: 523), ISIS 863552 (SEQ ID NO: 831), and ISIS 863553 (SEQ ID NO: 908) were considered tolerable in this study and were selected for further evaluation in a transgenic mouse model.

In the PCSK9 transgenic mice tolerability model, mice were dosed with 3'-THA conjugated oligonucleotides and plasma levels of alanine transaminase, aspartate transaminase, cholesterol, HDL-cholesterol, LDL-cholesterol and triglycerides were measured (Example 4). ISIS 863433, ISIS 863490, ISIS 863512, ISIS 863527, ISIS 863538, ISIS 863425, ISIS 863438, ISIS 863439, ISIS 863444, ISIS 863413, ISIS 863434, ISIS 863436, ISIS 863494, and ISIS 863539 were found tolerable. The selected oligonucleotide sequences were conjugated at the 5'-end with Trishexylamino-(THA)-C6GalNAC3 endcap (henceforth referred to as 5'-THA) and tested in the CD-1 mouse model. The 5'THA conjugated oligonucleotides are ISIS 845219, ISIS 863568, ISIS 863576, ISIS 863577, ISIS 863579, ISIS 863581, ISIS 863582, ISIS 863587, ISIS 863633, ISIS 863637, ISIS 863655, ISIS 863670, ISIS 863681, and ISIS 863682.

In the CD-1 mice tolerability model, mice were dosed for six weeks with varying doses of antisense oligonucleotide and tolerability markers, such as liver and kidney function markers (plasma levels of ALT, AST, albumin, BUN, creatinine, and bilirubin), hematology markers (blood cell counts for RBC, WBC, platelets, neutrophils, lymphocytes, and monocytes, as well as hemoglobin, hematocrit, and MCV content), and body and organ weights were measured (Example 5). Only those oligonucleotides were selected for further evaluation in the rat model, where treatment yielded plasma levels of such markers which were within the expected range after treatment with antisense olionucleotides. ISIS 863568, ISIS 863576, ISIS 863579, ISIS 863581, ISIS 863582, ISIS 863587, ISIS 863633, ISIS 863655, ISIS 863670, and ISIS 863681 were selected for further study in the rat model.

In the Sprague-Dawley rat model, similarly, the rats were dosed for 6 weeks with antisense oligonucleotides and tolerability markers, such as liver function markers (plasma levels of ALT, AST, albumin, BUN, creatinine, and bilirubin), kidney function markers (urine levels of creatinine and total protein), and weekly body weights, and final organ weights were measured (Example 6).

These oligonucleotides were also tested for their viscosity (Example 8) and all found to be optimal in their viscosity under the criteria tested.

ISIS 863568, ISIS 863579, ISIS 863581, ISIS 863582, ISIS 863587, ISIS 863633, ISIS 863655, ISIS 863670, and ISIS 863681 were tested in a dose-dependent four-week study in the PCSK9 transgenic mice model for efficacy (Example 7). At the end of 4 weeks, mice liver was analyzed for PCSK9 mRNA expression levels and the $ED_{50}$ was calculated. In addition, PCSK9 plasma protein levels, LDL-cholesterol plasma levels, and LDL-receptor levels in the liver were measured. It was observed that treatment with the antisense oligonucleotides resulted in inhibition of PCSK9 liver mRNA expression levels, reduction in LDL-cholesterol levels in the plasma, and corresponding increase in LDL receptor levels in the liver. Specifically, ISIS 863633 treatment was found to be efficacious.

ISIS 863568, ISIS 863579, ISIS 863581, ISIS 863582, ISIS 863587, ISIS 863633, ISIS 863655, ISIS 863670, and ISIS 863681 were tested for activity, pharmacokinetic profile and tolerability in a 12-week study in cynomolgus monkeys (Example 9). Treatment with the compounds that were fully cross-reactive with the rhesus monkey gene sequence caused reduction of PCSK9 mRNA expression in liver tissue. Specifically, treatment with ISIS 863633, ISIS 863670, and ISIS 863681 caused a reduction of PCSK9 mRNA expression in liver tissue, compared to the PBS control. It was noted that ISIS 863633 caused the highest reduction of PCSK9 mRNA expression compared to the PBS control. Changes in PCSK9 protein levels, LDL-cholesterol levels, total cholesterol levels, and hepatic LDL-receptor levels are a consequence of inhibition of PCSK9 mRNA levels. Treatment with ISIS 863633, ISIS 863670, and ISIS 863681 caused decreases in PCSK9 protein levels, LDL-cholesterol levels, total cholesterol levels, and induction of hepatic LDL-receptor levels, with ISIS 863633 causing the highest change. Treatment with the antisense oligonucleotides did not cause any changes in HDL-cholesterol or triglyceride levels. Hence, in terms of activity, ISIS 863633 was the most effective in the monkey study. Treatment with the compounds was well tolerated in the monkeys, in particular, treatment with ISIS 863633.

The new compounds were compared with previously designed compounds, including ISIS 405879 and ISIS 405995, which have previously been determined to be some of the most potent antisense compounds in vitro (see e.g., U.S. Pat. No. 8,084,437), as well as ISIS 431131 and ISIS 480604, which have been previously described in U.S. Pat. No. 9,127,276 (Example 10). The head-to-head comparison demonstrated that ISIS 863568, ISIS 863579, ISIS 863581, ISIS 863582, ISIS 863587, ISIS 863633, ISIS 863655, ISIS 863670, and ISIS 863681 were more efficacious than any of the previously publicly disclosed oligonucleotides.

Accordingly, provided herein are compounds with any one or more of the improved properties. In certain embodiments, the compounds as described herein are potent and tolerable.

EXAMPLES

The Examples below describe the screening process to identify lead compounds targeted to PCSK9. Out of over 1540 oligonucleotides that were screened, ISIS 863568, ISIS 863579, ISIS 863581, ISIS 863582, ISIS 863587, ISIS 863633, ISIS 863655, ISIS 863670, and ISIS 863681 emerged as the top lead compounds. In particular, ISIS 863633 exhibited the best combination of properties in terms of potency and tolerability out of over 1540 oligonucleotides.

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA). As provided herein, a designation of '0' for mRNA inhibition assays merely indicates that the antisense oligonucleotide did not inhibit mRNA expression levels.

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^m$CGAUCG," wherein mC indicates a cytosine base comprising a methyl group at the 5-position.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human PCSK9 in HepG2 Cells by 3-10-3 cEt Gapmers

Antisense oligonucleotides were designed targeting a PCSK9 nucleic acid and were tested for their effects on PCSK9 mRNA in vitro. The chimeric antisense oligonucleotides in the Tables below were designed as 3-10-3 cEt gapmers. The gapmers are 16 nucleosides in length, wherein the central gap segment is comprised of ten 2'-deoxynucleosides and is flanked by wing segments on the 5' end and the 3' end of three nucleosides each. Each nucleoside in the 5' wing segment and each nucleoside in the 3' wing segment has a cEt sugar modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human PCSK9 mRNA, designated herein as SEQ ID NO: 1 (GENBANK Accession No. NM_174936.3) or the human PCSK9 genomic sequence, designated herein as SEQ ID NO: 2 (GENBANK Accession No. NC_000001.11 truncated from nucleotides 55036001 to 55068000). 'n/a' indicates that the antisense oligonucleotide does not target that particular gene sequence with 100% complementarity.

The antisense oligonucleotides were tested in a series of experiments that had similar culture conditions. The results for each experiment are presented in separate tables shown below.

Study 1

Cultured HepG2 cells at a density of 20,000 cells per well were transfected using electroporation with 1,000 nM antisense oligonucleotide. ISIS 431131, previously disclosed in WO2014179620, was also included in the study as a benchmark oligonucleotide. After a treatment period of approximately 24 hours, RNA was isolated from the cells and PCSK9 mRNA levels were measured by quantitative real-time PCR. Human PCSK9 primer probe set from ABI (ID #Hs03037355_ml) was used to measure mRNA levels. PCSK9 mRNA levels were adjusted according to total RNA content, as measured by RIBOGREEN®. Results are presented as percent inhibition of PCSK9, relative to untreated control cells. Several of the newly designed oligonucleotides were more potent than the previously disclosed oligonucleotide, ISIS 431131.

TABLE 1

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 431131 | 1015 | 1034 | GTCACACTTGCTGGCCTGTC | 3 | N/A | N/A | 3 |
| 859373 | N/A | N/A | TCTGCCGTCCTTCCCA | 36 | 4562 | 4577 | 4 |
| 859377 | N/A | N/A | AGCATCTGCCGTCCTT | 62 | 4566 | 4581 | 5 |
| 859381 | N/A | N/A | TGTCAAGCACCACAGC | 31 | 5010 | 5025 | 6 |
| 859385 | N/A | N/A | TGACTTGTCAAGCACC | 61 | 5015 | 5030 | 7 |
| 859389 | N/A | N/A | ATAAGTGACTTGTCAA | 45 | 5020 | 5035 | 8 |
| 859393 | N/A | N/A | GCATTGTAAGTTCACT | 84 | 5138 | 5153 | 9 |
| 859397 | N/A | N/A | GCTTGCATTGTAAGTT | 29 | 5142 | 5157 | 10 |
| 859401 | N/A | N/A | GGTTTTCCCAGCTCTG | 85 | 5897 | 5912 | 11 |
| 859405 | N/A | N/A | CTCTGGTTTTCCCAGC | 72 | 5901 | 5916 | 12 |
| 859409 | N/A | N/A | CCACCTCTGGTTTTCC | 67 | 5905 | 5920 | 13 |
| 859413 | N/A | N/A | GTCTGCTCCAACTGCT | 43 | 6714 | 6729 | 14 |
| 859417 | N/A | N/A | CTCTTGTCTGCTCCAA | 55 | 6719 | 6734 | 15 |

TABLE 1-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 859421 | N/A | N/A | TTTAGCTCTTGTCTGC | 45 | 6724 | 6739 | 16 |
| 859425 | N/A | N/A | GCAAGTCCCTGCTAGA | 18 | 11238 | 11253 | 17 |
| 859429 | N/A | N/A | CACCTGCAAGTCCCTG | 15 | 11243 | 11258 | 18 |
| 859433 | N/A | N/A | ATTGCCACCTGCAAGT | 4 | 11248 | 11263 | 19 |
| 859437 | N/A | N/A | TCATTCTCTCCTCAGG | 58 | 11294 | 11309 | 20 |
| 859441 | N/A | N/A | TGGACCCACCACATTG | 34 | 11383 | 11398 | 21 |
| 859445 | N/A | N/A | TGCATGGACCCACCAC | 61 | 11387 | 11402 | 22 |
| 859449 | N/A | N/A | CATGTTGCATGGACCC | 61 | 11392 | 11407 | 23 |
| 859453 | N/A | N/A | ACAGTAGCCCCCCAAC | 46 | 11608 | 11623 | 24 |
| 859457 | N/A | N/A | TCACACAGTAGCCCCC | 52 | 11612 | 11627 | 25 |
| 859461 | N/A | N/A | AAAGTCACACAGTAGC | 51 | 11616 | 11631 | 26 |
| 859465 | N/A | N/A | GGTCACACAGTTTGGG | 58 | 11639 | 11654 | 27 |
| 859469 | N/A | N/A | A CATATGCAAGGTCAC | 74 | 11649 | 11664 | 28 |
| 859473 | N/A | N/A | ACTCAGACATATGCAA | 32 | 11655 | 11670 | 29 |
| 859477 | N/A | N/A | AGTGTCCCTCTTGGTC | 59 | 11950 | 11965 | 30 |
| 859481 | N/A | N/A | TGCCAGTGTCCCTCTT | 37 | 11954 | 11969 | 31 |
| 859485 | N/A | N/A | TGATCCTCTGCCAGTG | 58 | 11962 | 11977 | 32 |
| 859489 | N/A | N/A | TCTGTGATCCTCTGCC | 50 | 11966 | 11981 | 33 |
| 859493 | N/A | N/A | GGTCTCTGTGATCCTC | 67 | 11970 | 11985 | 34 |
| 859497 | N/A | N/A | AGCTCTAGGGCCCATG | 6 | 12671 | 12686 | 35 |
| 859501 | N/A | N/A | AGCCAGCTCTAGGGCC | 0 | 12675 | 12690 | 36 |
| 859505 | N/A | N/A | GTGGGTGCTCAAAACG | 28 | 12924 | 12939 | 37 |
| 859509 | N/A | N/A | AATAATGCCCCCGTAG | 26 | 13176 | 13191 | 38 |
| 859513 | N/A | N/A | CTGGTTAATAATGCCC | 47 | 13182 | 13197 | 39 |
| 859517 | N/A | N/A | CTGGATACATTGGCAG | 25 | 14125 | 14140 | 40 |
| 859521 | N/A | N/A | CTCTGAGTGTGTTAGG | 54 | 14473 | 14488 | 41 |
| 859525 | N/A | N/A | TGCTCTCTGAGTGTGT | 26 | 14477 | 14492 | 42 |
| 859529 | N/A | N/A | GCATGCTGAGCAGGTC | 78 | 14541 | 14556 | 43 |
| 859533 | N/A | N/A | TGTAGCATGCTGAGCA | 73 | 14545 | 14560 | 44 |
| 859537 | N/A | N/A | ATTCAGTGGCTGCTCT | 0 | 14755 | 14770 | 45 |
| 859541 | N/A | N/A | GAGCAATTCAGTGGCT | 24 | 14760 | 14775 | 46 |
| 859310 | 979 | 994 | TCCTCGGGCACATTCT | 34 | 16371 | 16386 | 47 |
| 468460 | 1075 | 1090 | TTGGCCACGCCGGCAT | 8 | 16705 | 16720 | 48 |
| 859545 | N/A | N/A | ATTTAGCAGCTACGGC | 35 | 17441 | 17456 | 49 |
| 859549 | N/A | N/A | CAACTATTTAGCAGCT | 36 | 17446 | 17461 | 50 |
| 859553 | N/A | N/A | AGGTTACCGCTGTCAG | 73 | 20914 | 20929 | 51 |

TABLE 1-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 859557 | N/A | N/A | GACCTAGGTTACCGCT | 33 | 20919 | 20934 | 52 |
| 859314 | 1498 | 1513 | CCACTCTGTGACACAA | 79 | 21470 | 21485 | 53 |
| 859318 | 1503 | 1518 | ATGTCCCACTCTGTGA | 49 | 21475 | 21490 | 54 |
| 859561 | N/A | N/A | CTCGAAGGTAAGCCGC | 66 | 21891 | 21906 | 55 |
| 859565 | N/A | N/A | CAGCACTGTCCTGCAG | 20 | 22880 | 22895 | 56 |
| 859569 | N/A | N/A | TTTTTGCTGGTTTGAG | 34 | 23030 | 23045 | 57 |
| 859573 | N/A | N/A | CACTTTTTTGCTGGTT | 58 | 23034 | 23049 | 58 |
| 859577 | N/A | N/A | AATTCCACTTTTTTGC | 15 | 23039 | 23054 | 59 |
| 859581 | N/A | N/A | ATCTGTGCACTATCCT | 28 | 23069 | 23084 | 60 |
| 859585 | N/A | N/A | TGGCATCTGTGCACTA | 55 | 23073 | 23088 | 61 |
| 859589 | N/A | N/A | TCTCACACGAGCATTA | 16 | 23176 | 23191 | 62 |
| 859593 | N/A | N/A | CTGCCTCTCACACGAG | 46 | 23181 | 23196 | 63 |
| 859597 | N/A | N/A | TCTTATGGAGGAGGAA | 23 | 23853 | 23868 | 64 |
| 859601 | N/A | N/A | TGTTTTCGACACAGGG | 68 | 24225 | 24240 | 65 |
| 859605 | N/A | N/A | GGCATGTTTTCGACAC | 68 | 24229 | 24244 | 66 |
| 859609 | N/A | N/A | CATCTTTTCAGTACTC | 43 | 26516 | 26531 | 67 |
| 859613 | N/A | N/A | ATCGCATCTTTTCAGT | 31 | 26520 | 26535 | 68 |
| 859322 | 2429 | 2444 | CTGTCACTGGAGCTCC | 26 | 27572 | 27587 | 69 |
| 859325 | 2495 | 2510 | GTCGGAACCATTTTAA | 34 | 27638 | 27653 | 70 |
| 859329 | 2501 | 2516 | GGACAAGTCGGAACCA | 29 | 27644 | 27659 | 71 |
| 859333 | 2505 | 2520 | AGAGGGACAAGTCGGA | 61 | 27648 | 27663 | 72 |
| 859337 | 3461 | 3476 | ATCTCCGCCAGGCCAG | 24 | 28604 | 28619 | 73 |
| 859341 | 3465 | 3480 | AAGCATCTCCGCCAGG | 68 | 28608 | 28623 | 74 |
| 859345 | 3470 | 3485 | CTTAGAAGCATCTCCG | 61 | 28613 | 28628 | 75 |
| 859349 | 3476 | 3491 | CCATGCCTTAGAAGCA | 58 | 28619 | 28634 | 76 |
| 859353 | 3538 | 3553 | TGTCTGCTTGCTTGGG | 62 | 28681 | 28696 | 77 |
| 859357 | 3544 | 3559 | GATAAATGTCTGCTTG | 37 | 28687 | 28702 | 78 |
| 859361 | 3593 | 3608 | GTCTAGAAAAGTTGGC | 63 | 28736 | 28751 | 79 |
| 859365 | 3597 | 3612 | ACAGGTCTAGAAAAGT | 64 | 28740 | 28755 | 80 |
| 859369 | 3606 | 3621 | AAAAGCAAAACAGGTC | 33 | 28749 | 28764 | 81 |

TABLE 2

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 431131 | 1015 | 1034 | GTCACACTTGCTGGCCTGTC | 0 | N/A | N/A | 3 |
| 859374 | N/A | N/A | ATCTGCCGTCCTTCCC | 42 | 4563 | 4578 | 82 |
| 859378 | N/A | N/A | CAGCATCTGCCGTCCT | 62 | 4567 | 4582 | 83 |
| 859382 | N/A | N/A | CTTGTCAAGCACCACA | 61 | 5012 | 5027 | 84 |
| 859386 | N/A | N/A | GTGACTTGTCAAGCAC | 10 | 5016 | 5031 | 85 |
| 859390 | N/A | N/A | TGTAAGTTCACTCATG | 56 | 5134 | 5149 | 86 |
| 859394 | N/A | N/A | TGCATTGTAAGTTCAC | 71 | 5139 | 5154 | 87 |
| 859398 | N/A | N/A | GGGCTTGCATTGTAAG | 13 | 5144 | 5159 | 88 |
| 859402 | N/A | N/A | TGGTTTTCCCAGCTCT | 78 | 5898 | 5913 | 89 |
| 859406 | N/A | N/A | CCTCTGGTTTTCCCAG | 61 | 5902 | 5917 | 90 |
| 859410 | N/A | N/A | TCCACCTCTGGTTTTC | 41 | 5906 | 5921 | 91 |
| 859414 | N/A | N/A | TTGTCTGCTCCAACTG | 39 | 6716 | 6731 | 92 |
| 859418 | N/A | N/A | GCTCTTGTCTGCTCCA | 71 | 6720 | 6735 | 93 |
| 859422 | N/A | N/A | TATAAATCTCCCATCC | 0 | 7280 | 7295 | 94 |
| 859426 | N/A | N/A | CTGCAAGTCCCTGCTA | 12 | 11240 | 11255 | 95 |
| 859430 | N/A | N/A | CCACCTGCAAGTCCCT | 26 | 11244 | 11259 | 96 |
| 859434 | N/A | N/A | CTCTCCTCAGGCCAGG | 64 | 11289 | 11304 | 97 |
| 859438 | N/A | N/A | CCCACCACATTGCATC | 37 | 11379 | 11394 | 98 |
| 859442 | N/A | N/A | ATGGACCCACCACATT | 10 | 11384 | 11399 | 99 |
| 859446 | N/A | N/A | TTGCATGGACCCACCA | 40 | 11388 | 11403 | 100 |
| 859450 | N/A | N/A | CGAGAACCGGTAAGGG | 34 | 11447 | 11462 | 101 |
| 859454 | N/A | N/A | CACAGTAGCCCCCCAA | 32 | 11609 | 11624 | 102 |
| 859458 | N/A | N/A | GTCACACAGTAGCCCC | 69 | 11613 | 11628 | 103 |
| 859462 | N/A | N/A | GCAAAGTCACACAGTA | 64 | 11618 | 11633 | 104 |
| 859466 | N/A | N/A | AGGTCACACAGTTTGG | 83 | 11640 | 11655 | 105 |
| 859470 | N/A | N/A | GACATATGCAAGGTCA | 40 | 11650 | 11665 | 106 |
| 859474 | N/A | N/A | TCCCTCTTGGTCTCTG | 55 | 11946 | 11961 | 107 |
| 859478 | N/A | N/A | CAGTGTCCCTCTTGGT | 67 | 11951 | 11966 | 108 |
| 859482 | N/A | N/A | CTGCCAGTGTCCCTCT | 1 | 11955 | 11970 | 109 |
| 859486 | N/A | N/A | GTGATCCTCTGCCAGT | 35 | 11963 | 11978 | 110 |
| 859490 | N/A | N/A | CTCTGTGATCCTCTGC | 68 | 11967 | 11982 | 111 |
| 859494 | N/A | N/A | GGGTCTCTGTGATCCT | 33 | 11971 | 11986 | 112 |
| 859498 | N/A | N/A | CAGCTCTAGGGCCCAT | 56 | 12672 | 12687 | 113 |
| 859502 | N/A | N/A | CAGCCAGCTCTAGGGC | 31 | 12676 | 12691 | 114 |
| 859506 | N/A | N/A | AGTGGGTGCTCAAAAC | 23 | 12925 | 12940 | 115 |
| 859510 | N/A | N/A | TTAATAATGCCCCCGT | 32 | 13178 | 13193 | 116 |

TABLE 2-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2: Start Site | SEQ ID: 2: Stop Site | SEQ ID NO |
|---|---|---|---|---|---|---|---|
| 859514 | N/A | N/A | CCTGGTTAATAATGCC | 36 | 13183 | 13198 | 117 |
| 859518 | N/A | N/A | GAGTGTGTTAGGAGCT | 83 | 14469 | 14484 | 118 |
| 859522 | N/A | N/A | TCTCTGAGTGTGTTAG | 21 | 14474 | 14489 | 119 |
| 859526 | N/A | N/A | CTTGCTCTCTGAGTGT | 42 | 14479 | 14494 | 120 |
| 859530 | N/A | N/A | AGCATGCTGAGCAGGT | 54 | 14542 | 14557 | 121 |
| 859534 | N/A | N/A | CTGTAGCATGCTGAGC | 71 | 14546 | 14561 | 122 |
| 859538 | N/A | N/A | AATTCAGTGGCTGCTC | 27 | 14756 | 14771 | 123 |
| 859542 | N/A | N/A | AGAGCAATTCAGTGGC | 42 | 14761 | 14776 | 124 |
| 859311 | 981 | 996 | CCTCCTCGGGCACATT | 14 | 16373 | 16388 | 125 |
| 468460 | 1075 | 1090 | TTGGCCACGCCGGCAT | 0 | 16705 | 16720 | 48 |
| 859546 | N/A | N/A | CTATTTAGCAGCTACG | 57 | 17443 | 17458 | 126 |
| 859550 | N/A | N/A | TCAACTATTTAGCAGC | 56 | 17447 | 17462 | 127 |
| 859554 | N/A | N/A | TAGGTTACCGCTGTCA | 47 | 20915 | 20930 | 128 |
| 859558 | N/A | N/A | GGACCTAGGTTACCGC | 49 | 20920 | 20935 | 129 |
| 859315 | 1499 | 1514 | CCCACTCTGTGACACA | 94 | 21471 | 21486 | 130 |
| 859319 | 1505 | 1520 | TGATGTCCCACTCTGT | 31 | 21477 | 21492 | 131 |
| 859562 | N/A | N/A | GTCCTGCAGCCTCTAG | 30 | 22873 | 22888 | 132 |
| 859566 | N/A | N/A | CCAGCACTGTCCTGCA | 54 | 22881 | 22896 | 133 |
| 859570 | N/A | N/A | TTTTTTGCTGGTTTGA | 33 | 23031 | 23046 | 134 |
| 859574 | N/A | N/A | CCACTTTTTTGCTGGT | 21 | 23035 | 23050 | 135 |
| 859578 | N/A | N/A | CAATTCCACTTTTTTG | 41 | 23040 | 23055 | 136 |
| 859582 | N/A | N/A | CATCTGTGCACTATCC | 48 | 23070 | 23085 | 137 |
| 859586 | N/A | N/A | ATGGCATCTGTGCACT | 30 | 23074 | 23089 | 138 |
| 859590 | N/A | N/A | CCTCTCACACGAGCAT | 48 | 23178 | 23193 | 139 |
| 859594 | N/A | N/A | TCTGCCTCTCACACGA | 29 | 23182 | 23197 | 140 |
| 859598 | N/A | N/A | TTCGACACAGGGTAGC | 67 | 24221 | 24236 | 141 |
| 859602 | N/A | N/A | ATGTTTTCGACACAGG | 66 | 24226 | 24241 | 142 |
| 859606 | N/A | N/A | TGGGCATGTTTTCGAC | 0 | 24231 | 24246 | 143 |
| 859610 | N/A | N/A | GCATCTTTTCAGTACT | 55 | 26517 | 26532 | 144 |
| 859614 | N/A | N/A | CATCGCATCTTTTCAG | 40 | 26521 | 26536 | 145 |
| 468484 | 2430 | 2445 | GCTGTCACTGGAGCTC | 46 | 27573 | 27588 | 146 |
| 859326 | 2497 | 2512 | AAGTCGGAACCATTTT | 56 | 27640 | 27655 | 147 |
| 859330 | 2502 | 2517 | GGGACAAGTCGGAACC | 57 | 27645 | 27660 | 148 |
| 859334 | 3458 | 3473 | TCCGCCAGGCCAGTGA | 33 | 28601 | 28616 | 149 |
| 859338 | 3462 | 3477 | CATCTCCGCCAGGCCA | 57 | 28605 | 28620 | 150 |
| 859342 | 3466 | 3481 | GAAGCATCTCCGCCAG | 56 | 28609 | 28624 | 151 |

TABLE 2-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID 2: Start Site | SEQ ID 2: Stop Site | SEQ ID NO |
|---|---|---|---|---|---|---|---|
| 859346 | 3472 | 3487 | GCCTTAGAAGCATCTC | 67 | 28615 | 28630 | 152 |
| 859350 | 3477 | 3492 | ACCATGCCTTAGAAGC | 41 | 28620 | 28635 | 153 |
| 859354 | 3540 | 3555 | AATGTCTGCTTGCTTG | 69 | 28683 | 28698 | 154 |
| 859358 | 3546 | 3561 | AAGATAAATGTCTGCT | 69 | 28689 | 28704 | 155 |
| 859362 | 3594 | 3609 | GGTCTAGAAAAGTTGG | 51 | 28737 | 28752 | 156 |
| 859366 | 3602 | 3617 | GCAAAACAGGTCTAGA | 52 | 28745 | 28760 | 157 |
| 859370 | 3632 | 3647 | ACCCAGAATAAATATC | 28 | 28775 | 28790 | 158 |

TABLE 3

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID 2: Start Site | SEQ ID 2: Stop Site | SEQ ID NO |
|---|---|---|---|---|---|---|---|
| 431131 | 1015 | 1034 | GTCACACTTGCTGGCCTGTC | 10 | N/A | N/A | 3 |
| 859375 | N/A | N/A | CATCTGCCGTCCTTCC | 28 | 4564 | 4579 | 159 |
| 859379 | N/A | N/A | CCAGCATCTGCCGTCC | 55 | 4568 | 4583 | 160 |
| 859383 | N/A | N/A | ACTTGTCAAGCACCAC | 66 | 5013 | 5028 | 161 |
| 859387 | N/A | N/A | AGTGACTTGTCAAGCA | 84 | 5017 | 5032 | 162 |
| 859391 | N/A | N/A | ATTGTAAGTTCACTCA | 70 | 5136 | 5151 | 163 |
| 859395 | N/A | N/A | TTGCATTGTAAGTTCA | 82 | 5140 | 5155 | 164 |
| 859399 | N/A | N/A | AAATTGAATGAATTGG | 26 | 5768 | 5783 | 165 |
| 859403 | N/A | N/A | CTGGTTTTCCCAGCTC | 73 | 5899 | 5914 | 166 |
| 859407 | N/A | N/A | ACCTCTGGTTTTCCCA | 77 | 5903 | 5918 | 167 |
| 859411 | N/A | N/A | TTCCACCTCTGGTTTT | 23 | 5907 | 5922 | 168 |
| 859415 | N/A | N/A | CTTGTCTGCTCCAACT | 22 | 6717 | 6732 | 169 |
| 859419 | N/A | N/A | AGCTCTTGTCTGCTCC | 81 | 6721 | 6736 | 170 |
| 859423 | N/A | N/A | ATTGAGGGAAAAAATC | 12 | 7468 | 7483 | 171 |
| 859427 | N/A | N/A | CCTGCAAGTCCCTGCT | 42 | 11241 | 11256 | 172 |
| 859431 | N/A | N/A | GCCACCTGCAAGTCCC | 47 | 11245 | 11260 | 173 |
| 859435 | N/A | N/A | ATTCTCTCCTCAGGCC | 52 | 11292 | 11307 | 174 |
| 859439 | N/A | N/A | GACCCACCACATTGCA | 48 | 11381 | 11396 | 175 |
| 859443 | N/A | N/A | CATGGACCCACCACAT | 25 | 11385 | 11400 | 176 |
| 859447 | N/A | N/A | GTTGCATGGACCCACC | 65 | 11389 | 11404 | 177 |
| 859451 | N/A | N/A | AGTAGCCCCCCAACTT | 0 | 11606 | 11621 | 178 |
| 859455 | N/A | N/A | ACACAGTAGCCCCCCA | 42 | 11610 | 11625 | 179 |
| 859459 | N/A | N/A | AGTCACACAGTAGCCC | 83 | 11614 | 11629 | 180 |

TABLE 3-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 859463 | N/A | N/A | CACACAGTTTGGGTGT | 37 | 11636 | 11651 | 181 |
| 859467 | N/A | N/A | ATATGCAAGGTCACAC | 49 | 11647 | 11662 | 182 |
| 859471 | N/A | N/A | AGACATATGCAAGGTC | 46 | 11651 | 11666 | 183 |
| 859475 | N/A | N/A | TGTCCCTCTTGGTCTC | 61 | 11948 | 11963 | 184 |
| 859479 | N/A | N/A | CCAGTGTCCCTCTTGG | 35 | 11952 | 11967 | 185 |
| 859483 | N/A | N/A | TCTGCCAGTGTCCCTC | 27 | 11956 | 11971 | 186 |
| 859487 | N/A | N/A | TGTGATCCTCTGCCAG | 42 | 11964 | 11979 | 187 |
| 859491 | N/A | N/A | TCTCTGTGATCCTCTG | 73 | 11968 | 11983 | 188 |
| 859495 | N/A | N/A | TCTAGGGCCCATGCTT | 21 | 12668 | 12683 | 189 |
| 859499 | N/A | N/A | CCAGCTCTAGGGCCCA | 53 | 12673 | 12688 | 190 |
| 859503 | N/A | N/A | GGCAGCCAGCTCTAGG | 42 | 12678 | 12693 | 191 |
| 859507 | N/A | N/A | CGCACAGTGGGTGCTC | 41 | 12930 | 12945 | 192 |
| 859511 | N/A | N/A | GGTTAATAATGCCCCC | 58 | 13180 | 13195 | 193 |
| 859515 | N/A | N/A | GCCTGGTTAATAATGC | 0 | 13184 | 13199 | 194 |
| 859519 | N/A | N/A | CTGAGTGTGTTAGGAG | 52 | 14471 | 14486 | 195 |
| 859523 | N/A | N/A | CTCTCTGAGTGTGTTA | 57 | 14475 | 14490 | 196 |
| 859527 | N/A | N/A | TGCTGAGCAGGTCCTT | 47 | 14538 | 14553 | 197 |
| 859531 | N/A | N/A | TAGCATGCTGAGCAGG | 79 | 14543 | 14558 | 198 |
| 859535 | N/A | N/A | TTCTGTAGCATGCTGA | 50 | 14548 | 14563 | 199 |
| 859539 | N/A | N/A | CAATTCAGTGGCTGCT | 62 | 14757 | 14772 | 200 |
| 859543 | N/A | N/A | ACAGAGCAATTCAGTG | 49 | 14763 | 14778 | 201 |
| 468460 | 1075 | 1090 | TTGGCCACGCCGGCAT | 29 | 16705 | 16720 | 48 |
| 859547 | N/A | N/A | ACTATTTAGCAGCTAC | 65 | 17444 | 17459 | 202 |
| 859551 | N/A | N/A | GTCAACTATTTAGCAG | 73 | 17448 | 17463 | 203 |
| 859555 | N/A | N/A | CTAGGTTACCGCTGTC | 60 | 20916 | 20931 | 204 |
| 859559 | N/A | N/A | GGGACCTAGGTTACCG | 31 | 20921 | 20936 | 205 |
| 859312 | 1495 | 1510 | CTCTGTGACACAAAGC | 69 | 21467 | 21482 | 206 |
| 859316 | 1501 | 1516 | GTCCCACTCTGTGACA | 66 | 21473 | 21488 | 207 |
| 859563 | N/A | N/A | GCACTGTCCTGCAGCC | 44 | 22878 | 22893 | 208 |
| 859567 | N/A | N/A | ATCCAGCACTGTCCTG | 47 | 22883 | 22898 | 209 |
| 859571 | N/A | N/A | CTTTTTTGCTGGTTTG | 77 | 23032 | 23047 | 210 |
| 859575 | N/A | N/A | TCCACTTTTTTGCTGG | 0 | 23036 | 23051 | 211 |
| 859579 | N/A | N/A | TGTGCACTATCCTGTA | 39 | 23066 | 23081 | 212 |
| 859583 | N/A | N/A | GCATCTGTGCACTATC | 73 | 23071 | 23086 | 213 |
| 859587 | N/A | N/A | AGATGGCATCTGTGCA | 65 | 23076 | 23091 | 214 |
| 859591 | N/A | N/A | GCCTCTCACACGAGCA | 57 | 23179 | 23194 | 215 |

TABLE 3-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 859595 | N/A | N/A | ACTCTGCCTCTCACAC | 27 | 23184 | 23199 | 216 |
| 859599 | N/A | N/A | TTTTCGACACAGGGTA | 69 | 24223 | 24238 | 217 |
| 859603 | N/A | N/A | CATGTTTTCGACACAG | 69 | 24227 | 24242 | 218 |
| 859607 | N/A | N/A | CTTTTCAGTACTCTAT | 28 | 26513 | 26528 | 219 |
| 859611 | N/A | N/A | CGCATCTTTTCAGTAC | 70 | 26518 | 26533 | 220 |
| 859615 | N/A | N/A | TCCATCGCATCTTTTC | 51 | 26523 | 26538 | 221 |
| 859320 | 2425 | 2440 | CACTGGAGCTCCTGGG | 45 | 27568 | 27583 | 222 |
| 859323 | 2431 | 2446 | GGCTGTCACTGGAGCT | 33 | 27574 | 27589 | 223 |
| 859327 | 2498 | 2513 | CAAGTCGGAACCATTT | 52 | 27641 | 27656 | 224 |
| 859331 | 2503 | 2518 | AGGGACAAGTCGGAAC | 28 | 27646 | 27661 | 225 |
| 859335 | 3459 | 3474 | CTCCGCCAGGCCAGTG | 25 | 28602 | 28617 | 226 |
| 859339 | 3463 | 3478 | GCATCTCCGCCAGGCC | 56 | 28606 | 28621 | 227 |
| 859343 | 3467 | 3482 | AGAAGCATCTCCGCCA | 63 | 28610 | 28625 | 228 |
| 859347 | 3474 | 3489 | ATGCCTTAGAAGCATC | 8 | 28617 | 28632 | 229 |
| 859351 | 3478 | 3493 | GACCATGCCTTAGAAG | 30 | 28621 | 28636 | 230 |
| 859355 | 3541 | 3556 | AAATGTCTGCTTGCTT | 51 | 28684 | 28699 | 231 |
| 859359 | 3589 | 3604 | AGAAAAGTTGGCTGTA | 37 | 28732 | 28747 | 232 |
| 859363 | 3595 | 3610 | AGGTCTAGAAAAGTTG | 74 | 28738 | 28753 | 233 |
| 859367 | 3604 | 3619 | AAGCAAAACAGGTCTA | 37 | 28747 | 28762 | 234 |
| 859371 | 3633 | 3648 | AACCCAGAATAAATAT | 30 | 28776 | 28791 | 235 |

TABLE 4

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 431131 | 1015 | 1034 | GTCACACTTGCTGGCCTGTC | 0 | N/A | N/A | 3 |
| 468460 | 1075 | 1090 | TTGGCCACGCCGGCAT | 25 | 16705 | 16720 | 48 |
| 859313 | 1497 | 1512 | CACTCTGTGACACAAA | 59 | 21469 | 21484 | 236 |
| 859317 | 1502 | 1517 | TGTCCCACTCTGTGAC | 10 | 21474 | 21489 | 237 |
| 859321 | 2428 | 2443 | TGTCACTGGAGCTCCT | 17 | 27571 | 27586 | 238 |
| 859324 | 2432 | 2447 | GGGCTGTCACTGGAGC | 46 | 27575 | 27590 | 239 |
| 859328 | 2499 | 2514 | ACAAGTCGGAACCATT | 60 | 27642 | 27657 | 240 |
| 859332 | 2504 | 2519 | GAGGGACAAGTCGGAA | 1 | 27647 | 27662 | 241 |
| 859336 | 3460 | 3475 | TCTCCGCCAGGCCAGT | 20 | 28603 | 28618 | 242 |

TABLE 4-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID 2: Start Site | SEQ ID 2: Stop Site | SEQ ID NO |
|---|---|---|---|---|---|---|---|
| 859340 | 3464 | 3479 | AGCATCTCCGCCAGGC | 60 | 28607 | 28622 | 243 |
| 859344 | 3468 | 3483 | TAGAAGCATCTCCGCC | 59 | 28611 | 28626 | 244 |
| 859348 | 3475 | 3490 | CATGCCTTAGAAGCAT | 0 | 28618 | 28633 | 245 |
| 859352 | 3480 | 3495 | CCGACCATGCCTTAGA | 63 | 28623 | 28638 | 246 |
| 859356 | 3542 | 3557 | TAAATGTCTGCTTGCT | 67 | 28685 | 28700 | 247 |
| 859360 | 3591 | 3606 | CTAGAAAAGTTGGCTG | 59 | 28734 | 28749 | 248 |
| 859364 | 3596 | 3611 | CAGGTCTAGAAAAGTT | 44 | 28739 | 28754 | 249 |
| 859368 | 3605 | 3620 | AAAGCAAAACAGGTCT | 62 | 28748 | 28763 | 250 |
| 859372 | N/A | N/A | TGCCGTCCTTCCCACC | 17 | 4560 | 4575 | 251 |
| 859376 | N/A | N/A | GCATCTGCCGTCCTTC | 40 | 4565 | 4580 | 252 |
| 859380 | N/A | N/A | TCCCAGCATCTGCCGT | 49 | 4570 | 4585 | 253 |
| 859384 | N/A | N/A | GACTTGTCAAGCACCA | 83 | 5014 | 5029 | 254 |
| 859388 | N/A | N/A | AAGTGACTTGTCAAGC | 77 | 5018 | 5033 | 255 |
| 859392 | N/A | N/A | CATTGTAAGTTCACTC | 77 | 5137 | 5152 | 256 |
| 859396 | N/A | N/A | CTTGCATTGTAAGTTC | 65 | 5141 | 5156 | 257 |
| 859400 | N/A | N/A | TTTCCCAGCTCTGTAT | 28 | 5894 | 5909 | 258 |
| 859404 | N/A | N/A | TCTGGTTTTCCCAGCT | 48 | 5900 | 5915 | 259 |
| 859408 | N/A | N/A | CACCTCTGGTTTTCCC | 78 | 5904 | 5919 | 260 |
| 859412 | N/A | N/A | CTTCCACCTCTGGTTT | 28 | 5908 | 5923 | 261 |
| 859416 | N/A | N/A | TCTTGTCTGCTCCAAC | 13 | 6718 | 6733 | 262 |
| 859420 | N/A | N/A | TAGCTCTTGTCTGCTC | 39 | 6722 | 6737 | 263 |
| 859424 | N/A | N/A | ACCCTAGGTGTACTTT | 27 | 7779 | 7794 | 264 |
| 859428 | N/A | N/A | ACCTGCAAGTCCCTGC | 31 | 11242 | 11257 | 265 |
| 859432 | N/A | N/A | TGCCACCTGCAAGTCC | 44 | 11246 | 11261 | 266 |
| 859436 | N/A | N/A | CATTCTCCTCAGGC | 38 | 11293 | 11308 | 267 |
| 859440 | N/A | N/A | GGACCCACCACATTGC | 19 | 11382 | 11397 | 268 |
| 859444 | N/A | N/A | GCATGGACCCACCACA | 56 | 11386 | 11401 | 269 |
| 859448 | N/A | N/A | TGTTGCATGGACCCAC | 53 | 11390 | 11405 | 270 |
| 859452 | N/A | N/A | CAGTAGCCCCCCAACT | 19 | 11607 | 11622 | 271 |
| 859456 | N/A | N/A | CACACAGTAGCCCCCC | 56 | 11611 | 11626 | 272 |
| 859460 | N/A | N/A | AAGTCACACAGTAGCC | 32 | 11615 | 11630 | 273 |
| 859464 | N/A | N/A | GTCACACAGTTTGGGT | 69 | 11638 | 11653 | 274 |
| 859468 | N/A | N/A | CATATGCAAGGTCACA | 59 | 11648 | 11663 | 275 |
| 859472 | N/A | N/A | TCAGACATATGCAAGG | 72 | 11653 | 11668 | 276 |
| 859476 | N/A | N/A | GTGTCCCTCTTGGTCT | 67 | 11949 | 11964 | 277 |
| 859480 | N/A | N/A | GCCAGTGTCCCTCTTG | 46 | 11953 | 11968 | 278 |

TABLE 4-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 859484 | N/A | N/A | CCTCTGCCAGTGTCCC | 34 | 11958 | 11973 | 279 |
| 859488 | N/A | N/A | CTGTGATCCTCTGCCA | 58 | 11965 | 11980 | 280 |
| 859492 | N/A | N/A | GTCTCTGTGATCCTCT | 71 | 11969 | 11984 | 281 |
| 859496 | N/A | N/A | GCTCTAGGGCCCATGC | 16 | 12670 | 12685 | 282 |
| 859500 | N/A | N/A | GCCAGCTCTAGGGCCC | 16 | 12674 | 12689 | 283 |
| 859504 | N/A | N/A | AGAGAAATGCATGCTA | 68 | 12841 | 12856 | 284 |
| 859508 | N/A | N/A | GGCGCACAGTGGGTGC | 0 | 12932 | 12947 | 285 |
| 859512 | N/A | N/A | TGGTTAATAATGCCCC | 40 | 13181 | 13196 | 286 |
| 859516 | N/A | N/A | TTGCCTGGTTAATAAT | 12 | 13186 | 13201 | 287 |
| 859520 | N/A | N/A | TCTGAGTGTGTTAGGA | 62 | 14472 | 14487 | 288 |
| 859524 | N/A | N/A | GCTCTCTGAGTGTGTT | 56 | 14476 | 14491 | 289 |
| 859528 | N/A | N/A | CATGCTGAGCAGGTCC | 66 | 14540 | 14555 | 290 |
| 859532 | N/A | N/A | GTAGCATGCTGAGCAG | 79 | 14544 | 14559 | 291 |
| 859536 | N/A | N/A | TCAGTGGCTGCTCTGA | 24 | 14753 | 14768 | 292 |
| 859540 | N/A | N/A | GCAATTCAGTGGCTGC | 33 | 14758 | 14773 | 293 |
| 859544 | N/A | N/A | TAGTTAACACACAGAA | 17 | 16208 | 16223 | 294 |
| 859548 | N/A | N/A | AACTATTTAGCAGCTA | 43 | 17445 | 17460 | 295 |
| 859552 | N/A | N/A | CGTCAACTATTTAGCA | 66 | 17449 | 17464 | 296 |
| 859556 | N/A | N/A | CCTAGGTTACCGCTGT | 33 | 20917 | 20932 | 297 |
| 859560 | N/A | N/A | GCACAGACCCTGACTG | 23 | 21567 | 21582 | 298 |
| 859564 | N/A | N/A | AGCACTGTCCTGCAGC | 48 | 22879 | 22894 | 299 |
| 859568 | N/A | N/A | TTTTGCTGGTTTGAGA | 52 | 23029 | 23044 | 300 |
| 859572 | N/A | N/A | ACTTTTTTGCTGGTTT | 70 | 23033 | 23048 | 301 |
| 859576 | N/A | N/A | ATTCCACTTTTTTGCT | 24 | 23038 | 23053 | 302 |
| 859580 | N/A | N/A | TCTGTGCACTATCCTG | 38 | 23068 | 23083 | 303 |
| 859584 | N/A | N/A | GGCATCTGTGCACTAT | 75 | 23072 | 23087 | 304 |
| 859588 | N/A | N/A | TCACACGAGCATTAAG | 34 | 23174 | 23189 | 305 |
| 859592 | N/A | N/A | TGCCTCTCACACGAGC | 38 | 23180 | 23195 | 306 |
| 859596 | N/A | N/A | TAGACAGGATCAACTC | 18 | 23406 | 23421 | 307 |
| 859600 | N/A | N/A | GTTTTCGACACAGGGT | 61 | 24224 | 24239 | 308 |
| 859604 | N/A | N/A | GCATGTTTTCGACACA | 63 | 24228 | 24243 | 309 |
| 859608 | N/A | N/A | ATCTTTTCAGTACTCT | 48 | 26515 | 26530 | 310 |
| 859612 | N/A | N/A | TCGCATCTTTTCAGTA | 31 | 26519 | 26534 | 311 |
| 859616 | N/A | N/A | AGCAGCTAGGCCACAG | 20 | 26841 | 26856 | 312 |

Study 2

Cultured HepG2 cells at a density of 20,000 cells per well were transfected using electroporation with 3,000 nM antisense oligonucleotide. After a treatment period of approximately 24 hours, RNA was isolated from the cells and PCSK9 mRNA levels were measured by quantitative real-time PCR. Human PCSK9 primer probe set from ABI (ID #Hs03037355 ml) was used to measure mRNA levels. PCSK9 mRNA levels were adjusted according to total RNA content, as measured by RIBOGREEN®. Results are presented as percent inhibition of PCSK9, relative to untreated control cells.

TABLE 5

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---------|---|---|---|---|---|---|---|
| 848304 | 757 | 772 | AACTTCAAGGCCAGCT | 66 | N/A | N/A | 313 |
| 848215 | 108 | 123 | CTGAACTGAACGGCGG | 68 | 3583 | 3598 | 314 |
| 848231 | 320 | 335 | GGCGAGGAGACCTAGA | 87 | 3795 | 3810 | 315 |
| 848247 | 485 | 500 | ACGCAAGGCTAGCACC | 77 | 3960 | 3975 | 316 |
| 848788 | N/A | N/A | GGCAAGCCCGCTTTCT | 88 | 4456 | 4471 | 317 |
| 848804 | N/A | N/A | CCCTTTTAAAGATTAG | 67 | 5053 | 5068 | 318 |
| 848820 | N/A | N/A | CCAGAGAAGAAACATC | 62 | 5524 | 5539 | 319 |
| 848836 | N/A | N/A | AAGAATCTGGAGCTGC | 84 | 6430 | 6445 | 320 |
| 848852 | N/A | N/A | CACTGAGGACCAAATT | 65 | 6806 | 6821 | 321 |
| 848868 | N/A | N/A | GCTATATAAAGGAATA | 65 | 7161 | 7176 | 322 |
| 848884 | N/A | N/A | CATGAGCAAGTCACTC | 65 | 7387 | 7402 | 323 |
| 848900 | N/A | N/A | AGTATAGTAGATGATA | 82 | 7720 | 7735 | 324 |
| 848262 | 614 | 629 | CGAGAGGTGGGTCTCC | 54 | 7887 | 7902 | 325 |
| 466848 | 673 | 688 | GTGAGGTATCCCCGGC | 88 | 7946 | 7961 | 326 |
| 848289 | 689 | 704 | GACATGCAGGATCTTG | 79 | 7962 | 7977 | 327 |
| 848916 | N/A | N/A | GGGAATTCTATACAGA | 72 | 8193 | 8208 | 328 |
| 848932 | N/A | N/A | CACCGAAGATGTGACA | 51 | 8521 | 8536 | 329 |
| 848948 | N/A | N/A | AAGGGAAAGGCCTGAG | 53 | 9040 | 9055 | 330 |
| 848964 | N/A | N/A | CCCCACAGGCAGCCTC | 61 | 9610 | 9625 | 331 |
| 848980 | N/A | N/A | CCGGAGGACAGACTAG | 27 | 10368 | 10383 | 332 |
| 848319 | 862 | 877 | TGGTATTCATCCGCCC | 60 | 10623 | 10638 | 333 |
| 848996 | N/A | N/A | AGCCAAACGGAGCTGG | 51 | 11093 | 11108 | 334 |
| 849012 | N/A | N/A | AAAGGAACAGGCTCTT | 56 | 11842 | 11857 | 335 |
| 849028 | N/A | N/A | CTCTAGGGCCCATGCT | 56 | 12669 | 12684 | 336 |
| 849044 | N/A | N/A | GGATACACAGGCTCGC | 96 | 13108 | 13123 | 337 |
| 849060 | N/A | N/A | GATGATGTGACCACTG | 86 | 13864 | 13879 | 338 |
| 849076 | N/A | N/A | GGCCAGCAAGGTGGGC | 35 | 14277 | 14292 | 339 |
| 849092 | N/A | N/A | TGCTAGTAGGTCTGGG | 72 | 14675 | 14690 | 340 |
| 849108 | N/A | N/A | CCAAAGGAAGACTTCA | 70 | 15400 | 15415 | 341 |
| 849124 | N/A | N/A | ATTTAAAGACTCAAAG | 16 | 15870 | 15885 | 342 |
| 849140 | N/A | N/A | ACATTTGTGGGAGAGG | 56 | 16250 | 16265 | 343 |
| 848334 | 984 | 999 | CGTCCTCCTCGGGCAC | 85 | 16376 | 16391 | 344 |

TABLE 5-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848348 | 1018 | 1033 | TCACACTTGCTGGCCT | 52 | 16648 | 16663 | 345 |
| 848364 | 1061 | 1076 | ATCCCGGCCGCTGACC | 57 | 16691 | 16706 | 346 |
| 468460 | 1075 | 1090 | TTGGCCACGCCGGCAT | 48 | 16705 | 16720 | 48 |
| 848379 | 1085 | 1100 | GCTGGCACCCTTGGCC | 57 | 16715 | 16730 | 347 |
| 849156 | N/A | N/A | AAGACATAAAGACATC | 89 | 17083 | 17098 | 348 |
| 849172 | N/A | N/A | CAGAAGGTTATTGATT | 68 | 17735 | 17750 | 349 |
| 849188 | N/A | N/A | TGCTAGTTATTAAGCA | 15 | 18080 | 18095 | 350 |
| 849204 | N/A | N/A | CAGTAACAGCTCTTTT | 80 | 19020 | 19035 | 351 |
| 849220 | N/A | N/A | CCTTATTATCCCTTTC | 70 | 19396 | 19411 | 352 |
| 849236 | N/A | N/A | CAACATCAAATTCTGC | 92 | 19658 | 19673 | 353 |
| 848395 | 1165 | 1180 | TTCCGAATAAACTCCA | 73 | 19996 | 20011 | 354 |
| 848411 | 1345 | 1360 | ACCTCGGGAGCTGAGG | 20 | 20176 | 20191 | 355 |
| 849252 | N/A | N/A | GATGGAGGTTTCGAGC | 87 | 20381 | 20396 | 356 |
| 849268 | N/A | N/A | TATCAAGTGGTTCTAA | 44 | 21039 | 21054 | 357 |
| 848427 | 1458 | 1473 | CACCAATGATGTCCTC | 45 | 21430 | 21445 | 358 |
| 849284 | N/A | N/A | TCTTATCGGCCAGGTG | 75 | 21810 | 21825 | 359 |
| 848443 | 1608 | 1623 | TGGCAGAGAAGTGGAT | 21 | 22101 | 22116 | 360 |
| 848459 | 1730 | 1745 | CCATACAGTCCTGCAA | 40 | 22512 | 22527 | 361 |
| 848475 | 1807 | 1822 | GAGCAGCTCAGCAGCT | 44 | 22589 | 22604 | 362 |
| 849300 | N/A | N/A | TACAGAAGAGCTGGAG | 61 | 22767 | 22782 | 363 |
| 849316 | N/A | N/A | ACACAGAGTGGTTTCA | 79 | 23262 | 23277 | 364 |
| 848489 | 1951 | 1966 | CTGCAGTTGGCCTGGG | 57 | 23571 | 23586 | 365 |
| 848505 | 2006 | 2021 | GTGGCAGTGGACACGG | 71 | 23626 | 23641 | 366 |
| 849332 | N/A | N/A | AGGAGAAGTAAGGTCA | 91 | 23828 | 23843 | 367 |
| 849348 | N/A | N/A | GGGCATGTTTTCGACA | 65 | 24230 | 24245 | 368 |
| 849364 | N/A | N/A | TTCCACCCAGAGATGG | 34 | 25105 | 25120 | 369 |
| 849380 | N/A | N/A | CGGTATGGTGGTGGCA | 71 | 25630 | 25645 | 370 |
| 849396 | N/A | N/A | GGGCAAGTGGATCCAA | 38 | 26364 | 26379 | 371 |
| 849412 | N/A | N/A | CCACACTTCATTTCTC | 35 | 27298 | 27313 | 372 |
| 848521 | 2225 | 2240 | GCAGGCCACGGTCACC | 67 | 27368 | 27383 | 373 |
| 848537 | 2483 | 2498 | TTAAAGCTCAGCCCCA | 67 | 27626 | 27641 | 374 |
| 848553 | 2560 | 2575 | CCCCGGAAAGGCGGAA | 39 | 27703 | 27718 | 375 |
| 848569 | 2704 | 2719 | CCGAGCACAGCTCGAC | 62 | 27847 | 27862 | 376 |
| 848584 | 2739 | 2754 | ACGGACATCGGCACAT | 92 | 27882 | 27897 | 377 |
| 848600 | 2776 | 2791 | GGCACGGAACAAGAGC | 87 | 27919 | 27934 | 378 |
| 848616 | 2888 | 2903 | ACCTTTCACACTCACC | 92 | 28031 | 28046 | 379 |

TABLE 5-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 468491 | 2971 | 2986 | TGCCATCCAGAAAGCT | 64 | 28114 | 28129 | 380 |
| 848646 | 3085 | 3100 | CACCTTTGGGTGTTGC | 80 | 28228 | 28243 | 381 |
| 848662 | 3132 | 3147 | CCACTGCACACTGCCG | 87 | 28275 | 28290 | 382 |
| 848678 | 3220 | 3235 | TGGTTCCAGGTTTCTT | 87 | 28363 | 28378 | 383 |
| 848693 | 3253 | 3268 | CCTGCTGTGTGAGCTT | 93 | 28396 | 28411 | 384 |
| 848709 | 3290 | 3305 | CTTCAGAGCCAGCCCA | 65 | 28433 | 28448 | 385 |
| 848725 | 3380 | 3395 | CCGAGCTTCCTGGTCT | 92 | 28523 | 28538 | 386 |
| 848741 | 3433 | 3448 | GGGTGATAACGGAAAA | 62 | 28576 | 28591 | 387 |
| 848756 | 3547 | 3562 | AAAGATAAATGTCTGC | 92 | 28690 | 28705 | 388 |
| 848772 | 3631 | 3646 | CCCAGAATAAATATCT | 89 | 28774 | 28789 | 389 |

TABLE 6

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | PCSK9 (% inhibition) | SEQ ID: 2 Start Site | SEQ ID 2: Stop Site | SEQ ID NO |
|---|---|---|---|---|---|---|---|
| 848216 | 123 | 138 | CTCCAGGCTCAGACCC | 82 | 3598 | 3613 | 390 |
| 848232 | 353 | 368 | GCCCATGAGGGCCAGG | 67 | 3828 | 3843 | 391 |
| 848248 | 486 | 501 | AACGCAAGGCTAGCAC | 62 | 3961 | 3976 | 392 |
| 848789 | N/A | N/A | CTATAATGGCAAGCCC | 76 | 4463 | 4478 | 393 |
| 848805 | N/A | N/A | CGTAGGGACGATTGTC | 65 | 5073 | 5088 | 394 |
| 848821 | N/A | N/A | ATGAACTTGAGGAGGC | 85 | 5558 | 5573 | 395 |
| 848837 | N/A | N/A | TTGGAAGAATCTGGAG | 81 | 6434 | 6449 | 396 |
| 848853 | N/A | N/A | CAACACTGAGGACCAA | 77 | 6809 | 6824 | 397 |
| 848869 | N/A | N/A | GGCAACACTTCTTAAA | 60 | 7219 | 7234 | 398 |
| 848885 | N/A | N/A | GTGCAGCCATGAGCAA | 73 | 7394 | 7409 | 399 |
| 848901 | N/A | N/A | ACAGAGTATAGTAGAT | 73 | 7724 | 7739 | 400 |
| 848263 | 616 | 631 | TGCGAGAGGTGGGTCT | 42 | 7889 | 7904 | 401 |
| 848275 | 674 | 689 | GGTGAGGTATCCCCGG | 67 | 7947 | 7962 | 402 |
| 848290 | 690 | 705 | AGACATGCAGGATCTT | 56 | 7963 | 7978 | 403 |
| 848917 | N/A | N/A | TCAAATGAAGATAGAC | 68 | 8237 | 8252 | 404 |
| 848933 | N/A | N/A | GAATACCCAGTCCCCT | 49 | 8548 | 8563 | 405 |
| 848949 | N/A | N/A | CTCAAGGGAAAGGCCT | 59 | 9043 | 9058 | 406 |
| 848965 | N/A | N/A | CATGGCAGCGGTGAAC | 47 | 9638 | 9653 | 407 |
| 848981 | N/A | N/A | GATCAAACCTGTCCCC | 42 | 10427 | 10442 | 408 |
| 848997 | N/A | N/A | TGCAGACCGTTTTCCA | 83 | 11221 | 11236 | 409 |

TABLE 6-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | PCSK9 (% inhibition) | SEQ ID: 2 Start Site | SEQ ID 2: Stop Site | SEQ ID NO |
|---|---|---|---|---|---|---|---|
| 849013 | N/A | N/A | GGAAAGGAACAGGCTC | 88 | 11844 | 11859 | 410 |
| 849029 | N/A | N/A | TTTGAGGGCGGCAGCC | 32 | 12687 | 12702 | 411 |
| 849045 | N/A | N/A | TGCTGGATACACAGGC | 79 | 13112 | 13127 | 412 |
| 849061 | N/A | N/A | TGTACCTGGGTTCTGC | 86 | 13885 | 13900 | 413 |
| 849077 | N/A | N/A | CACTAGATATTGAGCT | 55 | 14329 | 14344 | 414 |
| 849093 | N/A | N/A | CTATGCTAGTAGGTCT | 51 | 14678 | 14693 | 415 |
| 849109 | N/A | N/A | GGCCAAAGGAAGACTT | 22 | 15402 | 15417 | 416 |
| 849125 | N/A | N/A | CTGCAAGAAAGACAAC | 73 | 15889 | 15904 | 417 |
| 848320 | 887 | 902 | CACCAGGCTGCCTCCG | 49 | 16279 | 16294 | 418 |
| 848335 | 985 | 1000 | CCGTCCTCCTCGGGCA | 81 | 16377 | 16392 | 419 |
| 849141 | N/A | N/A | CATCAGACGGCCGTGC | 40 | 16416 | 16431 | 420 |
| 848349 | 1019 | 1034 | GTCACACTTGCTGGCC | 62 | 16649 | 16664 | 421 |
| 468459 | 1063 | 1078 | GCATCCCGGCCGCTGA | 76 | 16693 | 16708 | 422 |
| 468460 | 1075 | 1090 | TTGGCCACGCCGGCAT | 46 | 16705 | 16720 | 48 |
| 848380 | 1091 | 1106 | GCGCATGCTGGCACCC | 45 | 16721 | 16736 | 423 |
| 849157 | N/A | N/A | GATAACATAACAAAAG | 29 | 17096 | 17111 | 424 |
| 849173 | N/A | N/A | GCAGAAGGTTATTGAT | 64 | 17736 | 17751 | 425 |
| 849189 | N/A | N/A | ACAGCTGCTAGTTATT | 96 | 18085 18398 | 18100 18413 | 426 |
| 849205 | N/A | N/A | TGCTACTGTCAACAGT | 86 | 19032 | 19047 | 427 |
| 849221 | N/A | N/A | CAATAACCTTATTATC | 6 | 19402 | 19417 | 428 |
| 849237 | N/A | N/A | AGAGAACAGACTGAGG | 83 | 19727 | 19742 | 429 |
| 848396 | 1170 | 1185 | GGCTTTTCCGAATAAA | 43 | 20001 | 20016 | 430 |
| 849253 | N/A | N/A | GGCAGAGGACGCAGGG | 40 | 20538 | 20553 | 431 |
| 849269 | N/A | N/A | ACTATTCGGTGTATCA | 82 | 21050 | 21065 | 432 |
| 848428 | 1466 | 1481 | GCTGGAGGCACCAATG | 0 | 21438 | 21453 | 433 |
| 849285 | N/A | N/A | GTCTTATCGGCCAGGT | 86 | 21811 | 21826 | 434 |
| 848444 | 1617 | 1632 | TGACATCTTTGGCAGA | 39 | 22110 | 22125 | 435 |
| 848460 | 1731 | 1746 | ACCATACAGTCCTGCA | 19 | 22513 | 22528 | 436 |
| 848476 | 1814 | 1829 | GAAACTGGAGCAGCTC | 54 | 22596 | 22611 | 437 |
| 849301 | N/A | N/A | CATTGAAAATCCATCC | 83 | 22895 | 22910 | 438 |
| 849317 | N/A | N/A | CCCAAGGAAGACTGTT | 56 | 23318 | 23333 | 439 |
| 848490 | 1977 | 1992 | CCTCAGCTGGTGGAGC | 54 | 23597 | 23612 | 440 |
| 848506 | 2007 | 2022 | GGTGGCAGTGGACACG | 46 | 23627 | 23642 | 441 |
| 849333 | N/A | N/A | AGGTAATACCTTTTTC | 51 | 23871 | 23886 | 442 |
| 849349 | N/A | N/A | CACCATCCCTTGATGC | 46 | 24285 | 24300 | 443 |
| 849365 | N/A | N/A | GAAAACACCATCTTTC | 26 | 25118 | 25133 | 444 |

TABLE 6-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | PCSK9 (% inhibition) | SEQ ID: 2 Start Site | SEQ ID 2: Stop Site | SEQ ID NO |
|---|---|---|---|---|---|---|---|
| 849381 | N/A | N/A | GGCGGTATGGTGGTGG | 71 | 25632 | 25647 | 445 |
| 849397 | N/A | N/A | ACCCAGGGCAAGTGGA | 56 | 26369 | 26384 | 446 |
| 849413 | N/A | N/A | CCCCACCCACACTTCA | 53 | 27304 | 27319 | 447 |
| 848522 | 2227 | 2242 | TCGCAGGCCACGGTCA | 69 | 27370 | 27385 | 448 |
| 848538 | 2485 | 2500 | TTTTAAAGCTCAGCCC | 38 | 27628 | 27643 | 449 |
| 848554 | 2565 | 2580 | AGCAGCCCCGGAAAGG | 67 | 27708 | 27723 | 450 |
| 848570 | 2706 | 2721 | ACCCGAGCACAGCTCG | 90 | 27849 | 27864 | 451 |
| 848585 | 2741 | 2756 | CCACGGACATCGGCAC | 93 | 27884 | 27899 | 452 |
| 848601 | 2777 | 2792 | TGGCACGGAACAAGAG | 54 | 27920 | 27935 | 453 |
| 848617 | 2898 | 2913 | GGCCATCAGCACCTTT | 63 | 28041 | 28056 | 454 |
| 848632 | 2976 | 2991 | CTAGATGCCATCCAGA | 91 | 28119 | 28134 | 455 |
| 848647 | 3088 | 3103 | GGCCACCTTTGGGTGT | 46 | 28231 | 28246 | 456 |
| 848663 | 3141 | 3156 | GTGCATGCACCACTGC | 78 | 28284 | 28299 | 457 |
| 848679 | 3221 | 3236 | CTGGTTCCAGGTTTCT | 88 | 28364 | 28379 | 458 |
| 848694 | 3254 | 3269 | TCCTGCTGTGTGAGCT | 91 | 28397 | 28412 | 459 |
| 848710 | 3302 | 3317 | GAAGAGGCTTGGCTTC | 17 | 28445 | 28460 | 460 |
| 848726 | 3381 | 3396 | ACCGAGCTTCCTGGTC | 38 | 28524 | 28539 | 461 |
| 848742 | 3438 | 3453 | GGCCTGGGTGATAACG | 26 | 28581 | 28596 | 462 |
| 848757 | 3550 | 3565 | CCAAAAGATAAATGTC | 46 | 28693 | 28708 | 463 |
| 848773 | 3638 | 3653 | TACAAAACCCAGAATA | 59 | 28781 | 28796 | 464 |
| 848305 | 758 | 773 | CAACTTCAAGGCCAGC | 79 | N/A | N/A | 465 |
| 848412 | 1349 | 1364 | GATGACCTCGGGAGCT | 38 | N/A | N/A | 466 |

Study 3

Cultured HepG2 cells at a density of 20,000 cells per well were transfected using electroporation with 1,000 nM antisense oligonucleotide. After a treatment period of approximately 24 hours, RNA was isolated from the cells and PCSK9 mRNA levels were measured by quantitative real-time PCR. Human PCSK9 primer probe set from ABI (ID #Hs03037355_ml) was used to measure mRNA levels. PCSK9 mRNA levels were adjusted according to total RNA content, as measured by RIBOGREEN®. Results are presented as percent inhibition of PCSK9, relative to untreated control cells.

TABLE 7

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848205 | 4 | 19 | CACCAGAGCCCCATCG | 3 | 3479 | 3494 | 467 |
| 848221 | 189 | 204 | CTGGGAGCCGCTGCTG | 42 | 3664 | 3679 | 468 |
| 848237 | 389 | 404 | TGGCAGCGGCCACCAG | 0 | 3864 | 3879 | 469 |
| 848253 | 506 | 521 | GGCCAGGCCGTCCTCC | 51 | 3981 | 3996 | 470 |
| 848778 | N/A | N/A | CCGCACCTTGGCGCAG | 0 | 4035 | 4050 | 471 |

TABLE 7-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848794 | N/A | N/A | GAAACAGATGGAATAC | 28 | 4626 | 4641 | 472 |
| 848810 | N/A | N/A | ACCCAGCACACTCAGA | 0 | 5291 | 5306 | 473 |
| 848826 | N/A | N/A | GTACTCTGTGCAGTGG | 80 | 5748 | 5763 | 474 |
| 848842 | N/A | N/A | GAGTAGAACAGAGTCC | 54 | 6544 | 6559 | 475 |
| 848858 | N/A | N/A | TTAATAATCAGCCTTC | 46 | 6933 | 6948 | 476 |
| 848874 | N/A | N/A | TACAAATGCAGGCAGA | 40 | 7256 | 7271 | 477 |
| 848890 | N/A | N/A | CTCGACAACAGGTTTT | 65 | 7577 | 7592 | 478 |
| 848906 | N/A | N/A | AGGAACATGATGACAT | 0 | 7811 | 7826 | 479 |
| 848268 | 644 | 659 | CTGCAGGCGGCGGGCA | 0 | 7917 | 7932 | 480 |
| 848279 | 679 | 694 | ATCTTGGTGAGGTATC | 40 | 7952 | 7967 | 481 |
| 848294 | 695 | 710 | ATGGAAGACATGCAGG | 44 | 7968 | 7983 | 482 |
| 848922 | N/A | N/A | TAAAATGACTCAGGCT | 19 | 8406 | 8421 | 483 |
| 848938 | N/A | N/A | CATCAAGTTAGAGGCC | 49 | 8650 | 8665 | 484 |
| 848954 | N/A | N/A | TATACGGGTACCTTCT | 28 | 9143 | 9158 | 485 |
| 848970 | N/A | N/A | GCTCAGTGCAAACTGC | 0 | 10094 | 10109 | 486 |
| 848309 | 779 | 794 | CTCGATGTAGTCGACA | 62 | 10540 | 10555 | 487 |
| 848986 | N/A | N/A | CCCGAGAAGTGGAAAC | 12 | 10729 | 10744 | 488 |
| 849002 | N/A | N/A | CCAAGATCCCACGAGA | 56 | 11458 | 11473 | 489 |
| 849018 | N/A | N/A | GAGAAAGTGGTCCTGC | 35 | 12122 | 12137 | 490 |
| 849034 | N/A | N/A | CAGCAATAACTGATTT | 42 | 12825 | 12840 | 491 |
| 849044 | N/A | N/A | GGATACACAGGCTCGC | 83 | 13108 | 13123 | 337 |
| 849050 | N/A | N/A | CGCCTGAGAAGCTCAG | 44 | 13353 | 13368 | 492 |
| 849066 | N/A | N/A | CCACACAACGCACATC | 15 | 14043 | 14058 | 493 |
| 849082 | N/A | N/A | GACCAAACAGTGCTCG | 28 | 14360 | 14375 | 494 |
| 849098 | N/A | N/A | CTACAAAGACCTTTTC | 0 | 14849 | 14864 | 495 |
| 849114 | N/A | N/A | TAGGAGAAAGTAGGGA | 26 | 15533 | 15548 | 496 |
| 849130 | N/A | N/A | GAATATCAATATCTAA | 19 | 15983 | 15998 | 497 |
| 848325 | 931 | 946 | TCCCGGTGGTCACTCT | 2 | 16323 | 16338 | 498 |
| 848340 | 990 | 1005 | GGGTCCCGTCCTCCTC | 38 | 16382 | 16397 | 499 |
| 849146 | N/A | N/A | CCACATGAGAAAGACC | 0 | 16614 | 16629 | 500 |
| 848354 | 1026 | 1041 | CATGACTGTCACACTT | 23 | 16656 | 16671 | 501 |
| 848369 | 1074 | 1089 | TGGCCACGCCGGCATC | 17 | 16704 | 16719 | 502 |
| 468460 | 1075 | 1090 | TTGGCCACGCCGGCAT | 4 | 16705 | 16720 | 48 |
| 848385 | 1114 | 1129 | TGGCAGTTGAGCACGC | 0 | 16744 | 16759 | 503 |
| 849162 | N/A | N/A | GTCTAGAAAAAGTCCT | 65 | 17257 | 17272 | 504 |
| 849178 | N/A | N/A | CCGTGCCAGGTCATGC | 78 | 17957 | 17972 | 505 |

TABLE 7-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 849194 | N/A | N/A | CTGGGATACAGACACC | 42 | 18254 | 18269 | 506 |
| 849210 | N/A | N/A | AATTAAAAGACTCCAT | 18 | 19154 | 19169 | 507 |
| 849226 | N/A | N/A | TATTAGCAATTACACC | 45 | 19502 | 19517 | 508 |
| 849242 | N/A | N/A | TTACAGGCACAGAGTG | 25 | 19914 | 19929 | 509 |
| 848401 | 1228 | 1243 | CTGTACCCACCCGCCA | 11 | 20059 | 20074 | 510 |
| 849258 | N/A | N/A | AACAAGATTCCTTCCC | 30 | 20814 | 20829 | 511 |
| 849274 | N/A | N/A | GGCAGAACTCTGGCAC | 56 | 21163 | 21178 | 512 |
| 848417 | 1402 | 1417 | CCCAAAGTCCCCAGGG | 0 | 21374 | 21389 | 513 |
| 849290 | N/A | N/A | GGTGAAAGATGGTGAT | 10 | 22003 | 22018 | 514 |
| 848433 | 1544 | 1559 | CATCATGGCTGCAATG | 0 | 22037 | 22052 | 515 |
| 848449 | 1636 | 1651 | GGGAACCAGGCCTCAT | 25 | 22129 | 22144 | 516 |
| 848465 | 1736 | 1751 | TGCTGACCATACAGTC | 0 | 22518 | 22533 | 517 |
| 849306 | N/A | N/A | GTGCACTATCCTGTAG | 28 | 23065 | 23080 | 518 |
| 849322 | N/A | N/A | CAAAGACGGAAATGGG | 44 | 23462 | 23477 | 519 |
| 848481 | 1925 | 1940 | GCACCTGGCAATGGCG | 34 | 23545 | 23560 | 520 |
| 848495 | 1993 | 2008 | CGGGTCCCCATGCTGG | 0 | 23613 | 23628 | 521 |
| 849338 | N/A | N/A | TGCTTAGCACTCATCA | 0 | 24102 | 24117 | 522 |
| 849354 | N/A | N/A | CCTACATGCCAGCCTG | 73 | 24472 | 24487 | 523 |
| 849370 | N/A | N/A | AAAGAGATGCTGGCCT | 28 | 25228 | 25243 | 524 |
| 848511 | 2082 | 2097 | GCACAGGCGGCTTGTG | 28 | 25413 | 25428 | 525 |
| 849386 | N/A | N/A | CCATATTTATGCACAT | 62 | 25806 | 25821 | 526 |
| 849402 | N/A | N/A | TTTCAGTACTCTATAT | 12 | 26511 | 26526 | 527 |
| 848527 | 2372 | 2387 | AACGGCTGTCACGGCC | 42 | 27515 | 27530 | 528 |
| 848543 | 2507 | 2522 | AGAGAGGGACAAGTCG | 47 | 27650 | 27665 | 529 |
| 848559 | 2603 | 2618 | TTCCAGGCAAGGAGGC | 23 | 27746 | 27761 | 530 |
| 848575 | 2712 | 2727 | GGCAGCACCCGAGCAC | 72 | 27855 | 27870 | 531 |
| 848590 | 2757 | 2772 | ATAAAAGTCATTCTGC | 15 | 27900 | 27915 | 532 |
| 848606 | 2787 | 2802 | ATTGAATGCCTGGCAC | 36 | 27930 | 27945 | 533 |
| 848622 | 2919 | 2934 | CCACAGTTAGCTGGAG | 45 | 28062 | 28077 | 534 |
| 848637 | 3036 | 3051 | GCTCAGGAAACCAAGG | 12 | 28179 | 28194 | 535 |
| 848652 | 3122 | 3137 | CTGCCGAGTCAGTCCT | 66 | 28265 | 28280 | 536 |
| 848668 | 3172 | 3187 | TGCCGGGTAGTGGAGC | 49 | 28315 | 28330 | 537 |
| 848683 | 3226 | 3241 | CCCCTCTGGTTCCAGG | 43 | 28369 | 28384 | 538 |
| 848699 | 3261 | 3276 | GCTCAGTTCCTGCTGT | 18 | 28404 | 28419 | 539 |
| 848715 | 3317 | 3332 | AGCCGGGTGAAGTAAG | 26 | 28460 | 28475 | 540 |
| 848731 | 3386 | 3401 | CACTCACCGAGCTTCC | 73 | 28529 | 28544 | 541 |

TABLE 7-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848747 | 3471 | 3486 | CCTTAGAAGCATCTCC | 52 | 28614 | 28629 | 542 |
| 848762 | 3576 | 3591 | GTAAAAAGGCAACAGA | 36 | 28719 | 28734 | 543 |

TABLE 8

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848206 | 7 | 22 | CGCCACCAGAGCCCCA | 30 | 3482 | 3497 | 544 |
| 848222 | 207 | 222 | CGGAATCCTGGCTGGG | 55 | 3682 | 3697 | 545 |
| 848238 | 476 | 491 | TAGCACCAGCTCCTCG | 53 | 3951 | 3966 | 546 |
| 848254 | 520 | 535 | TGCTCGGGTGCTTCGG | 35 | 3995 | 4010 | 547 |
| 848779 | N/A | N/A | GGCTGCGGGTTCGCCC | 13 | 4070 | 4085 | 548 |
| 848795 | N/A | N/A | CGAGAATACCTCCGCC | 73 | 4682 | 4697 | 549 |
| 848811 | N/A | N/A | GCTGAGTAAGGACTTG | 64 | 5317 | 5332 | 550 |
| 848827 | N/A | N/A | TTCCGCTAAATAAAAA | 9 | 5781 | 5796 | 551 |
| 848843 | N/A | N/A | TCAGAGTAGAACAGAG | 51 | 6547 | 6562 | 552 |
| 848859 | N/A | N/A | GAGGGAGGTGCCAAGC | 31 | 6954 | 6969 | 553 |
| 848875 | N/A | N/A | CTACAAATGCAGGCAG | 63 | 7257 | 7272 | 554 |
| 848891 | N/A | N/A | AACTACGGGCCACACT | 7 | 7591 | 7606 | 555 |
| 848907 | N/A | N/A | ACGGATCCTGGCCCCA | 45 | 7834 | 7849 | 556 |
| 848269 | 663 | 678 | CCCGGCGGGCAGCCTG | 18 | 7936 | 7951 | 557 |
| 848280 | 680 | 695 | GATCTTGGTGAGGTAT | 1 | 7953 | 7968 | 558 |
| 848295 | 699 | 714 | GGCCATGGAAGACATG | 18 | 7972 | 7987 | 559 |
| 848923 | N/A | N/A | CTAGAGTCATGCTTTT | 0 | 8425 | 8440 | 560 |
| 848939 | N/A | N/A | GTGGAGAATCAGTGTG | 40 | 8683 | 8698 | 561 |
| 848955 | N/A | N/A | TTGAAGTCCAGCTCTC | 16 | 9258 | 9273 | 562 |
| 848971 | N/A | N/A | GCAATTCGGTTTGTCC | 65 | 10140 | 10155 | 563 |
| 848310 | 795 | 810 | AGACAGAGGAGTCCTC | 31 | 10556 | 10571 | 564 |
| 848987 | N/A | N/A | GATCATTTAAGGCAAG | 26 | 10850 | 10865 | 565 |
| 849003 | N/A | N/A | TCCCAAGATCCCACGA | 5 | 11460 | 11475 | 566 |
| 849019 | N/A | N/A | CAAGAGAAGCTTCTCC | 20 | 12152 | 12167 | 567 |
| 849035 | N/A | N/A | CTACAGCAATAACTGA | 46 | 12828 | 12843 | 568 |
| 849044 | N/A | N/A | GGATACACAGGCTCGC | 78 | 13108 | 13123 | 337 |
| 849051 | N/A | N/A | GAGCAGGGAGCTCATT | 0 | 13395 | 13410 | 569 |
| 849067 | N/A | N/A | CTAGAAGACAGCACAG | 15 | 14085 | 14100 | 570 |

TABLE 8-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID 2 Start Site | SEQ ID 2: Stop Site | SEQ ID NO |
|---|---|---|---|---|---|---|---|
| 849083 | N/A | N/A | CCGACCTGAAGACATC | 41 | 14380 | 14395 | 571 |
| 849099 | N/A | N/A | GCCCACCGCATAATCC | 18 | 14897 | 14912 | 572 |
| 849115 | N/A | N/A | GACAAAGGTTAGGGTA | 46 | 15549 | 15564 | 573 |
| 849131 | N/A | N/A | TGAATATCAATATCTA | 30 | 15984 | 15999 | 574 |
| 848326 | 939 | 954 | CCTCGATTTCCCGGTG | 30 | 16331 | 16346 | 575 |
| 848341 | 992 | 1007 | GCGGGTCCCGTCCTCC | 0 | 16384 | 16399 | 576 |
| 849147 | N/A | N/A | GACCACATGAGAAAGA | 0 | 16616 | 16631 | 577 |
| 848355 | 1029 | 1044 | TGCCATGACTGTCACA | 35 | 16659 | 16674 | 578 |
| 468460 | 1075 | 1090 | TTGGCCACGCCGGCAT | 19 | 16705 | 16720 | 48 |
| 848370 | 1076 | 1091 | CTTGGCCACGCCGGCA | 0 | 16706 | 16721 | 579 |
| 848386 | 1133 | 1148 | GCTAACCGTGCCCTTC | 20 | 16763 | 16778 | 580 |
| 849163 | N/A | N/A | CAGTAAGGGAGAGAAC | 3 | 17363 | 17378 | 581 |
| 849179 | N/A | N/A | CCCGTGCCAGGTCATG | 38 | 17958 | 17973 | 582 |
| 849195 | N/A | N/A | AGCTGCTAGTTATTTA | 44 | 18396 | 18411 | 583 |
| 849211 | N/A | N/A | GAAACAGGGACAGTTG | 25 | 19189 | 19204 | 584 |
| 849227 | N/A | N/A | GGAAGATATTAGCAAT | 78 | 19508 | 19523 | 585 |
| 849243 | N/A | N/A | CTTACAGGCACAGAGT | 27 | 19915 | 19930 | 586 |
| 848402 | 1238 | 1253 | GAGGACGCGGCTGTAC | 25 | 20069 | 20084 | 587 |
| 849259 | N/A | N/A | GTGGAACAAGATTCCT | 40 | 20818 | 20833 | 588 |
| 849275 | N/A | N/A | AGGCAGAACTCTGGCA | 56 | 21164 | 21179 | 589 |
| 848418 | 1414 | 1429 | CCAAAGTTGGTCCCCA | 0 | 21386 | 21401 | 590 |
| 848434 | 1546 | 1561 | AGCATCATGGCTGCAA | 49 | 22039 | 22054 | 591 |
| 848450 | 1641 | 1656 | CCTCAGGGAACCAGGC | 28 | 22134 | 22149 | 592 |
| 849291 | N/A | N/A | TGCCATCCTGCTTACC | 30 | 22209 | 22224 | 593 |
| 848466 | 1738 | 1753 | TGTGCTGACCATACAG | 20 | 22520 | 22535 | 594 |
| 849307 | N/A | N/A | CACCAAAATGCTGCAA | 39 | 23094 | 23109 | 595 |
| 849323 | N/A | N/A | GGCCTTAGAGTCAAAG | 0 | 23473 | 23488 | 596 |
| 468479 | 1926 | 1941 | AGCACCTGGCAATGGC | 47 | 23546 | 23561 | 597 |
| 848496 | 1997 | 2012 | GACACGGGTCCCCATG | 28 | 23617 | 23632 | 598 |
| 849339 | N/A | N/A | ACTAAGCTAAGTGCTT | 7 | 24113 | 24128 | 599 |
| 849355 | N/A | N/A | GCAAAATGGTGCTCTT | 52 | 24690 | 24705 | 600 |
| 849371 | N/A | N/A | ACCTAGAAACAACTCA | 23 | 25251 | 25266 | 601 |
| 848512 | 2084 | 2099 | CAGCACAGGCGGCTTG | 14 | 25415 | 25430 | 602 |
| 849387 | N/A | N/A | ATGCATATTGCATTTC | 44 | 25828 | 25843 | 603 |
| 849403 | N/A | N/A | GGCCAGACCACACTCC | 13 | 26808 | 26823 | 604 |
| 848528 | 2375 | 2390 | GGCAACGGCTGTCACG | 52 | 27518 | 27533 | 605 |
| 848544 | 2509 | 2524 | TGAGAGAGGGACAAGT | 27 | 27652 | 27667 | 606 |

TABLE 8-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848560 | 2613 | 2628 | AGTGAGTGAGTTCCAG | 65 | 27756 | 27771 | 607 |
| 848576 | 2713 | 2728 | TGGCAGCACCCGAGCA | 56 | 27856 | 27871 | 608 |
| 848591 | 2761 | 2776 | CTCAATAAAAGTCATT | 45 | 27904 | 27919 | 609 |
| 848607 | 2791 | 2806 | GAGGATTGAATGCCTG | 37 | 27934 | 27949 | 610 |
| 848623 | 2921 | 2936 | CTCCACAGTTAGCTGG | 35 | 28064 | 28079 | 611 |
| 848638 | 3045 | 3060 | GTAAAGGTGGCTCAGG | 46 | 28188 | 28203 | 612 |
| 848653 | 3123 | 3138 | ACTGCCGAGTCAGTCC | 29 | 28266 | 28281 | 613 |
| 848669 | 3180 | 3195 | GTGTACCCTGCCGGGT | 3 | 28323 | 28338 | 614 |
| 848684 | 3227 | 3242 | CCCCCTCTGGTTCCAG | 54 | 28370 | 28385 | 615 |
| 848700 | 3263 | 3278 | TGGCTCAGTTCCTGCT | 36 | 28406 | 28421 | 616 |
| 848716 | 3321 | 3336 | GCCCAGCCGGGTGAAG | 26 | 28464 | 28479 | 617 |
| 848732 | 3388 | 3403 | ATCACTCACCGAGCTT | 69 | 28531 | 28546 | 618 |
| 848748 | 3473 | 3488 | TGCCTTAGAAGCATCT | 68 | 28616 | 28631 | 619 |
| 848763 | 3578 | 3593 | CTGTAAAAGGCAACA | 52 | 28721 | 28736 | 620 |

TABLE 9

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848207 | 12 | 27 | GATCACGCCACCAGAG | 0 | 3487 | 3502 | 621 |
| 848223 | 209 | 224 | CGCGGAATCCTGGCTG | 1 | 3684 | 3699 | 622 |
| 848239 | 477 | 492 | CTAGCACCAGCTCCTC | 38 | 3952 | 3967 | 623 |
| 848255 | 533 | 548 | GGCTGTGGTTCCGTGC | 29 | 4008 | 4023 | 624 |
| 848780 | N/A | N/A | AAACAGCACCGCACCG | 0 | 4090 | 4105 | 625 |
| 848796 | N/A | N/A | CCGCACACGGTCGGCA | 35 | 4821 | 4836 | 626 |
| 848812 | N/A | N/A | GAACAAGGAAGAGGGC | 39 | 5341 | 5356 | 627 |
| 848828 | N/A | N/A | CAAAGACCCATCTGAA | 32 | 5803 | 5818 | 628 |
| 848844 | N/A | N/A | TCATGAATCAAGTCCA | 71 | 6650 | 6665 | 629 |
| 848860 | N/A | N/A | GCAGAGATCAATCACA | 36 | 6997 | 7012 | 630 |
| 848876 | N/A | N/A | TCCCATCCAGATGCTC | 34 | 7272 | 7287 | 631 |
| 848892 | N/A | N/A | ATTCAGGCAAAAATGG | 12 | 7608 | 7623 | 632 |
| 848270 | 665 | 680 | TCCCCGGCGGGCAGCC | 24 | 7938 | 7953 | 633 |
| 848281 | 681 | 696 | GGATCTTGGTGAGGTA | 23 | 7954 | 7969 | 634 |
| 848296 | 704 | 719 | AAGAAGGCCATGGAAG | 38 | 7977 | 7992 | 635 |
| 848908 | N/A | N/A | TGCCATTCCCAAAAAG | 0 | 8045 | 8060 | 636 |

TABLE 9-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848924 | N/A | N/A | CAAAGGAATTTTGGAC | 0 | 8442 | 8457 | 637 |
| 848940 | N/A | N/A | TGCCATGTGGAGAATC | 24 | 8689 | 8704 | 638 |
| 848956 | N/A | N/A | TCGAACCCAGGCTGGT | 0 | 9286 | 9301 | 639 |
| 848972 | N/A | N/A | CATGACATAACAGCAC | 24 | 10158 | 10173 | 640 |
| 848311 | 797 | 812 | AAAGACAGAGGAGTCC | 28 | 10558 | 10573 | 641 |
| 848988 | N/A | N/A | AAAGAGGATCATTTAA | 0 | 10856 | 10871 | 642 |
| 849004 | N/A | N/A | CAAGAACGACAAAGCT | 48 | 11493 | 11508 | 643 |
| 849020 | N/A | N/A | GGACACGGAAGAGGCA | 63 | 12166 | 12181 | 644 |
| 849036 | N/A | N/A | ACAGAGAAATGCATGC | 66 | 12843 | 12858 | 645 |
| 849044 | N/A | N/A | GGATACACAGGCTCGC | 81 | 13108 | 13123 | 337 |
| 849052 | N/A | N/A | CTCTATCTTCCAAACC | 22 | 13578 | 13593 | 646 |
| 849068 | N/A | N/A | ATACAGGCTTATCTAG | 3 | 14097 | 14112 | 647 |
| 849084 | N/A | N/A | CAATAGGCATCTACCA | 59 | 14444 | 14459 | 648 |
| 849100 | N/A | N/A | AGGACTTACAGCCCAC | 12 | 14907 | 14922 | 649 |
| 849116 | N/A | N/A | GCCCATGCAGGACAAA | 11 | 15559 | 15574 | 650 |
| 849132 | N/A | N/A | TATGAATATCAATATC | 0 | 15986 | 16001 | 651 |
| 468453 | 950 | 965 | CATGACCCTGCCCTCG | 45 | 16342 | 16357 | 652 |
| 848342 | 995 | 1010 | GAAGCGGGTCCCGTCC | 17 | 16387 | 16402 | 653 |
| 849148 | N/A | N/A | ACACAAGGACCACATG | 0 | 16623 | 16638 | 654 |
| 848356 | 1040 | 1055 | TGCCAGGTGGGTGCCA | 26 | 16670 | 16685 | 655 |
| 468460 | 1075 | 1090 | TTGGCCACGCCGGCAT | 0 | 16705 | 16720 | 48 |
| 848371 | 1077 | 1092 | CCTTGGCCACGCCGGC | 37 | 16707 | 16722 | 656 |
| 848387 | 1135 | 1150 | CCGCTAACCGTGCCCT | 17 | 16765 | 16780 | 657 |
| 849164 | N/A | N/A | CTTGAGCTGTGCGACC | 27 | 17497 | 17512 | 658 |
| 849180 | N/A | N/A | CCCCGTGCCAGGTCAT | 26 | 17959 | 17974 | 659 |
| 849196 | N/A | N/A | ACAACAGCCACATTTA | 56 | 18413 | 18428 | 660 |
| 849212 | N/A | N/A | TGTGAAACAGGGACAG | 17 | 19192 | 19207 | 661 |
| 849228 | N/A | N/A | TAATATATACATCCTA | 0 | 19564 | 19579 | 662 |
| 849244 | N/A | N/A | CCTTACAGGCACAGAG | 16 | 19916 | 19931 | 663 |
| 848403 | 1241 | 1256 | GTTGAGGACGCGGCTG | 19 | 20072 | 20087 | 664 |
| 849260 | N/A | N/A | CCAACGCGCGCGCGCG | 4 | 20870 | 20885 | 665 |
| 849276 | N/A | N/A | GAAAATCTGACTGCCC | 43 | 21180 | 21195 | 666 |
| 848419 | 1416 | 1431 | GGCCAAAGTTGGTCCC | 0 | 21388 | 21403 | 667 |
| 848435 | 1550 | 1565 | AGACAGCATCATGGCT | 43 | 22043 | 22058 | 668 |
| 848451 | 1656 | 1671 | TCAGTACCCGCTGGTC | 41 | 22149 | 22164 | 669 |
| 849292 | N/A | N/A | GGTCACACAGACCTCC | 24 | 22252 | 22267 | 670 |
| 848467 | 1744 | 1759 | CCCGAGTGTGCTGACC | 39 | 22526 | 22541 | 671 |

TABLE 9-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 849308 | N/A | N/A | TTCCACCAAAATGCTG | 7 | 23097 | 23112 | 672 |
| 848482 | 1927 | 1942 | CAGCACCTGGCAATGG | 10 | 23547 | 23562 | 673 |
| 848497 | 1998 | 2013 | GGACACGGGTCCCCAT | 32 | 23618 | 23633 | 674 |
| 849324 | N/A | N/A | GGCAAGCCCAGCCTCC | 0 | 23667 | 23682 | 675 |
| 849340 | N/A | N/A | AACGATAGCTAGAATT | 12 | 24143 | 24158 | 676 |
| 849356 | N/A | N/A | TGGTAGGGTTGTGGTT | 0 | 24782 | 24797 | 677 |
| 849372 | N/A | N/A | GCAAGAGCTAGGAAAC | 60 | 25265 | 25280 | 678 |
| 848513 | 2086 | 2101 | CTCAGCACAGGCGGCT | 41 | 25417 | 25432 | 679 |
| 849388 | N/A | N/A | ATGCATGCATATTGCA | 0 | 25832 | 25847 | 680 |
| 849404 | N/A | N/A | CTTCAGACTCCAGCCT | 0 | 26944 | 26959 | 681 |
| 848529 | 2378 | 2393 | GATGGCAACGGCTGTC | 0 | 27521 | 27536 | 682 |
| 848545 | 2511 | 2526 | GCTGAGAGAGGGACAA | 54 | 27654 | 27669 | 683 |
| 848561 | 2617 | 2632 | CCAGAGTGAGTGAGTT | 30 | 27760 | 27775 | 684 |
| 848577 | 2714 | 2729 | CTGGCAGCACCCGAGC | 52 | 27857 | 27872 | 685 |
| 848592 | 2762 | 2777 | GCTCAATAAAAGTCAT | 44 | 27905 | 27920 | 686 |
| 848608 | 2795 | 2810 | ACCTGAGGATTGAATG | 16 | 27938 | 27953 | 687 |
| 848624 | 2944 | 2959 | AATCAGGGAGCCCCCA | 0 | 28087 | 28102 | 688 |
| 848639 | 3047 | 3062 | GAGTAAAGGTGGCTCA | 19 | 28190 | 28205 | 689 |
| 848654 | 3124 | 3139 | CACTGCCGAGTCAGTC | 51 | 28267 | 28282 | 690 |
| 848670 | 3186 | 3201 | GCGAATGTGTACCCTG | 81 | 28329 | 28344 | 691 |
| 848685 | 3229 | 3244 | CGCCCCTCTGGTTCC | 57 | 28372 | 28387 | 692 |
| 848701 | 3264 | 3279 | CTGGCTCAGTTCCTGC | 69 | 28407 | 28422 | 693 |
| 848717 | 3330 | 3345 | AAATGAGGAGCCCAGC | 42 | 28473 | 28488 | 694 |
| 848733 | 3392 | 3407 | TGCCATCACTCACCGA | 48 | 28535 | 28550 | 695 |
| 848749 | 3482 | 3497 | CCCCGACCATGCCTTA | 43 | 28625 | 28640 | 696 |
| 848764 | 3580 | 3595 | GGCTGTAAAAGGCAA | 68 | 28723 | 28738 | 697 |

TABLE 10

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848208 | 15 | 30 | GCAGATCACGCCACCA | 0 | 3490 | 3505 | 698 |
| 848224 | 212 | 227 | GCGCGCGGAATCCTGG | 21 | 3687 | 3702 | 699 |
| 848240 | 478 | 493 | GCTAGCACCAGCTCCT | 37 | 3953 | 3968 | 700 |
| 468441 | 541 | 556 | TGGAAGGTGGCTGTGG | 0 | 4016 | 4031 | 701 |

TABLE 10-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848781 | N/A | N/A | CCGAGAGGAAACAGCA | 52 | 4098 | 4113 | 702 |
| 848797 | N/A | N/A | AGCAAACTCGCCCCGC | 55 | 4833 | 4848 | 703 |
| 848813 | N/A | N/A | GGCTCAGGGAACAAGG | 39 | 5349 | 5364 | 704 |
| 848829 | N/A | N/A | CACCATCATCGCTGAA | 39 | 5834 | 5849 | 705 |
| 848845 | N/A | N/A | GCAGACATACCTGCTT | 24 | 6693 | 6708 | 706 |
| 848861 | N/A | N/A | CTACATGTGCAGAGAT | 52 | 7005 | 7020 | 707 |
| 848877 | N/A | N/A | ATAAATCTCCCATCCA | 36 | 7279 | 7294 | 708 |
| 848893 | N/A | N/A | TTTCAAATGTGCCATT | 22 | 7621 | 7636 | 709 |
| 468443 | 666 | 681 | ATCCCCGGCGGGCAGC | 52 | 7939 | 7954 | 710 |
| 848282 | 682 | 697 | AGGATCTTGGTGAGGT | 47 | 7955 | 7970 | 711 |
| 848297 | 732 | 747 | CGCCACTCATCTTCAC | 23 | 8005 | 8020 | 712 |
| 848909 | N/A | N/A | GGCCTACTAAGCACAG | 49 | 8100 | 8115 | 713 |
| 848925 | N/A | N/A | TTCAAAGGAATTTTGG | 0 | 8444 | 8459 | 714 |
| 848941 | N/A | N/A | ACCCAGGTCCAGACTC | 44 | 8793 | 8808 | 715 |
| 848957 | N/A | N/A | GGTTAGACAGCCAATA | 48 | 9318 | 9333 | 716 |
| 848973 | N/A | N/A | CTAAATCATGACATAA | 14 | 10164 | 10179 | 717 |
| 848312 | 799 | 814 | GCAAAGACAGAGGAGT | 46 | 10560 | 10575 | 718 |
| 848989 | N/A | N/A | TCCAAGGTAAGTGCAG | 52 | 10924 | 10939 | 719 |
| 849005 | N/A | N/A | GACAAGAACGACAAAG | 46 | 11495 | 11510 | 720 |
| 849021 | N/A | N/A | GACAATGAAGAGGAGA | 69 | 12240 | 12255 | 721 |
| 849037 | N/A | N/A | CTCAATACCTGACAGA | 50 | 12854 | 12869 | 722 |
| 849044 | N/A | N/A | GGATACACAGGCTCGC | 81 | 13108 | 13123 | 337 |
| 849053 | N/A | N/A | TGGTAAAAGCCCCCAC | 39 | 13677 | 13692 | 723 |
| 849069 | N/A | N/A | ATACATTGGCAGACAG | 56 | 14121 | 14136 | 724 |
| 849085 | N/A | N/A | ACTCATCAATAGGCAT | 79 | 14450 | 14465 | 725 |
| 849101 | N/A | N/A | CATCACAGGACTTACA | 0 | 14913 | 14928 | 726 |
| 849117 | N/A | N/A | CAAGAGACTCACTGGG | 16 | 15581 | 15596 | 727 |
| 849133 | N/A | N/A | TGCCAAGAAGGACCCA | 61 | 16020 | 16035 | 728 |
| 848327 | 953 | 968 | GACCATGACCCTGCCC | 41 | 16345 | 16360 | 729 |
| 848343 | 997 | 1012 | TGGAAGCGGGTCCCGT | 11 | 16389 | 16404 | 730 |
| 849149 | N/A | N/A | TGCTCGACGAACACAA | 0 | 16633 | 16648 | 731 |
| 848357 | 1053 | 1068 | CGCTGACCACCCCTGC | 33 | 16683 | 16698 | 732 |
| 468460 | 1075 | 1090 | TTGGCCACGCCGGCAT | 7 | 16705 | 16720 | 48 |
| 848372 | 1078 | 1093 | CCCTTGGCCACGCCGG | 49 | 16708 | 16723 | 733 |
| 848388 | 1137 | 1152 | TGCCGCTAACCGTGCC | 10 | 16767 | 16782 | 734 |
| 849165 | N/A | N/A | GTGGAAGTCAAGCTGC | 42 | 17550 | 17565 | 735 |
| 849181 | N/A | N/A | GCCCCGTGCCAGGTCA | 58 | 17960 | 17975 | 736 |

TABLE 10-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 849197 | N/A | N/A | TAGGAGACAGCTAGTG | 25 | 18486 | 18501 | 737 |
| 849213 | N/A | N/A | CACAAACTTGAACAGA | 38 | 19248 | 19263 | 738 |
| 849229 | N/A | N/A | CTTAATATATACATCC | 0 | 19566 | 19581 | 739 |
| 849245 | N/A | N/A | GCCAAGGTCACCCCTT | 0 | 19963 | 19978 | 740 |
| 848404 | 1283 | 1298 | GACCAGCACGACCCCA | 13 | 20114 | 20129 | 741 |
| 849261 | N/A | N/A | ACCTAGGTTACCGCTG | 33 | 20918 | 20933 | 742 |
| 849277 | N/A | N/A | AGGAAAATCTGACTGC | 26 | 21182 | 21197 | 743 |
| 848420 | 1423 | 1438 | ACACAGCGGCCAAAGT | 0 | 21395 | 21410 | 744 |
| 848436 | 1552 | 1567 | GCAGACAGCATCATGG | 76 | 22045 | 22060 | 745 |
| 848452 | 1658 | 1673 | GGTCAGTACCCGCTGG | 29 | 22151 | 22166 | 746 |
| 849293 | N/A | N/A | CCTATTTAAGGTGGCG | 51 | 22311 | 22326 | 747 |
| 848468 | 1753 | 1768 | CGTGTAGGCCCCGAGT | 44 | 22535 | 22550 | 748 |
| 849309 | N/A | N/A | CAGAAATGCCTGCCCC | 64 | 23141 | 23156 | 749 |
| 848483 | 1928 | 1943 | GCAGCACCTGGCAATG | 0 | 23548 | 23563 | 750 |
| 848498 | 1999 | 2014 | TGGACACGGGTCCCCA | 2 | 23619 | 23634 | 751 |
| 849325 | N/A | N/A | CCTCACCCCAGGGCAA | 0 | 23678 | 23693 | 752 |
| 849341 | N/A | N/A | GTAACGATAGCTAGAA | 52 | 24145 | 24160 | 753 |
| 849357 | N/A | N/A | TGAACATGGTAGGGTT | 62 | 24788 | 24803 | 754 |
| 849373 | N/A | N/A | AGGCAAGAGCTAGGAA | 51 | 25267 | 25282 | 755 |
| 848514 | 2113 | 2128 | ACGCACTGGTTGGGCT | 5 | 25444 | 25459 | 756 |
| 849389 | N/A | N/A | GTTAAATAGATCAGAG | 15 | 25989 | 26004 | 757 |
| 849405 | N/A | N/A | CCCCATAGCCTGCCCC | 0 | 27058 | 27073 | 758 |
| 848530 | 2381 | 2396 | GCAGATGGCAACGGCT | 14 | 27524 | 27539 | 759 |
| 848546 | 2520 | 2535 | CCATGGAGGGCTGAGA | 3 | 27663 | 27678 | 760 |
| 848562 | 2619 | 2634 | ACCCAGAGTGAGTGAG | 29 | 27762 | 27777 | 761 |
| 848578 | 2715 | 2730 | GCTGGCAGCACCCGAG | 18 | 27858 | 27873 | 762 |
| 848593 | 2763 | 2778 | AGCTCAATAAAAGTCA | 61 | 27906 | 27921 | 763 |
| 848609 | 2820 | 2835 | GAAGAATCCTGCCTCC | 42 | 27963 | 27978 | 764 |
| 848625 | 2946 | 2961 | TTAATCAGGGAGCCCC | 31 | 28089 | 28104 | 765 |
| 848640 | 3050 | 3065 | GCAGAGTAAAGGTGGC | 38 | 28193 | 28208 | 766 |
| 848655 | 3125 | 3140 | ACACTGCCGAGTCAGT | 32 | 28268 | 28283 | 767 |
| 848671 | 3188 | 3203 | GTGCGAATGTGTACCC | 68 | 28331 | 28346 | 768 |
| 848686 | 3237 | 3252 | GGCAGGCACGCCCCCT | 17 | 28380 | 28395 | 769 |
| 848702 | 3265 | 3280 | TCTGGCTCAGTTCCTG | 51 | 28408 | 28423 | 770 |
| 848718 | 3332 | 3347 | AAAAATGAGGAGCCCA | 17 | 28475 | 28490 | 771 |
| 848734 | 3415 | 3430 | TTCCATGCCTGCAGGC | 35 | 28558 | 28573 | 772 |

TABLE 10-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848750 | 3502 | 3517 | GGACAGTTGTTGGCCC | 25 | 28645 | 28660 | 773 |
| 848765 | 3588 | 3603 | GAAAAGTTGGCTGTAA | 22 | 28731 | 28746 | 774 |

TABLE 11

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848209 | 51 | 66 | ACCTTCTAGGGTGTGG | 0 | 3526 | 3541 | 775 |
| 848225 | 242 | 257 | CTGAAGTTCAGGAGCA | 35 | 3717 | 3732 | 776 |
| 848241 | 479 | 494 | GGCTAGCACCAGCTCC | 58 | 3954 | 3969 | 777 |
| 848256 | 549 | 564 | CGCAGCGGTGGAAGGT | 15 | 4024 | 4039 | 778 |
| 848782 | N/A | N/A | GCGAAGAGCCCTCGGC | 33 | 4158 | 4173 | 779 |
| 848798 | N/A | N/A | GGGAAGAAGCTTCCCA | 0 | 4882 | 4897 | 780 |
| 848814 | N/A | N/A | AGAAAGTCAAAGGCTC | 74 | 5360 | 5375 | 781 |
| 848830 | N/A | N/A | GACACCATCATCGCTG | 67 | 5836 | 5851 | 782 |
| 848846 | N/A | /A | GGCAGACATACCTGCT | 0 | 6694 | 6709 | 783 |
| 848862 | N/A | N/A | GGCCTTAAGCTGCTTT | 10 | 7048 | 7063 | 784 |
| 848878 | N/A | N/A | ATATAAATCTCCCATC | 9 | 7281 | 7296 | 785 |
| 848894 | N/A | N/A | TCACATGGTTATATAA | 37 | 7640 | 7655 | 786 |
| 848271 | 667 | 682 | TATCCCCGGCGGGCAG | 35 | 7940 | 7955 | 787 |
| 848283 | 683 | 698 | CAGGATCTTGGTGAGG | 49 | 7956 | 7971 | 788 |
| 848298 | 740 | 755 | CAGCAGGTCGCCACTC | 5 | 8013 | 8028 | 789 |
| 848910 | N/A | N/A | AGCAATGGGCCTACTA | 0 | 8107 | 8122 | 790 |
| 848926 | N/A | N/A | AGCAACAGCTTCAAAG | 11 | 8453 | 8468 | 791 |
| 848942 | N/A | N/A | CTGATTAACCCATGGG | 46 | 8833 | 8848 | 792 |
| 848958 | N/A | N/A | TTACAGATAGAGGAAT | 0 | 9365 | 9380 | 793 |
| 848974 | N/A | N/A | GGACATGGAGTGAAGC | 7 | 10200 | 10215 | 794 |
| 848313 | 801 | 816 | GGGCAAAGACAGAGGA | 11 | 10562 | 10577 | 795 |
| 848990 | N/A | N/A | GGTAGAGTCACCATCA | 40 | 10953 | 10968 | 796 |
| 849006 | N/A | N/A | TCTCACAGCAACCTGT | 0 | 11548 | 11563 | 797 |
| 849022 | N/A | N/A | TCCTAACCCCCACAAC | 0 | 12373 | 12388 | 798 |
| 849038 | N/A | N/A | TGCAGGGCTAAAATCA | 34 | 12880 | 12895 | 799 |
| 849044 | N/A | N/A | GGATACACAGGCTCGC | 78 | 13108 | 13123 | 337 |
| 849054 | N/A | N/A | GGCAGGTGGGCCTGGT | 0 | 13689 | 13704 | 800 |
| 849070 | N/A | N/A | GGATACATTGGCAGAC | 41 | 14123 | 14138 | 801 |
| 849086 | N/A | N/A | GTGTTAGGAGCTTTCA | 60 | 14465 | 14480 | 802 |

TABLE 11-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 849102 | N/A | N/A | AGACACATCACAGGAC | 27 | 14918 | 14933 | 803 |
| 849118 | N/A | N/A | AAGAAGCAGGCACTGG | 32 | 15608 | 15623 | 804 |
| 849134 | N/A | N/A | AAGGAAAGGGAGGCCT | 0 | 16081 | 16096 | 805 |
| 848328 | 964 | 979 | TCGAAGTCGGTGACCA | 17 | 16356 | 16371 | 806 |
| 848344 | 999 | 1014 | TGTGGAAGCGGGTCCC | 24 | 16391 | 16406 | 807 |
| 848358 | 1055 | 1070 | GCCGCTGACCACCCCT | 0 | 16685 | 16700 | 808 |
| 468460 | 1075 | 1090 | TTGGCCACGCCGGCAT | 30 | 16705 | 16720 | 48 |
| 848373 | 1079 | 1094 | ACCCTTGGCCACGCCG | 30 | 16709 | 16724 | 809 |
| 848389 | 1145 | 1160 | TATGAGGGTGCCGCTA | 4 | 16775 | 16790 | 810 |
| 849150 | N/A | N/A | ACTTACCTATGAGGGT | 0 | 16782 | 16797 | 811 |
| 849166 | N/A | N/A | GGCTTACAGTGGAAGT | 8 | 17558 | 17573 | 812 |
| 849182 | N/A | N/A | TGCCCCGTGCCAGGTC | 41 | 17961 | 17976 | 813 |
| 849198 | N/A | N/A | CCAGGAGCCGTGGCCA | 12 | 18537 | 18552 | 814 |
| 849214 | N/A | N/A | ACACAAACTTGAACAG | 10 | 19249 | 19264 | 815 |
| 849230 | N/A | N/A | TCTTAATATATACATC | 0 | 19567 | 19582 | 816 |
| 849246 | N/A | N/A | GAACAAAGCCAAGGTC | 0 | 19970 | 19985 | 817 |
| 848405 | 1286 | 1301 | GGTGACCAGCACGACC | 0 | 20117 | 20132 | 818 |
| 849262 | N/A | N/A | CCTTGATAGGCCAGGG | 0 | 20937 | 20952 | 819 |
| 849278 | N/A | N/A | TCCCACTCAAATGTCC | 0 | 21205 | 21220 | 820 |
| 848421 | 1425 | 1440 | CCACACAGCGGCCAAA | 0 | 21397 | 21412 | 821 |
| 848437 | 1554 | 1569 | CGGCAGACAGCATCAT | 72 | 22047 | 22062 | 822 |
| 848453 | 1681 | 1696 | GGCAGGGCGGCCACCA | 0 | 22174 | 22189 | 823 |
| 849294 | N/A | N/A | AAAATATTGCACAGCC | 0 | 22353 | 22368 | 824 |
| 848469 | 1760 | 1775 | GGCCATCCGTGTAGGC | 0 | 22542 | 22557 | 825 |
| 849310 | N/A | N/A | AGCATTAAGACCCCAT | 21 | 23167 | 23182 | 826 |
| 848484 | 1929 | 1944 | GGCAGCACCTGGCAAT | 17 | 23549 | 23564 | 827 |
| 848499 | 2000 | 2015 | GTGGACACGGGTCCCC | 17 | 23620 | 23635 | 828 |
| 849326 | N/A | N/A | AGAAAGAGACCCCTCC | 0 | 23692 | 23707 | 829 |
| 849342 | N/A | N/A | AAACAATAGTAACGAT | 0 | 24153 | 24168 | 830 |
| 849358 | N/A | N/A | TCTGAACATGGTAGGG | 58 | 24790 | 24805 | 831 |
| 849374 | N/A | N/A | GCCCATCCCCATCAGA | 6 | 25303 | 25318 | 832 |
| 848515 | 2157 | 2172 | GGGCATGGCAGCAGGA | 17 | 25488 | 25503 | 833 |
| 849390 | N/A | N/A | CTTCAGCATGCAGCTC | 6 | 26093 | 26108 | 834 |
| 849406 | N/A | N/A | TGAAACTGATGGCCCC | 22 | 27070 | 27085 | 835 |
| 848531 | 2383 | 2398 | CAGCAGATGGCAACGG | 25 | 27526 | 27541 | 836 |
| 848547 | 2522 | 2537 | GGCCATGGAGGGCTGA | 0 | 27665 | 27680 | 837 |

TABLE 11-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848563 | 2623 | 2638 | AGGCACCCAGAGTGAG | 42 | 27766 | 27781 | 838 |
| 848579 | 2716 | 2731 | AGCTGGCAGCACCCGA | 20 | 27859 | 27874 | 839 |
| 848594 | 2770 | 2785 | GAACAAGAGCTCAATA | 13 | 27913 | 27928 | 840 |
| 848610 | 2822 | 2837 | GGGAAGAATCCTGCCT | 25 | 27965 | 27980 | 841 |
| 848626 | 2948 | 2963 | CATTAATCAGGGAGCC | 21 | 28091 | 28106 | 842 |
| 848641 | 3052 | 3067 | GAGCAGAGTAAAGGTG | 23 | 28195 | 28210 | 843 |
| 848656 | 3126 | 3141 | CACACTGCCGAGTCAG | 56 | 28269 | 28284 | 844 |
| 848672 | 3213 | 3228 | AGGTTTCTTCCTCTGT | 60 | 28356 | 28371 | 845 |
| 848687 | 3243 | 3258 | GAGCTTGGCAGGCACG | 67 | 28386 | 28401 | 846 |
| 848703 | 3266 | 3281 | TTCTGGCTCAGTTCCT | 20 | 28409 | 28424 | 847 |
| 848719 | 3334 | 3349 | GTAAAAATGAGGAGCC | 29 | 28477 | 28492 | 848 |
| 848735 | 3421 | 3436 | AAAAAGTTCCATGCCT | 9 | 28564 | 28579 | 849 |
| 848751 | 3506 | 3521 | GGAGGGACAGTTGTTG | 0 | 28649 | 28664 | 850 |
| 848766 | 3590 | 3605 | TAGAAAAGTTGGCTGT | 22 | 28733 | 28748 | 851 |

TABLE 12

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 848345 | 1012 | 1027 | TTGCTGGCCTGTCTGT | 3 | N/A | N/A | 852 |
| 848390 | 1148 | 1163 | GCCTATGAGGGTGCCG | 0 | N/A | N/A | 853 |
| 848454 | 1708 | 1723 | TGCCAACCTGCCCCAT | 8 | N/A | N/A | 854 |
| 848210 | 56 | 71 | CGGAAACCTTCTAGGG | 0 | 3531 | 3546 | 855 |
| 848226 | 244 | 259 | AGCTGAAGTTCAGGAG | 50 | 3719 | 3734 | 856 |
| 848242 | 480 | 495 | AGGCTAGCACCAGCTC | 37 | 3955 | 3970 | 857 |
| 848257 | 552 | 567 | TGGCGCAGCGGTGGAA | 0 | 4027 | 4042 | 858 |
| 848783 | N/A | N/A | CCACTACCCGTCCTCC | 0 | 4211 | 4226 | 859 |
| 848799 | N/A | N/A | CGGGAAGAAGCTTCCC | 0 | 4883 | 4898 | 860 |
| 848815 | N/A | N/A | CCCCACAACATCCCTC | 5 | 5377 | 5392 | 861 |
| 848831 | N/A | N/A | AAAGAACTGTGGACAT | 43 | 5935 | 5950 | 862 |
| 848847 | N/A | N/A | AGGCAGACATACCTGC | 0 | 6695 | 6710 | 863 |
| 848863 | N/A | N/A | CTGCAAGCTCTCCAGG | 17 | 7095 | 7110 | 864 |
| 848879 | N/A | N/A | CAAGAGTGACGGTTAT | 45 | 7295 | 7310 | 865 |
| 848895 | N/A | N/A | TATTATTCACATGGTT | 41 | 7646 | 7661 | 866 |
| 848272 | 668 | 683 | GTATCCCCGGCGGGCA | 37 | 7941 | 7956 | 867 |
| 848284 | 684 | 699 | GCAGGATCTTGGTGAG | 0 | 7957 | 7972 | 868 |

TABLE 12-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848299 | 743 | 758 | CTCCAGCAGGTCGCCA | 20 | 8016 | 8031 | 869 |
| 848911 | N/A | N/A | ATACATACTTGCTGTC | 21 | 8137 | 8152 | 870 |
| 848927 | N/A | N/A | TGGATAGCAACAGCTT | 70 | 8458 | 8473 | 871 |
| 848943 | N/A | N/A | TGCTGAGCTGATTAAC | 27 | 8840 | 8855 | 872 |
| 848959 | N/A | N/A | AATTATTATAACTGGT | 0 | 9381 | 9396 | 873 |
| 848975 | N/A | N/A | GGGCAGGATGGACATG | 4 | 10209 | 10224 | 874 |
| 848314 | 817 | 832 | TTCCACGGGATGCTCT | 3 | 10578 | 10593 | 875 |
| 848991 | N/A | N/A | TTAAAGGATCTGGTCC | 31 | 11011 | 11026 | 876 |
| 849007 | N/A | N/A | GTGTATGCAAAGTCAC | 55 | 11624 | 11639 | 877 |
| 849023 | N/A | N/A | AGGGAACAGTGGCTGC | 42 | 12407 | 12422 | 878 |
| 849039 | N/A | N/A | TTATTGAATGGTAAGA | 37 | 12905 | 12920 | 879 |
| 849044 | N/A | N/A | GGATACACAGGCTCGC | 77 | 13108 | 13123 | 337 |
| 849055 | N/A | N/A | CTGCAAGCATGGCCAG | 33 | 13710 | 13725 | 880 |
| 849071 | N/A | N/A | ACAACTGGATACATTG | 57 | 14129 | 14144 | 881 |
| 849087 | N/A | N/A | CACTTTGGTTTCTTCT | 28 | 14560 | 14575 | 882 |
| 849103 | N/A | N/A | CTTATGGCTTCGGTCA | 42 | 15107 | 15122 | 883 |
| 849119 | N/A | N/A | AGATACCAGGAGGGCT | 48 | 15730 | 15745 | 884 |
| 849135 | N/A | N/A | ATAGACAAGGAAAGGG | 68 | 16087 | 16102 | 885 |
| 848329 | 971 | 986 | CACATTCTCGAAGTCG | 25 | 16363 | 16378 | 886 |
| 848359 | 1056 | 1071 | GGCCGCTGACCACCCC | 19 | 16686 | 16701 | 887 |
| 468460 | 1075 | 1090 | TTGGCCACGCCGGCAT | 10 | 16705 | 16720 | 48 |
| 848374 | 1080 | 1095 | CACCCTTGGCCACGCC | 37 | 16710 | 16725 | 888 |
| 849151 | N/A | N/A | ATGGAGAGAGACCAGC | 20 | 16811 | 16826 | 889 |
| 849167 | N/A | N/A | CACCAGAGCCAGTGTT | 0 | 17590 | 17605 | 890 |
| 849183 | N/A | N/A | CTGCCCCGTGCCAGGT | 0 | 17962 | 17977 | 891 |
| 849199 | N/A | N/A | TGTCAAATGAGGTGTG | 15 | 18586 | 18601 | 892 |
| 849215 | N/A | N/A | ATGAGAAGGGCACACT | 0 | 19342 | 19357 | 893 |
| 849231 | N/A | N/A | AACTCTTAATATATAC | 0 | 19570 | 19585 | 894 |
| 849247 | N/A | N/A | AGGAACAAAGCCAAGG | 31 | 19972 | 19987 | 895 |
| 848406 | 1293 | 1308 | CGGCAGCGGTGACCAG | 0 | 20124 | 20139 | 896 |
| 849263 | N/A | N/A | GCCTTGATAGGCCAGG | 33 | 20938 | 20953 | 897 |
| 849279 | N/A | N/A | AGAGAAAGGAGCCCAA | 0 | 21290 | 21305 | 898 |
| 848422 | 1427 | 1442 | GTCCACACAGCGGCCA | 5 | 21399 | 21414 | 899 |
| 848438 | 1558 | 1573 | GGCTCGGCAGACAGCA | 58 | 22051 | 22066 | 900 |
| 849295 | N/A | N/A | GGCTTAAAGAACATAC | 28 | 22397 | 22412 | 901 |
| 848470 | 1772 | 1787 | GGCGACGGCTGTGGCC | 0 | 22554 | 22569 | 902 |

TABLE 12-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 849311 | N/A | N/A | GAGCATTAAGACCCCA | 32 | 23168 | 23183 | 903 |
| 468480 | 1930 | 1945 | AGGCAGCACCTGGCAA | 19 | 23550 | 23565 | 904 |
| 848500 | 2001 | 2016 | AGTGGACACGGGTCCC | 56 | 23621 | 23636 | 905 |
| 849327 | N/A | N/A | TCACACTTGTGAGGAC | 0 | 23737 | 23752 | 906 |
| 849343 | N/A | N/A | AAAGCAACGGGTGATG | 0 | 24170 | 24185 | 907 |
| 849359 | N/A | N/A | GTAAGATGGAAAGAGA | 55 | 24877 | 24892 | 908 |
| 849375 | N/A | N/A | CTGGGATGCTCCGTCT | 0 | 25324 | 25339 | 909 |
| 848516 | 2172 | 2187 | TGCATTCCAGACCTGG | 6 | 25503 | 25518 | 910 |
| 849391 | N/A | N/A | TGCTAACAACCTTCAG | 0 | 26103 | 26118 | 911 |
| 849407 | N/A | N/A | TACCATGCCAGTGCCA | 29 | 27098 | 27113 | 912 |
| 848532 | 2386 | 2401 | CGGCAGCAGATGGCAA | 27 | 27529 | 27544 | 913 |
| 848548 | 2527 | 2542 | TGCCAGGCCATGGAGG | 0 | 27670 | 27685 | 914 |
| 848564 | 2628 | 2643 | GGAGGAGGCACCCAGA | 20 | 27771 | 27786 | 915 |
| 468487 | 2720 | 2735 | GAGCAGCTGGCAGCAC | 42 | 27863 | 27878 | 916 |
| 848595 | 2771 | 2786 | GGAACAAGAGCTCAAT | 47 | 27914 | 27929 | 917 |
| 848611 | 2828 | 2843 | ATCCATGGGAAGAATC | 15 | 27971 | 27986 | 918 |
| 848627 | 2951 | 2966 | CTCCATTAATCAGGGA | 26 | 28094 | 28109 | 919 |
| 848642 | 3055 | 3070 | ATAGAGCAGAGTAAAG | 0 | 28198 | 28213 | 920 |
| 848657 | 3127 | 3142 | GCACACTGCCGAGTCA | 46 | 28270 | 28285 | 921 |
| 848673 | 3214 | 3229 | CAGGTTTCTTCCTCTG | 34 | 28357 | 28372 | 922 |
| 848688 | 3245 | 3260 | GTGAGCTTGGCAGGCA | 70 | 28388 | 28403 | 923 |
| 848704 | 3267 | 3282 | TTTCTGGCTCAGTTCC | 54 | 28410 | 28425 | 924 |
| 848720 | 3336 | 3351 | CCGTAAAAATGAGGAG | 17 | 28479 | 28494 | 925 |
| 848736 | 3423 | 3438 | GGAAAAGTTCCATGC | 57 | 28566 | 28581 | 926 |
| 468502 | 3508 | 3523 | AAGGAGGGACAGTTGT | 0 | 28651 | 28666 | 927 |
| 848767 | 3592 | 3607 | TCTAGAAAAGTTGGCT | 39 | 28735 | 28750 | 928 |

TABLE 13

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 848258 | 561 | 576 | ACGGATCCTTGGCGCA | 38 | N/A | N/A | 929 |
| 848300 | 753 | 768 | TCAAGGCCAGCTCCAG | 23 | N/A | N/A | 930 |
| 848346 | 1014 | 1029 | ACTTGCTGGCCTGTCT | 0 | N/A | N/A | 931 |
| 848391 | 1154 | 1169 | CTCCAGGCCTATGAGG | 0 | N/A | N/A | 932 |
| 848211 | 58 | 73 | TGCGGAAACCTTCTAG | 0 | 3533 | 3548 | 933 |

TABLE 13-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848227 | 258 | 273 | GAGGACTGTGCAGGAG | 42 | 3733 | 3748 | 934 |
| 848243 | 481 | 496 | AAGGCTAGCACCAGCT | 23 | 3956 | 3971 | 935 |
| 848784 | N/A | N/A | GGATATCCTGGCAGTG | 0 | 4350 | 4365 | 936 |
| 848800 | N/A | N/A | GAAAAAGCTAGTGGTC | 30 | 4905 | 4920 | 937 |
| 848816 | N/A | N/A | CTTGAAATGCCCTTTC | 0 | 5408 | 5423 | 938 |
| 848832 | N/A | N/A | TACATTTCAGACGGTG | 61 | 6279 | 6294 | 939 |
| 848848 | N/A | N/A | ATTATAGCAGCCACTA | 13 | 6761 | 6776 | 940 |
| 848864 | N/A | N/A | ATTTATTCAGCTCATG | 1 | 7114 | 7129 | 941 |
| 848880 | N/A | N/A | TGGGAAAGTCAAGAGT | 44 | 7304 | 7319 | 942 |
| 848896 | N/A | N/A | GCCAACTATTATTATT | 26 | 7655 | 7670 | 943 |
| 466846 | 669 | 684 | GGTATCCCCGGCGGGC | 45 | 7942 | 7957 | 944 |
| 848285 | 685 | 700 | TGCAGGATCTTGGTGA | 0 | 7958 | 7973 | 945 |
| 848912 | N/A | N/A | GATAAGTGCTCAATAC | 33 | 8149 | 8164 | 946 |
| 848928 | N/A | N/A | CTGGATAGCAACAGCT | 71 | 8459 | 8474 | 947 |
| 848944 | N/A | N/A | CGCCACAGGCCTTGGT | 30 | 8881 | 8896 | 948 |
| 848960 | N/A | N/A | CCAATTATTATAACTG | 21 | 9383 | 9398 | 949 |
| 848976 | N/A | N/A | AGCCAGGCTGTGCCAA | 0 | 10231 | 10246 | 950 |
| 848315 | 824 | 839 | CTCCAGGTTCCACGGG | 0 | 10585 | 10600 | 951 |
| 848992 | N/A | N/A | ATTAAAGGATCTGGTC | 2 | 11012 | 11027 | 952 |
| 849008 | N/A | N/A | CAGACATATGCAAGGT | 68 | 11652 | 11667 | 953 |
| 849024 | N/A | N/A | GCCCAAGGGAGAGGAG | 0 | 12421 | 12436 | 954 |
| 849040 | N/A | N/A | GTTATTATTGAATGGT | 80 | 12909 | 12924 | 955 |
| 849044 | N/A | N/A | GGATACACAGGCTCGC | 76 | 13108 | 13123 | 337 |
| 849056 | N/A | N/A | CAGGAGGCTGCAAGCA | 49 | 13717 | 13732 | 956 |
| 849072 | N/A | N/A | CAGGAAGCAGCCCAAG | 0 | 14175 | 14190 | 957 |
| 849088 | N/A | N/A | CTCCACTGATCAGTCC | 49 | 14582 | 14597 | 958 |
| 849104 | N/A | N/A | CCAAATATGCTGCAGA | 20 | 15185 | 15200 | 959 |
| 849120 | N/A | N/A | AGAGACAGGAAGCTGC | 63 | 15808 | 15823 | 960 |
| 849136 | N/A | N/A | CACAGAAACTACAGAG | 0 | 16199 | 16214 | 961 |
| 848330 | 974 | 989 | GGGCACATTCTCGAAG | 0 | 16366 | 16381 | 962 |
| 848360 | 1057 | 1072 | CGGCCGCTGACCACCC | 0 | 16687 | 16702 | 963 |
| 468460 | 1075 | 1090 | TTGGCCACGCCGGCAT | 0 | 16705 | 16720 | 48 |
| 848375 | 1081 | 1096 | GCACCCTTGGCCACGC | 24 | 16711 | 16726 | 964 |
| 849152 | N/A | N/A | CCAGATGGAGAGAGAC | 26 | 16815 | 16830 | 965 |
| 849168 | N/A | N/A | GGCTAGTGGGCTGCCT | 0 | 17613 | 17628 | 966 |
| 849184 | N/A | N/A | CCCTGCCCCGTGCCAG | 0 | 17964 | 17979 | 967 |

TABLE 13-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID 2: Start Site | SEQ ID 2: Stop Site | SEQ ID NO |
|---|---|---|---|---|---|---|---|
| 849200 | N/A | N/A | GCCTAACGCAGCTCTG | 62 | 18644 | 18659 | 968 |
| 849216 | N/A | N/A | GAGGAATGAGAAGGGC | 61 | 19347 | 19362 | 969 |
| 849232 | N/A | N/A | CCGCACGGTCACATGA | 19 | 19592 | 19607 | 970 |
| 849248 | N/A | N/A | GTGCCACAAGAAGCCC | 9 | 20268 20286 | 20283 20301 | 971 |
| 848407 | 1301 | 1316 | GAAGTTGCCGGCAGCG | 24 | 20132 | 20147 | 972 |
| 849264 | N/A | N/A | TAAATTCGGCCGCCAG | 9 | 20958 | 20973 | 973 |
| 848423 | 1433 | 1448 | AAAGAGGTCCACACAG | 0 | 21405 | 21420 | 974 |
| 849280 | N/A | N/A | CTGTTAGCATCACGGT | 25 | 21542 | 21557 | 975 |
| 848439 | 1574 | 1589 | GGCCAGGGTGAGCTCC | 0 | 22067 | 22082 | 976 |
| 849296 | N/A | N/A | GAGAGAGGAGGGCTTA | 0 | 22407 | 22422 | 977 |
| 848455 | 1716 | 1731 | AAAACAGCTGCCAACC | 0 | 22498 | 22513 | 978 |
| 848471 | 1774 | 1789 | CGGGCGACGGCTGTGG | 0 | 22556 | 22571 | 979 |
| 849312 | N/A | N/A | ACACGAGCATTAAGAC | 45 | 23172 | 23187 | 980 |
| 848485 | 1932 | 1947 | GCAGGCAGCACCTGGC | 7 | 23552 | 23567 | 981 |
| 848501 | 2002 | 2017 | CAGTGGACACGGGTCC | 37 | 23622 | 23637 | 982 |
| 849328 | N/A | N/A | CTGCAAGTCAGGCTTG | 20 | 23764 | 23779 | 983 |
| 849344 | N/A | N/A | TTTAAAGCAACGGGTG | 47 | 24173 | 24188 | 984 |
| 849360 | N/A | N/A | AGCTACACTGAGGCTC | 23 | 24906 | 24921 | 985 |
| 848517 | 2177 | 2192 | GACTTTGCATTCCAGA | 41 | 25508 | 25523 | 986 |
| 849376 | N/A | N/A | GGCAGAGGAAAGCCAG | 0 | 25355 | 25370 | 987 |
| 849392 | N/A | N/A | TGTCACATTCCAGGGC | 43 | 26171 | 26186 | 988 |
| 849408 | N/A | N/A | AGATAGACAGATGCCT | 8 | 27113 | 27128 | 989 |
| 848533 | 2402 | 2417 | CGCCAGGTGCCGGCTC | 0 | 27545 | 27560 | 990 |
| 848549 | 2550 | 2565 | GCGGAAGCATCCCCAT | 0 | 27693 | 27708 | 991 |
| 848565 | 2669 | 2684 | CCCCACAGTGAGGGAG | 20 | 27812 | 27827 | 992 |
| 848580 | 2727 | 2742 | ACATTGGGAGCAGCTG | 34 | 27870 | 27885 | 993 |
| 848596 | 2772 | 2787 | CGGAACAAGAGCTCAA | 70 | 27915 | 27930 | 994 |
| 848612 | 2832 | 2847 | CCCTATCCATGGGAAG | 39 | 27975 | 27990 | 995 |
| 848628 | 2959 | 2974 | AGCTAAGCCTCCATTA | 15 | 28102 | 28117 | 996 |
| 848643 | 3057 | 3072 | GCATAGAGCAGAGTAA | 0 | 28200 | 28215 | 997 |
| 848658 | 3128 | 3143 | TGCACACTGCCGAGTC | 49 | 28271 | 28286 | 998 |
| 848674 | 3215 | 3230 | CCAGGTTTCTTCCTCT | 58 | 28358 | 28373 | 999 |
| 848689 | 3246 | 3261 | TGTGAGCTTGGCAGGC | 39 | 28389 | 28404 | 1000 |
| 848705 | 3268 | 3283 | GTTTCTGGCTCAGTTC | 3 | 28411 | 28426 | 1001 |
| 848721 | 3338 | 3353 | ACCCGTAAAAATGAGG | 0 | 28481 | 28496 | 1002 |
| 848737 | 3425 | 3440 | ACGGAAAAAGTTCCAT | 18 | 28568 | 28583 | 1003 |

TABLE 13-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848752 | 3511 | 3526 | CTCAAGGAGGGACAGT | 33 | 28654 | 28669 | 1004 |
| 848768 | 3599 | 3614 | AAACAGGTCTAGAAAA | 17 | 28742 | 28757 | 1005 |

TABLE 14

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 468456 | 1015 | 1030 | CACTTGCTGGCCTGTC | 22 | N/A | N/A | 1006 |
| 848259 | 565 | 580 | CTCCACGGATCCTTGG | 0 | N/A | N/A | 1007 |
| 848301 | 754 | 769 | TTCAAGGCCAGCTCCA | 42 | N/A | N/A | 1008 |
| 848392 | 1159 | 1174 | ATAAACTCCAGGCCTA | 37 | N/A | N/A | 1009 |
| 848212 | 64 | 79 | CGTCGCTGCGGAAACC | 41 | 3539 | 3554 | 1010 |
| 848228 | 293 | 308 | GTCCACGCCGGCGGCG | 32 | 3768 | 3783 | 1011 |
| 848244 | 482 | 497 | CAAGGCTAGCACCAGC | 45 | 3957 | 3972 | 1012 |
| 848785 | N/A | N/A | GAAATCTGGGCAGGAT | 39 | 4362 | 4377 | 1013 |
| 848801 | N/A | N/A | CACCACAGCTAGTGAG | 28 | 5003 | 5018 | 1014 |
| 848817 | N/A | N/A | CACTATTTCCAGAACA | 20 | 5445 | 5460 | 1015 |
| 848833 | N/A | N/A | AATAATCTCATGTCAG | 77 | 6356 | 6371 | 1016 |
| 848849 | N/A | N/A | CAAATTATAGCAGCCA | 85 | 6764 | 6779 | 1017 |
| 848865 | N/A | N/A | GATTTATTCAGCTCAT | 65 | 7115 | 7130 | 1018 |
| 848881 | N/A | N/A | CCACAGTACCTATGAC | 0 | 7330 | 7345 | 1019 |
| 848897 | N/A | N/A | CAAATGCGGACCAAAA | 38 | 7694 | 7709 | 1020 |
| 848273 | 670 | 685 | AGGTATCCCCGGCGGG | 26 | 7943 | 7958 | 1021 |
| 848286 | 686 | 701 | ATGCAGGATCTTGGTG | 0 | 7959 | 7974 | 1022 |
| 848913 | N/A | N/A | CGATAAGTGCTCAATA | 25 | 8150 | 8165 | 1023 |
| 848929 | N/A | N/A | AAAGAAGGGACTTCAC | 29 | 8476 | 8491 | 1024 |
| 848945 | N/A | N/A | ACTTAGACTACGGGTT | 25 | 8931 | 8946 | 1025 |
| 848961 | N/A | N/A | TCCTTAAATGAATGTT | 41 | 9399 | 9414 | 1026 |
| 848977 | N/A | N/A | CTTGATCAGGCTGGGA | 0 | 10332 | 10347 | 1027 |
| 848316 | 833 | 848 | GGTAATCCGCTCCAGG | 59 | 10594 | 10609 | 1028 |
| 848993 | N/A | N/A | TCCCATTAAAGGATCT | 23 | 11016 | 11031 | 1029 |
| 849009 | N/A | N/A | ACACATGACCGACCAG | 0 | 11773 | 11788 | 1030 |
| 849025 | N/A | N/A | CTCCAGCCAAGCCCTT | 40 | 12570 | 12585 | 1031 |
| 849041 | N/A | N/A | TCTGGATACACTGTTG | 27 | 13008 | 13023 | 1032 |
| 849044 | N/A | N/A | GGATACACAGGCTCGC | 85 | 13108 | 13123 | 337 |
| 849057 | N/A | N/A | GGTCAGGAGGCTGCAA | 61 | 13720 | 13735 | 1033 |

TABLE 14-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 849073 | N/A | N/A | TGCTCAGGAAGCAGCC | 43 | 14179 | 14194 | 1034 |
| 849089 | N/A | N/A | CCCTAAGGCCTCCAGT | 41 | 14610 | 14625 | 1035 |
| 849105 | N/A | N/A | CTGAACAGCACCTCTG | 37 | 15220 | 15235 | 1036 |
| 849121 | N/A | N/A | TTAGAGACAGGAAGCT | 28 | 15810 | 15825 | 1037 |
| 849137 | N/A | N/A | CTTATAGTTAACACAC | 0 | 16212 | 16227 | 1038 |
| 848331 | 980 | 995 | CTCCTCGGGCACATTC | 7 | 16372 | 16387 | 1039 |
| 848361 | 1058 | 1073 | CCGGCCGCTGACCACC | 30 | 16688 | 16703 | 1040 |
| 468460 | 1075 | 1090 | TTGGCCACGCCGGCAT | 31 | 16705 | 16720 | 48 |
| 848376 | 1082 | 1097 | GGCACCCTTGGCCACG | 52 | 16712 | 16727 | 1041 |
| 849153 | N/A | N/A | GCCCAAGCCACCTCCC | 0 | 16840 | 16855 | 1042 |
| 849169 | N/A | N/A | AGGAAAGTCTCAGGGC | 78 | 17681 | 17696 | 1043 |
| 849185 | N/A | N/A | AGCCCTGCCCCGTGC | 18 | 17967 | 17982 | 1044 |
| 849201 | N/A | N/A | GGCCTAACGCAGCTCT | 34 | 18645 | 18660 | 1045 |
| 849217 | N/A | N/A | AGGCACCAAGAGGATG | 20 | 19370 | 19385 | 1046 |
| 849233 | N/A | N/A | GCGGATTTCAGACTTG | 80 | 19613 | 19628 | 1047 |
| 848408 | 1304 | 1319 | CCGGAAGTTGCCGGCA | 3 | 20135 | 20150 | 1048 |
| 849249 | N/A | N/A | CGTGCCACAAGAAGCC | 21 | 20269 20287 | 20284 20302 | 1049 |
| 849265 | N/A | N/A | GCCTTTAAATTCGGCC | 0 | 20963 | 20978 | 1050 |
| 848424 | 1435 | 1450 | GCAAAGAGGTCCACAC | 0 | 21407 | 21422 | 1051 |
| 849281 | N/A | N/A | GGCACTGGAGGTCCCG | 31 | 21583 | 21598 | 1052 |
| 848440 | 1582 | 1597 | CTCAACTCGGCCAGGG | 43 | 22075 | 22090 | 1053 |
| 849297 | N/A | N/A | TAGGAGAGAGGAGGGC | 21 | 22410 | 22425 | 1054 |
| 848456 | 1718 | 1733 | GCAAAACAGCTGCCAA | 24 | 22500 | 22515 | 1055 |
| 848472 | 1778 | 1793 | GCAGCGGGCGACGGCT | 0 | 22560 | 22575 | 1056 |
| 849313 | N/A | N/A | CTCTCACACGAGCATT | 11 | 23177 | 23192 | 1057 |
| 848486 | 1933 | 1948 | AGCAGGCAGCACCTGG | 35 | 23553 | 23568 | 1058 |
| 848502 | 2003 | 2018 | GCAGTGGACACGGGTC | 43 | 23623 | 23638 | 1059 |
| 849329 | N/A | N/A | GTATGGAACTGCAAGT | 0 | 23772 | 23787 | 1060 |
| 849345 | N/A | N/A | ATTTTAAAGCAACGGG | 75 | 24175 | 24190 | 1061 |
| 849361 | N/A | N/A | AAACCTAAAATAGTGG | 4 | 24928 | 24943 | 1062 |
| 849377 | N/A | N/A | GGGCAGAGGAAAGCCA | 12 | 25356 | 25371 | 1063 |
| 848518 | 2190 | 2205 | TTCCATGCTCCTTGAC | 11 | 25521 | 25536 | 1064 |
| 849393 | N/A | N/A | ATACACTCAGGTTTCT | 45 | 26199 | 26214 | 1065 |
| 849409 | N/A | N/A | ACCCAGGCGGTTCTGC | 10 | 27185 | 27200 | 1066 |
| 848534 | 2427 | 2442 | GTCACTGGAGCTCCTG | 59 | 27570 | 27585 | 1067 |
| 848550 | 2554 | 2569 | AAAGGCGGAAGCATCC | 23 | 27697 | 27712 | 1068 |

TABLE 14-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848566 | 2677 | 2692 | GTGAAATGCCCCACAG | 34 | 27820 | 27835 | 1069 |
| 848581 | 2729 | 2744 | GCACATTGGGAGCAGC | 58 | 27872 | 27887 | 1070 |
| 848597 | 2773 | 2788 | ACGGAACAAGAGCTCA | 77 | 27916 | 27931 | 1071 |
| 848613 | 2869 | 2884 | CAACGATGTTTGTCCC | 67 | 28012 | 28027 | 1072 |
| 848629 | 2962 | 2977 | GAAAGCTAAGCCTCCA | 69 | 28105 | 28120 | 1073 |
| 848644 | 3059 | 3074 | TGGCATAGAGCAGAGT | 49 | 28202 | 28217 | 1074 |
| 848659 | 3129 | 3144 | CTGCACACTGCCGAGT | 48 | 28272 | 28287 | 1075 |
| 848675 | 3216 | 3231 | TCCAGGTTTCTTCCTC | 63 | 28359 | 28374 | 1076 |
| 848690 | 3247 | 3262 | GTGTGAGCTTGGCAGG | 78 | 28390 | 28405 | 1077 |
| 848706 | 3269 | 3284 | CGTTTCTGGCTCAGTT | 55 | 28412 | 28427 | 1078 |
| 848722 | 3342 | 3357 | TGTTACCCGTAAAAAT | 0 | 28485 | 28500 | 1079 |
| 848738 | 3427 | 3442 | TAACGGAAAAAGTTCC | 64 | 28570 | 28585 | 1080 |
| 848753 | 3513 | 3528 | TGCTCAAGGAGGGACA | 27 | 28656 | 28671 | 1081 |
| 848769 | 3601 | 3616 | CAAAACAGGTCTAGAA | 43 | 28744 | 28759 | 1082 |

TABLE 15

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848302 | 755 | 770 | CTTCAAGGCCAGCTCC | 0 | N/A | N/A | 1083 |
| 848347 | 1016 | 1031 | ACACTTGCTGGCCTGT | 0 | N/A | N/A | 1084 |
| 848213 | 85 | 100 | CTGCAACCATGAGCGC | 4 | 3560 | 3575 | 1085 |
| 848229 | 309 | 324 | CTAGAGGCCGTGCGCG | 18 | 3784 | 3799 | 1086 |
| 848245 | 483 | 498 | GCAAGGCTAGCACCAG | 45 | 3958 | 3973 | 1087 |
| 848786 | N/A | N/A | GAAACTGGGAAATCTG | 0 | 4370 | 4385 | 1088 |
| 848802 | N/A | N/A | GTCAAGCACCACAGCT | 54 | 5009 | 5024 | 1089 |
| 848818 | N/A | N/A | CCTCAAGGGCTTGGTT | 0 | 5509 | 5524 | 1090 |
| 848834 | N/A | N/A | AATCTATGCAGCAAAA | 0 | 6407 | 6422 | 1091 |
| 848850 | N/A | N/A | AACAAATTATAGCAGC | 75 | 6766 | 6781 | 1092 |
| 848882 | N/A | N/A | GACCACAGTACCTATG | 30 | 7332 | 7347 | 1093 |
| 848898 | N/A | N/A | ACCAAATGCGGACCAA | 66 | 7696 | 7711 | 1094 |
| 848260 | 571 | 586 | GGCAACCTCCACGGAT | 53 | 7844 | 7859 | 1095 |
| 466847 | 671 | 686 | GAGGTATCCCCGGCGG | 73 | 7944 | 7959 | 1096 |
| 848287 | 687 | 702 | CATGCAGGATCTTGGT | 5 | 7960 | 7975 | 1097 |
| 848914 | N/A | N/A | TGCTTGGTACCCGATA | 39 | 8161 | 8176 | 1098 |

TABLE 15-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848930 | N/A | N/A | CCTAAAGAAGGGACTT | 18 | 8479 | 8494 | 1099 |
| 848946 | N/A | N/A | AGGCATTGACTTGTCA | 46 | 8956 | 8971 | 1100 |
| 848962 | N/A | N/A | TACCTAGCATCTGCTG | 0 | 9437 | 9452 | 1101 |
| 848978 | N/A | N/A | ACAGACTAGGAGCCTG | 0 | 10361 | 10376 | 1102 |
| 848317 | 852 | 867 | CCGCCCGGTACCGTGG | 0 | 10613 | 10628 | 1103 |
| 848994 | N/A | N/A | AGGCATCCCAGACAGG | 52 | 11042 | 11057 | 1104 |
| 849010 | N/A | N/A | GCACACATGACCGACC | 0 | 11775 | 11790 | 1105 |
| 849026 | N/A | N/A | CCCCATGCCAGCCCAA | 33 | 12604 | 12619 | 1106 |
| 849042 | N/A | N/A | ATTAATCTTCTGGATA | 13 | 13016 | 13031 | 1107 |
| 849044 | N/A | N/A | GGATACACAGGCTCGC | 82 | 13108 | 13123 | 337 |
| 849058 | N/A | N/A | GGACAGGGTCAGGAGG | 22 | 13726 | 13741 | 1108 |
| 849074 | N/A | N/A | GGATACAGGTGCTCAG | 55 | 14188 | 14203 | 1109 |
| 849090 | N/A | N/A | ACACACACTGTCTACC | 38 | 14629 | 14644 | 1110 |
| 849106 | N/A | N/A | CCTCAGGTGGAATCAG | 56 | 15306 | 15321 | 1111 |
| 849122 | N/A | N/A | GAATAACAGTGATGTC | 17 | 15852 | 15867 | 1112 |
| 849138 | N/A | N/A | ACCTTATAGTTAACAC | 4 | 16214 | 16229 | 1113 |
| 848332 | 982 | 997 | TCCTCCTCGGGCACAT | 21 | 16374 | 16389 | 1114 |
| 848362 | 1059 | 1074 | CCCGGCCGCTGACCAC | 0 | 16689 | 16704 | 1115 |
| 468460 | 1075 | 1090 | TTGGCCACGCCGGCAT | 0 | 16705 | 16720 | 48 |
| 848377 | 1083 | 1098 | TGGCACCCTTGGCCAC | 0 | 16713 | 16728 | 1116 |
| 849154 | N/A | N/A | GGTCAAGGCTGAACTC | 27 | 17014 | 17029 | 1117 |
| 849170 | N/A | N/A | TAGGAAAGTCTCAGGG | 36 | 17682 | 17697 | 1118 |
| 849186 | N/A | N/A | AGGCAATAGTGACTGT | 52 | 17985 | 18000 | 1119 |
| 849202 | N/A | N/A | CTGGAGACTGGAGGCC | 0 | 18657 | 18672 | 1120 |
| 849218 | N/A | N/A | GAAAGAGAGGCACCAA | 0 | 19377 | 19392 | 1121 |
| 849234 | N/A | N/A | TGCGGATTTCAGACTT | 24 | 19614 | 19629 | 1122 |
| 848393 | 1161 | 1176 | GAATAAACTCCAGGCC | 0 | 19992 | 20007 | 1123 |
| 848409 | 1322 | 1337 | GTAGAGGCAGGCATCG | 42 | 20153 | 20168 | 1124 |
| 849250 | N/A | N/A | CAGAAGGGTTCGGCCT | 32 | 20310 | 20325 | 1125 |
| 849266 | N/A | N/A | GGCTTTGTTTGCTTGA | 68 | 20980 | 20995 | 1126 |
| 848425 | 1437 | 1452 | GGGCAAAGAGGTCCAC | 0 | 21409 | 21424 | 1127 |
| 849282 | N/A | N/A | CATCAGGCCTACTTCA | 0 | 21624 | 21639 | 1128 |
| 848441 | 1603 | 1618 | GAGAAGTGGATCAGTC | 0 | 22096 | 22111 | 1129 |
| 849298 | N/A | N/A | TGCAAAAGGGCCTGG | 0 | 22482 | 22497 | 1130 |
| 848457 | 1720 | 1735 | CTGCAAACAGCTGCC | 13 | 22502 | 22517 | 1131 |
| 848473 | 1780 | 1795 | GCGCAGCGGGCGACGG | 0 | 22562 | 22577 | 1132 |
| 849314 | N/A | N/A | ATCCAGCCAGCTCCAC | 7 | 23207 | 23222 | 1133 |

TABLE 15-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848487 | 1934 | 1949 | TAGCAGGCAGCACCTG | 0 | 23554 | 23569 | 1134 |
| 848503 | 2004 | 2019 | GGCAGTGGACACGGGT | 26 | 23624 | 23639 | 1135 |
| 849330 | N/A | N/A | GGCAGAACCAGAGTAT | 0 | 23784 | 23799 | 1136 |
| 849346 | N/A | N/A | CAATAGTTGCCTATAC | 0 | 24201 | 24216 | 1137 |
| 849362 | N/A | N/A | AGACACACCCATTGGC | 8 | 24948 | 24963 | 1138 |
| 848519 | 2198 | 2213 | GGCCGGGATTCCATGC | 0 | 25529 | 25544 | 1139 |
| 849378 | N/A | N/A | ACGCAGCACCCCACCC | 0 | 25581 | 25596 | 1140 |
| 849394 | N/A | N/A | AAGGAGAGTTATACAC | 53 | 26209 | 26224 | 1141 |
| 849410 | N/A | N/A | GGACACAACCGTGTAT | 0 | 27220 | 27235 | 1142 |
| 848535 | 2447 | 2462 | ACCCATCCTGGGATGG | 0 | 27590 | 27605 | 1143 |
| 848551 | 2556 | 2571 | GGAAAGGCGGAAGCAT | 38 | 27699 | 27714 | 1144 |
| 848567 | 2684 | 2699 | TTGAATGGTGAAATGC | 65 | 27827 | 27842 | 1145 |
| 848582 | 2731 | 2746 | CGGCACATTGGGAGCA | 33 | 27874 | 27889 | 1146 |
| 848598 | 2774 | 2789 | CACGGAACAAGAGCTC | 68 | 27917 | 27932 | 1147 |
| 848614 | 2872 | 2887 | CCCCAACGATGTTTGT | 32 | 28015 | 28030 | 1148 |
| 848630 | 2964 | 2979 | CAGAAAGCTAAGCCTC | 72 | 28107 | 28122 | 1149 |
| 466853 | 3067 | 3082 | GCACAGCCTGGCATAG | 51 | 28210 | 28225 | 1150 |
| 848660 | 3130 | 3145 | ACTGCACACTGCCGAG | 1 | 28273 | 28288 | 1151 |
| 848676 | 3218 | 3233 | GTTCCAGGTTTCTTCC | 43 | 28361 | 28376 | 1152 |
| 848691 | 3248 | 3263 | TGTGTGAGCTTGGCAG | 22 | 28391 | 28406 | 1153 |
| 848707 | 3284 | 3299 | AGCCAGCCCAATCTGC | 0 | 28427 | 28442 | 1154 |
| 848723 | 3348 | 3363 | CCTCACTGTTACCCGT | 36 | 28491 | 28506 | 1155 |
| 848739 | 3429 | 3444 | GATAACGGAAAAAGTT | 0 | 28572 | 28587 | 1156 |
| 848754 | 3543 | 3558 | ATAAATGTCTGCTTGC | 52 | 28686 | 28701 | 1157 |
| 848770 | 3603 | 3618 | AGCAAAACAGGTCTAG | 60 | 28746 | 28761 | 1158 |

TABLE 16

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848303 | 756 | 771 | ACTTCAAGGCCAGCTC | 43 | N/A | N/A | 1159 |
| 848214 | 105 | 120 | AACTGAACGGCGGCGC | 0 | 3580 | 3595 | 1160 |
| 848230 | 311 | 326 | ACCTAGAGGCCGTGCG | 30 | 3786 | 3801 | 1161 |
| 848246 | 484 | 499 | CGCAAGGCTAGCACCA | 45 | 3959 | 3974 | 1162 |
| 848787 | N/A | N/A | GGCGAGGCAGAAACTG | 29 | 4379 | 4394 | 1163 |

TABLE 16-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 848803 | N/A | N/A | TCAAGGATAAGTGACT | 42 | 5026 | 5041 | 1164 |
| 848819 | N/A | N/A | AGAAACATCCTCAAGG | 38 | 5517 | 5532 | 1165 |
| 848835 | N/A | N/A | TAATCTATGCAGCAAA | 0 | 6408 | 6423 | 1166 |
| 848851 | N/A | N/A | CCAAATTTCCACATGA | 41 | 6797 | 6812 | 1167 |
| 848867 | N/A | N/A | AAGGAATACCTGAAGG | 22 | 7153 | 7168 | 1168 |
| 848883 | N/A | N/A | CCTCAGATACCTCTGC | 17 | 7359 | 7374 | 1169 |
| 848899 | N/A | N/A | GTATAGTAGATGATAA | 0 | 7719 | 7734 | 1170 |
| 848261 | 576 | 591 | TGCCAGGCAACCTCCA | 14 | 7849 | 7864 | 1171 |
| 848274 | 672 | 687 | TGAGGTATCCCCGGCG | 14 | 7945 | 7960 | 1172 |
| 848288 | 688 | 703 | ACATGCAGGATCTTGG | 16 | 7961 | 7976 | 1173 |
| 848915 | N/A | N/A | AGCCAGTAGTTACTGT | 9 | 8176 | 8191 | 1174 |
| 848931 | N/A | N/A | GAAGATGTGACATCCA | 28 | 8517 | 8532 | 1175 |
| 848947 | N/A | N/A | GAGCAGACTGATGGAA | 4 | 8971 | 8986 | 1176 |
| 848963 | N/A | N/A | GTGGTAACAGCCTCCT | 26 | 9526 | 9541 | 1177 |
| 848979 | N/A | N/A | GGACAGACTAGGAGCC | 4 | 10363 | 10378 | 1178 |
| 848318 | 858 | 873 | ATTCATCCGCCCGGTA | 0 | 10619 | 10634 | 1179 |
| 848995 | N/A | N/A | AGGTAGGCAGAGGCAT | 20 | 11052 | 11067 | 1180 |
| 849011 | N/A | N/A | GGCCGGGTCAGCACAC | 0 | 11785 | 11800 | 1181 |
| 849027 | N/A | N/A | GGCCCATGCTTGTGGC | 0 | 12663 | 12678 | 1182 |
| 849043 | N/A | N/A | AGGAATGGATTAATCT | 48 | 13024 | 13039 | 1183 |
| 849044 | N/A | N/A | GGATACACAGGCTCGC | 81 | 13108 | 13123 | 337 |
| 849059 | N/A | N/A | TCTAAGTGCAGGCGGT | 23 | 13776 | 13791 | 1184 |
| 849075 | N/A | N/A | CAGCAAGGTGGGCAGA | 10 | 14274 | 14289 | 1185 |
| 849091 | N/A | N/A | GCACAGTCCGAACTGT | 0 | 14660 | 14675 | 1186 |
| 849107 | N/A | N/A | GCGGAAATGGCCTGGC | 0 | 15353 | 15368 | 1187 |
| 849123 | N/A | N/A | GGAGAATAACAGTGAT | 62 | 15855 | 15870 | 1188 |
| 849139 | N/A | N/A | AACCTTATAGTTAACA | 0 | 16215 | 16230 | 1189 |
| 848333 | 983 | 998 | GTCCTCCTCGGGCACA | 18 | 16375 | 16390 | 1190 |
| 468457 | 1017 | 1032 | CACACTTGCTGGCCTG | 0 | 16647 | 16662 | 1191 |
| 848363 | 1060 | 1075 | TCCCGGCCGCTGACCA | 30 | 16690 | 16705 | 1192 |
| 468460 | 1075 | 1090 | TTGGCCACGCCGGCAT | 0 | 16705 | 16720 | 48 |
| 848378 | 1084 | 1099 | CTGGCACCCTTGGCCA | 0 | 16714 | 16729 | 1193 |
| 849155 | N/A | N/A | AGACATCACCGGATTT | 42 | 17074 | 17089 | 1194 |
| 849171 | N/A | N/A | CTGTAGGAAAGTCTCA | 49 | 17685 | 17700 | 1195 |
| 849187 | N/A | N/A | GGACACACAATCACCT | 14 | 18033 | 18048 | 1196 |
| 849203 | N/A | N/A | CAGTAACAGTTCTAAC | 0 | 18706 | 18721 | 1197 |
| 849219 | N/A | N/A | CTTATTATCCCTTTCC | 29 | 19395 | 19410 | 1198 |

TABLE 16-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 849235 | N/A | N/A | TCAAATTCTGCAGGAA | 0 | 19653 | 19668 | 1199 |
| 848394 | 1163 | 1178 | CCGAATAAACTCCAGG | 42 | 19994 | 20009 | 1200 |
| 848410 | 1324 | 1339 | GAGTAGAGGCAGGCAT | 0 | 20155 | 20170 | 1201 |
| 849251 | N/A | N/A | CCAAAGCCAGAAGGGT | 32 | 20317 | 20332 | 1202 |
| 849267 | N/A | N/A | TTCTAAGTGCCACGGG | 66 | 21029 | 21044 | 1203 |
| 848426 | 1455 | 1470 | CAATGATGTCCTCCCC | 0 | 21427 | 21442 | 1204 |
| 849283 | N/A | N/A | TCCCGATCAAATGTCC | 0 | 21772 | 21787 | 1205 |
| 848442 | 1606 | 1621 | GCAGAGAAGTGGATCA | 0 | 22099 | 22114 | 1206 |
| 849299 | N/A | N/A | TGCCAACCTGCAAAAA | 0 | 22490 | 22505 | 1207 |
| 848458 | 1728 | 1743 | ATACAGTCCTGCAAAA | 0 | 22510 | 22525 | 1208 |
| 848474 | 1803 | 1818 | AGCTCAGCAGCTCCTC | 11 | 22585 | 22600 | 1209 |
| 849315 | N/A | N/A | ATCCAGGAGGCCAAAG | 0 | 23228 | 23243 | 1210 |
| 848488 | 1937 | 1952 | GGGTAGCAGGCAGCAC | 0 | 23557 | 23572 | 1211 |
| 848504 | 2005 | 2020 | TGGCAGTGGACACGGG | 17 | 23625 | 23640 | 1212 |
| 849331 | N/A | N/A | GGAGAAGTAAGGTCAC | 52 | 23827 | 23842 | 1213 |
| 849347 | N/A | N/A | GTCAATAGTTGCCTAT | 33 | 24203 | 24218 | 1214 |
| 849363 | N/A | N/A | GTTCAAGGGTAAGCCG | 25 | 25011 | 25026 | 1215 |
| 849379 | N/A | N/A | TGGCACAAACTGACAC | 0 | 25619 | 25634 | 1216 |
| 849395 | N/A | N/A | TTAAGAGTGGACTCCT | 40 | 26260 | 26275 | 1217 |
| 849411 | N/A | N/A | CCAAAGTGCAGACGGC | 0 | 27260 | 27275 | 1218 |
| 848520 | 2222 | 2237 | GGCCACGGTCACCTGC | 0 | 27365 | 27380 | 1219 |
| 848536 | 2455 | 2470 | CCCCAGACACCCATCC | 26 | 27598 | 27613 | 1220 |
| 848552 | 2558 | 2573 | CCGGAAAGGCGGAAGC | 0 | 27701 | 27716 | 1221 |
| 848568 | 2700 | 2715 | GCACAGCTCGACCTGT | 3 | 27843 | 27858 | 1222 |
| 848583 | 2737 | 2752 | GGACATCGGCACATTG | 68 | 27880 | 27895 | 1223 |
| 848599 | 2775 | 2790 | GCACGGAACAAGAGCT | 19 | 27918 | 27933 | 1224 |
| 848615 | 2885 | 2900 | TTTCACACTCACCCCC | 7 | 28028 | 28043 | 1225 |
| 848631 | 2967 | 2982 | ATCCAGAAAGCTAAGC | 1 | 28110 | 28125 | 1226 |
| 848645 | 3072 | 3087 | TGCTAGCACAGCCTGG | 19 | 28215 | 28230 | 1227 |
| 848661 | 3131 | 3146 | CACTGCACACTGCCGA | 11 | 28274 | 28289 | 1228 |
| 848677 | 3219 | 3234 | GGTTCCAGGTTTCTTC | 61 | 28362 | 28377 | 1229 |
| 848692 | 3249 | 3264 | CTGTGTGAGCTTGGCA | 69 | 28392 | 28407 | 1230 |
| 848708 | 3288 | 3303 | TCAGAGCCAGCCCAAT | 8 | 28431 | 28446 | 1231 |
| 848724 | 3378 | 3393 | GAGCTTCCTGGTCTGT | 47 | 28521 | 28536 | 1232 |
| 848740 | 3431 | 3446 | GTGATAACGGAAAAAG | 65 | 28574 | 28589 | 1233 |

TABLE 16-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848755 | 3545 | 3560 | AGATAAATGTCTGCTT | 14 | 28688 | 28703 | 1234 |
| 848771 | 3616 | 3631 | TTCAAGTTACAAAAGC | 57 | 28759 | 28774 | 1235 |

TABLE 17

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848306 | 759 | 774 | GCAACTTCAAGGCCAG | 84 | N/A | N/A | 1236 |
| 848217 | 149 | 164 | AGCCAGTCTCACTGCC | 30 | 3624 | 3639 | 1237 |
| 848233 | 362 | 377 | GCTGACGGTGCCCATG | 51 | 3837 | 3852 | 1238 |
| 848249 | 487 | 502 | GAACGCAAGGCTAGCA | 5 | 3962 | 3977 | 1239 |
| 848790 | N/A | N/A | CCAAATCGGAACCCAC | 88 | 4478 | 4493 | 1240 |
| 848806 | N/A | N/A | ACAGAACTTTCCCTTC | 57 | 5114 | 5129 | 1241 |
| 848822 | N/A | N/A | TAAATTCGATTCCCAC | 32 | 5600 | 5615 | 1242 |
| 848838 | N/A | N/A | AGGCAGTAATGGGCAA | 92 | 6461 | 6476 | 1243 |
| 848854 | N/A | N/A | TCCAACACTGAGGACC | 93 | 6811 | 6826 | 1244 |
| 848870 | N/A | N/A | AAAGGCAACACTTCTT | 61 | 7222 | 7237 | 1245 |
| 848886 | N/A | N/A | CAATATTTACTGGTTG | 57 | 7409 | 7424 | 1246 |
| 848902 | N/A | N/A | CTTACAAATTACAACA | 59 | 7751 | 7766 | 1247 |
| 848264 | 622 | 637 | TCTGACTGCGAGAGGT | 71 | 7895 | 7910 | 1248 |
| 466849 | 675 | 690 | TGGTGAGGTATCCCCG | 48 | 7948 | 7963 | 1249 |
| 468444 | 691 | 706 | AAGACATGCAGGATCT | 30 | 7964 | 7979 | 1250 |
| 848918 | N/A | N/A | GACCAATGGGTTTGAT | 13 | 8311 | 8326 | 1251 |
| 848934 | N/A | N/A | GAGAATACCCAGTCCC | 50 | 8550 | 8565 | 1252 |
| 848950 | N/A | N/A | GCTCAAGGGAAAGGCC | 3 | 9044 | 9059 | 1253 |
| 848966 | N/A | N/A | GGACAAGAGTGCATCA | 6 | 10011 | 10026 | 1254 |
| 848982 | N/A | N/A | GGCCTTACCTGATCAA | 12 | 10437 | 10452 | 1255 |
| 848998 | N/A | N/A | CTAGAACCCTTCATTC | 0 | 11304 | 11319 | 1256 |
| 849014 | N/A | N/A | TCTCACCTGGTTGGAA | 31 | 11856 | 11871 | 1257 |
| 849030 | N/A | N/A | GTTAAGAGTGCAGGGT | 90 | 12708 | 12723 | 1258 |
| 849044 | N/A | N/A | GGATACACAGGCTCGC | 92 | 13108 | 13123 | 337 |
| 849046 | N/A | N/A | CCGTAGGTCTTGGCTA | 65 | 13166 | 13181 | 1259 |
| 849062 | N/A | N/A | AGCTGTACCTGGGTTC | 79 | 13888 | 13903 | 1260 |
| 849078 | N/A | N/A | CCTAGAGGAACCACTA | 51 | 14340 | 14355 | 1261 |
| 849094 | N/A | N/A | ACATGAATTTCAGGCA | 73 | 14731 | 14746 | 1262 |

TABLE 17-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 849110 | N/A | N/A | TCTCAGCCAGGCCAAA | 0 | 15411 | 15426 | 1263 |
| 849126 | N/A | N/A | CCCTATTATAGCCTTT | 67 | 15920 | 15935 | 1264 |
| 848321 | 890 | 905 | CTCCACCAGGCTGCCT | 0 | 16282 | 16297 | 1265 |
| 848336 | 986 | 1001 | CCCGTCCTCCTCGGGC | 0 | 16378 | 16393 | 1266 |
| 849142 | N/A | N/A | CCATCAGACGGCCGTG | 48 | 16417 | 16432 | 1267 |
| 848350 | 1020 | 1035 | TGTCACACTTGCTGGC | 45 | 16650 | 16665 | 1268 |
| 848365 | 1064 | 1079 | GGCATCCCGGCCGCTG | 62 | 16694 | 16709 | 1269 |
| 468460 | 1075 | 1090 | TTGGCCACGCCGGCAT | 0 | 16705 | 16720 | 48 |
| 848381 | 1098 | 1113 | GCAGGCTGCGCATGCT | 42 | 16728 | 16743 | 1270 |
| 849158 | N/A | N/A | TGCAAGCAGAAGATAG | 39 | 17153 | 17168 | 1271 |
| 849174 | N/A | N/A | CAGGAACTGACCTGAC | 21 | 17808 | 17823 | 1272 |
| 849190 | N/A | N/A | TACAGCTGCTAGTTAT | 59 | 18086 18399 | 18101 18414 | 1273 |
| 849206 | N/A | N/A | GTGCAGGCCATGGTCT | 68 | 19054 | 19069 | 1274 |
| 849222 | N/A | N/A | ATATACGAACTCAGGG | 0 | 19426 | 19441 | 1275 |
| 849238 | N/A | N/A | GGCCTTAAGAGAACAG | 46 | 19734 | 19749 | 1276 |
| 848397 | 1178 | 1193 | GACCAGCTGGCTTTTC | 2 | 20009 | 20024 | 1277 |
| 849254 | N/A | N/A | CCCAAAGAGTATTGGG | 0 | 20552 | 20567 | 1278 |
| 849270 | N/A | N/A | AACTATTCGGTGTATC | 67 | 21051 | 21066 | 1279 |
| 848413 | 1358 | 1373 | CCCAACTGTGATGACC | 0 | 21330 | 21345 | 1280 |
| 848429 | 1485 | 1500 | CAAAGCAGGTGCTGCA | 36 | 21457 | 21472 | 1281 |
| 849286 | N/A | N/A | AGGTAAGACAGCCTCC | 53 | 21856 | 21871 | 1282 |
| 848445 | 1619 | 1634 | GATGACATCTTTGGCA | 59 | 22112 | 22127 | 1283 |
| 848461 | 1732 | 1747 | GACCATACAGTCCTGC | 17 | 22514 | 22529 | 1284 |
| 848477 | 1816 | 1831 | GAGAAACTGGAGCAGC | 0 | 22598 | 22613 | 1285 |
| 849302 | N/A | N/A | TAGCAGATCGCTGACC | 67 | 22948 | 22963 | 1286 |
| 849318 | N/A | N/A | ACTCAAGCACCCTCAT | 0 | 23394 | 23409 | 1287 |
| 848491 | 1985 | 2000 | CATGCTGGCCTCAGCT | 11 | 23605 | 23620 | 1288 |
| 848507 | 2008 | 2023 | TGGTGGCAGTGGACAC | 71 | 23628 | 23643 | 1289 |
| 849334 | N/A | N/A | AATGAGGCAGGTAATA | 19 | 23879 | 23894 | 1290 |
| 849350 | N/A | N/A | CCTCAGGGCACCATCC | 72 | 24293 | 24308 | 1291 |
| 849366 | N/A | N/A | GGGAAAACACCATCTT | 31 | 25120 | 25135 | 1292 |
| 849382 | N/A | N/A | AGCATCTACCTGGCAA | 39 | 25666 | 25681 | 1293 |
| 849398 | N/A | N/A | GTGTACCCAGGGCAAG | 59 | 26373 | 26388 | 1294 |
| 849414 | N/A | N/A | AAGCACATGTCTAGCG | 8 | 27331 | 27346 | 1295 |
| 848523 | 2246 | 2261 | AGTCAGGGTCCAGCCC | 63 | 27389 | 27404 | 1296 |
| 848539 | 2487 | 2502 | CATTTTAAAGCTCAGC | 87 | 27630 | 27645 | 1297 |

TABLE 17-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848555 | 2580 | 2595 | CTCAAGGGCCAGGCCA | 70 | 27723 | 27738 | 1298 |
| 848571 | 2708 | 2723 | GCACCCGAGCACAGCT | 75 | 27851 | 27866 | 1299 |
| 848586 | 2743 | 2758 | GCCCACGGACATCGGC | 58 | 27886 | 27901 | 1300 |
| 848602 | 2778 | 2793 | CTGGCACGGAACAAGA | 8 | 27921 | 27936 | 1301 |
| 848618 | 2904 | 2919 | GATGAGGGCCATCAGC | 87 | 28047 | 28062 | 1302 |
| 848633 | 2978 | 2993 | GGCTAGATGCCATCCA | 64 | 28121 | 28136 | 1303 |
| 848648 | 3093 | 3108 | CCGCAGGCCACCTTTG | 12 | 28236 | 28251 | 1304 |
| 848664 | 3146 | 3161 | AGACAGTGCATGCACC | 10 | 28289 | 28304 | 1305 |
| 848680 | 3222 | 3237 | TCTGGTTCCAGGTTTC | 89 | 28365 | 28380 | 1306 |
| 848695 | 3255 | 3270 | TTCCTGCTGTGTGAGC | 63 | 28398 | 28413 | 1307 |
| 848711 | 3304 | 3319 | AAGAAGAGGCTTGGCT | 38 | 28447 | 28462 | 1308 |
| 848727 | 3382 | 3397 | CACCGAGCTTCCTGGT | 66 | 28525 | 28540 | 1309 |
| 848743 | 3446 | 3461 | GTGAATCAGGCCTGGG | 31 | 28589 | 28604 | 1310 |
| 848758 | 3558 | 3573 | GGACAGACCCAAAAGA | 71 | 28701 | 28716 | 1311 |
| 848774 | 3641 | 3656 | TGCTACAAAACCCAGA | 95 | 28784 | 28799 | 1312 |

TABLE 18

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 848218 | 153 | 168 | CCCGAGCCAGTCTCAC | 1 | 3628 | 3643 | 1313 |
| 848234 | 368 | 383 | CCTGGAGCTGACGGTG | 18 | 3843 | 3858 | 1314 |
| 848250 | 488 | 503 | GGAACGCAAGGCTAGC | 77 | 3963 | 3978 | 1315 |
| 848791 | N/A | N/A | TTCCAAACCAAATCGG | 46 | 4485 | 4500 | 1316 |
| 848807 | N/A | N/A | GGACAAAACTGCAAGT | 42 | 5170 | 5185 | 1317 |
| 848823 | N/A | N/A | TTCTAAATTCGATTCC | 61 | 5603 | 5618 | 1318 |
| 848839 | N/A | N/A | TTAGAAAGGCAGTAAT | 30 | 6467 | 6482 | 1319 |
| 848855 | N/A | N/A | CAAGGACGGCACCAAG | 37 | 6881 | 6896 | 1320 |
| 848871 | N/A | N/A | GAAGGGATGACTAAGT | 0 | 7242 | 7257 | 1321 |
| 848887 | N/A | N/A | AGGAAACCGTGGACCT | 60 | 7437 | 7452 | 1322 |
| 848903 | N/A | N/A | CCTACTTACAAATTAC | 4 | 7755 | 7770 | 1323 |
| 848265 | 633 | 648 | GGGCAGTGCGCTCTGA | 78 | 7906 | 7921 | 1324 |
| 848276 | 676 | 691 | TTGGTGAGGTATCCCC | 66 | 7949 | 7964 | 1325 |
| 848291 | 692 | 707 | GAAGACATGCAGGATC | 61 | 7965 | 7980 | 1326 |
| 848919 | N/A | N/A | GGCAGACCAATGGGTT | 10 | 8315 | 8330 | 1327 |
| 848935 | N/A | N/A | TAAGATTTGAAGCACT | 60 | 8580 | 8595 | 1328 |

TABLE 18-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 848951 | N/A | N/A | CTGAACTGTAAGCTCA | 46 | 9055 | 9070 | 1329 |
| 848967 | N/A | N/A | GGCACTAGCAGGAGTT | 62 | 10031 | 10046 | 1330 |
| 848983 | N/A | N/A | ATGGATTCAGCTCAGA | 66 | 10680 | 10695 | 1331 |
| 848999 | N/A | N/A | TCCAACTAGAACCCTT | 87 | 11309 | 11324 | 1332 |
| 849015 | N/A | N/A | CACTGAAGAGGTCTCA | 17 | 11867 | 11882 | 1333 |
| 849031 | N/A | N/A | AGGAACCTGAAGATCA | 72 | 12756 | 12771 | 1334 |
| 849044 | N/A | N/A | GGATACACAGGCTCGC | 85 | 13108 | 13123 | 337 |
| 849047 | N/A | N/A | TAATAATGCCCCCGTA | 49 | 13177 | 13192 | 1335 |
| 849063 | N/A | N/A | AGTTAGCCCAGGTGAG | 6 | 13951 | 13966 | 1336 |
| 849079 | N/A | N/A | CGCCACCCTAGAGGAA | 0 | 14346 | 14361 | 1337 |
| 849095 | N/A | N/A | AGCAATTCAGTGGCTG | 49 | 14759 | 14774 | 1338 |
| 849111 | N/A | N/A | CTCCAGCGCAGGTCTC | 35 | 15433 | 15448 | 1339 |
| 849127 | N/A | N/A | GTGTAAAATAAAGCCC | 77 | 15934 | 15949 | 1340 |
| 848322 | 900 | 915 | GGAGATACACCTCCAC | 15 | 16292 | 16307 | 1341 |
| 848337 | 987 | 1002 | TCCCGTCCTCCTCGGG | 8 | 16379 | 16394 | 1342 |
| 849143 | N/A | N/A | GGACAGTGACAGCTGG | 39 | 16524 | 16539 | 1343 |
| 848351 | 1021 | 1036 | CTGTCACACTTGCTGG | 8 | 16651 | 16666 | 1344 |
| 848366 | 1070 | 1085 | CACGCCGGCATCCCGG | 3 | 16700 | 16715 | 1345 |
| 468460 | 1075 | 1090 | TTGGCCACGCCGGCAT | 0 | 16705 | 16720 | 48 |
| 848382 | 1100 | 1115 | GCGCAGGCTGCGCATG | 0 | 16730 | 16745 | 1346 |
| 849159 | N/A | N/A | ATGCAAGTGAGTGAGT | 74 | 17187 | 17202 | 1347 |
| 849175 | N/A | N/A | GGAAAGAACAGCCTCC | 44 | 17842 | 17857 | 1348 |
| 849191 | N/A | N/A | GATACAGACACCCACC | 37 | 18250 | 18265 | 1349 |
| 849207 | N/A | N/A | TACCATAACTCCCCAC | 37 | 19123 | 19138 | 1350 |
| 849223 | N/A | N/A | ATCAAACTAGCCAACC | 0 | 19482 | 19497 | 1351 |
| 849239 | N/A | N/A | GAAGACGGAGTAAGGC | 81 | 19795 | 19810 | 1352 |
| 848398 | 1183 | 1198 | GGCTGGACCAGCTGGC | 0 | 20014 | 20029 | 1353 |
| 849255 | N/A | N/A | GGCCCAAAGAGTATTG | 0 | 20554 | 20569 | 1354 |
| 849271 | N/A | N/A | GAAACTATTCGGTGTA | 38 | 21053 | 21068 | 1355 |
| 848414 | 1370 | 1385 | GGCATTGGTGGCCCCA | 19 | 21342 | 21357 | 1356 |
| 848430 | 1492 | 1507 | TGTGACACAAAGCAGG | 84 | 21464 | 21479 | 1357 |
| 849287 | N/A | N/A | CGAAGGTAAGCCGCCT | 56 | 21889 | 21904 | 1358 |
| 848446 | 1626 | 1641 | CCTCATTGATGACATC | 0 | 22119 | 22134 | 1359 |
| 848462 | 1733 | 1748 | TGACCATACAGTCCTG | 19 | 22515 | 22530 | 1360 |
| 848478 | 1842 | 1857 | GCTCGCCCCGCCGCTT | 35 | 22624 | 22639 | 1361 |
| 849303 | N/A | N/A | GGCTGAGTCCAGAGTA | 89 | 22962 | 22977 | 1362 |

TABLE 18-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 849319 | N/A | N/A | GAAATGGGAATCTGCT | 0 | 23454 | 23469 | 1363 |
| 848492 | 1986 | 2001 | CCATGCTGGCCTCAGC | 32 | 23606 | 23621 | 1364 |
| 849335 | N/A | N/A | CAGCTATAGAGCGGCA | 0 | 24045 | 24060 | 1365 |
| 849351 | N/A | N/A | GAACAGCTCAGCCTCA | 0 | 24304 | 24319 | 1366 |
| 849367 | N/A | N/A | AGCCTTAGTTTCTCAG | 25 | 25135 | 25150 | 1367 |
| 848508 | 2047 | 2062 | TCCCAGTGGGAGCTGC | 0 | 25378 | 25393 | 1368 |
| 849383 | N/A | N/A | CCACAGCATCTACCTG | 80 | 25670 | 25685 | 1369 |
| 849399 | N/A | N/A | CCAGGAAGAGCACCTG | 17 | 26406 | 26421 | 1370 |
| 849415 | N/A | N/A | AGAAAGCACATGTCTA | 0 | 27334 | 27349 | 1371 |
| 848524 | 2250 | 2265 | AGCCAGTCAGGGTCCA | 55 | 27393 | 27408 | 1372 |
| 848540 | 2490 | 2505 | AACCATTTTAAAGCTC | 45 | 27633 | 27648 | 1373 |
| 848556 | 2582 | 2597 | CACTCAAGGGCCAGGC | 37 | 27725 | 27740 | 1374 |
| 848572 | 2709 | 2724 | AGCACCCGAGCACAGC | 89 | 27852 | 27867 | 1375 |
| 848587 | 2752 | 2767 | AGTCATTCTGCCCACG | 78 | 27895 | 27910 | 1376 |
| 848603 | 2779 | 2794 | CCTGGCACGGAACAAG | 51 | 27922 | 27937 | 1377 |
| 848619 | 2906 | 2921 | GAGATGAGGGCCATCA | 80 | 28049 | 28064 | 1378 |
| 848634 | 2999 | 3014 | GCGCACCTGTCTCCAG | 0 | 28142 | 28157 | 1379 |
| 848649 | 3110 | 3125 | TCCTAGGTGATGGCTC | 80 | 28253 | 28268 | 1380 |
| 848665 | 3148 | 3163 | TGAGACAGTGCATGCA | 37 | 28291 | 28306 | 1381 |
| 848681 | 3223 | 3238 | CTCTGGTTCCAGGTTT | 43 | 28366 | 28381 | 1382 |
| 848696 | 3256 | 3271 | GTTCCTGCTGTGTGAG | 78 | 28399 | 28414 | 1383 |
| 848712 | 3306 | 3321 | GTAAGAAGAGGCTTGG | 75 | 28449 | 28464 | 1384 |
| 848728 | 3383 | 3398 | TCACCGAGCTTCCTGG | 50 | 28526 | 28541 | 1385 |
| 848744 | 3451 | 3466 | GGCCAGTGAATCAGGC | 17 | 28594 | 28609 | 1386 |
| 848759 | 3563 | 3578 | AGAGAGGACAGACCCA | 83 | 28706 | 28721 | 1387 |
| 848775 | 3644 | 3659 | AAATGCTACAAAACCC | 67 | 28787 | 28802 | 1388 |
| 848307 | 760 | 775 | GGCAACTTCAAGGCCA | 0 | N/A | N/A | 1389 |

TABLE 19

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848219 | 181 | 196 | CGCTGCTGCAACGACG | 66 | 3656 | 3671 | 1390 |
| 848235 | 378 | 393 | ACCAGGACCGCCTGGA | 0 | 3853 | 3868 | 1391 |
| 848251 | 489 | 504 | CGGAACGCAAGGCTAG | 62 | 3964 | 3979 | 1392 |
| 848792 | N/A | N/A | GTCATAAAGAAATTGC | 47 | 4593 | 4608 | 1393 |

TABLE 19-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 848808 | N/A | N/A | TGGCAGAATTTTCCCC | 17 | 5249 | 5264 | 1394 |
| 848824 | N/A | N/A | TTTCATTCTAAATTCG | 58 | 5608 | 5623 | 1395 |
| 848840 | N/A | N/A | CTTTACCCAAAGCCTT | 0 | 6523 | 6538 | 1396 |
| 848856 | N/A | N/A | CATAGCGGGAGAACTT | 51 | 6908 | 6923 | 1397 |
| 848872 | N/A | N/A | GCAGAAGGGATGACTA | 53 | 7245 | 7260 | 1398 |
| 848888 | N/A | N/A | AGCCAGGAAACCGTGG | 63 | 7441 | 7456 | 1399 |
| 848904 | N/A | N/A | CCCTACTTACAAATTA | 40 | 7756 | 7771 | 1400 |
| 848266 | 640 | 655 | AGGCGGCGGGCAGTGC | 31 | 7913 | 7928 | 1401 |
| 848277 | 677 | 692 | CTTGGTGAGGTATCCC | 65 | 7950 | 7965 | 1402 |
| 848292 | 693 | 708 | GGAAGACATGCAGGAT | 64 | 7966 | 7981 | 1403 |
| 848920 | N/A | N/A | AGGCAGACCAATGGGT | 63 | 8316 | 8331 | 1404 |
| 848936 | N/A | N/A | CTAGAAGGTGGTGCAG | 0 | 8619 | 8634 | 1405 |
| 848952 | N/A | N/A | CCATAGTCAACTGTAC | 7 | 9097 | 9112 | 1406 |
| 848968 | N/A | N/A | AGCCAATGGGAGGCAC | 15 | 10042 | 10057 | 1407 |
| 848308 | 761 | 776 | GGGCAACTTCAAGGCC | 7 | 10522 | 10537 | 1408 |
| 848984 | N/A | N/A | GGGCAGAGCAAATGGA | 0 | 10691 | 10706 | 1409 |
| 849000 | N/A | N/A | GTTCACCCCAAGCTCT | 29 | 11420 | 11435 | 1410 |
| 849016 | N/A | N/A | CTCCACTGAAGAGGTC | 66 | 11870 | 11885 | 1411 |
| 849032 | N/A | N/A | GATTTAACCCTCCAAA | 0 | 12814 | 12829 | 1412 |
| 849044 | N/A | N/A | GGATACACAGGCTCGC | 86 | 13108 | 13123 | 337 |
| 849048 | N/A | N/A | GTTAATAATGCCCCCG | 80 | 13179 | 13194 | 1413 |
| 849064 | N/A | N/A | GCTGAGTTAGCCCAGG | 51 | 13955 | 13970 | 1414 |
| 849080 | N/A | N/A | AAACAGTGCTCGCCAC | 29 | 14356 | 14371 | 1415 |
| 849096 | N/A | N/A | TACAGAGCAATTCAGT | 33 | 14764 | 14779 | 1416 |
| 849112 | N/A | N/A | TGCCAGGCAGGTCCAG | 0 | 15506 | 15521 | 1417 |
| 849128 | N/A | N/A | CAATATCTAACAATAA | 0 | 15977 | 15992 | 1418 |
| 848323 | 905 | 920 | GTCTAGGAGATACACC | 72 | 16297 | 16312 | 1419 |
| 848338 | 988 | 1003 | GTCCCGTCCTCCTCGG | 33 | 16380 | 16395 | 1420 |
| 849144 | N/A | N/A | AATCAGCAGGTGGCTG | 0 | 16579 | 16594 | 1421 |
| 848352 | 1022 | 1037 | ACTGTCACACTTGCTG | 45 | 16652 | 16667 | 1422 |
| 848367 | 1072 | 1087 | GCCACGCCGGCATCCC | 27 | 16702 | 16717 | 1423 |
| 468460 | 1075 | 1090 | TTGGCCACGCCGGCAT | 2 | 16705 | 16720 | 48 |
| 848383 | 1105 | 1120 | AGCACGCGCAGGCTGC | 0 | 16735 | 16750 | 1424 |
| 849160 | N/A | N/A | CCACATCTGCCTGGCC | 0 | 17226 | 17241 | 1425 |
| 849176 | N/A | N/A | TGCCAGGTCATGCAAT | 0 | 17954 | 17969 | 1426 |
| 849192 | N/A | N/A | GGGATACAGACACCCA | 48 | 18252 | 18267 | 1427 |

TABLE 19-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID: 2 Stop Site | SEQ ID NO |
|---|---|---|---|---|---|---|---|
| 849208 | N/A | N/A | CCATACCATAACTCCC | 36 | 19126 | 19141 | 1428 |
| 849224 | N/A | N/A | CAATTACACCAGCAAT | 64 | 19496 | 19511 | 1429 |
| 849240 | N/A | N/A | CTGCGAAAATATTTTT | 32 | 19835 | 19850 | 1430 |
| 848399 | 1188 | 1203 | CCACAGGCTGGACCAG | 8 | 20019 | 20034 | 1431 |
| 849256 | N/A | N/A | CCTCAACCGCTCCCAT | 15 | 20631 | 20646 | 1432 |
| 849272 | N/A | N/A | GAGATAGGAAACTATT | 19 | 21060 | 21075 | 1433 |
| 848415 | 1388 | 1403 | GGTCACCGGCTGGTCT | 0 | 21360 | 21375 | 1434 |
| 848431 | 1500 | 1515 | TCCCACTCTGTGACAC | 93 | 21472 | 21487 | 1435 |
| 849288 | N/A | N/A | ACAGACACTAAGCTCT | 76 | 21910 | 21925 | 1436 |
| 848447 | 1628 | 1643 | GGCCTCATTGATGACA | 0 | 22121 | 22136 | 1437 |
| 848463 | 1734 | 1749 | CTGACCATACAGTCCT | 15 | 22516 | 22531 | 1438 |
| 848479 | 1850 | 1865 | CTCCATGCGCTCGCCC | 39 | 22632 | 22647 | 1439 |
| 849304 | N/A | N/A | CTAGAGATGGCTGAGT | 56 | 22970 | 22985 | 1440 |
| 849320 | N/A | N/A | ACGGAAATGGGAATCT | 0 | 23457 | 23472 | 1441 |
| 848493 | 1990 | 2005 | GTCCCCATGCTGGCCT | 33 | 23610 | 23625 | 1442 |
| 849336 | N/A | N/A | ATACAGAGATGTTAAG | 30 | 24079 | 24094 | 1443 |
| 849352 | N/A | N/A | TCTTATTCCAGGCTGG | 23 | 24362 | 24377 | 1444 |
| 849368 | N/A | N/A | AGCTGACCAGCTGTGT | 0 | 25180 | 25195 | 1445 |
| 848509 | 2064 | 2079 | TGCCAAGGTCCTCCAC | 18 | 25395 | 25410 | 1446 |
| 849384 | N/A | N/A | CAAAAACAGACCCAGC | 11 | 25733 | 25748 | 1447 |
| 849400 | N/A | N/A | AAATAGATGCTCCAGG | 35 | 26465 | 26480 | 1448 |
| 849416 | N/A | N/A | CGAGGAAAAGAAAGCA | 20 | 27342 | 27357 | 1449 |
| 848525 | 2254 | 2269 | CTGCAGCCAGTCAGGG | 1 | 27397 | 27412 | 1450 |
| 848541 | 2494 | 2509 | TCGGAACCATTTTAAA | 0 | 27637 | 27652 | 1451 |
| 848557 | 2585 | 2600 | CCCCACTCAAGGGCCA | 0 | 27728 | 27743 | 1452 |
| 848573 | 2710 | 2725 | CAGCACCCGAGCACAG | 23 | 27853 | 27868 | 1453 |
| 848588 | 2755 | 2770 | AAAAGTCATTCTGCCC | 62 | 27898 | 27913 | 1454 |
| 848604 | 2780 | 2795 | GCCTGGCACGGAACAA | 55 | 27923 | 27938 | 1455 |
| 848620 | 2909 | 2924 | CTGGAGATGAGGGCCA | 24 | 28052 | 28067 | 1456 |
| 848635 | 3021 | 3036 | GCACAGCCTGTGACCA | 71 | 28164 | 28179 | 1457 |
| 848650 | 3120 | 3135 | GCCGAGTCAGTCCTAG | 23 | 28263 | 28278 | 1458 |
| 848666 | 3150 | 3165 | GCTGAGACAGTGCATG | 47 | 28293 | 28308 | 1459 |
| 468497 | 3224 | 3239 | CCTCTGGTTCCAGGTT | 77 | 28367 | 28382 | 1460 |
| 848697 | 3257 | 3272 | AGTTCCTGCTGTGTGA | 44 | 28400 | 28415 | 1461 |
| 848713 | 3308 | 3323 | AAGTAAGAAGAGGCTT | 0 | 28451 | 28466 | 1462 |
| 848729 | 3384 | 3399 | CTCACCGAGCTTCCTG | 76 | 28527 | 28542 | 1463 |
| 848745 | 3456 | 3471 | CGCCAGGCCAGTGAAT | 44 | 28599 | 28614 | 1464 |

TABLE 19-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848760 | 3565 | 3580 | ACAGAGAGGACAGACC | 45 | 28708 | 28723 | 1465 |
| 848776 | 3661 | 3676 | AGTCACCATATTAATA | 63 | 28804 | 28819 | 1466 |

TABLE 20

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848432 | 1535 | 1550 | TGCAATGCCAGCCACG | 0 | N/A | N/A | 1467 |
| 848220 | 184 | 199 | AGCCGCTGCTGCAACG | 57 | 3659 | 3674 | 1468 |
| 848236 | 381 | 396 | GCCACCAGGACCGCCT | 28 | 3856 | 3871 | 1469 |
| 848252 | 492 | 507 | CCTCGGAACGCAAGGC | 38 | 3967 | 3982 | 1470 |
| 848793 | N/A | N/A | AGCATGAGTTCTGTGT | 43 | 4607 | 4622 | 1471 |
| 848809 | N/A | N/A | CAGCACACTCAGACAG | 47 | 5288 | 5303 | 1472 |
| 848825 | N/A | N/A | AAAAGGATTGGTCTAA | 0 | 5652 | 5667 | 1473 |
| 848841 | N/A | N/A | CCCTTTACCCAAAGCC | 71 | 6525 | 6540 | 1474 |
| 848857 | N/A | N/A | AATCAGCCTTCAAGGG | 39 | 6928 | 6943 | 1475 |
| 848873 | N/A | N/A | GGCAGAAGGGATGACT | 35 | 7246 | 7261 | 1476 |
| 848889 | N/A | N/A | TCGACAACAGGTTTTC | 58 | 7576 | 7591 | 1477 |
| 848905 | N/A | N/A | TGACATGGAAGAAACC | 34 | 7801 | 7816 | 1478 |
| 848267 | 642 | 657 | GCAGGCGGCGGGCAGT | 0 | 7915 | 7930 | 1479 |
| 848278 | 678 | 693 | TCTTGGTGAGGTATCC | 52 | 7951 | 7966 | 1480 |
| 848293 | 694 | 709 | TGGAAGACATGCAGGA | 26 | 7967 | 7982 | 1481 |
| 848921 | N/A | N/A | TGCATTGGCACAAGAA | 44 | 8340 | 8355 | 1482 |
| 848937 | N/A | N/A | AGTTAGAGGCCAGGAA | 25 | 8645 | 8660 | 1483 |
| 848953 | N/A | N/A | TCCCATAGTCAACTGT | 11 | 9099 | 9114 | 1484 |
| 848969 | N/A | N/A | TTGCAAAGCTTCCAGT | 7 | 10065 | 10080 | 1485 |
| 468446 | 775 | 790 | ATGTAGTCGACATGGG | 38 | 10536 | 10551 | 1486 |
| 848985 | N/A | N/A | CGAGAAGTGGAAACCA | 0 | 10727 | 10742 | 1487 |
| 849001 | N/A | N/A | GTGAAAGCTGAGTTCA | 6 | 11431 | 11446 | 1488 |
| 849017 | N/A | N/A | GGGTGGTAATTTGTCA | 15 | 12045 | 12060 | 1489 |
| 849033 | N/A | N/A | AATAACTGATTTAACC | 12 | 12821 | 12836 | 1490 |
| 849044 | N/A | N/A | GGATACACAGGCTCGC | 82 | 13108 | 13123 | 337 |
| 849049 | N/A | N/A | GTTCATTCCACTGCTT | 30 | 13216 | 13231 | 1491 |
| 849065 | N/A | N/A | CAACGCACATCGAGCA | 39 | 14038 | 14053 | 1492 |
| 849081 | N/A | N/A | ACCAAACAGTGCTCGC | 48 | 14359 | 14374 | 1493 |

TABLE 20-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 849097 | N/A | N/A | AATAAGGTCTGGCTCA | 43 | 14829 | 14844 | 1494 |
| 849113 | N/A | N/A | ACAGATGCCAGGCAGG | 10 | 15511 | 15526 | 1495 |
| 849129 | N/A | N/A | TCAATATCTAACAATA | 0 | 15978 | 15993 | 1496 |
| 848324 | 917 | 932 | CTGTATGCTGGTGTCT | 0 | 16309 | 16324 | 1497 |
| 848339 | 989 | 1004 | GGTCCCGTCCTCCTCG | 0 | 16381 | 16396 | 1498 |
| 849145 | N/A | N/A | CATGAGAAAGACCCCC | 0 | 16611 | 16626 | 1499 |
| 848353 | 1024 | 1039 | TGACTGTCACACTTGC | 56 | 16654 | 16669 | 1500 |
| 848368 | 1073 | 1088 | GGCCACGCCGGCATCC | 0 | 16703 | 16718 | 1501 |
| 468460 | 1075 | 1090 | TTGGCCACGCCGGCAT | 0 | 16705 | 16720 | 48 |
| 848384 | 1109 | 1124 | GTTGAGCACGCGCAGG | 58 | 16739 | 16754 | 1502 |
| 849161 | N/A | N/A | CTCCACCACATCTGCC | 30 | 17231 | 17246 | 1503 |
| 849177 | N/A | N/A | CGTGCCAGGTCATGCA | 74 | 17956 | 17971 | 1504 |
| 849193 | N/A | N/A | TGGGATACAGACACCC | 5 | 18253 | 18268 | 1505 |
| 849209 | N/A | N/A | TAAAAGACTCCATGCC | 0 | 19151 | 19166 | 1506 |
| 849225 | N/A | N/A | GCAATTACACCAGCAA | 84 | 19497 | 19512 | 1507 |
| 849241 | N/A | N/A | GCACAGAGTGATGGTT | 66 | 19908 | 19923 | 1508 |
| 848400 | 1190 | 1205 | CCCCACAGGCTGGACC | 34 | 20021 | 20036 | 1509 |
| 849257 | N/A | N/A | CTGCACCGGGCATGCG | 0 | 20686 | 20701 | 1510 |
| 849273 | N/A | N/A | CCCTACCATAGCCAGG | 36 | 21118 | 21133 | 1511 |
| 848416 | 1394 | 1409 | CCCCAGGGTCACCGGC | 38 | 21366 | 21381 | 1512 |
| 849289 | N/A | N/A | GCACACAGACACTAAG | 0 | 21914 | 21929 | 1513 |
| 848448 | 1633 | 1648 | AACCAGGCCTCATTGA | 0 | 22126 | 22141 | 1514 |
| 848464 | 1735 | 1750 | GCTGACCATACAGTCC | 9 | 22517 | 22532 | 1515 |
| 849305 | N/A | N/A | CTATCCTGTAGCATCA | 73 | 23060 | 23075 | 1516 |
| 849321 | N/A | N/A | GACGGAAATGGGAATC | 0 | 23458 | 23473 | 1517 |
| 848480 | 1875 | 1890 | GGCAGACCAGCTTGCC | 0 | 23495 | 23510 | 1518 |
| 848494 | 1991 | 2006 | GGTCCCCATGCTGGCC | 0 | 23611 | 23626 | 1519 |
| 849337 | N/A | N/A | TAGCACTCATCATTTC | 33 | 24098 | 24113 | 1520 |
| 849353 | N/A | N/A | GACGAGAATCAACTCT | 6 | 24383 | 24398 | 1521 |
| 849369 | N/A | N/A | CACCAGGACTCCTGTG | 4 | 25209 | 25224 | 1522 |
| 848510 | 2074 | 2089 | GGCTTGTGGGTGCCAA | 15 | 25405 | 25420 | 1523 |
| 849385 | N/A | N/A | CTCCAAGTGGAGTGGG | 0 | 25786 | 25801 | 1524 |
| 849401 | N/A | N/A | ACTAAAATAGATGCTC | 34 | 26469 | 26484 | 1525 |
| 849417 | N/A | N/A | TGCCAGAGCCCGAGGA | 0 | 27352 | 27367 | 1526 |
| 848526 | 2259 | 2274 | GGGCACTGCAGCCAGT | 0 | 27402 | 27417 | 1527 |
| 848542 | 2500 | 2515 | GACAAGTCGGAACCAT | 77 | 27643 | 27658 | 1528 |
| 848558 | 2598 | 2613 | GGCAAGGAGGCTGCCC | 0 | 27741 | 27756 | 1529 |

TABLE 20-continued

Inhibition of PCSK9 mRNA by 3-10-3 cEt gapmers targeting SEQ ID NO: 1 and 2

| ISIS No | SEQ ID: 1 Start Site | SEQ ID: 1 Stop Site | Sequence | % inhibition | SEQ ID: 2 Start Site | SEQ ID 2: Stop Site | SEQ ID NO |
|---|---|---|---|---|---|---|---|
| 848574 | 2711 | 2726 | GCAGCACCCGAGCACA | 70 | 27854 | 27869 | 1530 |
| 848589 | 2756 | 2771 | TAAAAGTCATTCTGCC | 56 | 27899 | 27914 | 1531 |
| 848605 | 2781 | 2796 | TGCCTGGCACGGAACA | 44 | 27924 | 27939 | 1532 |
| 848621 | 2915 | 2930 | AGTTAGCTGGAGATGA | 0 | 28058 | 28073 | 1533 |
| 848636 | 3027 | 3042 | ACCAAGGCACAGCCTG | 70 | 28170 | 28185 | 1534 |
| 848651 | 3121 | 3136 | TGCCGAGTCAGTCCTA | 69 | 28264 | 28279 | 1535 |
| 848667 | 3163 | 3178 | GTGGAGCGGGTTGGCT | 26 | 28306 | 28321 | 1536 |
| 848682 | 3225 | 3240 | CCCTCTGGTTCCAGGT | 23 | 28368 | 28383 | 1537 |
| 848698 | 3259 | 3274 | TCAGTTCCTGCTGTGT | 30 | 28402 | 28417 | 1538 |
| 848714 | 3311 | 3326 | GTGAAGTAAGAAGAGG | 47 | 28454 | 28469 | 1539 |
| 848730 | 3385 | 3400 | ACTCACCGAGCTTCCT | 63 | 28528 | 28543 | 1540 |
| 848746 | 3469 | 3484 | TTAGAAGCATCTCCGC | 44 | 28612 | 28627 | 1541 |
| 848761 | 3569 | 3584 | GGCAACAGAGAGGACA | 79 | 28712 | 28727 | 1542 |
| 848777 | 3666 | 3681 | TAAAAAGTCACCATAT | 9 | 28809 | 28824 | 1543 |

Example 2

Dose-Dependent Antisense Inhibition of Human PCSK9 in HepG2 Cells by 3-10-3 cEt Gapmers Select gapmers from Example 1 exhibiting in vitro inhibition of PCSK9 mRNA were tested at various doses in HepG2 cells. The antisense oligonucleotides were tested in a series of experiments that had similar culture conditions. The results for each experiment are presented in separate tables shown below.

Study 1

Cells were plated at a density of 20,000 cells per well and transfected using electroporation with 46.88 nM, 187.5 nM, 750 nM, and 3,000 nM concentrations of antisense oligonucleotide, as specified in the Tables below. ISIS 405879, previously disclosed in WO2008066776 was also included in the study as a benchmark oligonucleotide. After a treatment period of approximately 16 hours, RNA was isolated from the cells and PCSK9 mRNA levels were measured by quantitative real-time PCR. Human PCSK9 primer probe set from ABI (ID #Hs03037355_ml) was used to measure mRNA levels. PCSK9 mRNA levels were adjusted according to total RNA content, as measured by RIBOGREEN®. Results are presented as percent inhibition of PCSK9, relative to untreated control cells.

The half maximal inhibitory concentration ($IC_{50}$) of each oligonucleotide is also presented. PCSK9 mRNA levels were reduced in a dose-dependent manner in antisense oligonucleotide treated cells. Several of the newly designed antisense oligonucleotides demonstrated superior efficacy compared to the previously disclosed oligonucleotide, ISIS 405879. Specifically, ISIS 848542, ISIS 848593, ISIS 848597, ISIS 848598, ISIS 848630, ISIS 848833, ISIS 849040, ISIS 849171, and ISIS 849236 demonstrated superior efficacy compared to the previously disclosed oligonucleotide, ISIS 405879

TABLE 21

| ISIS No | 46.875 nM | 187.5 nM | 750 nM | 3,000 nM | $IC_{50}$ (µM) |
|---|---|---|---|---|---|
| 405879 | 13 | 6 | 3 | 29 | >3.00 |
| 466847 | 1 | 19 | 65 | 94 | 0.47 |
| 468497 | 12 | 27 | 60 | 83 | 0.48 |
| 848219 | 0 | 0 | 54 | 88 | 0.91 |
| 848241 | 0 | 5 | 31 | 63 | 1.78 |
| 848283 | 18 | 27 | 54 | 85 | 0.48 |
| 848306 | 0 | 19 | 53 | 91 | 0.62 |
| 848323 | 0 | 0 | 0 | 50 | >3.00 |
| 848376 | 0 | 3 | 12 | 43 | >3.00 |
| 848430 | 0 | 30 | 52 | 81 | 0.62 |
| 848431 | 67 | 79 | 92 | 96 | <0.05 |
| 848500 | 6 | 30 | 55 | 82 | 0.54 |
| 848539 | 0 | 0 | 0 | 55 | >3.00 |
| 848542 | 10 | 30 | 66 | 86 | 0.41 |
| 848560 | 12 | 32 | 76 | 91 | 0.33 |
| 848567 | 0 | 1 | 42 | 89 | 0.85 |
| 848570 | 23 | 27 | 67 | 87 | 0.35 |
| 848572 | 18 | 44 | 71 | 81 | 0.30 |
| 848574 | 0 | 5 | 68 | 95 | 0.55 |
| 848575 | 0 | 17 | 51 | 80 | 0.75 |
| 848576 | 11 | 18 | 45 | 74 | 0.86 |
| 848583 | 3 | 18 | 62 | 88 | 0.52 |
| 848584 | 0 | 22 | 54 | 89 | 0.57 |
| 848585 | 1 | 22 | 67 | 92 | 0.45 |
| 848593 | 0 | 25 | 53 | 83 | 0.63 |
| 848596 | 18 | 40 | 76 | 93 | 0.26 |
| 848597 | 22 | 42 | 78 | 87 | 0.24 |
| 848598 | 0 | 18 | 62 | 95 | 0.53 |
| 848616 | 0 | 14 | 55 | 88 | 0.66 |
| 848618 | 0 | 0 | 56 | 77 | 0.96 |
| 848619 | 3 | 7 | 41 | 74 | 1.07 |
| 848629 | 21 | 34 | 78 | 78 | 0.31 |

TABLE 21-continued

| ISIS No | 46.875 nM | 187.5 nM | 750 nM | 3,000 nM | IC$_{50}$ (µM) |
|---|---|---|---|---|---|
| 848630 | 7 | 22 | 65 | 83 | 0.50 |
| 848632 | 25 | 34 | 68 | 89 | 0.29 |
| 848635 | 0 | 0 | 49 | 83 | 0.92 |
| 848636 | 5 | 34 | 77 | 76 | 0.42 |
| 848649 | 5 | 10 | 43 | 78 | 0.89 |
| 848651 | 4 | 0 | 48 | 88 | 0.88 |
| 848652 | 0 | 6 | 28 | 80 | 1.16 |
| 848656 | 1 | 13 | 52 | 80 | 0.73 |
| 848670 | 0 | 38 | 84 | 85 | 0.39 |
| 848671 | 26 | 28 | 70 | 81 | 0.34 |
| 848672 | 0 | 11 | 27 | 73 | 1.37 |
| 848674 | 36 | 31 | 69 | 89 | 0.24 |
| 848677 | 2 | 32 | 69 | 90 | 0.41 |
| 848679 | 0 | 11 | 55 | 81 | 0.73 |
| 848680 | 11 | 20 | 64 | 81 | 0.52 |
| 848685 | 0 | 14 | 33 | 62 | 1.63 |
| 848687 | 0 | 25 | 63 | 90 | 0.51 |
| 848688 | 0 | 23 | 61 | 89 | 0.55 |
| 848690 | 15 | 21 | 78 | 84 | 0.39 |
| 848692 | 31 | 45 | 80 | 97 | 0.17 |
| 848693 | 8 | 23 | 69 | 88 | 0.44 |
| 848694 | 27 | 43 | 75 | 93 | 0.21 |
| 848701 | 0 | 10 | 39 | 77 | 1.02 |
| 848704 | 11 | 5 | 43 | 78 | 0.94 |
| 848725 | 0 | 9 | 51 | 81 | 0.79 |
| 848729 | 26 | 33 | 63 | 92 | 0.30 |
| 848731 | 0 | 15 | 60 | 89 | 0.55 |
| 848732 | 12 | 71 | 67 | 90 | 0.21 |
| 848736 | 6 | 18 | 40 | 73 | 1.00 |
| 848740 | 2 | 18 | 59 | 86 | 0.57 |
| 848748 | 9 | 42 | 60 | 85 | 0.39 |
| 848756 | 3 | 1 | 55 | 85 | 0.72 |
| 848759 | 18 | 37 | 75 | 94 | 0.28 |
| 848761 | 20 | 35 | 68 | 81 | 0.35 |
| 848764 | 0 | 8 | 37 | 64 | 1.52 |
| 848770 | 0 | 4 | 63 | 90 | 0.63 |
| 848771 | 3 | 23 | 57 | 93 | 0.50 |
| 848772 | 15 | 32 | 66 | 82 | 0.40 |
| 848774 | 0 | 8 | 64 | 90 | 0.61 |
| 848790 | 0 | 0 | 33 | 73 | 1.49 |
| 848795 | 9 | 42 | 62 | 91 | 0.35 |
| 848811 | 7 | 5 | 46 | 86 | 0.75 |
| 848814 | 17 | 20 | 64 | 89 | 0.43 |
| 848826 | 7 | 57 | 77 | 93 | 0.24 |
| 848830 | 0 | 35 | 45 | 86 | 0.62 |
| 848832 | 0 | 40 | 71 | 78 | 0.52 |
| 848833 | 19 | 43 | 68 | 81 | 0.32 |
| 848838 | 0 | 36 | 72 | 89 | 0.39 |
| 848841 | 5 | 24 | 62 | 86 | 0.50 |
| 848844 | 0 | 22 | 61 | 89 | 0.53 |
| 848849 | 9 | 48 | 79 | 92 | 0.26 |
| 848850 | 0 | 38 | 68 | 97 | 0.43 |
| 848854 | 2 | 7 | 58 | 84 | 0.66 |
| 848875 | 3 | 17 | 58 | 79 | 0.65 |
| 848890 | 0 | 6 | 27 | 65 | 1.74 |
| 848898 | 7 | 14 | 79 | 87 | 0.43 |
| 848927 | 12 | 25 | 75 | 95 | 0.35 |
| 848928 | 0 | 0 | 45 | 78 | 1.01 |
| 848971 | 0 | 21 | 54 | 82 | 0.65 |
| 848999 | 6 | 29 | 34 | 64 | 1.38 |
| 849007 | 0 | 4 | 41 | 78 | 1.02 |
| 849008 | 0 | 39 | 74 | 90 | 0.42 |
| 849013 | 4 | 17 | 47 | 86 | 0.67 |
| 849016 | 0 | 23 | 56 | 79 | 0.65 |
| 849020 | 0 | 13 | 40 | 67 | 1.28 |
| 849021 | 10 | 34 | 65 | 80 | 0.44 |
| 849030 | 2 | 28 | 58 | 86 | 0.52 |
| 849036 | 2 | 1 | 37 | 76 | 1.16 |
| 849040 | 28 | 55 | 79 | 96 | 0.15 |
| 849044 | 26 | 39 | 72 | 91 | 0.28 |
| 849048 | 0 | 30 | 60 | 79 | 0.61 |
| 849069 | 12 | 12 | 40 | 74 | 1.02 |
| 849071 | 2 | 31 | 65 | 92 | 0.42 |
| 849084 | 0 | 0 | 0 | 43 | >3.00 |
| 849085 | 20 | 39 | 64 | 89 | 0.31 |
| 849086 | 13 | 40 | 69 | 81 | 0.36 |
| 849106 | 20 | 24 | 55 | 80 | 0.53 |
| 849120 | 0 | 15 | 61 | 80 | 0.64 |
| 849123 | 9 | 48 | 82 | 84 | 0.27 |
| 849133 | 0 | 0 | 29 | 70 | 1.62 |
| 849135 | 25 | 54 | 79 | 95 | 0.17 |
| 849162 | 0 | 4 | 35 | 75 | 1.19 |
| 849169 | 34 | 63 | 72 | 83 | 0.12 |
| 849171 | 9 | 60 | 63 | 83 | 0.30 |
| 849177 | 0 | 16 | 69 | 75 | 0.68 |
| 849178 | 0 | 22 | 53 | 83 | 0.65 |
| 849181 | 6 | 8 | 39 | 84 | 0.86 |
| 849189 | 24 | 44 | 81 | 90 | 0.21 |
| 849200 | 0 | 0 | 34 | 70 | 1.48 |
| 849205 | 7 | 29 | 51 | 88 | 0.52 |
| 849216 | 0 | 15 | 28 | 66 | 1.66 |
| 849225 | 23 | 47 | 78 | 94 | 0.21 |
| 849227 | 7 | 35 | 74 | 94 | 0.34 |
| 849233 | 9 | 42 | 68 | 93 | 0.32 |
| 849236 | 0 | 1 | 57 | 88 | 0.73 |
| 849239 | 18 | 38 | 74 | 86 | 0.30 |
| 849266 | 0 | 22 | 66 | 86 | 0.51 |
| 849267 | 18 | 69 | 72 | 94 | 0.17 |
| 849285 | 3 | 18 | 45 | 84 | 0.71 |
| 849288 | 0 | 0 | 0 | 52 | >3.00 |
| 849303 | 18 | 33 | 57 | 72 | 0.54 |
| 849305 | 25 | 28 | 62 | 82 | 0.40 |
| 849309 | 10 | 18 | 59 | 82 | 0.57 |
| 849331 | 0 | 10 | 65 | 93 | 0.57 |
| 849332 | 0 | 0 | 48 | 76 | 1.09 |
| 849345 | 0 | 0 | 62 | 80 | 0.78 |
| 849354 | 0 | 0 | 43 | 64 | 1.49 |
| 849357 | 5 | 21 | 45 | 75 | 0.84 |
| 849358 | 0 | 10 | 45 | 79 | 0.88 |
| 849359 | 3 | 22 | 46 | 88 | 0.62 |
| 849372 | 0 | 15 | 29 | 82 | 1.04 |
| 849383 | 2 | 0 | 33 | 71 | 1.43 |
| 849386 | 11 | 18 | 51 | 84 | 0.60 |

Study 2

Cells were plated at a density of 20,000 cells per well and transfected using electroporation with 78.13 nM, 312.5 nM, 1,250 nM, and 5,000 nM concentrations of antisense oligonucleotide, as specified in the Tables below. ISIS 431131, previously disclosed in WO2014179620, was also included in the study as a benchmark oligonucleotide. After a treatment period of approximately 16 hours, RNA was isolated from the cells and PCSK9 mRNA levels were measured by quantitative real-time PCR. Human PCSK9 primer probe set from ABI (ID #Hs03037355_m1) was used to measure mRNA levels. PCSK9 mRNA levels were adjusted according to total RNA content, as measured by RIBOGREEN®. Results are presented as percent inhibition of PCSK9, relative to untreated control cells.

The half maximal inhibitory concentration (IC$_{50}$) of each oligonucleotide is also presented. PCSK9 mRNA levels were reduced in a dose-dependent manner in antisense oligonucleotide treated cells. Several of the newly designed antisense oligonucleotides demonstrated superior efficacy compared to the previously disclosed oligonucleotide, ISIS 431131

TABLE 22

| ISIS No | 78.125 nM | 312.5 nM | 1,250 nM | 5,000 nM | IC$_{50}$ (µM) |
|---|---|---|---|---|---|
| 431131 | 18 | 16 | 30 | 55 | >5 |
| 849169 | 23 | 57 | 86 | 92 | 0.28 |
| 859341 | 24 | 48 | 69 | 85 | 1.54 |
| 859346 | 27 | 54 | 80 | 94 | 0.27 |
| 859358 | 0 | 30 | 69 | 89 | 0.76 |

TABLE 22-continued

| ISIS No | 78.125 nM | 312.5 nM | 1,250 nM | 5,000 nM | IC$_{50}$ (µM) |
|---|---|---|---|---|---|
| 859361 | 28 | 53 | 73 | 94 | 0.30 |
| 859363 | 38 | 50 | 79 | 82 | 0.20 |
| 859384 | 19 | 59 | 76 | 94 | 0.30 |
| 859387 | 36 | 66 | 79 | 96 | 0.16 |
| 859392 | 14 | 33 | 63 | 81 | 0.96 |
| 859393 | 20 | 59 | 90 | 96 | 0.27 |
| 859394 | 43 | 65 | 80 | 96 | 0.12 |
| 859395 | 37 | 51 | 82 | 91 | 0.21 |
| 859401 | 27 | 64 | 88 | 94 | 0.20 |
| 859408 | 0 | 59 | 61 | 92 | 0.55 |
| 859419 | 22 | 58 | 77 | 84 | 0.31 |
| 859459 | 33 | 55 | 91 | 93 | 0.19 |
| 859462 | 31 | 56 | 78 | 96 | 0.24 |
| 859469 | 26 | 48 | 76 | 83 | 0.36 |
| 859472 | 19 | 35 | 67 | 87 | 0.56 |
| 859504 | 19 | 47 | 59 | 80 | 0.57 |
| 859529 | 19 | 50 | 88 | 94 | 0.32 |
| 859531 | 33 | 52 | 76 | 69 | 0.29 |
| 859532 | 24 | 55 | 79 | 90 | 0.30 |
| 859533 | 9 | 40 | 77 | 91 | 0.51 |
| 859534 | 25 | 49 | 85 | 85 | 0.70 |
| 859551 | 25 | 41 | 51 | 78 | 0.69 |
| 859552 | 0 | 17 | 53 | 78 | 1.36 |
| 859553 | 24 | 45 | 79 | 94 | 0.35 |
| 859561 | 28 | 54 | 71 | 92 | 0.30 |
| 859571 | 35 | 34 | 76 | 73 | 0.43 |
| 859584 | 19 | 51 | 85 | 95 | 0.32 |
| 859598 | 33 | 55 | 73 | 83 | 0.25 |
| 859601 | 23 | 39 | 63 | 90 | 0.50 |
| 859603 | 0 | 6 | 70 | 71 | 1.25 |
| 859605 | 9 | 42 | 67 | 83 | 0.62 |
| 859611 | 21 | 22 | 47 | 76 | 1.16 |

Example 3

Tolerability of 3'-Conjugated 3-10-3 cEt Gapmers Targeting Human PCSK9 in BALB/c Mice ISIS oligonucleotides selected from the studies above were conjugated with 3'-THA-C6-GalNAc3-(3R,5S)-5-(hydroxymethyl) pyrrolidin-3-ol phosphate endcap (henceforth referred to as 3'-THA). The hundred and sixty two 3'-THA-conjugated ISIS antisense oligonucleotides evaluated for changes in the levels of plasma chemistry markers are presented in the Table below. 'Parent Oligo' indicates the ISIS oligonucleotide that has been described in the studies above and that was conjugated with 3'-THA and tested in this study.

TABLE 23

3'-conjugated 3-10-3 cEt gapmers selected for tolerability evaluation in BALB/c mice

| ISIS No | Parent Oligo | SEQ ID NO |
|---|---|---|
| 863413 | 466847 | 1096 |
| 863415 | 848219 | 1390 |
| 863416 | 848241 | 777 |
| 863418 | 848306 | 1236 |
| 863419 | 848323 | 1419 |
| 863421 | 848430 | 1357 |
| 863422 | 848431 | 1435 |
| 863423 | 848500 | 905 |
| 863424 | 848539 | 1297 |
| 863425 | 848542 | 1528 |
| 863426 | 848560 | 607 |
| 863427 | 848567 | 1145 |
| 863428 | 848570 | 451 |
| 863429 | 848572 | 1375 |
| 863433 | 848583 | 1223 |
| 863434 | 848584 | 377 |
| 863435 | 848585 | 452 |
| 863436 | 848593 | 763 |
| 863437 | 848596 | 994 |
| 863438 | 848597 | 1071 |
| 863439 | 848598 | 1147 |
| 863440 | 848616 | 379 |
| 863441 | 848618 | 1302 |
| 863442 | 848619 | 1378 |
| 863443 | 848629 | 1073 |
| 863444 | 848630 | 1149 |
| 863445 | 848632 | 455 |
| 863446 | 848635 | 1457 |
| 863447 | 848636 | 1534 |
| 863448 | 848649 | 1380 |
| 863449 | 848651 | 1535 |
| 863451 | 848656 | 844 |
| 863452 | 848670 | 691 |
| 863453 | 848671 | 768 |
| 863457 | 848679 | 458 |
| 863458 | 848680 | 1306 |
| 863464 | 848693 | 384 |
| 863465 | 848694 | 459 |
| 863468 | 848725 | 386 |
| 863472 | 848736 | 926 |
| 863473 | 848740 | 1233 |
| 863474 | 848748 | 619 |
| 863475 | 848756 | 388 |
| 863476 | 848759 | 1387 |
| 863477 | 848761 | 1542 |
| 863478 | 848764 | 697 |
| 863479 | 848770 | 1158 |
| 863480 | 848771 | 1235 |
| 863481 | 848772 | 389 |
| 863482 | 848774 | 1312 |
| 863483 | 848790 | 1240 |
| 863484 | 848795 | 549 |
| 863485 | 848811 | 550 |
| 863486 | 848814 | 781 |
| 863487 | 848826 | 474 |
| 863488 | 848830 | 782 |
| 863489 | 848832 | 939 |
| 863490 | 848833 | 1016 |
| 863491 | 848838 | 1243 |
| 863492 | 848841 | 1474 |
| 863493 | 848844 | 629 |
| 863494 | 848849 | 1017 |
| 863495 | 848850 | 1092 |
| 863496 | 848854 | 1244 |
| 863497 | 848875 | 554 |
| 863498 | 848890 | 478 |
| 863499 | 848898 | 1094 |
| 863500 | 848927 | 871 |
| 863501 | 848928 | 947 |
| 863502 | 848971 | 563 |
| 863503 | 848999 | 1332 |
| 863504 | 849007 | 877 |
| 863505 | 849008 | 953 |
| 863506 | 849013 | 410 |
| 863507 | 849016 | 1411 |
| 863508 | 849020 | 644 |
| 863509 | 849021 | 721 |
| 863510 | 849030 | 1258 |
| 863511 | 849036 | 645 |
| 863512 | 849040 | 955 |
| 863513 | 849044 | 337 |
| 863514 | 849048 | 1413 |
| 863515 | 849069 | 724 |
| 863516 | 849071 | 881 |
| 863517 | 849084 | 648 |
| 863518 | 849085 | 725 |
| 863519 | 849086 | 802 |
| 863520 | 849106 | 1111 |

TABLE 23-continued

3'-conjugated 3-10-3 cEt gapmers selected
for tolerability evaluation in BALB/c mice

| ISIS No | Parent Oligo | SEQ ID NO |
|---|---|---|
| 863521 | 849120 | 960 |
| 863522 | 849123 | 1188 |
| 863523 | 849133 | 728 |
| 863524 | 849135 | 885 |
| 863525 | 849162 | 504 |
| 863526 | 849169 | 1043 |
| 863527 | 849171 | 1195 |
| 863531 | 849189 | 426 |
| 863532 | 849200 | 968 |
| 863533 | 849205 | 427 |
| 863535 | 849225 | 1507 |
| 863536 | 849227 | 585 |
| 863537 | 849233 | 1047 |
| 863538 | 849236 | 353 |
| 863539 | 849239 | 1352 |
| 863540 | 849266 | 1126 |
| 863541 | 849267 | 1203 |
| 863542 | 849285 | 434 |
| 863543 | 849288 | 1436 |
| 863544 | 849303 | 1362 |
| 863545 | 849305 | 1516 |
| 863546 | 849309 | 749 |
| 863547 | 849331 | 1213 |
| 863548 | 849332 | 367 |
| 863549 | 849345 | 1061 |
| 863550 | 849354 | 523 |
| 863551 | 849357 | 754 |
| 863552 | 849358 | 831 |
| 863553 | 849359 | 908 |
| 863554 | 849372 | 678 |
| 863555 | 849383 | 1369 |
| 863556 | 849386 | 526 |
| 884269 | 859561 | 55 |
| 884270 | 859459 | 180 |
| 884271 | 859395 | 164 |
| 884272 | 859603 | 218 |
| 884273 | 859504 | 284 |
| 884274 | 859394 | 87 |
| 884275 | 859598 | 141 |
| 884276 | 859531 | 198 |
| 884277 | 859469 | 28 |
| 884278 | 859346 | 152 |
| 884279 | 859361 | 79 |
| 884280 | 859472 | 276 |

BALB/c mice are a multipurpose mice model, frequently utilized for safety and efficacy testing. The mice were administered a single dose of oligonucleotide. Plasma levels of transaminases were measured using an automated clinical chemistry analyzer (Hitachi Olympus AU400e, Melville, N.Y.). ISIS oligonucleotides that caused changes in the levels of ALT and/or AST outside the expected range for antisense oligonucleotides were excluded in further studies. ISIS 863413, ISIS 863419, ISIS 863424, ISIS 863425, ISIS 863427, ISIS 863433, ISIS 863434, ISIS 863436, ISIS 863437, ISIS 863438, ISIS 863439, ISIS 863441, ISIS 863444, ISIS 863445, ISIS 863448, ISIS 863452, ISIS 863472, ISIS 863473, ISIS 863474, ISIS 863475, ISIS 863477, ISIS 863479, ISIS 863480, ISIS 863481, ISIS 863482, ISIS 863483, ISIS 863484, ISIS 863485, ISIS 863486, ISIS 863489, ISIS 863490, ISIS 863491, ISIS 863493, ISIS 863494, ISIS 863495, ISIS 863496, ISIS 863497, ISIS 863498, ISIS 863499, ISIS 863502, ISIS 863506, ISIS 863507, ISIS 863509, ISIS 863510, ISIS 863511, ISIS 863512, ISIS 863514, ISIS 863516, ISIS 863517, ISIS 863518, ISIS 863520, ISIS 863522, ISIS 863524, ISIS 863525, ISIS 863526, ISIS 863527, ISIS 863531, ISIS 863533, ISIS 863536, ISIS 863537, ISIS 863538, ISIS 863539, ISIS 863541, ISIS 863545, ISIS 863547, ISIS 863548, ISIS 863549, ISIS 863550, ISIS 863552, and ISIS 863553 were considered tolerable in this study and were selected for further evaluation.

Example 4

Effect of Antisense Inhibition of PCSK9 in Transgenic Mouse Model

A transgenic mouse model was developed at UCI using the human PCSK9 genomic construct, which was contained in fosmid ABC7-611722G24 and restricted with Nhe1 to produce a DNA fragment containing the entire genomic sequence as well as 8 Kb of 5' and 0.4 Kb of 3' noncoding sequence. PCSK9 transgenic mice were produced by random insertion via micronucleus injection. Progeny expressed human PCSK9 mRNA in the liver and secreted human PCSK9 plasma protein.

The efficacy of 3'-THA-conjugated ISIS oligonucleotides was evaluated in this model (referred to herein as Tg mice). The ISIS oligonucleotides tested are presented in the Table below. 'Parent ISIS No' indicates the ISIS oligonucleotide that has been described in the studies above and that was conjugated with 3'-THA and tested in this study.

TABLE 24

ISIS oligonucleotides tested in Tg mice

| ISIS No | Sequence | Parent ISIS No | SEQ ID NO |
|---|---|---|---|
| 863413 | GAGGTATCCCCGGCGG | 466847 | 1096 |
| 863419 | GTCTAGGAGATACACC | 848323 | 1419 |
| 863424 | CATTTTAAAGCTCAGC | 848539 | 1297 |
| 863425 | GACAAGTCGGAACCAT | 848542 | 1528 |
| 863427 | TTGAATGGTGAAATGC | 848567 | 1145 |
| 863433 | GGACATCGGCACATTG | 848583 | 1223 |
| 863434 | ACGGACATCGGCACAT | 848584 | 377 |
| 863436 | AGCTCAATAAAAGTCA | 848593 | 763 |
| 863437 | CGGAACAAGAGCTCAA | 848596 | 994 |
| 863438 | ACGGAACAAGAGCTCA | 848597 | 1071 |
| 863439 | CACGGAACAAGAGCTC | 848598 | 1147 |
| 863441 | GATGAGGGCCATCAGC | 848618 | 1302 |
| 863444 | CAGAAAGCTAAGCCTC | 848630 | 1149 |
| 863445 | CTAGATGCCATCCAGA | 848632 | 455 |
| 863448 | TCCTAGGTGATGGCTC | 848649 | 1380 |
| 863452 | GCGAATGTGTACCCTG | 848670 | 691 |
| 863472 | GGAAAAGTTCCATGC | 848736 | 926 |
| 863473 | GTGATAACGGAAAAG | 848740 | 1233 |
| 863474 | TGCCTTAGAAGCATCT | 848748 | 619 |
| 863475 | AAAGATAAATGTCTGC | 848756 | 388 |
| 863477 | GGCAACAGAGAGGACA | 848761 | 1542 |

TABLE 24-continued

ISIS oligonucleotides tested in Tg mice

| ISIS No | Sequence | Parent ISIS No | SEQ ID NO |
|---|---|---|---|
| 863479 | AGCAAAACAGGTCTAG | 848770 | 1158 |
| 863480 | TTCAAGTTACAAAAGC | 848771 | 1235 |
| 863481 | CCCAGAATAAATATCT | 848772 | 389 |
| 863482 | TGCTACAAAACCCAGA | 848774 | 1312 |
| 863483 | CCAAATCGGAACCCAC | 848790 | 1240 |
| 863484 | CGAGAATACCTCCGCC | 848795 | 549 |
| 863485 | GCTGAGTAAGGACTTG | 848811 | 550 |
| 863486 | AGAAAGTCAAAGGCTC | 848814 | 781 |
| 863489 | TACATTTCAGACGGTG | 848832 | 939 |
| 863490 | AATAATCTCATGTCAG | 848833 | 1016 |
| 863491 | AGGCAGTAATGGGCAA | 848838 | 1243 |
| 863493 | TCATGAATCAAGTCCA | 848844 | 629 |
| 863494 | CAAATTATAGCAGCCA | 848849 | 1017 |
| 863495 | AACAAATTATAGCAGC | 848850 | 1092 |
| 863496 | TCCAACACTGAGGACC | 848854 | 1244 |
| 863497 | CTACAAATGCAGGCAG | 848875 | 554 |
| 863498 | CTCGACAACAGGTTTT | 848890 | 478 |
| 863499 | ACCAAATGCGGACCAA | 848898 | 1094 |
| 863502 | GCAATTCGGTTTGTCC | 848971 | 563 |
| 863506 | GGAAAGGAACAGGCTC | 849013 | 410 |
| 863507 | CTCCACTGAAGAGGTC | 849016 | 1411 |
| 863509 | GACAATGAAGAGGAGA | 849021 | 721 |
| 863510 | GTTAAGAGTGCAGGGT | 849030 | 1258 |
| 863511 | ACAGAGAAATGCATGC | 849036 | 645 |
| 863512 | GTTATTATTGAATGGT | 849040 | 955 |
| 863514 | GTTAATAATGCCCCCG | 849048 | 1413 |
| 863516 | ACAACTGGATACATTG | 849071 | 881 |
| 863517 | CAATAGGCATCTACCA | 849084 | 648 |
| 863518 | ACTCATCAATAGGCAT | 849085 | 725 |
| 863520 | CCTCAGGTGGAATCAG | 849106 | 1111 |
| 863522 | GGAGAATAACAGTGAT | 849123 | 1188 |
| 863524 | ATAGACAAGGAAAGGG | 849135 | 885 |
| 863525 | GTCTAGAAAAAGTCCT | 849162 | 504 |
| 863526 | AGGAAAGTCTCAGGGC | 849169 | 1043 |
| 863527 | CTGTAGGAAAGTCTCA | 849171 | 1195 |
| 863531 | ACAGCTGCTAGTTATT | 849189 | 426 |
| 863533 | TGCTACTGTCAACAGT | 849205 | 427 |
| 863536 | GGAAGATATTAGCAAT | 849227 | 585 |
| 863537 | GCGGATTTCAGACTTG | 849233 | 1047 |
| 863538 | CAACATCAAATTCTGC | 849236 | 353 |
| 863539 | GAAGACGGAGTAAGGC | 849239 | 1352 |
| 863541 | TTCTAAGTGCCACGGG | 849267 | 1203 |
| 863545 | CTATCCTGTAGCATCA | 849305 | 1516 |
| 863547 | GGAGAAGTAAGGTCAC | 849331 | 1213 |
| 863548 | AGGAGAAGTAAGGTCA | 849332 | 367 |
| 863549 | ATTTTAAAGCAACGGG | 849345 | 1061 |
| 863550 | CCTACATGCCAGCCTG | 849354 | 523 |
| 863552 | TCTGAACATGGTAGGG | 849358 | 831 |
| 863553 | GTAAGATGGAAAGAGA | 849359 | 908 |

Treatment

PCSK9 transgenic mice were maintained on a 12-hour light/dark cycle and were fed ad libitum normal Purina mouse chow. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

The PCSK9 transgenic mice received subcutaneous injections of ISIS oligonucleotide at a dose of 2.5 mg/kg twice per week for 2 weeks. Two groups of mice received subcutaneous injections of PBS for 2 weeks. The saline-injected groups served as the control group to which oligonucleotide-treated groups were compared.

Plasma Chemistry Markers

To evaluate the effect of ISIS oligonucleotides on liver and kidney function of these mice, plasma levels of transaminases (ALT and AST), cholesterol (CHOL), HDL cholesterol (HDL), LDL cholesterol (LDL), and triglycerides (TRIG) were measured on day 12 using an automated clinical chemistry analyzer (Hitachi Olympus AU400e, Melville, N.Y.). The results are presented in the Table below. ISIS oligonucleotides that caused changes in the levels of any of the liver or kidney function markers outside the expected range for antisense oligonucleotides were excluded in further studies.

TABLE 25

Plasma chemistry markers in Tg mice plasma

| Treatment | ALT (IU/L) | AST (IU/L) | CHOL (mg/dL) | HDL (mg/dL) | LDL (mg/dL) | TRIG (mg/dL) |
|---|---|---|---|---|---|---|
| PBS | 17 | 37 | 114 | 73 | 35 | 65 |
| PBS | 23 | 102 | 105 | 68 | 32 | 76 |
| 863413 | 19 | 72 | 122 | 88 | 24 | 89 |
| 863419 | 15 | 44 | 115 | 73 | 31 | 104 |
| 863424 | 18 | 34 | 197 | 112 | 79 | 105 |
| 863425 | 25 | 53 | 143 | 101 | 36 | 104 |
| 863427 | 22 | 96 | 113 | 75 | 28 | 127 |
| 863433 | 17 | 54 | 92 | 67 | 19 | 61 |
| 863434 | 24 | 36 | 132 | 98 | 35 | 102 |

TABLE 25-continued

Plasma chemistry markers in Tg mice plasma

| Treatment | ALT (IU/L) | AST (IU/L) | CHOL (mg/dL) | HDL (mg/dL) | LDL (mg/dL) | TRIG (mg/dL) |
|---|---|---|---|---|---|---|
| 863436 | 17 | 50 | 124 | 81 | 31 | 96 |
| 863437 | 21 | 69 | 126 | 91 | 30 | 81 |
| 863438 | 18 | 66 | 57 | 39 | 15 | 54 |
| 863439 | 42 | 173 | 111 | 78 | 22 | 107 |
| 863441 | 20 | 57 | 84 | 58 | 20 | 56 |
| 863444 | 19 | 41 | 149 | 101 | 42 | 116 |
| 863445 | 20 | 36 | 169 | 111 | 48 | 111 |
| 863448 | 24 | 44 | 107 | 69 | 29 | 79 |
| 863452 | 20 | 67 | 114 | 78 | 23 | 100 |
| 863472 | 35 | 55 | 105 | 71 | 26 | 89 |
| 863473 | 23 | 67 | 152 | 105 | 38 | 130 |
| 863474 | 21 | 115 | 118 | 78 | 32 | 45 |
| 863475 | 23 | 87 | 179 | 112 | 62 | 92 |
| 863477 | 67 | 142 | 222 | 137 | 73 | 69 |
| 863479 | 29 | 60 | 142 | 96 | 32 | 90 |
| 863480 | 19 | 52 | 122 | 88 | 25 | 53 |
| 863481 | 28 | 50 | 223 | 132 | 70 | 115 |
| 863482 | 20 | 43 | 168 | 105 | 46 | 129 |
| 863483 | 19 | 34 | 174 | 110 | 47 | 139 |
| 863484 | 25 | 71 | 64 | 38 | 21 | 66 |
| 863485 | 19 | 71 | 170 | 113 | 42 | 110 |
| 863486 | 18 | 40 | 117 | 78 | 28 | 121 |
| 863489 | 38 | 68 | 90 | 66 | 18 | 89 |
| 863490 | 19 | 41 | 99 | 71 | 19 | 113 |
| 863491 | 20 | 40 | 148 | 99 | 35 | 146 |
| 863493 | 18 | 74 | 107 | 73 | 26 | 59 |
| 863494 | 19 | 41 | 149 | 106 | 32 | 104 |
| 863495 | 17 | 34 | 136 | 95 | 32 | 116 |
| 863496 | 545 | 275 | 136 | 97 | 31 | 29 |
| 863497 | 36 | 49 | 121 | 84 | 28 | 53 |
| 863498 | 23 | 44 | 181 | 122 | 42 | 98 |
| 863499 | 21 | 51 | 128 | 102 | 18 | 58 |
| 863502 | 34 | 144 | 116 | 84 | 22 | 86 |
| 863506 | 30 | 44 | 188 | 119 | 51 | 108 |
| 863507 | 19 | 46 | 108 | 78 | 18 | 100 |
| 863509 | 23 | 63 | 121 | 80 | 28 | 115 |
| 863510 | 40 | 71 | 149 | 111 | 28 | 51 |
| 863511 | 31 | 61 | 101 | 70 | 23 | 83 |
| 863512 | 21 | 52 | 83 | 59 | 14 | 103 |
| 863514 | 22 | 65 | 99 | 69 | 23 | 64 |
| 863516 | 18 | 52 | 117 | 73 | 33 | 122 |
| 863517 | 25 | 98 | 113 | 74 | 27 | 125 |
| 863518 | 35 | 116 | 96 | 65 | 23 | 70 |
| 863520 | 21 | 102 | 107 | 68 | 31 | 76 |
| 863522 | 31 | 55 | 89 | 56 | 24 | 77 |
| 863524 | 49 | 61 | 154 | 104 | 43 | 94 |
| 863525 | 20 | 58 | 208 | 116 | 66 | 155 |
| 863526 | 32 | 82 | 159 | 114 | 37 | 59 |
| 863527 | 25 | 112 | 98 | 66 | 23 | 101 |
| 863531 | 835 | 454 | 268 | 149 | 67 | 84 |
| 863533 | 0 | 109 | 276 | 152 | 80 | 98 |
| 863536 | 22 | 68 | 120 | 75 | 28 | 181 |
| 863537 | 29 | 102 | 134 | 97 | 27 | 52 |
| 863538 | 16 | 42 | 126 | 76 | 39 | 89 |
| 863539 | 22 | 53 | 100 | 65 | 25 | 64 |
| 863541 | 19 | 41 | 98 | 66 | 23 | 115 |
| 863545 | 28 | 53 | 109 | 73 | 25 | 114 |
| 863547 | 22 | 41 | 119 | 80 | 30 | 71 |
| 863548 | 550 | 433 | 188 | 125 | 33 | 60 |
| 863549 | 17 | 36 | 109 | 70 | 33 | 72 |
| 863550 | 32 | 62 | 158 | 98 | 43 | 77 |
| 863552 | 18 | 55 | 113 | 71 | 33 | 79 |
| 863553 | 18 | 43 | 103 | 62 | 30 | 86 |

Example 5

Tolerability of ISIS Oligonucleotides Targeting Human PCSK9 in CD1 Mice

ISIS oligonucleotides selected from the studies above were conjugated with 5'-Trishexylamino-(THA)-C6GalNAC3 endcap (henceforth referred to as 5'-THA). CD1® mice (Charles River, Mass.) are a multipurpose mice model, frequently utilized for safety and efficacy testing. The mice were treated with ISIS antisense oligonucleotides, selected from studies described above and conjugated with 5'-THA, and evaluated for changes in the levels of various plasma chemistry markers.

Study 1

Treatment

Groups of male CD1 mice were injected subcutaneously once a week for 6 weeks with 15 mg/kg of ISIS oligonucleotides. One group of male CD1 mice was injected subcutaneously once a week for 6 weeks with PBS. Mice were euthanized 48 hours after the last dose, and organs and plasma were harvested for further analysis.

The ISIS oligonucleotides tested are presented in the Table below. 'Unconjugated parent ISIS No.' refers to the ISIS oligonucleotide described in the in vitro studies above with the same sequence. '3'-THA counterpart ISIS No.' refers to the 3'THA conjugated oligonucleotide with the same sequence and evaluated in the transgenic mice study above.

TABLE 26

ISIS oligonucleotides tested in CD1 mice tolerability study

| ISIS No. | Unconjugated parent ISIS No. | 3'-THA counterpart ISIS No | Sequence | SEQ ID NO |
|---|---|---|---|---|
| 863576 | 848583 | 863433 | GGACATCGGCACATTG | 1223 |
| 863633 | 848833 | 863490 | AATAATCTCATGTCAG | 1016 |
| 863655 | 849040 | 863512 | GTTATTATTGAATGGT | 955 |
| 863670 | 849171 | 863527 | CTGTAGGAAAGTCTCA | 1195 |
| 863681 | 849236 | 863538 | CAACATCAAATTCTGC | 353 |

Plasma Chemistry Markers

To evaluate the effect of ISIS oligonucleotides on liver and kidney function, plasma levels of transaminases, bilirubin, creatinine, and BUN were measured using an automated clinical chemistry analyzer (Hitachi Olympus AU400e, Melville, N.Y.). The results are presented in the Table below. Treatment with the ISIS oligonucleotides did not cause any changes in the levels of any of the liver or kidney function markers outside the expected range for antisense oligonucleotides.

TABLE 27

Plasma chemistry markers in CD1 mice plasma at Day 45

|  | ALT (IU/L) | AST (IU/L) | ALB (g/dL) | BUN (mg/dL) | CRE (mg/dL) | TBIL (mg/dL) |
| --- | --- | --- | --- | --- | --- | --- |
| PBS | 25 | 41 | 2.6 | 20.1 | 0.07 | 0.13 |
| ISIS 863576 | 125 | 134 | 2.8 | 24.5 | 0.10 | 0.14 |

TABLE 27-continued

Plasma chemistry markers in CD1 mice plasma at Day 45

|  | ALT (IU/L) | AST (IU/L) | ALB (g/dL) | BUN (mg/dL) | CRE (mg/dL) | TBIL (mg/dL) |
| --- | --- | --- | --- | --- | --- | --- |
| ISIS 863633 | 35 | 60 | 2.6 | 21.8 | 0.10 | 0.14 |
| ISIS 863655 | 77 | 84 | 2.4 | 20.0 | 0.06 | 0.13 |
| ISIS 863670 | 25 | 61 | 2.7 | 22.5 | 0.09 | 0.15 |
| ISIS 863681 | 27 | 47 | 2.8 | 26.5 | 0.12 | 0.14 |

Hematology Assays

Blood obtained from all mice groups were analyzed for RBC, WBC, platelets, neutrophils, lymphocytes, and monocyte counts, as well as hemoglobin, HCT and MCV levels. The results are presented in the Table below. Treatment with the ISIS oligonucleotides did not cause any changes in the levels of any of the hematology markers outside the expected range for antisense oligonucleotides.

TABLE 28

Blood cell count in CD1 mice at Day 45

|  | RBC ($\times 10^6/\mu L$) | Platelets ($\times 10^3/\mu L$) | WBC ($\times 10^3/\mu L$) | Neutrophils ($\times 10^3/\mu L$) | Lymphocytes ($\times 10^3/\mu L$) | Monocytes ($\times 10^3/\mu L$) |
| --- | --- | --- | --- | --- | --- | --- |
| PBS | 9.0 | 1288 | 11.3 | 12.6 | 9128 | 515 |
| 863576 | 8.3 | 1251 | 9.4 | 18.8 | 6643 | 316 |
| 863633 | 9.4 | 1338 | 10.1 | 13.5 | 8009 | 698 |
| 863655 | 8.9 | 1320 | 8.0 | 10.0 | 5919 | 473 |
| 863670 | 9.7 | 1335 | 8.3 | 21.3 | 6514 | 402 |
| 863681 | 9.5 | 1329 | 7.6 | 11.0 | 6376 | 310 |

TABLE 29

Hematology markers in CD1 mice at Day 45

|  | Hemoglobin (g/dL) | HCT (%) | MCV (fL) |
| --- | --- | --- | --- |
| PBS | 14.0 | 43 | 48 |
| 863576 | 12.9 | 40 | 48 |
| 863633 | 14.6 | 45 | 49 |
| 863655 | 14.1 | 44 | 50 |
| 863670 | 14.7 | 44 | 46 |
| 863681 | 14.6 | 45 | 47 |

Body and Organ Weight Measurements

To evaluate the effect of ISIS oligonucleotides on the overall health of the animals, body and organ weights were measured. Body weights were measured every week and are presented in the Table below. Organ weights were measured and the data is also presented in the Table below. The results indicate that effect of treatment with antisense oligonucleotides on body and organ weights was within the expected range for antisense oligonucleotides.

TABLE 30

Body weights (g) in CD1 mice

|  | Baseline (day 1) | Week 1 (day 8) | Week 2 (day 15) | Week 3 (day 22) | Week 4 (day 29) | Week 5 (day 36) | Week 6 (day 43) |
| --- | --- | --- | --- | --- | --- | --- | --- |
| PBS | 46 | 48 | 49 | 48 | 50 | 49 | 49 |
| 863576 | 29 | 33 | 35 | 36 | 38 | 38 | 39 |
| 863633 | 27 | 32 | 33 | 34 | 36 | 37 | 39 |
| 863655 | 28 | 33 | 33 | 35 | 37 | 38 | 39 |
| 863670 | 27 | 31 | 32 | 33 | 36 | 36 | 38 |
| 863681 | 28 | 33 | 33 | 35 | 37 | 38 | 40 |

TABLE 31

Organ weights (g) in CD1 mice

|  | Liver | Spleen | Kidney |
|---|---|---|---|
| PBS | 2.25 | 0.16 | 0.63 |
| 863576 | 2.32 | 0.19 | 0.59 |
| 863633 | 2.25 | 0.11 | 0.50 |
| 863655 | 2.55 | 0.15 | 0.61 |
| 863670 | 1.89 | 0.11 | 0.51 |
| 863681 | 2.25 | 0.10 | 0.47 |

Study 2

Treatment

Groups of male CD1 mice were injected subcutaneously once a week for 6 weeks with 15 mg/kg of ISIS oligonucleotides. One group of male CD1 mice was injected subcutaneously once a week for 6 weeks with PBS. Mice were euthanized 48 hours after the last dose, and organs and plasma were harvested for further analysis.

The ISIS oligonucleotides tested are presented in the Table below. 'Unconjugated parent ISIS No.' refers to the ISIS oligonucleotide described in the in vitro studies above with the same sequence. '3'-THA counterpart ISIS No.' refers to the 3'THA conjugated oligonucleotide with the same sequence and described in the transgenic mice study above.

TABLE 32

ISIS oligonucleotides tested in CD1 mice tolerability study

| ISIS No. | Unconjugated parent ISIS No. | 3'-THA counterpart ISIS No | Sequence | SEQ ID NO |
|---|---|---|---|---|
| 863568 | 848542 | 863425 | GACAAGTCGGAACCAT | 1528 |
| 863581 | 848597 | 863438 | ACGGAACAAGAGCTCA | 1071 |
| 863582 | 848598 | 863439 | CACGGAACAAGAGCTC | 1147 |
| 863587 | 848630 | 863444 | CAGAAAGCTAAGCCTC | 1149 |

Plasma Chemistry Markers

To evaluate the effect of ISIS oligonucleotides on liver and kidney function, plasma levels of transaminases, bilirubin, creatinine, and BUN were measured using an automated clinical chemistry analyzer (Hitachi Olympus AU400e, Melville, N.Y.).

The results are presented in the Table below. Treatment with the ISIS oligonucleotides did not cause any changes in the levels of any of the liver or kidney function markers outside the expected range for antisense oligonucleotides.

TABLE 33

Plasma chemistry markers in CD1 mice plasma at Day 45

|  | ALT (IU/L) | AST (IU/L) | ALB (g/dL) | BUN (mg/dL) | CRE (mg/dL) | TBIL (mg/dL) |
|---|---|---|---|---|---|---|
| PBS | 25 | 51 | 2.6 | 25.8 | 0.10 | 0.12 |
| ISIS 863568 | 72 | 67 | 2.6 | 20.4 | 0.10 | 0.14 |
| ISIS 863581 | 74 | 77 | 2.7 | 25.0 | 0.10 | 0.14 |
| ISIS 863582 | 71 | 89 | 2.8 | 24.4 | 0.11 | 0.13 |
| ISIS 863587 | 60 | 60 | 2.5 | 24.6 | 0.11 | 0.10 |

Hematology Assays

Blood obtained from all mice groups were analyzed for RBC, WBC, platelets, neutrophils, lymphocytes, and monocyte counts, as well as hemoglobin, HCT and MCV levels. The results are presented in the Table below. Treatment with the ISIS oligonucleotides did not cause any changes in the levels of any of the hematology markers outside the expected range for antisense oligonucleotides.

TABLE 34

Blood cell count in CD1 mice at Day 45

|  | RBC ($\times 10^6/\mu L$) | Platelets ($\times 10^3/\mu L$) | WBC ($\times 10^3/\mu L$) | Neutrophils ($\times 10^3/\mu L$) | Lymphocytes ($\times 10^3/\mu L$) | Monocytes ($\times 10^3/\mu L$) |
|---|---|---|---|---|---|---|
| PBS | 9.6 | 853 | 3.9 | 12 | 3174 | 129 |
| 863568 | 10.3 | 859 | 7.8 | 15 | 6060 | 347 |
| 863581 | 9.4 | 812 | 8.0 | 17 | 6162 | 359 |

TABLE 34-continued

Blood cell count in CD1 mice at Day 45

| | RBC (× 10⁶/μL) | Platelets (× 10³/μL) | WBC (× 10³/μL) | Neutrophils (× 10³/μL) | Lymphocytes (× 10³/μL) | Monocytes (× 10³/μL) |
|---|---|---|---|---|---|---|
| 863582 | 9.1 | 868 | 10.5 | 21 | 6671 | 713 |
| 863587 | 9.6 | 903 | 9.8 | 10 | 8233 | 344 |

TABLE 35

Hematology markers in CD1 mice at Day 45

| | Hemoglobin (g/dL) | HCT (%) | MCV (fL) |
|---|---|---|---|
| PBS | 14.5 | 44 | 46 |
| 863568 | 16.2 | 47 | 46 |
| 863581 | 14.5 | 43 | 46 |
| 863582 | 13.5 | 41 | 45 |
| 863587 | 15.0 | 45 | 47 |

Body and Organ Weight Measurements

To evaluate the effect of ISIS oligonucleotides on the overall health of the animals, body and organ weights were measured. Body weights were measured every week and are presented in the Table below. Organ weights were measured and the data is also presented in the Table below. The results indicate that effect of treatment with antisense oligonucleotides on body and organ weights was within the expected range for antisense oligonucleotides.

TABLE 36

Body weights (g) in CD1 mice

| | Baseline (day 1) | Week 1 (day 9) | Week 2 (day 16) | Week 3 (day 23) | Week 4 (day 30) | Week 5 (day 37) | Week 6 (day 43) |
|---|---|---|---|---|---|---|---|
| PBS | 30 | 33 | 36 | 36 | 37 | 39 | 39 |
| 863568 | 29 | 32 | 34 | 34 | 36 | 39 | 38 |
| 863581 | 29 | 33 | 35 | 36 | 36 | 39 | 39 |
| 863582 | 31 | 34 | 36 | 36 | 37 | 40 | 41 |
| 863587 | 30 | 35 | 37 | 37 | 39 | 41 | 43 |

TABLE 37

Organ weights (g) in CD1 mice

| | Liver | Spleen | Kidney |
|---|---|---|---|
| PBS | 2.06 | 0.11 | 0.59 |
| 863568 | 2.46 | 0.10 | 0.54 |
| 863581 | 2.23 | 0.13 | 0.56 |
| 863582 | 2.52 | 0.16 | 0.63 |
| 863587 | 2.94 | 0.16 | 0.64 |

Study 3
Treatment

Groups of male CD1 mice were injected subcutaneously once a week for 6 weeks with 5 mg/kg or 15 mg/kg of ISIS oligonucleotides. One group of male CD1 mice was injected subcutaneously once a week for 6 weeks with PBS. Mice were euthanized 48 hours after the last dose, and organs and plasma were harvested for further analysis.

The ISIS oligonucleotides tested are presented in the Table below. 'Unconjugated parent ISIS No.' refers to the ISIS oligonucleotide described in the in vitro studies above with the same sequence. '3'-THA counterpart ISIS No.' refers to the 3'THA conjugated oligonucleotide with the same sequence and described in the transgenic mice study above.

TABLE 38

ISIS oligonucleotides tested in CD1 mice tolerability study

| ISIS No. | Unconjugated parent ISIS No. | 3'-THA counterpart ISIS No | Sequence | SEQ ID NO |
|---|---|---|---|---|
| 845219 | 466847 | 863413 | GAGGTATCCCCGGCGG | 1096 |
| 863577 | 848584 | 863434 | ACGGACATCGGCACAT | 377 |
| 863579 | 848593 | 863436 | AGCTCAATAAAAGTCA | 763 |
| 863637 | 848849 | 863494 | CAAATTATAGCAGCCA | 1017 |
| 863682 | 849239 | 863539 | GAAGACGGAGTAAGGC | 1352 |

Plasma Chemistry Markers

To evaluate the effect of ISIS oligonucleotides on liver and kidney function, plasma levels of transaminases, bilirubin, creatinine, and BUN were measured using an automated clinical chemistry analyzer (Hitachi Olympus AU400e, Melville, N.Y.).

The results are presented in the Table below. ISIS oligonucleotides that caused changes in the levels of any of the liver or kidney function markers outside the expected range for antisense oligonucleotides were excluded in further studies.

TABLE 39

Plasma chemistry markers in CD1 mice plasma at Day 45

| | Dose (mg/kg) | ALT (IU/L) | AST (IU/L) | ALB (g/dL) | BUN (mg/dL) | CRE (mg/dL) | TBIL (mg/dL) |
|---|---|---|---|---|---|---|---|
| PBS | — | 26 | 62 | 2.5 | 19.5 | 0.08 | 0.18 |
| 845219 | 5 | 96 | 64 | 2.4 | 19.3 | 0.08 | 0.15 |
| | 15 | 187 | 115 | 2.3 | 22.0 | 0.07 | 0.17 |
| 863577 | 5 | 176 | 160 | 2.5 | 17.2 | 0.09 | 0.13 |
| | 15 | 621 | 492 | 2.5 | 15.6 | 0.10 | 0.20 |
| 863579 | 5 | 50 | 50 | 2.5 | 19.9 | 0.10 | 0.13 |
| | 15 | 87 | 70 | 2.4 | 20.3 | 0.11 | 0.13 |
| 863637 | 5 | 321 | 301 | 1.7 | 19.3 | 0.05 | 0.19 |
| | 15 | 508 | 472 | 2.4 | 20.5 | 0.09 | 0.22 |
| 863682 | 5 | 306 | 156 | 2.3 | 20.0 | 0.06 | 0.13 |
| | 15 | 373 | 212 | 2.4 | 21.0 | 0.06 | 0.14 |

Hematology Assays

Blood obtained from all mice groups were analyzed for RBC, WBC, platelets, neutrophils, lymphocytes, and monocyte counts, as well as hemoglobin, HCT and MCV levels. The results are presented in the Table below. ISIS oligonucleotides that caused changes in the levels of any of the hematology markers outside the expected range for antisense oligonucleotides were excluded in further studies.

TABLE 40

Blood cell count in CD1 mice at Day 45

| | Dose (mg/kg) | RBC (× 10$^6$/μL) | Platelets (× 10$^3$/μL) | WBC (× 10$^3$/μL) | Neutrophils (× 10$^3$/μL) | Lymphocytes (× 10$^3$/μL) | Monocytes (× 10$^3$/μL) |
|---|---|---|---|---|---|---|---|
| PBS | — | 9.4 | 1218 | 8.8 | 13 | 7078 | 367 |
| 845219 | 5 | 9.4 | 1349 | 7.2 | 13 | 5749 | 444 |
| | 15 | 9.3 | 1263 | 7.2 | 13 | 5664 | 511 |
| 863577 | 5 | 9.2 | 1401 | 8.0 | 17 | 5851 | 650 |
| | 15 | 8.2 | 1299 | 10.0 | 10 | 7718 | 1034 |
| 863579 | 5 | 10.0 | 1252 | 9.0 | 16 | 6876 | 587 |
| | 15 | 9.6 | 1256 | 8.2 | 11 | 6645 | 415 |
| 863637 | 5 | 9.0 | 956 | 5.7 | 14 | 4266 | 448 |
| | 15 | 9.3 | 843 | 6.8 | 13 | 5044 | 696 |
| 863682 | 5 | 9.4 | 1040 | 5.9 | 13 | 4581 | 447 |
| | 15 | 9.0 | 800 | 8.3 | 8 | 6757 | 694 |

TABLE 41

Hematology markers in CD1 mice at Day 45

| | Dose (mg/kg) | Hemoglobin (g/dL) | HCT (%) | MCV (fL) |
|---|---|---|---|---|
| PBS | — | 14.1 | 45 | 48 |
| 845219 | 5 | 14.2 | 45 | 49 |
| | 15 | 13.8 | 43 | 46 |
| 863577 | 5 | 13.9 | 45 | 49 |
| | 15 | 12.2 | 39 | 48 |
| 863579 | 5 | 14.9 | 47 | 48 |
| | 15 | 15.3 | 48 | 50 |
| 863637 | 5 | 13.5 | 42 | 47 |
| | 15 | 13.8 | 43 | 47 |
| 863682 | 5 | 14.5 | 45 | 48 |
| | 15 | 13.6 | 43 | 48 |

Body and Organ Weight Measurements

To evaluate the effect of ISIS oligonucleotides on the overall health of the animals, body and organ weights were measured. Body weights were measured every week and are presented in the Table below. Organ weights were measured and the data is also presented in the Table below. The results indicate that effect of treatment with the antisense oligonucleotides on body and organ weights was within the expected range for antisense oligonucleotides.

TABLE 42

Body weights (g) in CD1 mice

| | Dose (mg/kg) | Baseline (day 1) | Week 1 (day 8) | Week 2 (day 15) | Week 3 (day 22) | Week 4 (day 29) | Week 5 (day 36) | Week 6 (day 42) |
|---|---|---|---|---|---|---|---|---|
| PBS | — | 27 | 30 | 32 | 32 | 33 | 35 | 35 |
| 845219 | 5 | 28 | 33 | 34 | 35 | 37 | 40 | 39 |
| | 15 | 29 | 33 | 34 | 35 | 36 | 38 | 38 |
| 863577 | 5 | 26 | 31 | 32 | 33 | 34 | 37 | 35 |
| | 15 | 27 | 31 | 31 | 32 | 34 | 36 | 35 |
| 863579 | 5 | 28 | 32 | 33 | 32 | 36 | 38 | 36 |
| | 15 | 27 | 32 | 33 | 32 | 36 | 38 | 37 |
| 863637 | 5 | 28 | 33 | 34 | 35 | 36 | 37 | 38 |
| | 15 | 27 | 32 | 34 | 34 | 36 | 38 | 38 |
| 863682 | 5 | 26 | 32 | 33 | 32 | 35 | 37 | 36 |
| | 15 | 27 | 31 | 32 | 33 | 34 | 36 | 36 |

TABLE 43

Organ weights (g) in CD1 mice

| | Dose (mg/kg) | Liver | Spleen | Kidney |
|---|---|---|---|---|
| PBS | — | 1.84 | 0.08 | 0.50 |
| 845219 | 5 | 2.42 | 0.13 | 0.54 |
| | 15 | 2.41 | 0.15 | 0.54 |
| 863577 | 5 | 2.47 | 0.11 | 0.58 |
| | 15 | 2.62 | 0.15 | 0.59 |
| 863579 | 5 | 2.53 | 0.13 | 0.57 |
| | 15 | 2.82 | 0.12 | 0.54 |
| 863637 | 5 | 2.38 | 0.17 | 0.52 |
| | 15 | 2.67 | 0.22 | 0.58 |
| 863682 | 5 | 1.79 | 0.11 | 0.54 |
| | 15 | 2.13 | 0.21 | 0.53 |

Example 6

Tolerability of ISIS Oligonucleotides Targeting Human PCSK9 in Sprague-Dawley Rats Sprague-Dawley rats are a multipurpose model used for safety and efficacy evaluations. The rats were treated with ISIS antisense oligonucleotides from the studies described in the Examples above and evaluated for changes in the levels of various plasma chemistry markers.

Treatment

Male Sprague-Dawley rats were maintained on a 12-hour light/dark cycle and fed ad libitum with Purina normal rat chow, diet 5001. Groups of 4 Sprague-Dawley rats each were injected subcutaneously once a week for 6 weeks with 15 mg/kg of ISIS oligonucleotide. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured and the results are presented in the Table below expressed in IU/L. Plasma levels of bilirubin (TBIL), BUN, albumin (ALB), and creatinine (CRE) were also measured using the same clinical chemistry analyzer and the results are also presented in the Table below expressed in mg/dL. Plasma levels of albumin were also measured using the same clinical chemistry analyzer and the results are also presented in the Table below expressed in g/dL.

TABLE 44

Liver function markers in Sprague-Dawley rats

| | ALT (IU/L) | AST (IU/L) | ALB (g/dL) | BUN (mg/dL) | CRE (mg/dL) | TBIL (mg/dL) |
|---|---|---|---|---|---|---|
| PBS | 20 | 64 | 3.1 | 13 | 0.2 | 0.1 |
| 863568 | 40 | 70 | 3.5 | 14 | 0.2 | 0.2 |
| 863576 | 39 | 94 | 3.7 | 16 | 0.3 | 0.1 |
| 863579 | 33 | 91 | 3.3 | 14 | 0.2 | 0.1 |
| 863581 | 36 | 154 | 2.8 | 18 | 0.3 | 0.2 |
| 863582 | 38 | 122 | 2.9 | 20 | 0.3 | 0.1 |
| 863587 | 38 | 87 | 3.0 | 12 | 0.2 | 0.1 |
| 863633 | 26 | 78 | 3.0 | 16 | 0.3 | 0.1 |
| 863655 | 27 | 84 | 3.1 | 15 | 0.2 | 0.1 |
| 863670 | 30 | 91 | 3.2 | 15 | 0.2 | 0.1 |
| 863681 | 29 | 81 | 3.2 | 14 | 0.2 | 0.1 |

Kidney Function

To evaluate the effect of ISIS oligonucleotides on kidney function, urine levels of blood creatinine and total protein were measured using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies. 'N/A' indicates that data is not available for that group.

TABLE 45

Kidney function markers (mg/dL) in Sprague-Dawley rats

|  | CRE (mg/dL) | TP (mg/dL) |
|---|---|---|
| PBS | 79 | 59 |
| 863568 | 111 | 137 |
| 863576 | N/A | N/A |
| 863579 | 93 | 117 |
| 863581 | 54 | 75 |
| 863582 | 71 | 91 |
| 863587 | 64 | 86 |
| 863633 | 100 | 85 |
| 863655 | 85 | 117 |
| 863670 | 89 | 104 |
| 863681 | 144 | 142 |

Body and Organ Weights

To evaluate the effect of ISIS oligonucleotides on the overall health of the animals, body and organ weights were measured. Body weights were measured every week and are presented in the Table below. Organ weights were measured and the data is also presented in the Table below. The results indicate that effect of treatment with antisense oligonucleotides on body and organ weights was within the expected range for antisense oligonucleotides.

TABLE 46

Body weights (g)

|  | Baseline (day 1) | Week 1 (day 8) | Week 2 (day 15) | Week 3 (day 22) | Week 4 (day 29) | Week5 (day 36) | Week 6 (day 43) |
|---|---|---|---|---|---|---|---|
| PBS | 201 | 267 | 344 | 389 | 433 | 451 | 470 |
| 863568 | 200 | 265 | 334 | 371 | 404 | 419 | 435 |
| 863576 | 272 | 327 | 361 | 389 | 417 | 424 | 435 |
| 863579 | 264 | 313 | 357 | 379 | 407 | 420 | 430 |
| 863581 | 195 | 258 | 329 | 361 | 397 | 411 | 430 |
| 863582 | 204 | 273 | 350 | 387 | 423 | 440 | 458 |
| 863587 | 205 | 273 | 353 | 398 | 439 | 459 | 474 |
| 863633 | 271 | 319 | 361 | 377 | 401 | 406 | 417 |
| 863655 | 195 | 256 | 330 | 366 | 406 | 417 | 435 |
| 863670 | 189 | 249 | 319 | 351 | 384 | 394 | 406 |
| 863681 | 275 | 312 | 364 | 386 | 415 | 426 | 435 |

TABLE 47

Organ weights (g)

|  | Liver | Spleen | Kidney |
|---|---|---|---|
| PBS | 12 | 0.8 | 3.4 |
| 863568 | 16 | 1.2 | 3.3 |
| 863576 | 12 | 1.3 | 3.0 |
| 863579 | 11 | 1.0 | 3.0 |
| 863581 | 13 | 2.0 | 3.1 |
| 863582 | 14 | 2.1 | 3.5 |
| 863587 | 14 | 1.1 | 3.4 |
| 863633 | 12 | 1.6 | 3.2 |
| 863655 | 11 | 1.7 | 3.4 |
| 863670 | 12 | 1.0 | 2.9 |
| 863681 | 12 | 1.1 | 3.3 |

Example 7

Effect of Antisense Inhibition of PCSK9 in Transgenic Mouse Model

A transgenic mouse model developed at UCI and has never been described in the literature. The human PCSK9 genomic construct contained in fosmid ABC7-611722G24 was restricted with Nhe1 to produce a DNA fragment containing the entire genomic sequence as well as 8 Kb of 5' and 0.4 Kb of 3' noncoding sequence. PCSK9 transgenic mice were produced by random insertion via micronucleus injection. Progeny expressed human PCSK9 mRNA in the liver and secreted human PCSK9 plasma protein.

Treatment

Transgenic mice were maintained on a 12-hour light/dark cycle and were fed ad libitum normal Purina mouse chow. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

The Tg mice were divided into 27 groups of 3 mice each. Groups received subcutaneous injections of ISIS oligonucleotide at a dose of 0.25 mg/kg, 1.00 mg/kg, or 5.00 mg/kg once per week for 4 weeks. One group of 4 mice received subcutaneous injections of PBS once per week for 4 weeks. The saline-injected group served as the control group to which oligonucleotide-treated groups were compared.

RNA analysis

On day 26, RNA was extracted from liver for real-time PCR analysis of measurement of mRNA expression of PCSK9. Results are presented as percent change of mRNA, relative to PBS control, normalized with RIBOGREEN®. As shown in the Table below, treatment with ISIS antisense oligonucleotides resulted in significant reduction of PCSK9 mRNA in comparison to the PBS control.

TABLE 48

Percent inhibition of PCSK9 mRNA in the transgenic mice liver relative to the PBS control

|  | Weekly Dose (mg/kg) | % Inhibition | $ED_{50}$ |
|---|---|---|---|
| 863568 | 0.25 | 26 | 0.5 |
|  | 1 | 76 |  |
|  | 5 | 95 |  |
| 863579 | 0.25 | 9 | 1.4 |
|  | 1 | 41 |  |
|  | 5 | 84 |  |

TABLE 48-continued

Percent inhibition of PCSK9 mRNA in the
transgenic mice liver relative to the PBS control

| ISIS No | Weekly Dose (mg/kg) | % Inhibition | $ED_{50}$ |
|---|---|---|---|
| 863581 | 0.25 | 12 | 0.6 |
|  | 1 | 73 |  |
|  | 5 | 80 |  |
| 863582 | 0.25 | 32 | 0.5 |
|  | 1 | 71 |  |
|  | 5 | 91 |  |
| 863587 | 0.25 | 27 | 0.5 |
|  | 1 | 71 |  |
|  | 5 | 87 |  |
| 863633 | 0.25 | 60 | 0.2 |
|  | 1 | 96 |  |
|  | 5 | 99 |  |
| 863655 | 0.25 | 37 | 0.3 |
|  | 1 | 94 |  |
|  | 5 | 99 |  |
| 863670 | 0.25 | 0 | 1.0 |
|  | 1 | 62 |  |
|  | 5 | 87 |  |
| 863681 | 0.25 | 25 | 0.9 |
|  | 1 | 45 |  |
|  | 5 | 94 |  |

Protein Analysis

PCSK9 plasma protein was measured by a human-specific ELISA kit (R&D Systems). Results are presented as percent change of protein levels, relative to PBS control. As shown in the Table below, treatment with ISIS antisense oligonucleotides resulted in significant reduction of PCSK9 plasma protein levels in comparison to the PBS control.

TABLE 49

Percent inhibition of PCSK9 plasma protein in
the transgenic mice relative to the PBS control

| ISIS No | Weekly Dose (mg/kg) | % Inhibition | $ED_{50}$ |
|---|---|---|---|
| 863568 | 0.25 | 37 | 0.4 |
|  | 1 | 74 |  |
|  | 5 | 97 |  |
| 863579 | 0.25 | 5 | 1.5 |
|  | 1 | 41 |  |
|  | 5 | 81 |  |
| 863581 | 0.25 | 31 | 0.6 |
|  | 1 | 59 |  |
|  | 5 | 91 |  |
| 863582 | 0.25 | 25 | 0.5 |
|  | 1 | 73 |  |
|  | 5 | 95 |  |
| 863587 | 0.25 | 33 | 0.4 |
|  | 1 | 77 |  |
|  | 5 | 93 |  |
| 863633 | 0.25 | 50 | 0.3 |
|  | 1 | 97 |  |
|  | 5 | 99 |  |
| 863655 | 0.25 | 44 | 0.3 |
|  | 1 | 93 |  |
|  | 5 | 99 |  |
| 863670 | 0.25 | 23 | 1.6 |
|  | 1 | 38 |  |
|  | 5 | 72 |  |
| 863681 | 0.25 | 28 | 0.8 |
|  | 1 | 54 |  |
|  | 5 | 89 |  |

LDL-Cholesterol Levels

Levels of LDL-cholesterol in the plasma were measured by an automated clinical chemistry analyzer (Hitachi Olympus AU400e, Melville, N.Y.). Levels of LDL receptor (LDLr) protein in the liver were also measured. Results are presented as percent change of levels, relative to PBS control. As shown in the Table below, treatment with several ISIS antisense oligonucleotides resulted in significant reduction of levels of LDL-cholesterol in the plasma in comparison to the PBS control. Correspondingly, it was observed that treatment with ISIS antisense oligonucleotides resulted in dose-dependent liver LDLr protein increases in the mice.

TABLE 50

Inhibition of LDL-cholesterol levels in the
plasma relative to the PBS control

| ISIS No | Weekly Dose (mg/kg) | % inhibition |
|---|---|---|
| 863568 | 0.25 | 7 |
|  | 1 | 41 |
|  | 5 | 59 |
| 863579 | 0.25 | 0 |
|  | 1 | 15 |
|  | 5 | 33 |
| 863581 | 0.25 | 30 |
|  | 1 | 17 |
|  | 5 | 41 |
| 863582 | 0.25 | 23 |
|  | 1 | 28 |
|  | 5 | 50 |
| 863587 | 0.25 | 20 |
|  | 1 | 38 |
|  | 5 | 38 |
| 863633 | 0.25 | 27 |
|  | 1 | 66 |
|  | 5 | 71 |
| 863655 | 0.25 | 29 |
|  | 1 | 58 |
|  | 5 | 74 |
| 863670 | 0.25 | 19 |
|  | 1 | 0 |
|  | 5 | 39 |
| 863681 | 0.25 | 21 |
|  | 1 | 23 |
|  | 5 | 35 |

TABLE 51

Percent increase of liver LDLr in the
transgenic mice relative to the PBS control

| ISIS No | Weekly Dose (mg/kg) | % increase |
|---|---|---|
| 863568 | 0.25 | 3 |
|  | 1 | 61 |
|  | 5 | 245 |
| 863579 | 0.25 | −46 |
|  | 1 | −5 |
|  | 5 | 132 |
| 863581 | 0.25 | −44 |
|  | 1 | 6 |
|  | 5 | 73 |
| 863582 | 0.25 | −19 |
|  | 1 | 93 |
|  | 5 | 191 |
| 863587 | 0.25 | −6 |
|  | 1 | −10 |
|  | 5 | 95 |
| 863633 | 0.25 | −22 |
|  | 1 | 131 |
|  | 5 | 269 |
| 863655 | 0.25 | 0 |
|  | 1 | 129 |
|  | 5 | 207 |
| 863670 | 0.25 | 9 |
|  | 1 | 81 |
|  | 5 | 78 |

TABLE 51-continued

Percent increase of liver LDLr in the
transgenic mice relative to the PBS control

| | Weekly Dose (mg/kg) | % increase |
|---|---|---|
| 863681 | 0.25 | 123 |
| | 1 | 360 |
| | 5 | 222 |

Example 8

Measurement of Viscosity of Antisense Oligonucleotides Targeting Human PCSK9

The viscosity of select antisense oligonucleotides from the studies described above was measured with the aim of screening out antisense oligonucleotides which have a viscosity of more than 40 centipoise (cP). Oligonucleotides having a viscosity greater than 40 cP would have less than optimal viscosity.

Oligonucleotides (32-35 mg) were weighed into a glass vial, 120 µL of water was added and the antisense oligonucleotide was dissolved into solution by heating the vial at 50° C. Part (75 µL) of the pre-heated sample was pipetted to a micro-viscometer (Cambridge). The temperature of the micro-viscometer was set to 25° C. and the viscosity of the sample was measured. Another part (20 µL) of the pre-heated sample was pipetted into 10 mL of water for UV reading at 260 nM at 85° C. (Cary UV instrument). The results are presented in the Table below, where the concentration of each antisense oligonucleotide was 350 mg/ml, and indicate that all the antisense oligonucleotides solutions were optimal in their viscosity under the criterion stated above.

TABLE 52

Viscosity of antisense oligonucleotides targeting human PCSK9

| ISIS No | Viscosity (cP) | Concentration (mg/mL) |
|---|---|---|
| 863568 | 39 | 325 |
| 863576 | 20 | 325 |
| 863579 | 19 | 325 |
| 863581 | 25 | 300 |
| 863582 | 17 | 300 |
| 863587 | 14 | 325 |
| 863633 | 12 | 325 |
| 863655 | 10 | 325 |
| 863670 | 21 | 325 |
| 863681 | 15 | 325 |

Example 9

Effect of ISIS Antisense Oligonucleotides Targeting Human PCSK9 in Cynomolgus Monkeys Cynomolgus monkeys were treated with ISIS antisense oligonucleotides selected from studies described in the Examples above. Antisense oligonucleotide efficacy and tolerability, as well as their pharmacokinetic profile in the liver and kidney, were evaluated.

At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well. The human antisense oligonucleotides tested are cross-reactive with the rhesus genomic sequence (the complement of GENBANK Accession No. NW_005092960.1 truncated from nucleotides 83474000 to 83501000, designated herein as SEQ ID NO: 1544). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 1544 is presented in the Table below. "Start site" indicates the 5'-most nucleotide to which the gapmer is targeted in the rhesus monkey gene sequence.

TABLE 53

Antisense oligonucleotides complementary to the rhesus PCSK9 genomic sequence (SEQ ID NO: 1544)

| ISIS No | Target Start Site | Mismatches | Target Stop Site | SEQ ID NO |
|---|---|---|---|---|
| 863568 | 25252 | 1 | 25267 | 1528 |
| 863579 | 25510 | 2 | 25525 | 763 |
| 863581 | 25520 | 1 | 25535 | 1071 |
| 863582 | 25521 | 1 | 25536 | 1147 |
| 863587 | 25712 | 2 | 25727 | 1149 |
| 863633 | 3911 | 0 | 3926 | 1016 |
| 863655 | 10464 | 1 | 10479 | 955 |
| 863670 | 15306 | 0 | 15321 | 1195 |
| 863681 | 17270 | 0 | 17285 | 353 |

Treatment

Prior to the study, the monkeys were kept in quarantine during which the animals were observed daily for general health. The monkeys were 2-4 years old and weighed 2-4 kg. Nine groups of 5 randomly assigned male cynomolgus monkeys each were injected subcutaneously with ISIS oligonucleotide or PBS in clockwise rotation between four different sites on the backs of the monkeys (i.e. left, right, top, and bottom) on each day of dosing; one site per dose. The monkeys were dosed twice a week (days 1, 5, 9, and 14) for the first two weeks, and then subsequently once a week for 10 weeks (days 21, 28, 35, 42, 49, 56, 63, 70, 77, and 84) with 10 mg/kg of ISIS oligonucleotide. A control group of 5 cynomolgus monkeys was injected with PBS in a similar manner and served as the control group.

During the study period, the monkeys were observed twice daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. Scheduled euthanasia of the animals was conducted on day 86 approximately 48 hours post-dose by exsanguination while under deep anesthesia. The protocols described in the Example were approved by the Institutional Animal Care and Use Committee (IACUC).

Target Reduction

RNA Analysis

On day 86, RNA was extracted from liver for real-time PCR analysis of measurement of mRNA expression of PCSK9. Results are presented as percent change of mRNA, relative to PBS control, normalized with RIBOGREEN®. As shown in the Table below, treatment with ISIS antisense oligonucleotides, ISIS 863633, ISIS 863670, and ISIS 863681, which had no mismatches with the rhesus gene, resulted in significant reduction of PCSK9 mRNA in comparison to the PBS control.

TABLE 54

Percent inhibition of PCSK9 mRNA in the cynomolgus monkey liver relative to the PBS control

|  | % inhibition |
|---|---|
| 863655 | 46 |
| 863633 | 88 |
| 863568 | 74 |
| 863579 | 35 |
| 863582 | 55 |
| 863581 | 53 |
| 863587 | 36 |
| 863670 | 84 |
| 863681 | 87 |

Protein Analysis

Approximately 1 mL of blood was collected from all available animals on day −7 (pre-treatment), Days 16, 30, 58, and 86 (approximately 48 hours post-dose on Days 14, 28, 56, and 84, respectively) and placed in tubes containing the potassium salt of EDTA. The tubes were centrifuged (3000 rpm for 10 min at 4° C.) to obtain plasma. The results are presented in the Table below as a percentage increase or decrease over the levels at Day −7 (pre-treatment levels). As shown in the Table below, treatment with ISIS antisense oligonucleotides, ISIS 863633, ISIS 863670, and ISIS 863681, which had no mismatches with the rhesus gene, resulted in significant reduction of PCSK9 protein levels.

Liver tissue was also analyzed for levels of LDL receptor (LDLr) protein induction levels. The results are presented in the Table below. The data demonstrates that treatment with the three antisense oligonucleotides that are homologous to the rhesus monkey genomic sequence resulted in hepatic LDLr protein induction after 12 weeks of treatment.

TABLE 55

Plasma protein levels (% of pre-treatment levels) in the cynomolgus monkey

|  | Day 16 | Day 30 | Day 86 |
|---|---|---|---|
| PBS | 34 | 36 | 18 |
| 863655 | −13 | −2 | −36 |
| 863633 | −90 | −91 | −91 |
| 863568 | −19 | −14 | −22 |
| 863579 | 34 | 36 | 18 |
| 863582 | 8 | 2 | 35 |
| 863581 | 16 | 8 | 11 |
| 863587 | −3 | 1 | −12 |
| 863670 | −79 | −83 | −86 |
| 863681 | −80 | −82 | −86 |

TABLE 56

Hepatic LDLr protein levels (% of PBS control) in the cynomolgus monkey

|  | % increase |
|---|---|
| 863655 | 98 |
| 863633 | 399 |
| 863568 | 243 |
| 863579 | 163 |
| 863582 | 115 |
| 863581 | 156 |
| 863587 | 158 |
| 863670 | 521 |
| 863681 | 417 |

Plasma Lipid Levels

To evaluate the effect of ISIS oligonucleotides on total cholesterol, LDL-Cholesterol, HDL-cholesterol, and triglyceride levels, monkeys were fasted overnight prior to blood collection. Approximately 1.7 mL of blood samples were collected from all the study groups. Blood was collected in tubes without anticoagulant for serum separation. The tubes were kept at room temperature for a minimum of 90 minutes and then centrifuged at 3,000 rpm for 10 minutes at room temperature to obtain serum. Levels were measured using a Toshiba 200FR NEO chemistry analyzer (Toshiba Co., Japan). The data demonstrates that treatment with the three antisense oligonucleotides with homology with the rhesus monkey genomic sequence resulted in significant reduction of plasma total cholesterol and LDL-cholesterol. As expected, reduction of human PCSK9 levels did not affect plasma HDL-cholesterol or triglyceride levels.

TABLE 57

Plasma lipid levels (mg/dL) in cynomolgus monkey on Day 86

|  | Total cholesterol | LDL-cholesterol | HDL-cholesterol | Triglycerides |
|---|---|---|---|---|
| PBS | 146 | 37 | 110 | 71 |
| 863655 | 152 | 73 | 71 | 46 |
| 863633 | 115 | 17 | 99 | 57 |
| 863568 | 128 | 32 | 99 | 51 |
| 863579 | 109 | 44 | 71 | 45 |
| 863582 | 137 | 38 | 103 | 37 |
| 863581 | 174 | 51 | 122 | 34 |
| 863587 | 140 | 45 | 102 | 35 |
| 863670 | 95 | 17 | 83 | 45 |
| 863681 | 109 | 19 | 99 | 29 |

Tolerability Studies

Clinical Chemistry Parameters

To evaluate the effect of ISIS oligonucleotides on hepatic function, monkeys were fasted overnight prior to blood collection. Approximately 1.7 mL of blood samples were collected from all the study groups. Blood was collected in tubes without anticoagulant for serum separation. The tubes were kept at room temperature for a minimum of 90 minutes and then centrifuged at 3,000 rpm for 10 minutes at room temperature to obtain serum. Levels of total bilirubin (TBIL), aspartate aminotransferase (AST), alanine aminotransferase (ALT), and albumin (ALB) were measured using a Toshiba 200FR NEO chemistry analyzer (Toshiba Co., Japan). The results indicate that antisense oligonucleotides had no effect on liver function outside the expected range for antisense oligonucleotides. Specifically, ISIS 863633 was observed to be well tolerated.

TABLE 58

Plasma Chemistry markers in cynomolgus monkey on Day 86

|        | ALT (IU/L) | AST (IU/L) | Bilirubin (mg/dL) | ALB (g/dL) |
|--------|------------|------------|-------------------|------------|
| PBS    | 65         | 64         | 0.2               | 4.1        |
| 863655 | 63         | 59         | 0.3               | 3.5        |
| 863633 | 47         | 70         | 0.3               | 4.0        |
| 863568 | 44         | 64         | 0.3               | 4.1        |
| 863579 | 50         | 52         | 0.2               | 4.1        |
| 863582 | 42         | 57         | 0.2               | 4.2        |
| 863581 | 55         | 61         | 0.3               | 4.2        |
| 863587 | 110        | 76         | 0.3               | 3.9        |
| 863670 | 42         | 64         | 0.3               | 4.1        |
| 863681 | 62         | 60         | 0.3               | 4.1        |

Kidney Function

To evaluate the effect of ISIS oligonucleotides on kidney function, monkeys were fasted overnight prior to blood collection. Approximately 1.7 mL of blood samples were collected from all the study groups. Blood was collected in tubes without anticoagulant for serum separation. The tubes were kept at room temperature for a minimum of 90 minutes and then centrifuged at 3,000 rpm for 10 minutes at room temperature to obtain serum. Levels of BUN and creatinine were measured using a Toshiba 200FR NEO chemistry analyzer (Toshiba Co., Japan). Results are presented in the Table below, expressed in mg/dL.

The plasma chemistry data indicate that most of the ISIS oligonucleotides did not have any effect on the kidney function outside the expected range for antisense oligonucleotides. Specifically, ISIS 863633 was observed to be well tolerated.

TABLE 59

Plasma BUN and creatinine levels (mg/dL) in cynomolgus monkeys at day 86

|        | BUN | Creatinine |
|--------|-----|------------|
| PBS    | 31  | 0.8        |
| 863655 | 26  | 0.8        |
| 863633 | 27  | 0.8        |
| 863568 | 27  | 0.9        |
| 863579 | 24  | 0.8        |
| 863582 | 24  | 0.8        |
| 863581 | 27  | 0.8        |
| 863587 | 24  | 0.8        |
| 863670 | 26  | 1.0        |
| 863681 | 23  | 0.8        |

Hematology

To evaluate any effect of ISIS oligonucleotides in cynomolgus monkeys on hematologic parameters, approximately 0.5 mL of blood was collected from each of the available study animals in tubes containing $K_2$-EDTA. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA120 hematology analyzer (Bayer, USA). The data is presented in the Tables below.

The data indicate the oligonucleotides did not cause any changes in hematologic parameters outside the expected range for antisense oligonucleotides at this dose. Specifically, ISIS 863633 was observed to be well tolerated.

TABLE 60

Blood cell counts in cynomolgus monkeys on day 86

|        | RBC ($\times 10^6/\mu L$) | Platelets ($\times 10^3/\mu L$) | WBC ($\times 10^3/\mu L$) | Neutrophils ($\times 10^3/\mu L$) | Lymphocytes ($\times 10^3/\mu L$) | Monocytes ($\times 10^3/\mu L$) |
|--------|------|-----|------|-----|-----|-----|
| PBS    | 5.5  | 340 | 9.0  | 3.1 | 5.4 | 0.3 |
| 863655 | 5.6  | 361 | 9.7  | 3.7 | 5.4 | 0.3 |
| 863633 | 5.6  | 395 | 11.4 | 4.5 | 6.5 | 0.3 |
| 863568 | 5.8  | 409 | 12.1 | 602 | 5.4 | 0.3 |
| 863579 | 5.9  | 390 | 8.0  | 2.2 | 5.3 | 0.3 |
| 863582 | 5.6  | 333 | 8.9  | 3.0 | 5.5 | 0.3 |
| 863581 | 5.8  | 382 | 8.2  | 2.4 | 5.3 | 0.3 |
| 863587 | 6.0  | 348 | 8.8  | 2.3 | 6.0 | 0.2 |
| 863670 | 5.4  | 417 | 10.7 | 4.3 | 5.9 | 0.3 |
| 863681 | 5.6  | 408 | 9.0  | 3.1 | 5.5 | 0.2 |

TABLE 61

Hematologic parameters in cynomolgus monkeys on day 86

|        | Hemoglobin (g/dL) | HCT (%) |
|--------|-------------------|---------|
| PBS    | 12.8              | 45      |
| 863655 | 13.0              | 43      |
| 863633 | 12.9              | 43      |
| 863568 | 13.0              | 44      |
| 863579 | 13.5              | 46      |
| 863582 | 12.4              | 43      |
| 863581 | 13.0              | 44      |
| 863587 | 13.5              | 46      |
| 863670 | 12.7              | 43      |
| 863681 | 12.7              | 43      |

Overall, the results of the study indicate that ISIS 863633 is the most potent and well tolerated compound of those tested for inhibiting PCSK9 and is an important candidate for the treatment of cardiovascular diseases, specifically for lowering LDL-cholesterol levels.

Example 10

Comparative Inhibition of Antisense Oligonucleotides Targeting Human PCSK9 in a Dose Response Assay The unconjugated parent oligonucleotides of the antisense oligonucleotides tested in the monkey study were compared with previously designed compounds. ISIS 848542, ISIS 848593, ISIS 848597, ISIS 848598, ISIS 848630, ISIS 848833, ISIS 849040, ISIS 849171, and ISIS 849236 were tested for efficacy with ISIS 405879 and ISIS 405995, which have previously been determined to be some of the most potent antisense compounds in vitro (see e.g., U.S. Pat. No. 8,084,437), as well as ISIS 431131 and ISIS 480604, which have been previously described in U.S. Pat. No. 9,127,276.

Cells were plated at a density of 10,000 cells per well and 39.1 nM, 156.25 nM, 625 nM, 2,500 nM, and 10,000 nM concentrations of antisense oligonucleotide was added to the medium for free uptake of oligonucleotide by the cells. After a treatment period of approximately 48 hours, RNA was isolated from the cells and PCSK9 mRNA levels were measured by quantitative real-time PCR. Human PCSK9 primer probe set from ABI (ID #Hs03037355_m1) was used to measure mRNA levels. PCSK9 mRNA levels were adjusted according to total RNA content, as measured by RIBOGREEN®. Results are presented as percent inhibition of PCSK9, relative to untreated control cells.

The half maximal inhibitory concentration ($IC_{50}$) of each oligonucleotide is also presented. PCSK9 mRNA levels were reduced in a dose-dependent manner in antisense oligonucleotide treated cells. ISIS 848542, ISIS 848593, ISIS 848597, ISIS 848598, ISIS 848630, ISIS 848833, ISIS 849040, ISIS 849171, and ISIS 849236 demonstrated superior efficacy compared to all previously disclosed oligonucleotides.

TABLE 62

| ISIS No | 39.1 nM | 156.25 nM | 625.0 nM | 2500.0 nM | 10000.0 nM | $IC_{50}$ (µM) |
|---|---|---|---|---|---|---|
| 405879 | 0 | 0 | 0 | 0 | 0 | >10 |
| 405995 | 0 | 0 | 0 | 0 | 0 | >10 |
| 431131 | 0 | 3 | 0 | 0 | 5 | >10 |
| 480604 | 0 | 1 | 19 | 31 | 36 | >10 |
| 848542 | 9 | 37 | 70 | 83 | 88 | 0.4 |
| 848593 | 19 | 36 | 51 | 53 | 69 | 1.1 |
| 848597 | 41 | 67 | 78 | 86 | 91 | 0.04 |
| 848598 | 41 | 64 | 76 | 85 | 90 | 0.1 |
| 848630 | 0 | 17 | 59 | 79 | 85 | 0.9 |
| 848833 | 4 | 66 | 88 | 93 | 94 | 0.2 |
| 849040 | 41 | 93 | 98 | 99 | 98 | <0.03 |
| 849171 | 0 | 52 | 86 | 94 | 96 | 0.3 |
| 849236 | 0 | 26 | 71 | 89 | 95 | 0.6 |

What is claimed:

1. An oligomeric compound comprising a modified oligonucleotide according to the following formula: $A_{ks} A_{ks} T_{ks} A_{ds} A_{ds} T_{ds} {}^{m}C_{ds} T_{ds} {}^{m}C_{ds} A_{ds} T_{ds} G_{ds} T_{ds} {}^{m}C_{ks} A_{ks} G_{k}$ (SEQ ID NO: 1016); wherein,
A=an adenine,
${}^{m}$C=a 5-methylcytosine,
G=a guanine,
T=a thymine,
k=a cEt modified nucleoside,
d=β-D-2'-deoxyribonucleoside, and
s=a phosphorothioate internucleoside linkage.

2. A pharmaceutical composition comprising the oligomeric compound of claim 1, and a pharmaceutically acceptable diluent or carrier.

3. The pharmaceutical composition of claim 2, wherein the pharmaceutically acceptable diluent comprises water or phosphate buffered saline (PBS).

4. The pharmaceutical composition of claim 3, consisting essentially of the modified oligonucleotide and water or PBS.

5. An oligomeric compound comprising a modified oligonucleotide and a conjugate group according to the following formula: GalNAc$_{3}$-7$_{a\text{-}o}$, $A_{ks} A_{ks} T_{ks} A_{ds} A_{ds} T_{ds} {}^{m}C_{ds} T_{ds} {}^{m}C_{ds} A_{ds} T_{ds} G_{ds} T_{ds} {}^{m}C_{ks} A_{ks} G_{k}$ (SEQ ID NO: 1016); wherein,
A=an adenine,
${}^{m}$C=a 5-methylcytosine,
G=a guanine,
T=a thymine,
k=a cEt modified nucleoside,
d=β-D-2'-deoxyribonucleoside,
s=a phosphorothioate internucleoside linkage, and GalNAc$_{3\text{-}7a\text{-}o}$ =

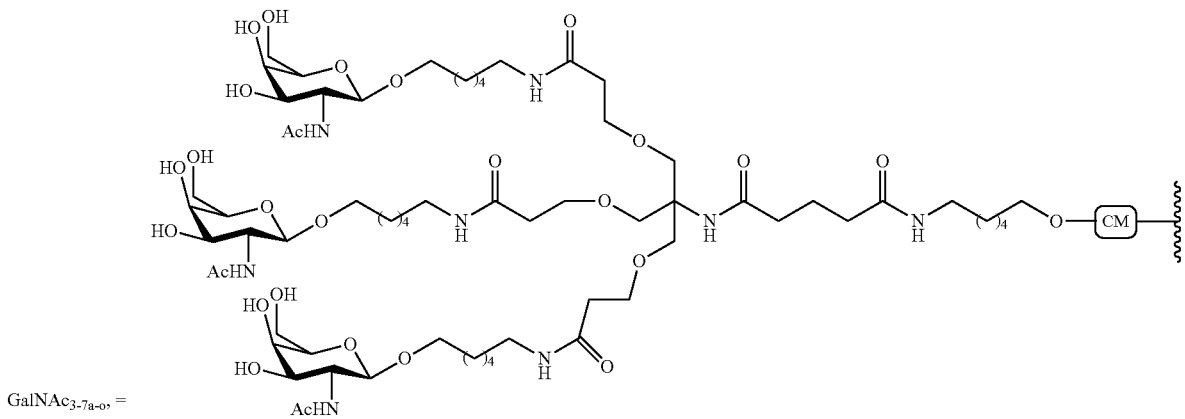

, wherein the cleavable moiety (CM) comprises a phosphodiester bond.

6. A pharmaceutical composition comprising the oligomeric compound of claim 5, and a pharmaceutically acceptable diluent or carrier.

7. The pharmaceutical composition of claim 6, wherein the pharmaceutically acceptable diluent comprises water or phosphate buffered saline (PBS).

8. The pharmaceutical composition of claim 7, consisting essentially of the modified oligonucleotide and water or PBS.

9. A method of treating, preventing, or ameliorating a disease associated with PCSK9 in an individual comprising administering to the individual a compound according to claim 1 or claim 5, wherein the disease is hypercholesterolemia, dyslipidemia or mixed dyslipidemia.

10. The method of claim 9, wherein administering the compound inhibits or reduces LDL-cholesterol levels and total cholesterol levels and improves the induction of hepatic LDL receptor levels.

11. A method of inhibiting expression of PCSK9 in a cell comprising contacting the cell with a compound according to claim 1 or claim 5.

12. The method of claim 11, wherein the cell is in the liver of an individual.

13. The method of claim 12, wherein the individual has, or is at risk of having, hypercholesterolemia, dyslipidemia or mixed dyslipidemia.

14. A method of reducing or inhibiting LDL-cholesterol levels and total cholesterol levels in an individual having, or at risk of having, a disease associated with PCSK9 comprising administering to the individual a compound according to claim 1 or claim 5.

15. The method of claim 14, wherein the individual has, or is at risk of having, hypercholesterolemia, dyslipidemia, or mixed dyslipidemia.

* * * * *

SEQUENCE LISTING

<160> NUMBER OF SEQ ID NOS: 1550

<210> SEQ ID NO 1
<211> LENGTH: 3731
<212> TYPE: DNA
<213> ORGANISM: Homo sapiens

<400> SEQUENCE: 1

```
gtccgatggg gctctggtgg cgtgatctgc gcgcccagg cgtcaagcac ccacaccta      60 gaaggtttcc gcagcgacgt cgaggcgctc atggttgcag gcgggcgccg ccgttcagtt   120
cagggtctga gcctggagga gtgagccagg cagtgagact ggctcgggcg ggccgggacg   180
cgtcgttgca gcagcggctc ccagctccca gccaggattc cgcgcgcccc ttcacgcgcc   240
ctgctcctga acttcagctc ctgcacagtc ctccccaccg caaggctcaa ggcgccgccg   300
gcgtggaccg cgcacggcct ctaggtctcc tcgccaggac agcaacctct cccctggccc   360
tcatgggcac cgtcagctcc aggcggtcct ggtggccgct gccactgctg ctgctgctgc   420
tgctgctcct gggtcccgcg ggcgcccgtg cgcaggagga cgaggacggc gactacgagg   480
agctggtgct agccttgcgt tccgaggagg acggcctggc cgaagcaccc gagcacggaa   540
ccacagccac cttccaccgc tgcgccaagg atccgtggag gttgcctggc acctacgtgg   600
tggtgctgaa ggaggagacc cacctctcgc agtcagagcg cactgcccgc cgcctgcagg   660
cccaggctgc ccgccgggga taccctcacc agatcctgca tgtcttccat ggccttcttc   720
ctggcttcct ggtgaagatg agtggcgacc tgctggagct ggccttgaag ttgccccatg   780
tcgactacat cgaggaggac tcctctgtct ttgcccagag catcccgtgg aacctggagc   840
ggattacccc tccacggtac cgggcggatg aataccagcc ccccgacgga ggcagcctgg   900
tggaggtgta tctcctagac accagcatac agagtgacca ccgggaaatc gagggcaggg   960
tcatggtcac cgacttcgag aatgtgcccg aggaggacgg gacccgcttc cacagacagg  1020
```

```
ccagcaagtg tgacagtcat ggcacccacc tggcaggggt ggtcagcggc cgggatgccg   1080
gcgtggccaa gggtgccagc atgcgcagcc tgcgcgtgct caactgccaa gggaagggca   1140
cggttagcgg caccctcata ggcctggagt ttattcggaa aagccagctg gtccagcctg   1200
tggggccact ggtggtgctg ctgccccctgg cgggtgggta cagccgcgtc ctcaacgccg   1260
cctgccagcg cctggcgagg gctggggtcg tgctggtcac cgctgccggc aacttccggg   1320
acgatgcctg cctctactcc ccagcctcag ctcccgaggt catcacagtt ggggccacca   1380
atgcccaaga ccagccggtg accctgggga cttttgggac caactttggc cgctgtgtgg   1440
acctctttgc cccaggggag gacatcattg gtgcctccag cgactgcagc acctgctttg   1500
tgtcacagag tgggacatca caggctgctg cccacgtggc tggcattgca gccatgatgc   1560
tgtctgccga gccggagctc accctggccg agttgaggca gagactgatc cacttctctg   1620
ccaaagatgt catcaatgag gcctggttcc ctgaggacca gcgggtactg acccccaacc   1680
tggtggccgc cctgcccccc agcacccatg ggcaggttg gcagctgttt tgcaggactg   1740
tatggtcagc acactcgggg cctacacgga tggccacagc cgtcgcccgc tgcgcccccag   1800 atgaggagct gctgagctgc tccagtttct ccaggagtgg aagcggcgg ggcgagcgca   1860 tggaggccca aggggcaag ctggtctgcc gggcccacaa cgcttttggg ggtgaggtg   1920 tctacgccat tgccaggtgc tgcctgctac cccaggccaa ctgcagcgtc cacacagctc   1980
caccagctga ggccagcatg ggacccgtg tccactgcca caacagggc cacgtcctca   2040 caggctgcag ctcccactgg gaggtggagg accttggcac ccacaagccg cctgtgctga   2100
ggccacgagg tcagcccaac cagtgcgtgg ccacaggga ggccagcatc cacgcttcct   2160
gctgccatgc cccaggtctg gaatgcaaag tcaaggagca tggaatcccg gcccctcagg   2220
agcaggtgac cgtggcctgc gaggagggct ggaccctgac tggctgcagt gccctccctg   2280
ggacctccca cgtcctgggg gcctacgccg tagacaacac gtgtgtagtc aggagccggg   2340
acgtcagcac tacaggcagc accagcgaag gggccgtgac agccgttgcc atctgctgcc   2400
ggagccggca cctggcgcag gcctcccagg agctccagtg acagccccat cccaggatgg   2460 gtgtctgggga gggtcaagg gctggggctg agctttaaaa tggttccgac ttgtccctct   2520
ctcagccctc catggcctgg cacgaggga tgggatgct tccgcctttc cggggctgct   2580
ggcctggccc ttgagtgggg cagcctcctt gcctggaact cactcactct gggtgcctcc   2640
tccccaggtg gaggtgccag gaagctccct ccctcactgt ggggcatttc accattcaaa   2700
caggtcgagc tgtgctcggg tgctgccagc tgctcccaat gtgccgatgt ccgtgggcag   2760
aatgactttt attgagctct tgttccgtgc caggcattca atcctcaggt ctccaccaag   2820
gaggcaggat tcttcccatg gataggggag gggcggtag ggctgcagg acaaacatc   2880 gttggggggt gagtgtgaaa ggtgctgatg gccctcatct ccagctaact gtggagaagc   2940
ccctgggggc tccctgatta atggaggctt agctttctgg atggcatcta gccagaggct   3000
ggagacaggt gcgcccctgg tggtcacagg ctgtgccttg gtttcctgag ccacctttac   3060
tctgctctat gccaggctgt gctagcaaca cccaaaggtg gcctgcgggg agccatcacc   3120
taggactgac tcgcagtgt gcagtggtgc atgcactgtc tcagccaacc cgctccacta   3180
cccggcaggg tacacattcg caccctact tcacagagga agaaacctgg aaccagaggg   3240
ggcgtgcctg ccaagctcac acagcaggaa ctgagccaga acgcagatt gggctggctc   3300 tgaagccaag cctcttctta cttcacccgg ctgggctcct catttttacg ggtaacagtg   3360
aggctgggaa ggggaacaca gaccaggaag ctcggtgagt gatggcagaa cgatgcctgc   3420
```

| | |
|---|---|
| aggcatggaa cttttttccgt tatcacccag gcctgattca ctggcctggc ggagatgctt | 3480 |
| ctaaggcatg gtcggggagg agggccaaca actgtccctc cttgagcacc agccccaccc | 3540 |
| aagcaagcag acatttatct tttgggtctg tcctctctgt tgccttttta cagccaactt | 3600 |
| ttctagacct gttttgcttt tgtaacttga agatatttat tctgggtttt gtagcatttt | 3660 |
| tattaatatg gtgactttt aaaataaaaa caaacaaacg ttgtcctaac aaaaaaaaaa | 3720 |
| aaaaaaaaaa a | 3731 |

<210> SEQ ID NO 2
<211> LENGTH: 32000
<212> TYPE: DNA
<213> ORGANISM: Homo sapiens

<400> SEQUENCE: 2

| | |
|---|---|
| gtgaccatga gcggtagttg ccagtggtat tcacaaatat acccttttctc ctccttctgg | 60 |
| gcacttggtg tgattgcagt ttcctacatt tgaccttagg tgtggtcatg tgtctcgctt | 120 |
| aggagaagga aatgtgaacg gaagtgttgt gggtcacttt tgtgtggaag ctgcatggag | 180 |
| tcacctcttt gctttccgtc agcctcagtg ttcagcaatg ttctgaatga tggttgcttt | 240 |
| atcagtctgg ttctggggtg agggtaatga agtagtgaag caaagtcctt gatggacatg | 300 |
| tgaggtgaga cagaaataaa cctttgacat ttcaagcccc tgagatttgg ggcgtgcatg | 360 |
| tgctggaagc agaacctagc ctattctgat ggattcctcc agcactgctc gtgggaagac | 420 |
| atcatcaata tagagcattc atgtgcccctt tatctcgaaa ttccacttcc aggaatttat | 480 |
| gaaacagata ctctcacatg tgcaaacagc tatggataag gacagacatg gcaacttgga | 540 |
| ttgcaatagc aaaagacaga acaaccaac ggaaacacca accaatagga aattggctaa | 600 |
| agacattgtg aaacatacat agaatgaaat aatctgcaac cagaaaaata aggcagtaga | 660 |
| tgtatgtgta ccagtgtggt ttttattccg agattagggc taggttaaga cgtcagatta | 720 |
| agttgtccct ctccaccccca ccaatataaa taaaaagtta aaagtaaatc ataaactatt | 780 |
| tttacaattt taaaaagtgg gttaaagagc ccatccaagt agttttataa aagtagacta | 840 |
| tctccgaaaa gatacccaat aaataggtat attactttcc tggggctgtt ataacaagtt | 900 |
| tctacaaatt tgctggcttc aaataacaaa aacgtattct cttgcagtta tggaagccag | 960 |
| aagtatggaa tgaagggttg cagggtggtg ccctctccca aagctctagg ggaggaacat | 1020 |
| tccttgcttc ttccagctcc tttgggggct cctggcattc cttggcttat gtcggcacag | 1080 |
| ctctaatcgg cgcctccatt gttacatagg tgtttctgtg tctcaagtat ctctccctt | 1140 |
| tctcttctga tatcagtcat tggatttagg gaccatccta aacccaggat aatctcctca | 1200 |
| tgagatcctt aggtcaatta catctgcaaa gatctcattt ccaaataagg tcacattcaa | 1260 |
| aagtaccagg ggttagtctt agacttatct ttttggggga cacgattcaa cccactaccg | 1320 |
| tgggtaacag tggttttccc tcagaaggtg gtggttcagg agtgggagga agatgaactt | 1380 |
| ttcactgtat atccttttcaa actattcacg ttttaaaaaa aacatttttca tgtaaattta | 1440 |
| aaaaaattga acattcacac aaaaagatgc cccctccctt gcaaaaaaga gtatgcccgt | 1500 |
| tcaaaatgtt gaaatgtaca ctcacagcaa tggtggctgc agactccaag tttctgaggt | 1560 |
| tggagaaggt agccagggag cataaaagtg agttctatct actcattcag tctatgaggg | 1620 |
| gaaggcaatg gctagaaaag cattttgagg gacagtaaaa gtggcatttt tagagggagg | 1680 |
| aagccttgag gatgcttgtg gggtgaaggg aaagaataac tcaggaagag gcatttaggg | 1740 |

```
ataagaggag gagaggagat agtggaggta ggtgatccct gcggaggcca gattggggca    1800
ggggagtgtc agctgagtat aagaggatgg tccctctgc cctgaaggag gaaggcagga     1860
ggggaaaagg atgggtgttg acccagaaag cacttgtggt ggaggggagg ccccagaaga    1920
ggcttctgac ttaccctgat tgctggtacc tctcagggga gctggctgct tatttgctgg    1980
ccagggtgtg ggggaaccca tttgagaaga gggagaaggt gacacaattc ctttgggcaa    2040
cttatgggag gggtaattgg tgagggatga aagccctgcc aagtggcagg aggcccagct    2100
ggggctgccc ctcataagag tgcagtggag gatatgggat gagaagtgac tgcccctctg    2160
gttccatctg tcgcagagcc cagggtgctt ccttcctccc ccacctccct cagaacacac    2220
ccactgcatg ctggacagca gccccttcc tgggcctggg gacatccatg tccctctgtg     2280
cacaggcttc atcattctct gggtgcacgg taacgacccc ggtaggtgag aggccaaggt    2340
cccaaagggg agcagcaggg aaagttagct cccatctatt cttgctccag ggagggcctt    2400
tgatgaggaa gctgccaaaa gcacattgca aatacaattc caattacagg caacaggaag    2460
gagaaccacc tctgccacct ctgtcagcaa accatgagct cctactctgt gctgcgatgg    2520
cgggctcgat ggggataact ctgaccttac ctcatggagt cactgtcaac ccactggttg    2580
cactgtcttt gtgcactggc tctctggagt gaggtctttg caaacaaagt ggaaagagca    2640
tcaactttgg actccagcac ctagattcag agcaggccat ttcactcgga atctgctgtg    2700
catctgcaag ggaggatcat aaattcgcct ttgtttcttc ccagtatcga cagcccttcc    2760
agaaagagca agcctcatgt catgccacat gtacaatctg aggccaggag ctctcttttcc   2820 ccttttcatc ctcctgcctg gtacacaata ggtgtttact ggatgcttgt ccagttgatt    2880
tcttgaacat ggtgtgtaaa aggaatcttt gcaaattgaa tcttctggaa agctgagctt    2940
gtgcctacca tagaattctg aatgtaccta tatgacgtct ttgcaaactt aaaacctgaa    3000
tctttgtagt ataaatccct tgaaatgcat gtaggctgga catcaaaagc aagcaatctc    3060
ttcaaggagc agctagttgg taaggtcagt gtgcagggtg cataaagggc agaggccgga    3120
gggggtccag gctaagttta gaaggctgcc aggttaaggc cagtggaaag aattcggtgg    3180
gcagcgagga gtccacagta ggattgattc agaagtctca ctggtcagca ggagacaagg    3240
tggacccagg aaacactgaa aaggtgggcc cggcagaact tggagtctgg catcccacgc    3300
agggtgagag gcgggagagg aggagcccct agggcgccgg cctgccttcc agcccagtta    3360
ggatttggga gttttttctt ccctctgcgc gtaatctgac gctgtttggg gagggcgagg    3420
ccgaaacctg atcctccagt ccgggggttc cgttaatgtt taatcagata ggatcgtccg    3480
atggggctct ggtggcgtga tctgcgcgcc ccaggcgtca agcacccaca ccctagaagg    3540
tttccgcagc gacgtcgagg cgctcatggt tgcaggcggg cgccgccgtt cagttcaggg    3600
tctgagcctg gaggagtgag ccaggcagtg agactggctc gggcgggccg ggacgcgtcg    3660
ttgcagcagc ggctcccagc tcccagccag gattccgcgc gccccttcac gcgccctgct    3720
cctgaacttc agctcctgca cagtcctccc caccgcaagg ctcaaggcgc cgccggcgtg    3780
gaccgcgcac ggcctctagg tctcctcgcc aggacagcaa cctctcccct ggccctcatg    3840
ggcaccgtca gctccaggcg gtcctggtgg ccgctgccac tgctgctgct gctgctgctg    3900
ctcctgggtc ccgcgggcgc ccgtgcgcag gaggacgagg acggcgacta cgaggagctg    3960
gtgctagcct tgcgttccga ggaggacggc ctggccgaag cacccgagca cggaaccaca    4020
gccaccttcc accgctgcgc caaggtgcgg gtgtagggat gggaggccgg ggcgaacccg    4080
cagccgggac ggtgcggtgc tgtttcctct cgggcctcag tttcccccca tgtaagagag    4140
```

```
gaagtggagt gcaggtcgcc gagggctctt cgcttggcac gatcttgggg actgcaggca    4200
aggcggcggg ggaggacggg tagtggggag cacggtggag agcggggacg gccggctctt    4260
tggggacttg ctggggcgtg cggctgcgct attcagtggg aaggttcgcg gggttgggag    4320
acccggaggc cgaggaaggg cgagcagagc actgccagga tatcctgccc agatttccca    4380
gtttctgcct cgccgcggca caggtgggtg aaggagtgaa tgcctggaac gtactgggaa    4440
ctgcaccagg cacagagaaa gcgggcttgc cattatagtg ggttccgatt tggtttggaa    4500
aacatgggca gcggagggtg gagggcctgg agagaaggcc ctacccgaga caggggcggg    4560
gtgggaagga cggcagatgc tgggagcacg aggcaatttc tttatgacac agaactcatg    4620
ctctagtatt ccatctgttt cagccgaaga aaagaaccag ctgaaggggc aggggagaag    4680
gggcggaggt attctcgagg cccattggcg tcctttagga ctcaggcagg aagggccct    4740 tggtgctctg gagccggagg tggtgcgcct ggtactggga ccccggagct gagcccggcg    4800
cctcagccca cctggctgtc tgccgaccgt gtgcggggcg agtttgctca acaactctgc    4860
cagcttctgg ccctcaggct gtgggaagct tcttcccggg gcgagaccac tagcttttc    4920 taagtattac cagcccagga cttggctgag gttctgtgtc ccccagcttg gagtcagatg    4980
tggggttgaa tcttggcttc ctctcactag ctgtggtgct tgacaagtca cttatccttg    5040
agcctccatt gcctaatctt taaaagggag gtgacaatcg tccctacggc tcagtggcag    5100
cagatgggga gatgaaggga aagttctgtt gaccatgagt gaacttacaa tgcaagcccc    5160 gggggggatca cttgcagttt tgtccctgtc tgcagtgtga cctgttggtg acattgtctt    5220
tgctccaaac cacagctcct ggggcagagg ggaaaattct gccactcaca gctgcctgcc    5280
cacgcttctg tctgagtgtg ctgggtggca ggatggcaag tccttactca gctcagtata    5340
gccctcttcc ttgttccctg agcctttgac tttctcgagg gatgttgtgg ggttgtggcc    5400
aggataagaa agggcatttc aagttaccac tgctccaaaa caactgttct ggaaatagtg    5460
agtaccccat cctgagaggt gagtaagcag aggctgtatg accacctgaa ccaagcccct    5520
gaggatgttt cttctctggt ggaagtttgg aacaggagcc tcctcaagtt catttattca    5580
ttcattcaat ggttattttg tgggaatcga atttagaatg aaaatatttt ttggcaagca    5640
gaaaataatt tttagaccaa tccttttctt ttagtcatga gaaactgagg cccagagaga    5700
ggaggtcacc ccaggtgcat tagaactggg tttccagaac tgacactcca ctgcacagag    5760
tactctccca attcattcaa ttttttattta gcggaaggca ttttcagatg ggtctttgaa    5820
gcattagtag gagttcagcg atgatggtgt catgagaatt ttattctagg attaggaggt    5880
accatgaaca aagatacaga gctgggaaaa ccagaggtgg aagataagga gcacatgtcc    5940
acagttcttt ttcttttttt tttgagatgg agtttcgctc ttgttcccca ggctggagtg    6000
caatggtgca gtctcagctc actgcaacat ctgtctcccg ggttcaagtg gttctcctgc    6060
ctcagcctcc caagaagctg ggattacagg tacctgccac cacgcccggc taatttttgt    6120
atttttagta gagaagggt ttcaccacgt tggccaggct agtcgcaaac tcctgacctc    6180
ctcagtggat ccgaggaggt gatcctcccg cctcagcctc ccaaagtgct cgaattacag    6240
gtgtgagcca ccacgcctgg cctccacagt tctttatcca ccgtctgaaa tgtaaaatgt    6300
tacgaaaacc aaaagttttt tttgtgattt atttgatggt agcacctgac gtgaactgac    6360
atgagattat ttttaattta gttgtgtgaa tatgcatatt catatatttt gctgcataga    6420
ttacagtatg cagctccaga ttcttccaag cagactctga ttgcccatta ctgcctttct    6480
```

-continued

| | | | | | |
|---|---|---|---|---|---|
| aaaatccaaa | caagttctga | ggttcaaaac | cgttttggcc | ctaaggcttt | gggtaaaggg | 6540 |
| ggtggactct | gttctactct | gactggagtc | caagatgcat | atatacagag | atatgggtga | 6600 |
| tggggctgca | aggtaggttg | aggtaggggc | caaggaggag | catggagttt | ggacttgatt | 6660 |
| catgaggctg | tggggagcca | gtgaaggttc | ttaagcaggt | atgtctgcct | gagagcagtt | 6720 |
| ggagcagaca | agagctaaaa | accaaacaaa | tcaccataga | tagtggctgc | tataatttgt | 6780 |
| ttgtcccctc | caaatctcat | gtggaaattt | ggtcctcagt | gttggaagtg | gggcctaatg | 6840 |
| ggaggtgttt | gggtcatggg | ggaggaaccc | ctgtgaaagg | cttggtgccg | tccttgtgat | 6900 |
| aatgagtaag | ttctcccgct | atgatttccc | ttgaaggctg | attattaaaa | agagcttggc | 6960 |
| acctccctct | cttctctctt | gcttcttctc | ttgccatgtg | attgatctct | gcacatgtag | 7020 |
| gctccccttc | accttctgcc | atcagtgaaa | gcagcttaag | gccctcacca | gaagcagatg | 7080 |
| ctggtgccat | gcttcctgga | gagcttgcag | aatcatgagc | tgaataaatc | ccttttcctt | 7140 |
| gtaaattact | caccttcagg | tattcccttta | tatagcaaca | caaaaggact | aagacagtgg | 7200 |
| ccttgacttt | tctctctctt | taagaagtgt | tgcctttgct | cacttagtca | tcccttctgc | 7260 |
| ctgcatttgt | agagcatctg | gatgggagat | ttatataacc | gtcactcttg | actttcccag | 7320 |
| caggcctatg | tcataggtac | tgtggtctct | acaatacagc | agaggtatct | gaggctccga | 7380 |
| gaggttgagt | gacttgctca | tggctgcaca | accagtaaat | attggagctg | gaattcaggt | 7440 |
| ccacggtttc | ctggctccaa | agcccatgat | ttttcccctc | aatttattct | gactggggca | 7500 |
| tgggggaggg | ggtggccttt | gggcagggcc | accaggagcg | accaggcccg | tagagagctg | 7560 |
| ggtgcaggta | cagaggaaaa | cctgttgtcg | agtgtggccc | gtagttccca | tttttgcctg | 7620 |
| aatggcacat | ttgaaagtgt | tatataacca | tgtgaataat | aatagttggc | ctatatgagt | 7680 |
| tctttaatttt | gcttttttggt | ccgcatttgg | taacttcttt | atcatctact | atactctgtt | 7740 |
| gtgtctcttt | tgttgtaatt | tgtaagtagg | ggtgagataa | agtacaccta | gggtttgctg | 7800 |
| ggtttcttcc | atgtcatcat | gttcctcctt | gcatggggcc | aggatccgtg | gaggttgcct | 7860 |
| ggcacctacg | tggtggtgct | gaaggaggag | acccacctct | cgcagtcaga | gcgcactgcc | 7920 |
| cgccgcctgc | aggcccaggc | tgcccgccgg | ggatacctca | ccaagatcct | gcatgtcttc | 7980 |
| catggccttc | ttcctggctt | cctggtgaag | atgagtggcg | acctgctgga | gctggtgagc | 8040 |
| cacccttttt | gggaatggca | cttcctgata | gggctgggcc | actgcatata | cactggggac | 8100 |
| tgtgcttagt | aggcccattg | ctgaaaatca | gaaggggaca | gcaagtatgt | attgagcact | 8160 |
| tatcgggtac | caagcacagt | aactactggc | tttctgtata | gaattcccctt | taagcctggc | 8220 |
| catgccccag | tggtacgtct | atcttcattt | gaaagacgag | gagactgaag | ttcagagggg | 8280 |
| accacacaga | cagctagggg | tagagcctgg | atcaaaccca | ttggtctgcc | tgccagccat | 8340 |
| tcttgtgcca | atgcatctgc | tgcctacgga | aacctgtagg | gacaaggccc | tgggatgttc | 8400 |
| agtggagcct | gagtcatttt | ataaaaaagc | atgactctag | ggtccaaaat | tcctttgaag | 8460 |
| ctgttgctat | ccagagtgaa | gtcccttctt | taggacaggg | tggccctcct | ccctcctgga | 8520 |
| tgtcacatct | tcggtggagg | ggcagaaagg | ggactgggta | ttctcctcac | cctggcccta | 8580 |
| gtgcttcaaa | tcttaaaaaa | acgttttttat | ttgtgcttct | gcaccacctt | ctagcccacc | 8640 |
| tcgtttcctg | gcctctaact | tgatgagagc | gtgtgtcatt | ttcacactga | ttctccacat | 8700 |
| ggcaggcggt | gcttcttagc | ctcctgcaga | cagtgaggcc | ccacggtctt | gtccaaggtc | 8760 |
| acacagcgtg | taatgggcag | ggtcagagtc | tggagtctgg | acctgggtct | cctagctgca | 8820 |
| ctgcactgct | gccccatggg | ttaatcagct | cagcataccg | tggctgaaca | gctacctcat | 8880 |

```
accaaggcct gtggcgccat gacagggatt gacagggtcc ctgccttgga aacccgtagt    8940
ctaagtagag gagactgaca agtcaatgcc ttccatcagt ctgctcaaca cacgtttacc    9000
aagtgcctac tgtgtgctgc agaggcgaag atgacacagc tcaggccttt cccttgagct    9060
tacagttcag gaggagagac tgaccagtga ctgccagtac agttgactat gggacaatgt    9120
gctcagcctt ggggagagac gaagaaggta cccgtatagc accagatgac aggcacgagc    9180
cccacaggcc agggcagctg ctcagaggag agtaggccaa gcagaaggca aacagaaggc    9240
tgcaggcatt tgccatcgag agctggactt caaactgggc atcataccag cctgggttcg    9300
agtcctgccc agcccttat tggctgtcta accctgagca aatcccttca cctctctgag    9360
cctcattcct ctatctgtaa accagttata ataattggaa cattcattta aggactaaat    9420
gaggtcgtga agcattcagc agatgctagg tacggaaact cgctgaagtg ggggcaggtt    9480
aagaagcctc tggggatacg aaggcatcca gggactagtt gtggcaggag gctgttacca    9540
cttaggtctg aagggtaagg agagggaata gctttccctc tgcccagttg gagccggtgg    9600
catggaggag aggctgcctg tggggaatca cccgagggtt caccgctgcc atgcgcaggg    9660
agtcaggagg tagggaggga gtggggcaga tgcacaccat tttttttttt ttttgagact    9720
ctgttgccca gactggagtg cagtggtgcc atatctgcac ctctgcctcc cgggttcaag    9780
ctcactgcaa cctctgcctc ccgggttcaa gcgattctcc tgcctcagcc tcccgagtag    9840
ctgggactac aggtgtgtgc caccatgcct ggctaatttt tgtatttta atagagatgg    9900
ggtttcacca tgttggccag gctggtctcg aactctcgac ctcaggtgat cccccacctc    9960
ggcctcccaa agtgctggga ttacaggcgt gagtcaccgc tcccagctgc tgatgcactc   10020
ttgtccttct aactcctgct agtgcctccc attggctgag cccaactgga agctttgcaa   10080
gggagctggt gctgcagttt gcactgagca ggctggagaa ggctggagaa tagactaggg   10140
gacaaaccga attgccagtg ctgttatgtc atgatttagg catggagtcc agggcctgag   10200
cttcactcca tgtccatcct gcccagagcc ttggcacagc ctggctccca gacaagatgt   10260
caagttcaga atccttccta aaaggaatcc tctatgccag accgtgttgc agggatatgg   10320
gagtgctggg ctcccagcct gatcaaggag cgagaaaact caggctccta gtctgtcctc   10380
cggggcacta gcagggacaa ggtgggaggc tgctgggctg ggatgtgggg acaggtttga   10440
tcaggtaagg ccaggctgtg gctgtgtttg ctgctgtcca aatggcttaa gcagagtccc   10500
ccggcctctc tggcttctgc aggccttgaa gttgccccat gtcgactaca tcgaggagga   10560
ctcctctgtc tttgcccaga gcatcccgtg aacctggag cggattaccc ctccacggta   10620
ccgggcggat gaataccagc ccccggtaa gaccccatc tgtgccctgc cccaccccat   10680
ctgagctgaa tccatttgct ctgccctggc ctggcctccc tgctggtggt ttccacttct   10740
cggggggctt tgggactcag cacctccact gacccctttt tttctgtccc atccccatcc   10800
cctgcagccc ccactgcctg ccttcctgtt gccccacaaa tgcaaaagtc ttgccttaaa   10860
tgatcctctt ttccttcttt tctcttgttt tccttttctc accatttgga atggcccagc   10920
aggctgcact tacccttggaa ggagggttca tctgatggtg actctaccta gggcccccag   10980
gcctctataa ctcccagtgc cctgcagact ggaccagatc ctttaatggg atagacacaa   11040
ccctgtctgg gatgcctctg cctaccttcc tgttttgctg ctccacctgc ctccagctcc   11100
gtttggcttc ctggggctcc ctgcctgggc cactttgtgt cttccctcta ggcctttctt   11160
tccactgttc cctctgcctg gtgtggcctg gctatggaag ggagggagga ggagcggcca   11220
```

```
tggaaaacgg tctgcattct agcagggact tgcaggtggc aattcagtcg ggaagactc    11280
tagatgcacc tggcctgagg agagaatgaa gggttctagt tggactgtgt taagtttgag   11340
gtgcccatgg tgtgaggtct ggagctcagc gcagagatga tgcaatgtgg tgggtccatg   11400
caacatggtg ccaggacgca gagcttgggg tgaactcagc tttcacccct taccggttct   11460
cgtgggatct tgggaagcca ctttcttcta tgagctttgt cgttcttgtc tgtaaaatgg   11520
gcacataacc ctgtccctgt ccttctcaca ggttgctgtg agactccaat gagttgaagg   11580
atgtgcagat gcttttggaa gtgaaaagtt gggggggctac tgtgtgactt tgcatacacc   11640
caaactgtgt gaccttgcat atgtctgagt tgctgccatt gcaacagatc agagctggtg   11700
ggctgggtgt ggagaaaggg tttgtgtggg ggacatcctc tggcaagggt ggcagcagca   11760
gaagtgaggg gcctggtcgg tcatgtgtgc tgacccggcc tgggcagcct gtggccaggg   11820
agaggacagc tcctctgtag aagagcctg ttcctttcca accaggtgag acctcttcag   11880
tggagccctg gagcccctg tactccacat cagtgcctca gggacctccc ggagcaggct   11940
aatatcagag accaagaggg acactggcag aggatcacag agaccccagt ccaggcaggg   12000
actgagaaga tcttgccccc taagttagtt cctagcact gctgtgacaa attaccaccc    12060
cctcggttgg aacaagttga ttctctgcag tcctggaggc cagaagcctg aatcagtgtc   12120
ggcaggacca ctttctcccg ggggctcca gggagaagct tctcttgcct cttccgtgtc    12180
ccaacagcgg cagcacacca atcccagcct ctgtcttcac acagccttct ctgtgtctct   12240
ctcctcttca ttgtctcata aggacacttg tcattggatt tagggcccac tggatcctcc   12300
aggatgatct catgtgggga accttaacca catctgcaag gaccctttt ccaaataagg    12360
tcacagccac aggttgtggg ggttaggatg tgagtgtatc tctttggcag ccactgttcc   12420
ctcctctccc ttgggccaga agcagacgtg gggccctttc ttccccatag gatgcccatg   12480
gattgcccc cttcccgctt ccccgagtg tctgtgggag gtggcaggaa tggcaggcag    12540
gggtgtggaa ccccttctgg agtcatatca agggcttggc tggaggaagt cctcctggag   12600
ctgttgggct ggcatggggc aggctggctg ggcccagcag cagcttcttc attcatgggg   12660
aggccacaag catgggccct agagctggct gccgccctca aacccagacc ctgcactctt   12720
aactgtgtga ccttgcatac gtcactcacc ctctctgatc ttcaggttcc tctgcaaaag   12780
ggaggtaatg ataaccctca ctctgggggg ctgtttggag ggttaaatca gttattgctg   12840
tagcatgcat ttctctgtca ggtattgagt gaggtgctgt gattttagcc ctgcattttt   12900
cttttcttac cattcaataa taacgttttg agcaccact gtgcgccagg caccatatta   12960
ggtgctgggg atacaaatgt gaatgaaatg aatgtggtct cttcccccaa cagtgtatcc   13020
agaagattaa tccattcctt aaacaaatgc tacttgacac agattagttc tggataggct   13080
gagagctctg aaggagtgca ggcagctgcg agcctgtgta tccagcagaa ggatcaggaa   13140
aggattcctg gaggaagcgc tgttctagcc aagacctacg ggggcattat taaccaggca   13200
aaggggacgg tgtccaagca gtggaatgaa cgtggattga agctgtgagg caggaggag    13260
tgtggcctgt gcagaaggga ccgaggctgg tgagaccagg agggcctggg tggcctccag   13320
gtcagatgtg aaaggaagaa cttggccaca gtctgagctt tcaggcgta tggcagggct    13380
gcctggtgag agggaatgag ctccctgctc tggaggtatg caagcaggac tgggctctca   13440
cctgccagag gccacagagc tttcagagg ctggaagagg ccactccaag gcctcttttgc   13500
ccctgagagt ggtggctctt cttgaggcca ccttgccacg ctgtcacagg gaactagcag   13560
cccctgcctc acccgggggt ttggaagata gagggaggcc taggaagggc cctgtgtctc   13620
```

```
atccgagctg ggccccttte cagcctctca ctggaaggaa gcccaaggat gttcctgtgg    13680
gggcttttac caggcccacc tgccctctgc tggccatgct tgcagcctcc tgaccctgtc    13740
ccagcaggac agtgggctgg tgtgagcggg caggaaccgc ctgcacttag aaggtgtggg    13800
gctgcctccc cgagcttcca tctgccgctg ggcccacacc ccaggccag gatgggacc     13860
ccacagtggt cacatcatct tgcagcagaa cccaggtaca gctcctggag cagatggtgg    13920
tcccaagcac gggtgggacc agaaaggact ctcacctggg ctaactcagc tgcagcctca    13980
gttccctcct cacacacgac gaggaacatg gactggaagc ctgcccagca ggccttctgc    14040
tcgatgtgcg ttgtgtggct tacgtccagg gagggaagca gcctctgtgc tgtcttctag    14100
ataagcctgt attccccggg ctgtctgcca atgtatccag ttgtcccgtc agcctggaag    14160
ctctgaggga aaaccttggg ctgcttcctg agcacctgta tccccctgcag ccagcccggg   14220
gcctctgcta ggagcagact gagcatggct tatgggcctg gcaccatctg gcctctgccc    14280
accttgctgg ccttgtcttg tgtctgcccc ttcgacattc catagcccag ctcaatatct    14340
agtggttcct ctagggtggc gagcactgtt tggtctccag atgtcttcag gtcggagctc    14400
acagcgctct cagccacccc ttcccagtgt agcaccgggc acatggtaga tgcctattga    14460
tgagtgaaag ctcctaacac actcagagag caaggactcc gcctcatccc acagcctggg    14520
aggagaggca gactgccaag gacctgctca gcatgctaca gaagaaacca aagtgcccac    14580
gggactgatc agtggagctt cctgccgaga ctggaggcct tagggcaggg tagacagtgt    14640
gtgtgcaggc tggggactca cagttcggac tgtgcccaga cctactagca tagtgggtgg    14700
gtgggaggat gcgggactgg gggccgacct tgcctgaaat tcatgtggga tctcagagca    14760
gccactgaat tgctctgtag ggggctaaat agtggccccc acagatacac acacccagac    14820
agagcctgtg agccagacct tatttggaga aaaggtcttt gtagatgtaa ttaagcatct    14880
caagatggca tcatctggat tatgcggtgg gctgtaagtc ctgtgatgtg tctttatgag    14940
agaaaggcag agggagattt gacacacaca ggaggggcca cgtggagaca gaggtggaga    15000
ttggagaaat gtggccacaa gccagggaac accagcagcc accagaagcc ggaagacgtg    15060
aggcagggtt cttcccagag ccttcgctgc tgagtctggg aatttgtgac cgaagccata    15120
agaagtgggt acacgccctg agcctcccac acttgctcac ctgtcctgag atgagaatct    15180
ctactctgca gcatatttgg aggatcactg cgggggccac agaggtgctg ttcagatggc    15240
acttcagaag actcaggaga ccctggggca ggagcagttt gactgacagc ccagagggct    15300
gccctctgat tccacctgag gccctgcttt tcctggctgc aggggttcca gggccaggcc    15360
atttccgctg gcgcaggact ctgctagcag caacctgcct gaagtcttcc tttggcctgg    15420
ctgagagttt ctgagacctg cgctggagcg gaggtgcttc cttccttgct tcctttcttc    15480
ctctctccct tctccatcca gcaggctgga cctgcctggc atctgtgagc tctccctact    15540
ttctcctata ccctaacctt tgtcctgcat gggcgactcc cccagtgagt ctcttgcagc    15600
ttttacccca gtgcctgctt cttggagaat ccaaactgat ccagttaggg atgataaagt    15660
gtagggtagg cgctcggtga ctgttttctc tgaggttgtg actcgtgtga ggcagaagca    15720
gtccccgtga gccctcctgg tatcttgtgg agtggagaac gcttggacct ggagccagga    15780
ggcccagaca tacatcctgt ccgagctgca gcttcctgtc tctaaaatga gccggccagc    15840
gcaggtggcc agacatcact gttattctcc tttgagtctt taaatcttgt tgtctttctt    15900
gcagactcgg tgagctgtga aaggctataa taggggcttt atttttacact ttgatactat   15960
```

```
tttttgaaca ttcatattat tgttagatat tgatattcat atgaaggagc aggatgactt    16020
gggtccttct tggcagtagc attgccagct gatggccttg gacagttacc tgccctctct    16080
aggcctccct ttccttgtct atgaaataca ttatagaata ggatgtagtg tgtgaggatt    16140
ttttggaggt taaacgagtg aatatattta aggcgctttc accagtgcct gggatgtgct    16200
ctgtagtttc tgtgtgttaa ctataaggtt gactttatgc tcattccctc ctctcccaca    16260
aatgtcgcct tggaaagacg gaggcagcct ggtggaggtg tatctcctag acaccagcat    16320
acagagtgac caccgggaaa tcgagggcag ggtcatggtc accgacttcg agaatgtgcc    16380
cgaggaggac gggacccgct tccacagaca ggtaagcacg gccgtctgat gggagggctg    16440
cctctgccca tatccccatc ctggaggtgg gtggggactg ccaccccaga gcgttgcagc    16500
tgtactcctg ggttgcaccc ccccagctg tcactgtccc ctccctgcca tcagttgtgg     16560
gaagggcgtt catccatcca gccacctgct gatttgttat agggtggagg gggggtcttt    16620
ctcatgtggt ccttgtgttc gtcgagcagg ccagcaagtg tgacagtcat ggcacccacc    16680
tggcaggggt ggtcagcggc cgggatgccg gcgtggccaa gggtgccagc atgcgcagcc    16740
tgcgcgtgct caactgccaa gggaagggca cggttagcgg caccctcata ggtaagtgat    16800
ggccccagac gctggtctct ctccatctgg acctggcctg ggaggtggct tgggctgggc    16860
ccagggagag ctaatgtctc ctaaccaaga atgctgtggc agcctctgcc gcagagccag    16920
agaaccagag tgccaaggct ggcagggttc ccagtgccca cgagtgcaga tgaagaaacc    16980
caggccccaa gagggtcatg caggtagccc agggagttca gccttgaccc tgggtcaatg    17040
acctttccac agttccacac tgctccccctt ttaaaatccg gtgatgtctt tatgtctttt    17100
gttatgttat cttcaatgtg gagggactcg aggtgatcta agcaaacttt ttctatcttc    17160
tgcttgcata cctctgagac caggggactc actcacttgc atgactgggc cctgcaggtc    17220
acactggcca ggcagatgtg gtggaggaac tggcagagga cttttctag actgtgacta    17280 catttagtcc acccagcggc ccccctatga agtccagttg agaactagga ctctgggggc    17340
cggtggacag agaagaggga gggttctctc ccttactgac ttccttctgt ggccagacat    17400
tgagcaaggc ctctgtacag catgtcctgg ggctggcctt gccgtagctg ctaaatagtt    17460
gacgaaacca gtccagagag gggaggtgac tgccagggtc gcacagctca agctggggaa    17520
ctcgctggga aaactgtcag ctctgggcag cagcttgact tccactgtaa gcccagccc    17580 ccagggtcaa acactggctc tggtgctggc agaggcagcc cactagcctg tttcaaaggc    17640
tgagaaggcc caggagtctg ccctgtgctc caccagttct gccctgagac tttcctacag    17700
agtacaggtt ttgatgttca gttttaaagg caagaatcaa taaccttctg ccccatcagg    17760 tgacccttg tgcctgtccc acccctttat tgactgacct cggctcagtc aggtcagttc     17820
ctgaaggtca gtgtgtggag gggaggctgt tctttcccag aaaggccttc cccaggcctg    17880
gtgctctggc ctctggagga cttcctggag aagtcccttc tttggggtcc cagtcagtgt    17940
atgggaagcc cttattgcat gacctggcac ggggcagggg ctcaacagtc actattgcct    18000
tccttgccac tgccatttcc tcctctgtaa gcaggtgatt gtgtgtccag tctgagcaca    18060
gagataagca cacagcaggt gcttaataac tagcagctgt aggctgggcg cggtggctca    18120
tgcctgtaat cccagcactt tgggaggccg aggtgggcag atcacctgag gtcaggagtt    18180
cgagaccagc ctgttcaaca tggtgaaacc ccgtctctac taaaaataca aaaattagcc    18240
aggcatggtg gtgggtgtct gtatcccagc tacttgggag gctaaggcag gagaatcgct    18300
tgaacccagg aggtggaggt tgcagtgagc tgagatcgtg ccactgcaat ccagcctgag    18360
```

```
tgatagagcg agattccatc tcaaaaataa ataagtaaat aactagcagc tgtaaatgtg    18420
gctgttgttc ttcacctcca cactcagtgc cactccactc cctccctccg tggtgtgagg    18480
ggcctcacta gctgtctcct aggaggagca tggctgtgag attccagctc catccttggc    18540
cacggctcct ggagacatct tagaggccag gatccagaag gctcccacac ctcatttgac    18600
aggggagaag ctgtcagttc caggtccccT tgcacatcag gccagagct gcgttaggcc     18660
tccagtctcc aggccactgg gccagagctc acaggctggc agagggttag aactgttact    18720
ggtggctggg tgcagtggct cacgcctgta atcttagcac tttgggaggg caaggcggga    18780
ggatcatgag gtcaggacat cgagaccatc cttgctaaca cggtgaagcc ccgtctctac    18840
taaaactaca aaaaattagc cgggcgtggt ggcaggcgcc tgtagtccca gctactcagg    18900
aggctgaggc aggagaatgg cgtgaacccg ggaggcggag cttgcagtga ccgagattg     18960
cgccactgca ctccagcctg ggcaatagag cgagactccg tctggaaaga aaaaaaaaaa    19020
aaagagctgt tactgttgac agtagcatga ggtagaccat ggcctgcacc aaaatggggg    19080
agtggagtgc cactgaggcc agaaggaacc acaccctcaa gggtggggag ttatggtatg    19140
gggggtccta ggcatggagt cttttaattc tttagacaat cctgggagca actgtccctg    19200
tttcacagag ggcggggcca cacagctggt gagtgggcag ccaagactct gttcaagttt    19260
gtgtgggtcc aacacttgcg gccacggtgg aggggcatct gagccaggcc tcagagagtg    19320
gcggggaag ttgggtgggg aagtgtgccc ttctcattcc tctgaggctc atcctcttgg      19380
tgcctctctt tcatggaaag ggataataag gttattgtga ggatcccctg agttcgtata    19440
ttcagacgct tagacagagc caggcacaga gaagggcccg gggttggcta gtttgattgc    19500
tggtgtaatt gctaatatct tccagtttgt attggtcaag gttctgcaga gaagcagaac    19560
cagtaggatg tatatattaa gagtttcaag ctcatgtgac cgtgcgggct ggcaagtctg    19620
aaatccgcag ggcaggccag gcaggctggc aattcctgca gaatttgatg ttgcaatact    19680
gagtcctaag gcagtcctgg ggcagaattc cttcttccct gggaggcctc agtctgttct    19740
cttaaggcct tcaactgatt aaatgaggcc tgcccaagtt atagagagta acctgcctta    19800
ctccgtcttc tgatttaaat gttagtcaca tctaaaaaat attttcgcag cagcatttcc    19860
actggctttt gaccaaacat caggccacaa agttgatccc caaaattaac catcactctg    19920
tgcctgtaag ggaggggctg ggaaggggga gcaggtctcc ccaaggggtg accttggctt    19980
tgttcctccc aggcctggag tttattcgga aaagccagct ggtccagcct gtggggccac    20040
tggtggtgct gctgcccctg gcgggtgggt acagccgcgt cctcaacgcc gcctgccagc    20100
gcctggcgag ggctggggtc gtgctggtca ccgctgccgg caacttccgg gacgatgcct    20160
gcctctactc cccagcctca gctcccgagg taggtgctgg ggctgctgcc ccaaggcgcg    20220
ggtagggggc ggagggcgga gggcggaggg agggcgggcg ggcaggcggg cttcttgtgg    20280
cacgtgggct tcttgtggca cgttcctgga ggccgaaccc ttctggcttt ggaaggagtc    20340
gtcagagacc cccgccatgc gggaggctgg ggaggaaggg gctcgaaacc tccatcatcg    20400
cagagtctga atagcagtgg ccccgccatg cgcccacgta gcggcgccta cgtagccacg    20460
cccccacacc ccgtcctggc cactctccct cctgaaggtc ttctggtacc cgccccctcc    20520
ccatctccat ccccaggccc tgcgtcctct gcccaatact cttttgggcct ccctgttgtc    20580
cagctctctc cgcggctcca tgactgacaa cttgagcaag gctaatgtga atgggagcgg    20640
ttgagggctc agacctctca cccgaggaac atccacagag tgtgccgcat gcccggtgca    20700
```

```
gtgtggctgc ggggacacag acacggagcc tcggccctga ggagctgggg ggcagtgacc   20760
gtccctcctc tgacccacca ctcctccagt gtcaggacac tgcgggtatc taggggaagg   20820
aatcttgttc cacttcaagt ctggaacttc aagtctgtgt gtgtgcgtgc gcgcgcgcgc   20880 gttggggtg  ggggttgcag agcagatgcg tacctgacag cggtaaccta ggtccccct   20940 ggcctatcaa ggcttccctg gcggccgaat ttaaaggcat caagcaaaca aagcccaaca   21000
catctctgcc ttgtcctctc agtttccccc cgtggcactt agaaccactt gatacaccga   21060
atagtttcct atctccccca ctaggatgta aactccacag gggcattggg aatgctgcct   21120
ggctatggta gggacagagg ggagcaccag ggcggggcag gggtgccaga gttctgcctg   21180
ggcagtcaga ttttccttag gagggggacat ttgagtggga cccaaacagg tgtatagcag  21240
ttgtccagcc cagctggcaa ggcctgagtc tgcctctgca acccctctct gggctcctt    21300 tctctgccac ccacctcctc acctttccag gtcatcacag ttggggccac caatgcccaa   21360
gaccagccgg tgaccctggg gactttgggg accaactttg ccgctgtgt  ggacctcttt   21420 gccccagggg aggacatcat tggtgcctcc agcgactgca gcacctgctt tgtgtcacag   21480
agtgggacat cacaggctgc tgcccacgtg gctggtaagt caccacccca ctgcctcggc   21540
caccgtgatg ctaacagccc cttggcagt  cagggtctgt gccgggacct ccagtgccag   21600
gctctgtgca ggggaccag  agatgaagta ggcctgatgg tgccttcaag gacactcagt   21660
ctgatgaggg aggcgagtgc acagaggaaa cacgaggtca gggctgtatt agagggagcc   21720
cagaggaggc acctgcccag cccgagggtc agagaaggca tcttggagga gggacatttg   21780
atcgggagct tgatggatga ataggagttc acctggccga taagacagca actaccaagg   21840
cttagaggtg tgagaggagg ctgtcttacc tcactgagta aggactgcag gcggcttacc   21900
ttcgagaaga gagcttagtg tctgtgtgca cgtgtgtttg tgtgtatgtg tgtgcgtgtg   21960
tgcactggca ggagtcccct gctggggcag gagggccggg ccatcaccat cttttcaccat  22020 tcacccctgc accaggcatt gcagccatga tgctgtctgc cgagccggag ctcaccctgg   22080
ccgagttgag gcagagactg atccacttct ctgccaaaga tgtcatcaat gaggcctggt   22140
tccctgagga ccagcgggta ctgaccccca acctggtggc cgccctgccc cccagcaccc   22200
atggggcagg taagcaggat ggcagggtgg gcaagtccag gctgggcctt gggaggtctg   22260
tgtgaccttg acagtctctc ccttctccct tgtctgtgta aggaggatga cgccacctta   22320
aataggatta aatgagaatg gggctctgaa agggctgtgc aatattttca taacgtgttt   22380
ttatagagac agttgagtat gttctttaag ccctcctctc tcctaccatg aactaaagat   22440
ttctgtggag gtcccctcac tcccagcacc ccctcctcat cccaggccct ttttgcaggt   22500
tggcagctgt tttgcaggac tgtatggtca gcacactcgg ggcctacacg gatggccaca   22560
gccgtcgccc gctgcgcccc agatgaggag ctgctgagct gctccagttt ctccaggagt   22620
gggaagcggc ggggcgagcg catggaggtg actgtacccc tccttcgtgt gtgtgtgtgt   22680
gtgtgtgtgt gtgtgtgtgt gtgtgtgtgt gtgtgtgtca gtgctgggcc tcagggacc    22740 cccagcaagc ccctccatcc tccagactcc agctcttctg taagcttaca gggctggcca   22800
gaccaggagt ggggcactcc tcacttcacg cggctgggg  ctgctggaga gagccacagc   22860
gggaagggtt tcctagaggc tgcaggacag tgctggatgg attttcaatg ctcacctggg   22920
tgtgagcgtg cggcagggcc gcgtgagggt cagcgatctg ctactctgga ctcagccatc   22980
tctaggcccc tctcactcag gtgctccatg gttctgggag ctgagaaatc tcaaaccagc   23040
aaaaaagtgg aattgatgtt gatgctacag gatagtgcac agatgccatc tggttgcagc   23100
```

```
attttggtgg aagggcagtg cccagctagg agagtgagga ggggcaggca tttctggctt    23160
gaggagatgg ggtcttaatg ctcgtgtgag aggcagagtg ggtggagtgg agctggctgg    23220
atccttgctt tggcctcctg gatttctctc tatctccatt ttgaaaccac tctgtgtttg    23280
gaagaacttt tgagtattca gagctgccca ctggcagaac agtcttcctt gggcaggagt    23340
gagctccttg tccccagaag gctgggtctg gctggcccct ggcagggaca ctgatgaggg    23400
tgcttgagtt gatcctgtct agtccctttc tgtgttttca agcccattc taaagcagat     23460 tcccatttcc gtctttgact ctaaggccca aggggcaag  ctggtctgcc gggcccacaa    23520
cgcttttggg ggtgagggtg tctacgccat tgccaggtgc tgcctgctac cccaggccaa    23580
ctgcagcgtc cacacagctc caccagctga ggccagcatg gggacccgtg tccactgcca    23640
ccaacagggc cacgtcctca caggtaggag gctgggcttg ccctggggtg aggagggggtc   23700 tctttctcct tatgcaccca ctgcccgcga ggcttggtcc tcacaagtgt gatccatgag    23760
actcaagcct gacttgcagt tccatactct ggttctgcca cttccatgcc ctttgagcct    23820
gggcaggtga ccttacttct cctcatctca gcttcctcct ccataagagg gaaaaggta    23880 ttacctgcct cattgtgttg caaggagatg ggcagcatct agggcactgg cctggagtat    23940
cgcaggtgct ttgcctaagg tggtgcagtc caggagaggc agctccagag agaggccccc    24000
ggctggggct gaaaggaggg cagacctcgg tttgaatttc accctgccgc tctatagctg    24060
tgtgacttgg gcaaattact taacatctct gtatgaggaa atgatgagtg ctaagcactt    24120
agcttagtgc cggacaata  taaattctag ctatcgttac tattgttttc atcacccgtt    24180
gctttaaaat ccagcctctg gtataggcaa ctattgacgg gctaccctgt gtcgaaaaca    24240
tgcccaggca ggtagcagga agtcacagat ggggacctct tggggcatca agggatggtg    24300
ccctgaggct gagctgttct ggttgggtgg agcatgagag gtctgggaag acagtgggac    24360
tccagcctgg aataagaggc tcagagttga ttctcgtctg agcacgtcca ggggaaccac    24420
tgagggtttg ggaacaggag agtgagggtg agaacctggt tctgggcaca gcaggctggc    24480
atgtaggatg gatgttcagg aaagatgagc atagtcaggt ggctggtgcc cttgtccagg    24540
ggagaggctc cgtcaggttc aggggtcctg gcttggaggg aagtccgcca tgctctaatc    24600
acgctcccct ttggaagtgc tcagccgatg agctcacagg cacatgtcag tttgaagtca    24660
tggaatctga ctccatgaag cgcacctcaa agagcaccat tttgcagcta agggaactgc    24720
aggctggaca tgctgagtgg ctgccccgag cccttgcagc taggacatag agaatgctag    24780
taaccacaac cctaccatgt tcagagcaca tgccaggctc catgctgggg cttcgcacgt    24840
gtcatcttca cagtgtccct gtgagtaggt gtggtttctc tttccatctt acaaatgagt    24900
aaacagagcc tcagtgtagc taagtaacca ctattttagg tttcttagcc aatgggtgtg    24960
tctgactcct aagcccatgg agggcattct gaggtggttc agacagaccc cggcttaccc    25020
ttgaacttct gcctgctggc tgcataggga ggggctgggg ggagtttgag catctccaggc   25080 catagagccc ctgcctcact gtctccatct ctgggtggaa agatggtgtt ttccctgaga    25140
aactaaggct cagagaggtt gaatggctct cccaaggtca cacagctggt cagctgcaga    25200
gttgagaaca caggagtcct ggtgctcagg ccagcatctc ttttttttctt tgagttgttt   25260 ctaggttttcc tagctcttgc ctcagacctt aaagagagag ggtctgatgg ggatgggcac   25320
tggagacgga gcatcccagc atttcacatc tgagctggct ttcctctgcc ccaggctgca    25380
gctcccactg ggaggtggag gaccttggca cccacaagcc gcctgtgctg aggccacgag    25440
```

```
gtcagcccaa ccagtgcgtg ggccacaggg aggccagcat ccacgcttcc tgctgccatg    25500
ccccaggtct ggaatgcaaa gtcaaggagc atggaatccc ggcccctcag gagcaggtga    25560
agaggcccgt gaggccgggt gggtggggtg ctgcgtgtct ctcctgcaca gcttttctgt    25620
gtcagtttgt gccaccacca taccgccatg catcagggtg gcggtttgcc aggtagatgc    25680
tgtgggcagc ttccgccatt gtgtggacag catgtatatg tgtctctgtg tggctgggtc    25740 tgttttttgct tttgtccaga tcagtaaggt ttgctacctg ggtaccccac tccacttgga    25800
gtagaatgtg cataaatatg gcataaagaa atgcaatatg catgcattta ttgattgatc    25860
tatttttttc tgagatgggg tcttgctgtg ttgcccaggc tggtctcaaa ttcctgggct    25920
caagcaatcc tctggtctca gcctccccaa gtgttgggat tataggcatg agccgctgca    25980
cctggcctct ctgatctatt taacaaacct gctgggaggg tctcagggtc aggagcagca    26040
ctgggctctg aggacacaga gctcactcag ccgtgaccca gagggggtgc ctgagctgca    26100
tgctgaaggt tgttagcatg accagcaagg caagaaaagg ccctgccgag attagcaagg    26160
catgtgccaa gccctggaat gtgacagccg ggccttctag aaacctgagt gtataactct    26220
ccttaaaagc cagtaggagc tcctcaaaag gcagccctaa ggagtccact cttaaatgaa    26280
ctcagagtca gttttaaaat gcaagtctgt gttgattctg gtctggatgg tgcattcctc    26340
gagagcaaaa gacagtcttg gtcttggatc cacttgccct gggtacactg agggctgcta    26400
ggttccaggt gctcttcctg gcactgggga gggatacagg cccaagagac atgctgttct    26460
ccctcctgga gcatctattt tagtggagga agacagaaaa caaaccatta atatagagta    26520
ctgaaaagat gcgatggaga aaactatagc aaggaaggga atggggtggg agagaggtca    26580
ggagaggtct cgctgacaag gtggacgaaa caggccatga ggcagagaac atgttccagg    26640
caaagcaaag gcccccaggt ggggatgtgc agggagtacc aggaaaccag agaggtggga    26700
atagttatga gatgggggt gcctcagagg ggacagggcc aagtcaggtg agacctgagg    26760
gtcacagtca gcagtgagct ggggccatgc aggggtctgg cctcagagga gtgtggtctg    26820
gcctggatct gaacctctca ctgtggccta gctgctgagc tgagaagaga tgacaaggac    26880
cttgggcaga agcagggaga ctggaggag gcggtggagg gtccaggcgt tggggcgggg    26940
ctcaggctgg agtctgaagg gagcctgcag gcctggtggg tggatgtggg tgggagaggg    27000
ggaggatggc accaaggctc gggccctgg acagatggag ttgccattaa gtgggatggg    27060
gcaggctatg gggccatcag tttcagaggg atgagtttgg cactggcatg gtaggcatct    27120
gtctatctcc acgccctca aaccaggcat gaagcaggag ctcacgtgtt tggtcagcca    27180
tggtgcagaa ccgcctgggt gggaggtgcg gggtgggaga tacacggttg tgtcccaaat    27240
gggctctgag ccagcgaggg ccgtctgcac tttggcctca cagaaggatg tcggagggag    27300
aaatgaagtg tgggtggggg tcccgggcca cgctagacat gtgctttctt ttcctcgggc    27360
tctggcaggt gaccgtggcc tgcgaggagg gctggaccct gactggctgc agtgccctcc    27420
ctgggacctc ccacgtcctg ggggcctacg ccgtagacaa cacgtgtgta gtcaggagcc    27480
gggacgtcag cactacaggc agcaccagcg aaggggccgt gacagccgtt gccatctgct    27540
gccggagccg gcacctggcg caggcctccc aggagctcca gtgacagccc catcccagga    27600
tgggtgtctg gggagggtca agggctgggg ctgagcttta aaatggttcc gacttgtccc    27660
tctctcagcc ctccatggcc tggcacgagg ggatggggat gcttccgcct tccggggct    27720 gctggcctgg cccttgagtg gggcagcctc cttgcctgga actcactcac tctgggtgcc    27780
tcctccccag gtggaggtgc caggaagctc cctccctcac tgtgggcat ttcaccattc    27840
```

```
aaacaggtcg agctgtgctc gggtgctgcc agctgctccc aatgtgccga tgtccgtggg    27900
cagaatgact tttattgagc tcttgttccg tgccaggcat tcaatcctca ggtctccacc    27960
aaggaggcag gattcttccc atggataggg gaggggcgg taggggctgc agggacaaac     28020
atcgttgggg ggtgagtgtg aaggtgctg atggccctca tctccagcta actgtggaga    28080
agcccctggg ggctccctga ttaatggagg cttagctttc tggatggcat ctagccagag    28140
gctggagaca ggtgcgcccc tggtggtcac aggctgtgcc ttggtttcct gagccacctt    28200
tactctgctc tatgccaggc tgtgctagca acacccaaag gtggcctgcg gggagccatc    28260
acctaggact gactcggcag tgtgcagtgg tgcatgcact gtctcagcca acccgctcca    28320
ctacccggca gggtacacat tcgcacccct acttcacaga ggaagaaacc tggaaccaga    28380
gggggcgtgc ctgccaagct cacacagcag gaactgagcc agaaacgcag attgggctgg    28440
ctctgaagcc aagcctcttc ttacttcacc cggctgggct cctcattttt acgggtaaca    28500
gtgaggctgg aaggggaac acagaccagg aagctcggtg agtgatggca gaacgatgcc    28560
tgcaggcatg gaacttttc cgttatcacc caggcctgat tcactggcct ggcggagatg     28620
cttctaaggc atggtcgggg gagagggcca acaactgtcc ctccttgagc accagcccca    28680
cccaagcaag cagacattta tcttttgggt ctgtcctctc tgttgccttt ttacagccaa    28740
cttttctaga cctgttttgc ttttgtaact tgaagatatt tattctgggt tttgtagcat    28800
ttttattaat atggtgactt tttaaaataa aaacaaacaa acgttgtcct aactcttgca    28860
tagacttgac tgcctagggt gatgccttgc ttatactagg aactgggtaa gtttgttgaa    28920
tagttgagta agccaagtat ttgatgagta cttttatctt gagtacaagt attgggcaag    28980
tactggtgat gtgaacttac tccttgtgcc tatcctagga atgaaatgaa tgtcttcctg    29040
cagctcccct gaccaccctg acagtcaaag tgcctcctcc ttggtgacag gtgccctaca    29100
gcactctaga tgctctgttg tcctgacctc ccaatgccct tttcattctt ttctccccag    29160
tacctggcac acagcctggc ccgagtattt acggaataag ttacagtgcc agatgcttct    29220
gtaatgagcc agtgctaagt ccatggcttt tttcatgatt taaaattcag aacagtctca    29280
gattgggtgc aatggctcac acctgtaatc tcagtacttt gggaggctga ggcaggagga    29340
ttgcttgtgt ttaggaattc aagaccctgg gcaacagtga gaccccgtct ctataaaaaa    29400
atttaaaaga ttagcgaggt gtggtagcac atgcctgtgg tcccggctac tcaggaggct    29460
gatatgggag gcttgcttga gctgggaggc tgagggtgca gtgagctgta attacatcat    29520
cactgcactg cagcctgggt tacagagtgc ataatgatcc cattcaatgt gggacctcca    29580
ggccctccac tctaaggctg gtgaatatag ctgtcttaag caagttctct ctctctctag    29640
acagcccatg tcataaggaa tctcaggcaa aattcctccc agattacatt ttctgacaat    29700
tcagtgtcat atatggaaag cattcaagag ttgacagatg gcaatggctt gaacacccaa    29760
ctgtgttatc tctgcccgtt ggaacctagg cctgtggtgc aaccctagac tctctctcct    29820
tcccctccac agaatcaagt atcagctggt tagagatcca caccctgaca gctctgtgat    29880
gttggaacaa cttggttctt gcagagggtt agcaggtggt caccagggat cggggaggaa    29940
ggggtgtggc ttgcaggaag gcgaaaatct ggactagcaa ataggaagg ggacccatgt     30000
gagcaacgct ggccactagg aatgagactg agacctgtgg gatctagcaa gaagcccagt    30060
gtgaccagcg acacgatcta tgctggggac cacttgggag agccaaaagc tttggtggag    30120
atgaatggag accatcaacc taagttcagc atcctcctct aagctttgca gatgaatcct    30180
```

```
gaaatggtca gccccctccag agaaaagaac agcaacaggc tcagaggacc cacagtcccc   30240
tttattagtg taaagtacta agaggaatca acagcattta gcaccaggca caggctcgtg   30300
ttcccccgcc cactacggct gtgttctgat atatgaagaa tggcggcaag actccaactc   30360 tgttttttgaa aaatttattt tatactctta gaagctaaga actttgccac acatgaacca   30420
aatttagaat taaggttctt ccctagtgta tctacttcct tttgaaattt tataaacaag   30480
attttataca caagaggtag cagaggaaaa ttccagtctg cttgttccaa gctcagaagg   30540
taactgcaca cacctcgatg ttagcaggga aggtggggca ggacagggta agtctgatga   30600
tacggcactc tagttcctaa aactgactgt agttgtcagt gaccgtgtga ggactccagg   30660
agaagtcgtg gtgagatgcc cgctgggatg cttgttttct ttcccaggat gccttcaacg   30720
ggcagaatcg gccatcttaa gatcggcctc actaagggag cttcttgaga acacacagca   30780
ttattgagtt aattgtgcaa ttcctgctct gtttgcagac cattttgaaa ggtttataaa   30840
aacatcttca tccaaaaaat tggcagtaaa aatgacaact cttccaaggt aagcctgtca   30900
taactgtcac tgttgtacta cattaaaaaa agtcatcagc aggttcattg actgtagctg   30960
tcagcaatca agtggttacc agcaaagtga aaacgatggt cattgcagca acaatataag   31020
caacatgatc tgaagcgtat aatatacacg gtggacgatc ctgatgaagc ttacagtga   31080 ggacggcagg tgctagggt gcggaaggcg ttgtttccat aggaaataag gggactagaa   31140
gtggcaattt cactcctgat tttgggctcc tgagagtgca gtcgccagcg atgatatccc   31200
agtgtggatc atcgccagca tttcaaggtc atgtcccaca caatctcttg gtgaggatgt   31260
gggcggagag aaggtgagaa tagggtaggg gaaacagtag gacaggaagt attcacgtac   31320
tcaaaaccaa tggtagaaca tcacatttca aactgcaaga ccattggaac cgtctgaagt   31380
ttgccactcg cctctgtccg tttctctaag ggtacagttc tgctcttaag tgctggccct   31440
tccatcttct cagtgtgttt gacaaaggcc actgccaacc tccagcaagt cacagaataa   31500
caatgaagtc tgacagcaca gaaaccctca ctgccagaga atgaaaagac tgggccatgg   31560
cgagagcaca gtaatgagat gccatctgcc tggccacatg cccacacaat gccacagcag   31620
ccagacaggc acttcagggc tggctgcgcc tctgtgactt ggcaaatctg acagtgaaaa   31680
cctggcactt cctaaggctc cctagttctg tgcatggtga gatgaaaata aggcaggacc   31740
tgtaactaaa ggcaaaacag ggccgaaaat gtgagcaatt caaaatacaa aatgtacaaa   31800 atatatga aatatgtggg tgtaaacctc tcccccacac cataaaaggg agctggtata    31860
aatgagtgaa tggtgctata ctttggaaat acgactaaat ggatggttat tcaattgctt   31920
tatatttatt tctgggaaaa taaatcttaa accttgactg acttttcagt gttaattagt   31980
catgttgagg agaaacaaat                                              32000
```

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
gtcacacttg ctggcctgtc                                              20

<210> SEQ ID NO 4
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 4
tctgccgtcc ttccca                                                    16

<210> SEQ ID NO 5
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 5
agcatctgcc gtcctt                                                    16

<210> SEQ ID NO 6
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 6
tgtcaagcac cacagc                                                    16

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
tgacttgtca agcacc                                                    16

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
ataagtgact tgtcaa                                                    16

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
gcattgtaag ttcact                                                    16

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
gcttgcattg taagtt                                                    16
```

```
<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
ggttttccca gctctg                                                       16

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
ctctggtttt cccagc                                                       16

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
ccacctctgg ttttcc                                                       16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
gtctgctcca actgct                                                       16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
ctcttgtctg ctccaa                                                       16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
tttagctctt gtctgc                                                       16

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 17
gcaagtccct gctaga                                                          16

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
cacctgcaag tccctg                                                          16

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
attgccacct gcaagt                                                          16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
tcattctctc ctcagg                                                          16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
tggacccacc acattg                                                          16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
tgcatggacc caccac                                                          16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
catgttgcat ggaccc                                                          16

<210> SEQ ID NO 24
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
acagtagccc cccaac                                                       16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 25
tcacacagta gccccc                                                       16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
aaagtcacac agtagc                                                       16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
ggtcacacag tttggg                                                       16

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
acatatgcaa ggtcac                                                       16

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 29
actcagacat atgcaa                                                       16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
```
agtgtccctc ttggtc                                                    16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
tgccagtgtc cctctt                                                    16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
tgatcctctg ccagtg                                                    16

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 33
tctgtgatcc tctgcc                                                    16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
ggtctctgtg atcctc                                                    16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 35
agctctaggg cccatg                                                    16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
agccagctct agggcc                                                    16

<210> SEQ ID NO 37
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 37
gtgggtgctc aaaacg                                                    16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
aataatgccc ccgtag                                                    16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
ctggttaata atgccc                                                    16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
ctggatacat tggcag                                                    16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
ctctgagtgt gttagg                                                    16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
tgctctctga gtgtgt                                                    16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
gcatgctgag caggtc                                                    16
```

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
tgtagcatgc tgagca                                                    16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
attcagtggc tgctct                                                    16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
gagcaattca gtggct                                                    16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
tcctcgggca cattct                                                    16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
ttggccacgc cggcat                                                    16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
atttagcagc tacggc                                                    16

<210> SEQ ID NO 50
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 50
caactattta gcagct                                                       16

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
aggttaccgc tgtcag                                                       16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
gacctaggtt accgct                                                       16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
ccactctgtg acacaa                                                       16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
atgtcccact ctgtga                                                       16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
ctcgaaggta agccgc                                                       16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
cagcactgtc ctgcag                                                       16

```
<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
tttttgctgg tttgag                                                      16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
cacttttttg ctggtt                                                      16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
aattccactt ttttgc                                                      16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
atctgtgcac tatcct                                                      16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
tggcatctgt gcacta                                                      16

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
tctcacacga gcatta                                                      16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 63
ctgcctctca cacgag                                              16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
tcttatggag gaggaa                                              16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
tgttttcgac acaggg                                              16

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
ggcatgtttt cgacac                                              16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
catcttttca gtactc                                              16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
atcgcatctt ttcagt                                              16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
ctgtcactgg agctcc                                              16

<210> SEQ ID NO 70
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 70
gtcggaacca tttaa                                               16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
ggacaagtcg gaacca                                              16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
agagggacaa gtcgga                                              16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
atctccgcca ggccag                                              16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
aagcatctcc gccagg                                              16

<210> SEQ ID NO 75
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 75
cttagaagca tctccg                                              16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
```
ccatgcctta gaagca                                           16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
tgtctgcttg cttggg                                           16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
gataaatgtc tgcttg                                           16

<210> SEQ ID NO 79
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
gtctagaaaa gttggc                                           16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
acaggtctag aaaagt                                           16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
aaaagcaaaa caggtc                                           16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
atctgccgtc cttccc                                           16

<210> SEQ ID NO 83
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 83
cagcatctgc cgtcct                                                       16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
cttgtcaagc accaca                                                       16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
gtgacttgtc aagcac                                                       16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
tgtaagttca ctcatg                                                       16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
tgcattgtaa gttcac                                                       16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
gggcttgcat tgtaag                                                       16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
tggttttccc agctct                                                       16
```

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
cctctggttt tcccag                                                          16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
tccacctctg gttttc                                                          16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
ttgtctgctc caactg                                                          16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
gctcttgtct gctcca                                                          16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
tataaatctc ccatcc                                                          16

<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
ctgcaagtcc ctgcta                                                          16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
ccacctgcaa gtccct					16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
ctctcctcag gccagg					16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
cccaccacat tgcatc					16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
atggacccac cacatt					16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
ttgcatggac ccacca					16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
cgagaaccgg taaggg					16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
cacagtagcc ccccaa					16

<210> SEQ ID NO 103

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
gtcacacagt agcccc                                                        16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
gcaaagtcac acagta                                                        16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
aggtcacaca gtttgg                                                        16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
gacatatgca aggtca                                                        16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
tccctcttgg tctctg                                                        16

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
cagtgtccct cttggt                                                        16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
```
ctgccagtgt ccctct                                                    16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
gtgatcctct gccagt                                                    16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
ctctgtgatc ctctgc                                                    16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
gggtctctgt gatcct                                                    16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
cagctctagg gcccat                                                    16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
cagccagctc tagggc                                                    16

<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
agtgggtgct caaaac                                                    16

<210> SEQ ID NO 116
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 116
ttaataatgc ccccgt                                                     16

<210> SEQ ID NO 117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 117
cctggttaat aatgcc                                                     16

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
gagtgtgtta ggagct                                                     16

<210> SEQ ID NO 119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 119
tctctgagtg tgttag                                                     16

<210> SEQ ID NO 120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 120
cttgctctct gagtgt                                                     16

<210> SEQ ID NO 121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 121
agcatgctga gcaggt                                                     16

<210> SEQ ID NO 122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 122
ctgtagcatg ctgagc                                                     16
```

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
aattcagtgg ctgctc         16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
agagcaattc agtggc         16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
cctcctcggg cacatt         16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
ctatttagca gctacg         16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
tcaactattt agcagc         16

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
taggttaccg ctgtca         16

<210> SEQ ID NO 129
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 129
ggacctaggt taccgc                                                       16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 130
cccactctgt gacaca                                                       16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
tgatgtccca ctctgt                                                       16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
gtcctgcagc ctctag                                                       16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 133
ccagcactgt cctgca                                                       16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 134 tttttttgctg gtttga                                                      16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135 ccacttttttt gctggt                                                      16

```
<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
caattccact tttttg                                                  16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 137
catctgtgca ctatcc                                                  16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 138
atggcatctg tgcact                                                  16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 139
cctctcacac gagcat                                                  16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140
tctgcctctc acacga                                                  16

<210> SEQ ID NO 141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 141
ttcgacacag ggtagc                                                  16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 142
atgttttcga cacagg                                                    16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
tgggcatgtt ttcgac                                                    16

<210> SEQ ID NO 144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 144
gcatcttttc agtact                                                    16

<210> SEQ ID NO 145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 145
catcgcatct tttcag                                                    16

<210> SEQ ID NO 146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 146
gctgtcactg gagctc                                                    16

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 147
aagtcggaac catttt                                                    16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
gggacaagtc ggaacc                                                    16

<210> SEQ ID NO 149
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 149
tccgccaggc cagtga                                                  16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 150
catctccgcc aggcca                                                  16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 151
gaagcatctc cgccag                                                  16

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 152
gccttagaag catctc                                                  16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 153
accatgcctt agaagc                                                  16

<210> SEQ ID NO 154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 154
aatgtctgct tgcttg                                                  16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
```
aagataaatg tctgct                                                    16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
ggtctagaaa agttgg                                                    16

<210> SEQ ID NO 157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 157
gcaaaacagg tctaga                                                    16

<210> SEQ ID NO 158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 158
acccagaata aatatc                                                    16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 159
catctgccgt ccttcc                                                    16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160
ccagcatctg ccgtcc                                                    16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
acttgtcaag caccac                                                    16

<210> SEQ ID NO 162
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 162
agtgacttgt caagca                                                        16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 163
attgtaagtt cactca                                                        16

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 164
ttgcattgta agttca                                                        16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
aaattgaatg aattgg                                                        16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 166 ctggtttcc cagctc                                                         16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 167
acctctggtt ttccca                                                        16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
ttccacctct ggtttt                                                        16
```

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
cttgtctgct ccaact                                                    16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 170
agctcttgtc tgctcc                                                    16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 171
attgagggaa aaaatc                                                    16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 172
cctgcaagtc cctgct                                                    16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
gccacctgca agtccc                                                    16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 174
attctctcct caggcc                                                    16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 175
gacccaccac attgca                                                         16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 176
catggaccca ccacat                                                         16

<210> SEQ ID NO 177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 177
gttgcatgga cccacc                                                         16

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 178
agtagccccc caactt                                                         16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 179
acacagtagc ccccca                                                         16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 180
agtcacacag tagccc                                                         16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 181
cacacagttt gggtgt                                                         16

<210> SEQ ID NO 182

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 182
atatgcaagg tcacac                                                         16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 183
agacatatgc aaggtc                                                         16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 184
tgtccctctt ggtctc                                                         16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 185
ccagtgtccc tcttgg                                                         16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
tctgccagtg tccctc                                                         16

<210> SEQ ID NO 187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 187
tgtgatcctc tgccag                                                         16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 188
tctctgtgat cctctg                                                        16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 189
tctagggccc atgctt                                                        16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 190
ccagctctag ggccca                                                        16

<210> SEQ ID NO 191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 191
ggcagccagc tctagg                                                        16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
cgcacagtgg gtgctc                                                        16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 193
ggttaataat gccccc                                                        16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 194
gcctggttaa taatgc                                                        16

<210> SEQ ID NO 195
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 195
ctgagtgtgt taggag                                                    16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 196
ctctctgagt gtgtta                                                    16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 197
tgctgagcag gtcctt                                                    16

<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 198
tagcatgctg agcagg                                                    16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 199
ttctgtagca tgctga                                                    16

<210> SEQ ID NO 200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 200
caattcagtg gctgct                                                    16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 201
acagagcaat tcagtg                                                    16
```

-continued

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 202
actatttagc agctac                                                     16

<210> SEQ ID NO 203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 203
gtcaactatt tagcag                                                     16

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 204
ctaggttacc gctgtc                                                     16

<210> SEQ ID NO 205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 205
gggacctagg ttaccg                                                     16

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 206
ctctgtgaca caaagc                                                     16

<210> SEQ ID NO 207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 207
gtcccactct gtgaca                                                     16

<210> SEQ ID NO 208
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 208
gcactgtcct gcagcc                                                        16

<210> SEQ ID NO 209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 209
atccagcact gtcctg                                                        16

<210> SEQ ID NO 210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 210 ctttttgct ggtttg                                                         16

<210> SEQ ID NO 211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 211
tccacttttt tgctgg                                                        16

<210> SEQ ID NO 212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 212
tgtgcactat cctgta                                                        16

<210> SEQ ID NO 213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 213
gcatctgtgc actatc                                                        16

<210> SEQ ID NO 214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 214
agatggcatc tgtgca                                                        16

```
<210> SEQ ID NO 215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 215
gcctctcaca cgagca                                                       16

<210> SEQ ID NO 216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 216
actctgcctc tcacac                                                       16

<210> SEQ ID NO 217
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 217
ttttcgacac agggta                                                       16

<210> SEQ ID NO 218
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 218
catgttttcg acacag                                                       16

<210> SEQ ID NO 219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 219
cttttcagta ctctat                                                       16

<210> SEQ ID NO 220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 220
cgcatctttt cagtac                                                       16

<210> SEQ ID NO 221
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 221
tccatcgcat cttttc                                                16

<210> SEQ ID NO 222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 222
cactggagct cctggg                                                16

<210> SEQ ID NO 223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 223
ggctgtcact ggagct                                                16

<210> SEQ ID NO 224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 224
caagtcggaa ccattt                                                16

<210> SEQ ID NO 225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 225
agggacaagt cggaac                                                16

<210> SEQ ID NO 226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 226
ctccgccagg ccagtg                                                16

<210> SEQ ID NO 227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 227
gcatctccgc caggcc                                                16

<210> SEQ ID NO 228
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 228
agaagcatct ccgcca                                                    16

<210> SEQ ID NO 229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 229
atgccttaga agcatc                                                    16

<210> SEQ ID NO 230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 230
gaccatgcct tagaag                                                    16

<210> SEQ ID NO 231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 231
aaatgtctgc ttgctt                                                    16

<210> SEQ ID NO 232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 232
agaaaagttg gctgta                                                    16

<210> SEQ ID NO 233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 233
aggtctagaa aagttg                                                    16

<210> SEQ ID NO 234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 234
```
aagcaaaaca ggtcta                                                        16

<210> SEQ ID NO 235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 235
aacccagaat aaatat                                                        16

<210> SEQ ID NO 236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 236
cactctgtga cacaaa                                                        16

<210> SEQ ID NO 237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 237
tgtcccactc tgtgac                                                        16

<210> SEQ ID NO 238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 238
tgtcactgga gctcct                                                        16

<210> SEQ ID NO 239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 239
gggctgtcac tggagc                                                        16

<210> SEQ ID NO 240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 240
acaagtcgga accatt                                                        16

<210> SEQ ID NO 241
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 241
gagggacaag tcggaa                                                 16

<210> SEQ ID NO 242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 242
tctccgccag gccagt                                                 16

<210> SEQ ID NO 243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 243
agcatctccg ccaggc                                                 16

<210> SEQ ID NO 244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 244
tagaagcatc tccgcc                                                 16

<210> SEQ ID NO 245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 245
catgccttag aagcat                                                 16

<210> SEQ ID NO 246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 246
ccgaccatgc cttaga                                                 16

<210> SEQ ID NO 247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 247
taaatgtctg cttgct                                                 16
```

<210> SEQ ID NO 248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 248
ctagaaaagt tggctg                                                    16

<210> SEQ ID NO 249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 249
caggtctaga aaagtt                                                    16

<210> SEQ ID NO 250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 250
aaagcaaaac aggtct                                                    16

<210> SEQ ID NO 251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 251
tgccgtcctt cccacc                                                    16

<210> SEQ ID NO 252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 252
gcatctgccg tccttc                                                    16

<210> SEQ ID NO 253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 253
tcccagcatc tgccgt                                                    16

<210> SEQ ID NO 254
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 254
gacttgtcaa gcacca                                                        16

<210> SEQ ID NO 255
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 255
aagtgacttg tcaagc                                                        16

<210> SEQ ID NO 256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 256
cattgtaagt tcactc                                                        16

<210> SEQ ID NO 257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 257
cttgcattgt aagttc                                                        16

<210> SEQ ID NO 258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 258
tttcccagct ctgtat                                                        16

<210> SEQ ID NO 259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 259
tctggttttc ccagct                                                        16

<210> SEQ ID NO 260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 260
cacctctggt tttccc                                                        16

<210> SEQ ID NO 261
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 261
cttccacctc tggttt                                                         16

<210> SEQ ID NO 262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 262
tcttgtctgc tccaac                                                         16

<210> SEQ ID NO 263
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 263
tagctcttgt ctgctc                                                         16

<210> SEQ ID NO 264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 264
accctaggtg tacttt                                                         16

<210> SEQ ID NO 265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 265
acctgcaagt ccctgc                                                         16

<210> SEQ ID NO 266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 266
tgccacctgc aagtcc                                                         16

<210> SEQ ID NO 267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 267
```

```
cattctctcc tcaggc                                           16

<210> SEQ ID NO 268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 268
ggacccacca cattgc                                           16

<210> SEQ ID NO 269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 269
gcatggaccc accaca                                           16

<210> SEQ ID NO 270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 270
tgttgcatgg acccac                                           16

<210> SEQ ID NO 271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 271
cagtagcccc ccaact                                           16

<210> SEQ ID NO 272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 272
cacacagtag cccccc                                           16

<210> SEQ ID NO 273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 273
aagtcacaca gtagcc                                           16

<210> SEQ ID NO 274
<211> LENGTH: 16
<212> TYPE: DNA
```

<213> ORGANISM: Artificial sequence
<220> FEATURE:
<223> OTHER INFORMATION: Synthetic oligonucleotide

<400> SEQUENCE: 274
gtcacacagt ttgggt                                                   16

<210> SEQ ID NO 275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 275
catatgcaag gtcaca                                                   16

<210> SEQ ID NO 276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 276
tcagacatat gcaagg                                                   16

<210> SEQ ID NO 277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 277
gtgtccctct tggtct                                                   16

<210> SEQ ID NO 278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 278
gccagtgtcc ctcttg                                                   16

<210> SEQ ID NO 279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 279
cctctgccag tgtccc                                                   16

<210> SEQ ID NO 280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 280
ctgtgatcct ctgcca                                                   16

<210> SEQ ID NO 281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 281
gtctctgtga tcctct                                                   16

<210> SEQ ID NO 282
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 282
gctctagggc ccatgc                                                   16

<210> SEQ ID NO 283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 283
gccagctcta gggccc                                                   16

<210> SEQ ID NO 284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 284
agagaaatgc atgcta                                                   16

<210> SEQ ID NO 285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 285
ggcgcacagt gggtgc                                                   16

<210> SEQ ID NO 286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 286
tggttaataa tgcccc                                                   16

<210> SEQ ID NO 287
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 287
ttgcctggtt aataat                                                       16

<210> SEQ ID NO 288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 288
tctgagtgtg ttagga                                                       16

<210> SEQ ID NO 289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 289
gctctctgag tgtgtt                                                       16

<210> SEQ ID NO 290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 290
catgctgagc aggtcc                                                       16

<210> SEQ ID NO 291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 291
gtagcatgct gagcag                                                       16

<210> SEQ ID NO 292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 292
tcagtggctg ctctga                                                       16

<210> SEQ ID NO 293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 293
gcaattcagt ggctgc                                                       16

```
<210> SEQ ID NO 294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 294
tagttaacac acagaa                                                   16

<210> SEQ ID NO 295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 295
aactatttag cagcta                                                   16

<210> SEQ ID NO 296
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 296
cgtcaactat ttagca                                                   16

<210> SEQ ID NO 297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 297
cctaggttac cgctgt                                                   16

<210> SEQ ID NO 298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 298
gcacagaccc tgactg                                                   16

<210> SEQ ID NO 299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 299
agcactgtcc tgcagc                                                   16

<210> SEQ ID NO 300
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 300
ttttgctggt ttgaga                                                    16

<210> SEQ ID NO 301
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 301
acttttttgc tggttt                                                    16

<210> SEQ ID NO 302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 302
attccacttt tttgct                                                    16

<210> SEQ ID NO 303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 303
tctgtgcact atcctg                                                    16

<210> SEQ ID NO 304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 304
ggcatctgtg cactat                                                    16

<210> SEQ ID NO 305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 305
tcacacgagc attaag                                                    16

<210> SEQ ID NO 306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 306
tgcctctcac acgagc                                                    16

<210> SEQ ID NO 307
<211> LENGTH: 16
```

<212> TYPE: DNA
<213> ORGANISM: Artificial sequence
<220> FEATURE:
<223> OTHER INFORMATION: Synthetic oligonucleotide

<400> SEQUENCE: 307
tagacaggat caactc                                                   16

<210> SEQ ID NO 308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 308
gttttcgaca cagggt                                                   16

<210> SEQ ID NO 309
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 309
gcatgttttc gacaca                                                   16

<210> SEQ ID NO 310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 310
atcttttcag tactct                                                   16

<210> SEQ ID NO 311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 311
tcgcatcttt tcagta                                                   16

<210> SEQ ID NO 312
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 312
agcagctagg ccacag                                                   16

<210> SEQ ID NO 313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 313

```
aacttcaagg ccagct                                                    16

<210> SEQ ID NO 314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 314
ctgaactgaa cggcgg                                                    16

<210> SEQ ID NO 315
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 315
ggcgaggaga cctaga                                                    16

<210> SEQ ID NO 316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 316
acgcaaggct agcacc                                                    16

<210> SEQ ID NO 317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 317
ggcaagcccg ctttct                                                    16

<210> SEQ ID NO 318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 318 ccctttaaa gattag                                                     16

<210> SEQ ID NO 319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 319
ccagagaaga aacatc                                                    16

<210> SEQ ID NO 320
<211> LENGTH: 16
<212> TYPE: DNA
<213> ORGANISM: Artificial sequence
```

<220> FEATURE:
<223> OTHER INFORMATION: Synthetic oligonucleotide

<400> SEQUENCE: 320
aagaatctgg agctgc                                                         16

<210> SEQ ID NO 321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 321
cactgaggac caaatt                                                         16

<210> SEQ ID NO 322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 322
gctatataaa ggaata                                                         16

<210> SEQ ID NO 323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 323
catgagcaag tcactc                                                         16

<210> SEQ ID NO 324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 324
agtatagtag atgata                                                         16

<210> SEQ ID NO 325
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 325
cgagaggtgg gtctcc                                                         16

<210> SEQ ID NO 326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 326
gtgaggtatc cccggc                                                         16

<210> SEQ ID NO 327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 327
gacatgcagg atcttg                                                    16

<210> SEQ ID NO 328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 328
gggaattcta tacaga                                                    16

<210> SEQ ID NO 329
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 329
caccgaagat gtgaca                                                    16

<210> SEQ ID NO 330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 330
aagggaaagg cctgag                                                    16

<210> SEQ ID NO 331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 331
ccccacaggc agcctc                                                    16

<210> SEQ ID NO 332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 332
ccggaggaca gactag                                                    16

<210> SEQ ID NO 333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 333
tggtattcat ccgccc                                                   16

<210> SEQ ID NO 334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 334
agccaaacgg agctgg                                                   16

<210> SEQ ID NO 335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 335
aaaggaacag gctctt                                                   16

<210> SEQ ID NO 336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 336
ctctagggcc catgct                                                   16

<210> SEQ ID NO 337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 337
ggatacacag gctcgc                                                   16

<210> SEQ ID NO 338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 338
gatgatgtga ccactg                                                   16

<210> SEQ ID NO 339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 339
ggccagcaag gtgggc                                                   16

<210> SEQ ID NO 340

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 340
tgctagtagg tctggg                                                     16

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 341
ccaaaggaag acttca                                                     16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 342
atttaaagac tcaaag                                                     16

<210> SEQ ID NO 343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 343
acatttgtgg gagagg                                                     16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 344
cgtcctcctc gggcac                                                     16

<210> SEQ ID NO 345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 345
tcacacttgc tggcct                                                     16

<210> SEQ ID NO 346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 346
```

```
atcccggccg ctgacc                                                       16

<210> SEQ ID NO 347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 347
gctggcaccc ttggcc                                                       16

<210> SEQ ID NO 348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 348
aagacataaa gacatc                                                       16

<210> SEQ ID NO 349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 349
cagaaggtta ttgatt                                                       16

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 350
tgctagttat taagca                                                       16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 351
cagtaacagc tctttt                                                       16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 352
ccttattatc cctttc                                                       16

<210> SEQ ID NO 353
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 353
caacatcaaa ttctgc                                                    16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
ttccgaataa actcca                                                    16

<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 355
acctcgggag ctgagg                                                    16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 356
gatggaggtt tcgagc                                                    16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
tatcaagtgg ttctaa                                                    16

<210> SEQ ID NO 358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 358
caccaatgat gtcctc                                                    16

<210> SEQ ID NO 359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 359
tcttatcggc caggtg                                                    16
```

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 360
tggcagagaa gtggat                                            16

<210> SEQ ID NO 361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 361
ccatacagtc ctgcaa                                            16

<210> SEQ ID NO 362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 362
gagcagctca gcagct                                            16

<210> SEQ ID NO 363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 363
tacagaagag ctggag                                            16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
acacagagtg gtttca                                            16

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
ctgcagttgg cctggg                                            16

<210> SEQ ID NO 366
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 366
gtggcagtgg acacgg                                                         16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 367
aggagaagta aggtca                                                         16

<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
gggcatgttt tcgaca                                                         16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
ttccacccag agatgg                                                         16

<210> SEQ ID NO 370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 370
cggtatggtg gtggca                                                         16

<210> SEQ ID NO 371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 371
gggcaagtgg atccaa                                                         16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 372
ccacacttca tttctc                                                         16

```
<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 373
gcaggccacg gtcacc                                                   16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 374
ttaaagctca gcccca                                                   16

<210> SEQ ID NO 375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 375
ccccggaaag gcggaa                                                   16

<210> SEQ ID NO 376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 376
ccgagcacag ctcgac                                                   16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 377
acggacatcg gcacat                                                   16

<210> SEQ ID NO 378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 378
ggcacggaac aagagc                                                   16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 379
acctttcaca ctcacc                                                    16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 380
tgccatccag aaagct                                                    16

<210> SEQ ID NO 381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 381
cacctttggg tgttgc                                                    16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 382
ccactgcaca ctgccg                                                    16

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 383
tggttccagg tttctt                                                    16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 384
cctgctgtgt gagctt                                                    16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 385
cttcagagcc agccca                                                    16

<210> SEQ ID NO 386
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 386
ccgagcttcc tggtct                                                    16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 387
gggtgataac ggaaaa                                                    16

<210> SEQ ID NO 388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 388
aaagataaat gtctgc                                                    16

<210> SEQ ID NO 389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 389
cccagaataa atatct                                                    16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 390
ctccaggctc agaccc                                                    16

<210> SEQ ID NO 391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 391
gcccatgagg gccagg                                                    16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 392
```
aacgcaaggc tagcac                                                   16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 393
ctataatggc aagccc                                                   16

<210> SEQ ID NO 394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 394
cgtagggacg attgtc                                                   16

<210> SEQ ID NO 395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 395
atgaacttga ggaggc                                                   16

<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 396
ttggaagaat ctggag                                                   16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 397
caacactgag gaccaa                                                   16

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 398
ggcaacactt cttaaa                                                   16

<210> SEQ ID NO 399
<211> LENGTH: 16
<212> TYPE: DNA
<213> ORGANISM: Artificial sequence -continued

```
<220> FEATURE:
<223> OTHER INFORMATION: Synthetic oligonucleotide

<400> SEQUENCE: 399
gtgcagccat gagcaa                                                         16

<210> SEQ ID NO 400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 400
acagagtata gtagat                                                         16

<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 401
tgcgagaggt gggtct                                                         16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 402
ggtgaggtat ccccgg                                                         16

<210> SEQ ID NO 403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 403
agacatgcag gatctt                                                         16

<210> SEQ ID NO 404
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 404
tcaaatgaag atagac                                                         16

<210> SEQ ID NO 405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 405
gaatacccag tcccct                                                         16
```

```
<210> SEQ ID NO 406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 406
ctcaagggaa aggcct                                                    16

<210> SEQ ID NO 407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 407
catggcagcg gtgaac                                                    16

<210> SEQ ID NO 408
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 408
gatcaaacct gtcccc                                                    16

<210> SEQ ID NO 409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 409
tgcagaccgt tttcca                                                    16

<210> SEQ ID NO 410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 410
ggaaaggaac aggctc                                                    16

<210> SEQ ID NO 411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 411
tttgagggcg gcagcc                                                    16

<210> SEQ ID NO 412
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 412
tgctggatac acaggc                                               16

<210> SEQ ID NO 413
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 413
tgtacctggg ttctgc                                               16

<210> SEQ ID NO 414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 414
cactagatat tgagct                                               16

<210> SEQ ID NO 415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 415
ctatgctagt aggtct                                               16

<210> SEQ ID NO 416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 416
ggccaaagga agactt                                               16

<210> SEQ ID NO 417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 417
ctgcaagaaa gacaac                                               16

<210> SEQ ID NO 418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 418
caccaggctg cctccg                                               16

<210> SEQ ID NO 419
```

-continued

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 419
ccgtcctcct cgggca                                                        16

<210> SEQ ID NO 420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 420
catcagacgg ccgtgc                                                        16

<210> SEQ ID NO 421
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 421
gtcacacttg ctggcc                                                        16

<210> SEQ ID NO 422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 422
gcatcccggc cgctga                                                        16

<210> SEQ ID NO 423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 423
gcgcatgctg gcaccc                                                        16

<210> SEQ ID NO 424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 424
gataacataa caaaag                                                        16

<210> SEQ ID NO 425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 425
```

-continued gcagaaggtt attgat                                                16

<210> SEQ ID NO 426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 426
acagctgcta gttatt                                                16

<210> SEQ ID NO 427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 427
tgctactgtc aacagt                                                16

<210> SEQ ID NO 428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 428
caataacctt attatc                                                16

<210> SEQ ID NO 429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 429
agagaacaga ctgagg                                                16

<210> SEQ ID NO 430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 430
ggcttttccg aataaa                                                16

<210> SEQ ID NO 431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 431
ggcagaggac gcaggg                                                16

<210> SEQ ID NO 432
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 432
actattcggt gtatca                                                   16

<210> SEQ ID NO 433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 433
gctggaggca ccaatg                                                   16

<210> SEQ ID NO 434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 434
gtcttatcgg ccaggt                                                   16

<210> SEQ ID NO 435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 435
tgacatcttt ggcaga                                                   16

<210> SEQ ID NO 436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 436
accatacagt cctgca                                                   16

<210> SEQ ID NO 437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 437
gaaactggag cagctc                                                   16

<210> SEQ ID NO 438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 438
cattgaaaat ccatcc                                                   16
```

<210> SEQ ID NO 439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 439
cccaaggaag actgtt                                                        16

<210> SEQ ID NO 440
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 440
cctcagctgg tggagc                                                        16

<210> SEQ ID NO 441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 441
ggtggcagtg gacacg                                                        16

<210> SEQ ID NO 442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 442
aggtaatacc tttttc                                                        16

<210> SEQ ID NO 443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 443
caccatccct tgatgc                                                        16

<210> SEQ ID NO 444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 444
gaaaacacca tctttc                                                        16

<210> SEQ ID NO 445
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 445
ggcggtatgg tggtgg                                                        16

<210> SEQ ID NO 446
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 446
acccagggca agtgga                                                        16

<210> SEQ ID NO 447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 447
ccccacccac acttca                                                        16

<210> SEQ ID NO 448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 448
tcgcaggcca cggtca                                                        16

<210> SEQ ID NO 449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 449
ttttaaagct cagccc                                                        16

<210> SEQ ID NO 450
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 450
agcagccccg gaaagg                                                        16

<210> SEQ ID NO 451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 451
acccgagcac agctcg                                                        16

```
<210> SEQ ID NO 452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 452
ccacggacat cggcac                                                   16

<210> SEQ ID NO 453
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 453
tggcacggaa caagag                                                   16

<210> SEQ ID NO 454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 454
ggccatcagc accttt                                                   16

<210> SEQ ID NO 455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 455
ctagatgcca tccaga                                                   16

<210> SEQ ID NO 456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 456
ggccaccttt gggtgt                                                   16

<210> SEQ ID NO 457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 457
gtgcatgcac cactgc                                                   16

<210> SEQ ID NO 458
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 458
ctggttccag gtttct                                                     16

<210> SEQ ID NO 459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 459
tcctgctgtg tgagct                                                     16

<210> SEQ ID NO 460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 460
gaagaggctt ggcttc                                                     16

<210> SEQ ID NO 461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 461
accgagcttc ctggtc                                                     16

<210> SEQ ID NO 462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 462
ggcctgggtg ataacg                                                     16

<210> SEQ ID NO 463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 463
ccaaaagata aatgtc                                                     16

<210> SEQ ID NO 464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 464
tacaaaaccc agaata                                                     16

<210> SEQ ID NO 465
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 465
caacttcaag gccagc                                                   16

<210> SEQ ID NO 466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 466
gatgacctcg ggagct                                                   16

<210> SEQ ID NO 467
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 467
caccagagcc ccatcg                                                   16

<210> SEQ ID NO 468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 468
ctgggagccg ctgctg                                                   16

<210> SEQ ID NO 469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 469
tggcagcggc caccag                                                   16

<210> SEQ ID NO 470
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 470
ggccaggccg tcctcc                                                   16

<210> SEQ ID NO 471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 471
```
ccgcaccttg gcgcag                                               16

<210> SEQ ID NO 472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 472
gaaacagatg gaatac                                               16

<210> SEQ ID NO 473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 473
acccagcaca ctcaga                                               16

<210> SEQ ID NO 474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 474
gtactctgtg cagtgg                                               16

<210> SEQ ID NO 475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 475
gagtagaaca gagtcc                                               16

<210> SEQ ID NO 476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 476
ttaataatca gccttc                                               16

<210> SEQ ID NO 477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 477
tacaaatgca ggcaga                                               16

<210> SEQ ID NO 478
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 478
ctcgacaaca ggtttt                                               16

<210> SEQ ID NO 479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 479
aggaacatga tgacat                                               16

<210> SEQ ID NO 480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 480
ctgcaggcgg cgggca                                               16

<210> SEQ ID NO 481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 481
atcttggtga ggtatc                                               16

<210> SEQ ID NO 482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 482
atggaagaca tgcagg                                               16

<210> SEQ ID NO 483
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 483
taaaatgact caggct                                               16

<210> SEQ ID NO 484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 484
catcaagtta gaggcc                                               16
```

<210> SEQ ID NO 485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 485
tatacgggta ccttct                                                    16

<210> SEQ ID NO 486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 486
gctcagtgca aactgc                                                    16

<210> SEQ ID NO 487
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 487
ctcgatgtag tcgaca                                                    16

<210> SEQ ID NO 488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 488
cccgagaagt ggaaac                                                    16

<210> SEQ ID NO 489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 489
ccaagatccc acgaga                                                    16

<210> SEQ ID NO 490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 490
gagaaagtgg tcctgc                                                    16

<210> SEQ ID NO 491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 491
cagcaataac tgattt                                              16

<210> SEQ ID NO 492
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 492
cgcctgagaa gctcag                                              16

<210> SEQ ID NO 493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 493
ccacacaacg cacatc                                              16

<210> SEQ ID NO 494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 494
gaccaaacag tgctcg                                              16

<210> SEQ ID NO 495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 495
ctacaaagac cttttc                                              16

<210> SEQ ID NO 496
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 496
taggagaaag taggga                                              16

<210> SEQ ID NO 497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 497
gaatatcaat atctaa                                              16

<210> SEQ ID NO 498

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 498
tcccggtggt cactct                                                       16

<210> SEQ ID NO 499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 499
gggtcccgtc ctcctc                                                       16

<210> SEQ ID NO 500
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 500
ccacatgaga aagacc                                                       16

<210> SEQ ID NO 501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 501
catgactgtc acactt                                                       16

<210> SEQ ID NO 502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 502
tggccacgcc ggcatc                                                       16

<210> SEQ ID NO 503
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 503
tggcagttga gcacgc                                                       16

<210> SEQ ID NO 504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 504
```
gtctagaaaa agtcct 16

<210> SEQ ID NO 505
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 505
ccgtgccagg tcatgc 16

<210> SEQ ID NO 506
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 506
ctgggataca gacacc 16

<210> SEQ ID NO 507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 507
aattaaaaga ctccat 16

<210> SEQ ID NO 508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 508
tattagcaat tacacc 16

<210> SEQ ID NO 509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 509
ttacaggcac agagtg 16

<210> SEQ ID NO 510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 510
ctgtacccac ccgcca 16

<210> SEQ ID NO 511
<211> LENGTH: 16
<212> TYPE: DNA

<210> SEQ ID NO 511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 511
aacaagattc cttccc                    16

<210> SEQ ID NO 512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 512
ggcagaactc tggcac                    16

<210> SEQ ID NO 513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 513
cccaaagtcc ccaggg                    16

<210> SEQ ID NO 514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 514
ggtgaaagat ggtgat                    16

<210> SEQ ID NO 515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 515
catcatggct gcaatg                    16

<210> SEQ ID NO 516
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 516
gggaaccagg cctcat                    16

<210> SEQ ID NO 517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 517
tgctgaccat acagtc                    16

```
<210> SEQ ID NO 518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 518
gtgcactatc ctgtag                                                    16

<210> SEQ ID NO 519
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 519
caaagacgga aatggg                                                    16

<210> SEQ ID NO 520
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 520
gcacctggca atggcg                                                    16

<210> SEQ ID NO 521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 521
cgggtcccca tgctgg                                                    16

<210> SEQ ID NO 522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 522
tgcttagcac tcatca                                                    16

<210> SEQ ID NO 523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 523
cctacatgcc agcctg                                                    16

<210> SEQ ID NO 524
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 524
aaagagatgc tggcct                                                    16

<210> SEQ ID NO 525
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 525
gcacaggcgg cttgtg                                                    16

<210> SEQ ID NO 526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 526
ccatatttat gcacat                                                    16

<210> SEQ ID NO 527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 527
tttcagtact ctatat                                                    16

<210> SEQ ID NO 528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 528
aacggctgtc acggcc                                                    16

<210> SEQ ID NO 529
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 529
agagagggac aagtcg                                                    16

<210> SEQ ID NO 530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 530
ttccaggcaa ggaggc                                                    16

```
<210> SEQ ID NO 531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 531
ggcagcaccc gagcac                                                     16

<210> SEQ ID NO 532
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 532
ataaaagtca ttctgc                                                     16

<210> SEQ ID NO 533
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 533
attgaatgcc tggcac                                                     16

<210> SEQ ID NO 534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 534
ccacagttag ctggag                                                     16

<210> SEQ ID NO 535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 535
gctcaggaaa ccaagg                                                     16

<210> SEQ ID NO 536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 536
ctgccgagtc agtcct                                                     16

<210> SEQ ID NO 537
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 537
tgccgggtag tggagc                                                    16

<210> SEQ ID NO 538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 538
cccctctggt tccagg                                                    16

<210> SEQ ID NO 539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 539
gctcagttcc tgctgt                                                    16

<210> SEQ ID NO 540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 540
agccgggtga agtaag                                                    16

<210> SEQ ID NO 541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 541
cactcaccga gcttcc                                                    16

<210> SEQ ID NO 542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 542
ccttagaagc atctcc                                                    16

<210> SEQ ID NO 543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 543 gtaaaaggc aacaga                                                     16

<210> SEQ ID NO 544
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 544
cgccaccaga gcccca                                                    16

<210> SEQ ID NO 545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 545
cggaatcctg gctggg                                                    16

<210> SEQ ID NO 546
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 546
tagcaccagc tcctcg                                                    16

<210> SEQ ID NO 547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 547
tgctcgggtg cttcgg                                                    16

<210> SEQ ID NO 548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 548
ggctgcgggt tcgccc                                                    16

<210> SEQ ID NO 549
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 549
cgagaatacc tccgcc                                                    16

<210> SEQ ID NO 550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 550
```
gctgagtaag gacttg 16

<210> SEQ ID NO 551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 551
ttccgctaaa taaaaa 16

<210> SEQ ID NO 552
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 552
tcagagtaga acagag 16

<210> SEQ ID NO 553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 553
gagggaggtg ccaagc 16

<210> SEQ ID NO 554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 554
ctacaaatgc aggcag 16

<210> SEQ ID NO 555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 555
aactacgggc cacact 16

<210> SEQ ID NO 556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 556
acggatcctg gcccca 16

<210> SEQ ID NO 557
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 557
cccggcgggc agcctg                                                        16

<210> SEQ ID NO 558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 558
gatcttggtg aggtat                                                        16

<210> SEQ ID NO 559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 559
ggccatggaa gacatg                                                        16

<210> SEQ ID NO 560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 560
ctagagtcat gctttt                                                        16

<210> SEQ ID NO 561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 561
gtggagaatc agtgtg                                                        16

<210> SEQ ID NO 562
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 562
ttgaagtcca gctctc                                                        16

<210> SEQ ID NO 563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 563
gcaattcggt ttgtcc                                                        16
```

```
<210> SEQ ID NO 564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 564
agacagagga gtcctc                                                      16

<210> SEQ ID NO 565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 565
gatcatttaa ggcaag                                                      16

<210> SEQ ID NO 566
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 566
tcccaagatc ccacga                                                      16

<210> SEQ ID NO 567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 567
caagagaagc ttctcc                                                      16

<210> SEQ ID NO 568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 568
ctacagcaat aactga                                                      16

<210> SEQ ID NO 569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 569
gagcagggag ctcatt                                                      16

<210> SEQ ID NO 570
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 570
ctagaagaca gcacag                                                   16

<210> SEQ ID NO 571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 571
ccgacctgaa gacatc                                                   16

<210> SEQ ID NO 572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 572
gcccaccgca taatcc                                                   16

<210> SEQ ID NO 573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 573
gacaaaggtt agggta                                                   16

<210> SEQ ID NO 574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 574
tgaatatcaa tatcta                                                   16

<210> SEQ ID NO 575
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 575
cctcgatttc ccggtg                                                   16

<210> SEQ ID NO 576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 576
gcgggtcccg tcctcc                                                   16

<210> SEQ ID NO 577
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 577
gaccacatga gaaaga                                                       16

<210> SEQ ID NO 578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 578
tgccatgact gtcaca                                                       16

<210> SEQ ID NO 579
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 579
cttggccacg ccggca                                                       16

<210> SEQ ID NO 580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 580
gctaaccgtg cccttc                                                       16

<210> SEQ ID NO 581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 581
cagtaaggga gagaac                                                       16

<210> SEQ ID NO 582
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 582
cccgtgccag gtcatg                                                       16

<210> SEQ ID NO 583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 583
```
agctgctagt tattta                                                                      16

<210> SEQ ID NO 584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 584
gaaacaggga cagttg                                                                      16

<210> SEQ ID NO 585
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 585
ggaagatatt agcaat                                                                      16

<210> SEQ ID NO 586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 586
cttacaggca cagagt                                                                      16

<210> SEQ ID NO 587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 587
gaggacgcgg ctgtac                                                                      16

<210> SEQ ID NO 588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 588
gtggaacaag attcct                                                                      16

<210> SEQ ID NO 589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 589
aggcagaact ctggca                                                                      16

<210> SEQ ID NO 590
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 590
ccaaagttgg tcccca                                                   16

<210> SEQ ID NO 591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 591
agcatcatgg ctgcaa                                                   16

<210> SEQ ID NO 592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 592
cctcagggaa ccaggc                                                   16

<210> SEQ ID NO 593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 593
tgccatcctg cttacc                                                   16

<210> SEQ ID NO 594
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 594
tgtgctgacc atacag                                                   16

<210> SEQ ID NO 595
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 595
caccaaaatg ctgcaa                                                   16

<210> SEQ ID NO 596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 596
ggccttagag tcaaag                                                   16
```

<210> SEQ ID NO 597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 597
agcacctggc aatggc                                                         16

<210> SEQ ID NO 598
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 598
gacacgggtc cccatg                                                         16

<210> SEQ ID NO 599
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 599
actaagctaa gtgctt                                                         16

<210> SEQ ID NO 600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 600
gcaaaatggt gctctt                                                         16

<210> SEQ ID NO 601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 601
acctagaaac aactca                                                         16

<210> SEQ ID NO 602
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 602
cagcacaggc ggcttg                                                         16

<210> SEQ ID NO 603
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 603
atgcatattg catttc                              16

<210> SEQ ID NO 604
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 604
ggccagacca cactcc                              16

<210> SEQ ID NO 605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 605
ggcaacggct gtcacg                              16

<210> SEQ ID NO 606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 606
tgagagaggg acaagt                              16

<210> SEQ ID NO 607
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 607
agtgagtgag ttccag                              16

<210> SEQ ID NO 608
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 608
tggcagcacc cgagca                              16

<210> SEQ ID NO 609
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 609
ctcaataaaa gtcatt                              16

```
<210> SEQ ID NO 610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 610
gaggattgaa tgcctg                                                    16

<210> SEQ ID NO 611
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 611
ctccacagtt agctgg                                                    16

<210> SEQ ID NO 612
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 612
gtaaaggtgg ctcagg                                                    16

<210> SEQ ID NO 613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 613
actgccgagt cagtcc                                                    16

<210> SEQ ID NO 614
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 614
gtgtaccctg ccgggt                                                    16

<210> SEQ ID NO 615
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 615
ccccctctgg ttccag                                                    16

<210> SEQ ID NO 616
<211> LENGTH: 16
<212> TYPE: DNA
<213> ORGANISM: Artificial sequence
<220> FEATURE:
<223> OTHER INFORMATION: Synthetic oligonucleotide
```

-continued

<400> SEQUENCE: 616
tggctcagtt cctgct                                    16

<210> SEQ ID NO 617
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 617
gcccagccgg gtgaag                                    16

<210> SEQ ID NO 618
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 618
atcactcacc gagctt                                    16

<210> SEQ ID NO 619
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 619
tgccttagaa gcatct                                    16

<210> SEQ ID NO 620
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 620
ctgtaaaaag gcaaca                                    16

<210> SEQ ID NO 621
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 621
gatcacgcca ccagag                                    16

<210> SEQ ID NO 622
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 622
cgcggaatcc tggctg                                    16

<210> SEQ ID NO 623
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 623
ctagcaccag ctcctc                                                  16

<210> SEQ ID NO 624
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 624
ggctgtggtt ccgtgc                                                  16

<210> SEQ ID NO 625
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 625
aaacagcacc gcaccg                                                  16

<210> SEQ ID NO 626
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 626
ccgcacacgg tcggca                                                  16

<210> SEQ ID NO 627
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 627
gaacaaggaa gagggc                                                  16

<210> SEQ ID NO 628
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 628
caaagaccca tctgaa                                                  16

<210> SEQ ID NO 629
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 629
```
tcatgaatca agtcca                                         16

<210> SEQ ID NO 630
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 630
gcagagatca atcaca                                         16

<210> SEQ ID NO 631
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 631
tcccatccag atgctc                                         16

<210> SEQ ID NO 632
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 632
attcaggcaa aaatgg                                         16

<210> SEQ ID NO 633
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 633
tccccggcgg gcagcc                                         16

<210> SEQ ID NO 634
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 634
ggatcttggt gaggta                                         16

<210> SEQ ID NO 635
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 635
aagaaggcca tggaag                                         16

<210> SEQ ID NO 636
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 636
tgccattccc aaaaag                                                    16

<210> SEQ ID NO 637
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 637
caaaggaatt ttggac                                                    16

<210> SEQ ID NO 638
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 638
tgccatgtgg agaatc                                                    16

<210> SEQ ID NO 639
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 639
tcgaacccag gctggt                                                    16

<210> SEQ ID NO 640
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 640
catgacataa cagcac                                                    16

<210> SEQ ID NO 641
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 641
aaagacagag gagtcc                                                    16

<210> SEQ ID NO 642
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 642
aaagaggatc atttaa                                                    16

```
<210> SEQ ID NO 643
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 643
caagaacgac aaagct                                                      16

<210> SEQ ID NO 644
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 644
ggacacggaa gaggca                                                      16

<210> SEQ ID NO 645
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 645
acagagaaat gcatgc                                                      16

<210> SEQ ID NO 646
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 646
ctctatcttc caaacc                                                      16

<210> SEQ ID NO 647
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 647
atacaggctt atctag                                                      16

<210> SEQ ID NO 648
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 648
caataggcat ctacca                                                      16

<210> SEQ ID NO 649
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 649
aggacttaca gcccac                                                        16

<210> SEQ ID NO 650
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 650
gcccatgcag gacaaa                                                        16

<210> SEQ ID NO 651
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 651
tatgaatatc aatatc                                                        16

<210> SEQ ID NO 652
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 652
catgaccctg ccctcg                                                        16

<210> SEQ ID NO 653
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 653
gaagcgggtc ccgtcc                                                        16

<210> SEQ ID NO 654
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 654
acacaaggac cacatg                                                        16

<210> SEQ ID NO 655
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 655
tgccaggtgg gtgcca                                                        16

<210> SEQ ID NO 656
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 656
ccttggccac gccggc                                                 16

<210> SEQ ID NO 657
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 657
ccgctaaccg tgccct                                                 16

<210> SEQ ID NO 658
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 658
cttgagctgt gcgacc                                                 16

<210> SEQ ID NO 659
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 659
ccccgtgcca ggtcat                                                 16

<210> SEQ ID NO 660
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 660
acaacagcca cattta                                                 16

<210> SEQ ID NO 661
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 661
tgtgaaacag ggacag                                                 16

<210> SEQ ID NO 662
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 662
```
taatatatac atccta                                                    16

<210> SEQ ID NO 663
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 663
ccttacaggc acagag                                                    16

<210> SEQ ID NO 664
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 664
gttgaggacg cggctg                                                    16

<210> SEQ ID NO 665
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 665
ccaacgcgcg cgcgcg                                                    16

<210> SEQ ID NO 666
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 666
gaaaatctga ctgccc                                                    16

<210> SEQ ID NO 667
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 667
ggccaaagtt ggtccc                                                    16

<210> SEQ ID NO 668
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 668
agacagcatc atggct                                                    16

<210> SEQ ID NO 669
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 669
tcagtacccg ctggtc                                                   16

<210> SEQ ID NO 670
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 670
ggtcacacag acctcc                                                   16

<210> SEQ ID NO 671
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 671
cccgagtgtg ctgacc                                                   16

<210> SEQ ID NO 672
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 672
ttccaccaaa atgctg                                                   16

<210> SEQ ID NO 673
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 673
cagcacctgg caatgg                                                   16

<210> SEQ ID NO 674
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 674
ggacacgggt ccccat                                                   16

<210> SEQ ID NO 675
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 675
ggcaagccca gcctcc                                                   16

<210> SEQ ID NO 676
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 676
aacgatagct agaatt                                                    16

<210> SEQ ID NO 677
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 677
tggtagggtt gtggtt                                                    16

<210> SEQ ID NO 678
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 678
gcaagagcta ggaaac                                                    16

<210> SEQ ID NO 679
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 679
ctcagcacag gcggct                                                    16

<210> SEQ ID NO 680
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 680
atgcatgcat attgca                                                    16

<210> SEQ ID NO 681
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 681
cttcagactc cagcct                                                    16

<210> SEQ ID NO 682
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 682
gatggcaacg gctgtc          16

<210> SEQ ID NO 683
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 683
gctgagagag ggacaa          16

<210> SEQ ID NO 684
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 684
ccagagtgag tgagtt          16

<210> SEQ ID NO 685
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 685
ctggcagcac ccgagc          16

<210> SEQ ID NO 686
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 686
gctcaataaa agtcat          16

<210> SEQ ID NO 687
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 687
acctgaggat tgaatg          16

<210> SEQ ID NO 688
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 688
aatcagggag ccccca          16

```
<210> SEQ ID NO 689
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 689
gagtaaaggt ggctca                                                    16

<210> SEQ ID NO 690
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 690
cactgccgag tcagtc                                                    16

<210> SEQ ID NO 691
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 691
gcgaatgtgt accctg                                                    16

<210> SEQ ID NO 692
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 692
cgccccctct ggttcc                                                    16

<210> SEQ ID NO 693
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 693
ctggctcagt tcctgc                                                    16

<210> SEQ ID NO 694
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 694
aaatgaggag cccagc                                                    16

<210> SEQ ID NO 695
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 695
tgccatcact caccga                                                    16

<210> SEQ ID NO 696
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 696
ccccgaccat gcctta                                                    16

<210> SEQ ID NO 697
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 697
ggctgtaaaa aggcaa                                                    16

<210> SEQ ID NO 698
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 698
gcagatcacg ccacca                                                    16

<210> SEQ ID NO 699
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 699
gcgcgcggaa tcctgg                                                    16

<210> SEQ ID NO 700
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 700
gctagcacca gctcct                                                    16

<210> SEQ ID NO 701
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 701
tggaaggtgg ctgtgg                                                    16

<210> SEQ ID NO 702
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 702
ccgagaggaa acagca                                                        16

<210> SEQ ID NO 703
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 703
agcaaactcg ccccgc                                                        16

<210> SEQ ID NO 704
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 704
ggctcaggga acaagg                                                        16

<210> SEQ ID NO 705
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 705
caccatcatc gctgaa                                                        16

<210> SEQ ID NO 706
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 706
gcagacatac ctgctt                                                        16

<210> SEQ ID NO 707
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 707
ctacatgtgc agagat                                                        16

<210> SEQ ID NO 708
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 708
```
ataaatctcc catcca                                          16

<210> SEQ ID NO 709
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 709
tttcaaatgt gccatt                                          16

<210> SEQ ID NO 710
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 710
atccccggcg ggcagc                                          16

<210> SEQ ID NO 711
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 711
aggatcttgg tgaggt                                          16

<210> SEQ ID NO 712
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 712
cgccactcat cttcac                                          16

<210> SEQ ID NO 713
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 713
ggcctactaa gcacag                                          16

<210> SEQ ID NO 714
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 714
ttcaaaggaa ttttgg                                          16

<210> SEQ ID NO 715
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 715
acccaggtcc agactc                                              16

<210> SEQ ID NO 716
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 716
ggttagacag ccaata                                              16

<210> SEQ ID NO 717
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 717
ctaaatcatg acataa                                              16

<210> SEQ ID NO 718
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 718
gcaaagacag aggagt                                              16

<210> SEQ ID NO 719
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 719
tccaaggtaa gtgcag                                              16

<210> SEQ ID NO 720
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 720
gacaagaacg acaaag                                              16

<210> SEQ ID NO 721
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 721
gacaatgaag aggaga                                              16

```
<210> SEQ ID NO 722
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 722 ctcaataacct gacaga                                                   16

<210> SEQ ID NO 723
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 723
tggtaaaagc ccccac                                                    16

<210> SEQ ID NO 724
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 724
atacattggc agacag                                                    16

<210> SEQ ID NO 725
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 725
actcatcaat aggcat                                                    16

<210> SEQ ID NO 726
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 726
catcacagga cttaca                                                    16

<210> SEQ ID NO 727
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 727
caagagactc actggg                                                    16

<210> SEQ ID NO 728
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 728
tgccaagaag gaccca                                                    16

<210> SEQ ID NO 729
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 729
gaccatgacc ctgccc                                                    16

<210> SEQ ID NO 730
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 730
tggaagcggg tcccgt                                                    16

<210> SEQ ID NO 731
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 731
tgctcgacga acacaa                                                    16

<210> SEQ ID NO 732
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 732
cgctgaccac ccctgc                                                    16

<210> SEQ ID NO 733
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 733
cccttggcca cgccgg                                                    16

<210> SEQ ID NO 734
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 734
tgccgctaac cgtgcc                                                    16

<210> SEQ ID NO 735
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 735
gtggaagtca agctgc                                                         16

<210> SEQ ID NO 736
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 736
gccccgtgcc aggtca                                                         16

<210> SEQ ID NO 737
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 737
taggagacag ctagtg                                                         16

<210> SEQ ID NO 738
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 738
cacaaacttg aacaga                                                         16

<210> SEQ ID NO 739
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 739
cttaatatat acatcc                                                         16

<210> SEQ ID NO 740
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 740
gccaaggtca cccctt                                                         16

<210> SEQ ID NO 741
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 741
```
gaccagcacg accccca                                                          16

<210> SEQ ID NO 742
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 742
acctaggtta ccgctg                                                           16

<210> SEQ ID NO 743
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 743
aggaaaatct gactgc                                                           16

<210> SEQ ID NO 744
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 744
acacagcggc caaagt                                                           16

<210> SEQ ID NO 745
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 745
gcagacagca tcatgg                                                           16

<210> SEQ ID NO 746
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 746
ggtcagtacc cgctgg                                                           16

<210> SEQ ID NO 747
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 747
cctatttaag gtggcg                                                           16

<210> SEQ ID NO 748
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 748
cgtgtaggcc ccgagt                                                    16

<210> SEQ ID NO 749
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 749
cagaaatgcc tgcccc                                                    16

<210> SEQ ID NO 750
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 750
gcagcacctg gcaatg                                                    16

<210> SEQ ID NO 751
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 751
tggacacggg tcccca                                                    16

<210> SEQ ID NO 752
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 752
cctcacccca gggcaa                                                    16

<210> SEQ ID NO 753
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 753
gtaacgatag ctagaa                                                    16

<210> SEQ ID NO 754
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 754
tgaacatggt agggtt                                                    16
```

-continued

<210> SEQ ID NO 755
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 755
aggcaagagc taggaa                                                       16

<210> SEQ ID NO 756
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 756
acgcactggt tgggct                                                       16

<210> SEQ ID NO 757
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 757
gttaaataga tcagag                                                       16

<210> SEQ ID NO 758
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 758
ccccatagcc tgcccc                                                       16

<210> SEQ ID NO 759
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 759
gcagatggca acggct                                                       16

<210> SEQ ID NO 760
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 760
ccatggaggg ctgaga                                                       16

<210> SEQ ID NO 761
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 761
acccagagtg agtgag                                                    16

<210> SEQ ID NO 762
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 762
gctggcagca cccgag                                                    16

<210> SEQ ID NO 763
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 763
agctcaataa aagtca                                                    16

<210> SEQ ID NO 764
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 764
gaagaatcct gcctcc                                                    16

<210> SEQ ID NO 765
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 765
ttaatcaggg agcccc                                                    16

<210> SEQ ID NO 766
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 766
gcagagtaaa ggtggc                                                    16

<210> SEQ ID NO 767
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 767
acactgccga gtcagt                                                    16

```
<210> SEQ ID NO 768
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 768
gtgcgaatgt gtaccc                                                   16

<210> SEQ ID NO 769
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 769
ggcaggcacg cccct                                                    16

<210> SEQ ID NO 770
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 770
tctggctcag ttcctg                                                   16

<210> SEQ ID NO 771
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 771
aaaaatgagg agccca                                                   16

<210> SEQ ID NO 772
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 772
ttccatgcct gcaggc                                                   16

<210> SEQ ID NO 773
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 773
ggacagttgt tggccc                                                   16

<210> SEQ ID NO 774
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 774
gaaaagttgg ctgtaa                                                        16

<210> SEQ ID NO 775
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 775
accttctagg gtgtgg                                                        16

<210> SEQ ID NO 776
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 776
ctgaagttca ggagca                                                        16

<210> SEQ ID NO 777
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 777
ggctagcacc agctcc                                                        16

<210> SEQ ID NO 778
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 778
cgcagcggtg gaaggt                                                        16

<210> SEQ ID NO 779
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 779
gcgaagagcc ctcggc                                                        16

<210> SEQ ID NO 780
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 780
gggaagaagc ttccca                                                        16

<210> SEQ ID NO 781
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 781
agaaagtcaa aggctc                                                    16

<210> SEQ ID NO 782
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 782
gacaccatca tcgctg                                                    16

<210> SEQ ID NO 783
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 783
ggcagacata cctgct                                                    16

<210> SEQ ID NO 784
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 784
ggccttaagc tgcttt                                                    16

<210> SEQ ID NO 785
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 785
atataaatct cccatc                                                    16

<210> SEQ ID NO 786
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 786
tcacatggtt atataa                                                    16

<210> SEQ ID NO 787
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 787
```
tatccccggc gggcag                                                16

<210> SEQ ID NO 788
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 788
caggatcttg gtgagg                                                16

<210> SEQ ID NO 789
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 789
cagcaggtcg ccactc                                                16

<210> SEQ ID NO 790
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 790
agcaatgggc ctacta                                                16

<210> SEQ ID NO 791
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 791
agcaacagct tcaaag                                                16

<210> SEQ ID NO 792
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 792
ctgattaacc catggg                                                16

<210> SEQ ID NO 793
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 793
ttacagatag aggaat                                                16

<210> SEQ ID NO 794
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 794
ggacatggag tgaagc                                                      16

<210> SEQ ID NO 795
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 795
gggcaaagac agagga                                                      16

<210> SEQ ID NO 796
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 796
ggtagagtca ccatca                                                      16

<210> SEQ ID NO 797
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 797
tctcacagca acctgt                                                      16

<210> SEQ ID NO 798
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 798
tcctaacccc cacaac                                                      16

<210> SEQ ID NO 799
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 799
tgcagggcta aaatca                                                      16

<210> SEQ ID NO 800
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 800
ggcaggtggg cctggt                                                      16
```

```
<210> SEQ ID NO 801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 801
ggatacattg gcagac                                                       16

<210> SEQ ID NO 802
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 802
gtgttaggag ctttca                                                       16

<210> SEQ ID NO 803
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 803
agacacatca caggac                                                       16

<210> SEQ ID NO 804
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 804
aagaagcagg cactgg                                                       16

<210> SEQ ID NO 805
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 805
aaggaaaggg aggcct                                                       16

<210> SEQ ID NO 806
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 806
tcgaagtcgg tgacca                                                       16

<210> SEQ ID NO 807
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 807
tgtggaagcg ggtccc                                                         16

<210> SEQ ID NO 808
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 808
gccgctgacc acccct                                                         16

<210> SEQ ID NO 809
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 809
acccttggcc acgccg                                                         16

<210> SEQ ID NO 810
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 810
tatgagggtg ccgcta                                                         16

<210> SEQ ID NO 811
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 811
acttacctat gagggt                                                         16

<210> SEQ ID NO 812
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 812
ggcttacagt ggaagt                                                         16

<210> SEQ ID NO 813
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 813
tgccccgtgc caggtc                                                         16

<210> SEQ ID NO 814
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 814
ccaggagccg tggcca                                                       16

<210> SEQ ID NO 815
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 815
acacaaactt gaacag                                                       16

<210> SEQ ID NO 816
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 816
tcttaatata tacatc                                                       16

<210> SEQ ID NO 817
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 817
gaacaaagcc aaggtc                                                       16

<210> SEQ ID NO 818
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 818
ggtgaccagc acgacc                                                       16

<210> SEQ ID NO 819
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 819
ccttgatagg ccaggg                                                       16

<210> SEQ ID NO 820
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 820
```
tcccactcaa atgtcc                                                    16

<210> SEQ ID NO 821
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 821
ccacacagcg gccaaa                                                    16

<210> SEQ ID NO 822
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 822
cggcagacag catcat                                                    16

<210> SEQ ID NO 823
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 823
ggcagggcgg ccacca                                                    16

<210> SEQ ID NO 824
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 824
aaaatattgc acagcc                                                    16

<210> SEQ ID NO 825
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 825
ggccatccgt gtaggc                                                    16

<210> SEQ ID NO 826
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 826
agcattaaga ccccat                                                    16

<210> SEQ ID NO 827
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 827
ggcagcacct ggcaat                                                      16

<210> SEQ ID NO 828
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 828
gtggacacgg gtcccc                                                      16

<210> SEQ ID NO 829
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 829
agaaagagac ccctcc                                                      16

<210> SEQ ID NO 830
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 830
aaacaatagt aacgat                                                      16

<210> SEQ ID NO 831
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 831
tctgaacatg gtaggg                                                      16

<210> SEQ ID NO 832
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 832
gcccatcccc atcaga                                                      16

<210> SEQ ID NO 833
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 833
gggcatggca gcagga                                                      16
```

<210> SEQ ID NO 834
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 834
cttcagcatg cagctc                                                 16

<210> SEQ ID NO 835
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 835
tgaaactgat ggcccc                                                 16

<210> SEQ ID NO 836
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 836
cagcagatgg caacgg                                                 16

<210> SEQ ID NO 837
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 837
ggccatggag ggctga                                                 16

<210> SEQ ID NO 838
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 838
aggcacccag agtgag                                                 16

<210> SEQ ID NO 839
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 839
agctggcagc acccga                                                 16

<210> SEQ ID NO 840
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 840
gaacaagagc tcaata                16

<210> SEQ ID NO 841
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 841
gggaagaatc ctgcct                16

<210> SEQ ID NO 842
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 842
cattaatcag ggagcc                16

<210> SEQ ID NO 843
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 843
gagcagagta aaggtg                16

<210> SEQ ID NO 844
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 844
cacactgccg agtcag                16

<210> SEQ ID NO 845
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 845
aggtttcttc ctctgt                16

<210> SEQ ID NO 846
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 846
gagcttggca ggcacg                16

```
<210> SEQ ID NO 847
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 847
ttctggctca gttcct                                                     16

<210> SEQ ID NO 848
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 848
gtaaaaatga ggagcc                                                     16

<210> SEQ ID NO 849
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 849
aaaaagttcc atgcct                                                     16

<210> SEQ ID NO 850
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 850
ggagggacag ttgttg                                                     16

<210> SEQ ID NO 851
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 851
tagaaaagtt ggctgt                                                     16

<210> SEQ ID NO 852
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 852
ttgctggcct gtctgt                                                     16

<210> SEQ ID NO 853
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 853
gcctatgagg gtgccg                                               16

<210> SEQ ID NO 854
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 854
tgccaacctg ccccat                                               16

<210> SEQ ID NO 855
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 855
cggaaacctt ctaggg                                               16

<210> SEQ ID NO 856
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 856
agctgaagtt caggag                                               16

<210> SEQ ID NO 857
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 857
aggctagcac cagctc                                               16

<210> SEQ ID NO 858
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 858
tggcgcagcg gtggaa                                               16

<210> SEQ ID NO 859
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 859
ccactacccg tcctcc                                               16

<210> SEQ ID NO 860
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 860
cgggaagaag cttccc                                               16

<210> SEQ ID NO 861
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 861
ccccacaaca tccctc                                               16

<210> SEQ ID NO 862
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 862
aaagaactgt ggacat                                               16

<210> SEQ ID NO 863
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 863
aggcagacat acctgc                                               16

<210> SEQ ID NO 864
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 864
ctgcaagctc tccagg                                               16

<210> SEQ ID NO 865
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 865
caagagtgac ggttat                                               16

<210> SEQ ID NO 866
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 866
```
tattattcac atggtt                                              16

<210> SEQ ID NO 867
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 867
gtatccccgg cgggca                                              16

<210> SEQ ID NO 868
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 868
gcaggatctt ggtgag                                              16

<210> SEQ ID NO 869
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 869
ctccagcagg tcgcca                                              16

<210> SEQ ID NO 870
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 870
atacatactt gctgtc                                              16

<210> SEQ ID NO 871
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 871
tggatagcaa cagctt                                              16

<210> SEQ ID NO 872
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 872
tgctgagctg attaac                                              16

<210> SEQ ID NO 873
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 873
aattattata actggt                                                   16

<210> SEQ ID NO 874
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 874
gggcaggatg gacatg                                                   16

<210> SEQ ID NO 875
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 875
ttccacggga tgctct                                                   16

<210> SEQ ID NO 876
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 876
ttaaaggatc tggtcc                                                   16

<210> SEQ ID NO 877
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 877
gtgtatgcaa agtcac                                                   16

<210> SEQ ID NO 878
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 878
agggaacagt ggctgc                                                   16

<210> SEQ ID NO 879
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 879
ttattgaatg gtaaga                                                   16
```

```
<210> SEQ ID NO 880
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 880
ctgcaagcat ggccag                                                    16

<210> SEQ ID NO 881
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 881
acaactggat acattg                                                    16

<210> SEQ ID NO 882
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 882
cactttggtt tcttct                                                    16

<210> SEQ ID NO 883
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 883
cttatggctt cggtca                                                    16

<210> SEQ ID NO 884
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 884
agataccagg agggct                                                    16

<210> SEQ ID NO 885
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 885
atagacaagg aaaggg                                                    16

<210> SEQ ID NO 886
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 886
cacattctcg aagtcg                                                    16

<210> SEQ ID NO 887
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 887
ggccgctgac cacccc                                                    16

<210> SEQ ID NO 888
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 888
cacccttggc cacgcc                                                    16

<210> SEQ ID NO 889
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 889
atggagagag accagc                                                    16

<210> SEQ ID NO 890
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 890
caccagagcc agtgtt                                                    16

<210> SEQ ID NO 891
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 891
ctgccccgtg ccaggt                                                    16

<210> SEQ ID NO 892
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 892
tgtcaaatga ggtgtg                                                    16

<210> SEQ ID NO 893

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 893
atgagaaggg cacact                                                     16

<210> SEQ ID NO 894
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 894
aactcttaat atatac                                                     16

<210> SEQ ID NO 895
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 895
aggaacaaag ccaagg                                                     16

<210> SEQ ID NO 896
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 896
cggcagcggt gaccag                                                     16

<210> SEQ ID NO 897
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 897
gccttgatag gccagg                                                     16

<210> SEQ ID NO 898
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 898
agagaaagga gcccaa                                                     16

<210> SEQ ID NO 899
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 899
```
gtccacacag cggcca                                                    16

<210> SEQ ID NO 900
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 900
ggctcggcag acagca                                                    16

<210> SEQ ID NO 901
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 901
ggcttaaaga acatac                                                    16

<210> SEQ ID NO 902
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 902
ggcgacggct gtggcc                                                    16

<210> SEQ ID NO 903
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 903
gagcattaag acccca                                                    16

<210> SEQ ID NO 904
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 904
aggcagcacc tggcaa                                                    16

<210> SEQ ID NO 905
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 905
agtggacacg ggtccc                                                    16

<210> SEQ ID NO 906
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 906
tcacacttgt gaggac                                                      16

<210> SEQ ID NO 907
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 907
aaagcaacgg gtgatg                                                      16

<210> SEQ ID NO 908
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 908
gtaagatgga aagaga                                                      16

<210> SEQ ID NO 909
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 909
ctgggatgct ccgtct                                                      16

<210> SEQ ID NO 910
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 910
tgcattccag acctgg                                                      16

<210> SEQ ID NO 911
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 911
tgctaacaac cttcag                                                      16

<210> SEQ ID NO 912
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 912
taccatgcca gtgcca                                                      16
```

<210> SEQ ID NO 913
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 913
cggcagcaga tggcaa                                                    16

<210> SEQ ID NO 914
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 914
tgccaggcca tggagg                                                    16

<210> SEQ ID NO 915
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 915
ggaggaggca cccaga                                                    16

<210> SEQ ID NO 916
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 916
gagcagctgg cagcac                                                    16

<210> SEQ ID NO 917
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 917
ggaacaagag ctcaat                                                    16

<210> SEQ ID NO 918
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 918
atccatggga agaatc                                                    16

<210> SEQ ID NO 919
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 919
ctccattaat caggga                                                         16

<210> SEQ ID NO 920
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 920
atagagcaga gtaaag                                                         16

<210> SEQ ID NO 921
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 921
gcacactgcc gagtca                                                         16

<210> SEQ ID NO 922
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 922
caggtttctt cctctg                                                         16

<210> SEQ ID NO 923
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 923
gtgagcttgg caggca                                                         16

<210> SEQ ID NO 924
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 924
tttctggctc agttcc                                                         16

<210> SEQ ID NO 925
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 925
ccgtaaaaat gaggag                                                         16
```

```
<210> SEQ ID NO 926
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 926
ggaaaaagtt ccatgc                                                      16

<210> SEQ ID NO 927
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 927
aaggagggac agttgt                                                      16

<210> SEQ ID NO 928
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 928
tctagaaaag ttggct                                                      16

<210> SEQ ID NO 929
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 929
acggatcctt ggcgca                                                      16

<210> SEQ ID NO 930
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 930
tcaaggccag ctccag                                                      16

<210> SEQ ID NO 931
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 931
acttgctggc ctgtct                                                      16

<210> SEQ ID NO 932
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 932
ctccaggcct atgagg                                                         16

<210> SEQ ID NO 933
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 933
tgcggaaacc ttctag                                                         16

<210> SEQ ID NO 934
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 934
gaggactgtg caggag                                                         16

<210> SEQ ID NO 935
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 935
aaggctagca ccagct                                                         16

<210> SEQ ID NO 936
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 936
ggatatcctg gcagtg                                                         16

<210> SEQ ID NO 937
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 937
gaaaaagcta gtggtc                                                         16

<210> SEQ ID NO 938
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 938
cttgaaatgc cctttc                                                         16

<210> SEQ ID NO 939
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 939
tacatttcag acggtg                                                     16

<210> SEQ ID NO 940
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 940
attatagcag ccacta                                                     16

<210> SEQ ID NO 941
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 941
atttattcag ctcatg                                                     16

<210> SEQ ID NO 942
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 942
tgggaaagtc aagagt                                                     16

<210> SEQ ID NO 943
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 943
gccaactatt attatt                                                     16

<210> SEQ ID NO 944
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 944
ggtatccccg gcgggc                                                     16

<210> SEQ ID NO 945
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 945
```
tgcaggatct tggtga                                                        16

<210> SEQ ID NO 946
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 946
gataagtgct caatac                                                        16

<210> SEQ ID NO 947
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 947
ctggatagca acagct                                                        16

<210> SEQ ID NO 948
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 948
cgccacaggc cttggt                                                        16

<210> SEQ ID NO 949
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 949
ccaattatta taactg                                                        16

<210> SEQ ID NO 950
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 950
agccaggctg tgccaa                                                        16

<210> SEQ ID NO 951
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 951
ctccaggttc cacggg                                                        16

<210> SEQ ID NO 952
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 952
attaaaggat ctggtc                                                    16

<210> SEQ ID NO 953
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 953
cagacatatg caaggt                                                    16

<210> SEQ ID NO 954
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 954
gcccaaggga gaggag                                                    16

<210> SEQ ID NO 955
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 955
gttattattg aatggt                                                    16

<210> SEQ ID NO 956
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 956
caggaggctg caagca                                                    16

<210> SEQ ID NO 957
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 957
caggaagcag cccaag                                                    16

<210> SEQ ID NO 958
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 958
ctccactgat cagtcc                                                    16
```

<210> SEQ ID NO 959
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 959
ccaaatatgc tgcaga                                                    16

<210> SEQ ID NO 960
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 960
agagacagga agctgc                                                    16

<210> SEQ ID NO 961
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 961
cacagaaact acagag                                                    16

<210> SEQ ID NO 962
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 962
gggcacattc tcgaag                                                    16

<210> SEQ ID NO 963
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 963
cggccgctga ccaccc                                                    16

<210> SEQ ID NO 964
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 964
gcacccttgg ccacgc                                                    16

<210> SEQ ID NO 965
<211> LENGTH: 16
<212> TYPE: DNA
<213> ORGANISM: Artificial sequence
<220> FEATURE:
<223> OTHER INFORMATION: Synthetic oligonucleotide -continued

```
<400> SEQUENCE: 965
ccagatggag agagac                                                          16

<210> SEQ ID NO 966
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 966
ggctagtggg ctgcct                                                          16

<210> SEQ ID NO 967
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 967
ccctgccccg tgccag                                                          16

<210> SEQ ID NO 968
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 968
gcctaacgca gctctg                                                          16

<210> SEQ ID NO 969
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 969
gaggaatgag aagggc                                                          16

<210> SEQ ID NO 970
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 970
ccgcacggtc acatga                                                          16

<210> SEQ ID NO 971
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 971
gtgccacaag aagccc                                                          16

<210> SEQ ID NO 972
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 972
gaagttgccg gcagcg                                                     16

<210> SEQ ID NO 973
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 973
taaattcggc cgccag                                                     16

<210> SEQ ID NO 974
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 974
aaagaggtcc acacag                                                     16

<210> SEQ ID NO 975
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 975
ctgttagcat cacggt                                                     16

<210> SEQ ID NO 976
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 976
ggccagggtg agctcc                                                     16

<210> SEQ ID NO 977
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 977
gagagaggag ggctta                                                     16

<210> SEQ ID NO 978
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 978
```
aaaacagctg ccaacc                                           16

<210> SEQ ID NO 979
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 979
cgggcgacgg ctgtgg                                           16

<210> SEQ ID NO 980
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 980
acacgagcat taagac                                           16

<210> SEQ ID NO 981
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 981
gcaggcagca cctggc                                           16

<210> SEQ ID NO 982
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 982
cagtggacac gggtcc                                           16

<210> SEQ ID NO 983
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 983
ctgcaagtca ggcttg                                           16

<210> SEQ ID NO 984
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 984
tttaaagcaa cgggtg                                           16

<210> SEQ ID NO 985
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 985
agctacactg aggctc                                                    16

<210> SEQ ID NO 986
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 986
gactttgcat tccaga                                                    16

<210> SEQ ID NO 987
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 987
ggcagaggaa agccag                                                    16

<210> SEQ ID NO 988
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 988
tgtcacattc cagggc                                                    16

<210> SEQ ID NO 989
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 989
agatagacag atgcct                                                    16

<210> SEQ ID NO 990
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 990
cgccaggtgc cggctc                                                    16

<210> SEQ ID NO 991
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 991
gcggaagcat ccccat                                                    16
```

<210> SEQ ID NO 992
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 992
ccccacagtg agggag                                                         16

<210> SEQ ID NO 993
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 993
acattgggag cagctg                                                         16

<210> SEQ ID NO 994
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 994
cggaacaaga gctcaa                                                         16

<210> SEQ ID NO 995
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 995
ccctatccat gggaag                                                         16

<210> SEQ ID NO 996
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 996
agctaagcct ccatta                                                         16

<210> SEQ ID NO 997
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 997
gcatagagca gagtaa                                                         16

<210> SEQ ID NO 998
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 998
tgcacactgc cgagtc                                                    16

<210> SEQ ID NO 999
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 999
ccaggtttct tcctct                                                    16

<210> SEQ ID NO 1000
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1000
tgtgagcttg gcaggc                                                    16

<210> SEQ ID NO 1001
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1001
gtttctggct cagttc                                                    16

<210> SEQ ID NO 1002
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1002
acccgtaaaa atgagg                                                    16

<210> SEQ ID NO 1003
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1003
acggaaaaag ttccat                                                    16

<210> SEQ ID NO 1004
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1004
ctcaaggagg gacagt                                                    16

```
<210> SEQ ID NO 1005
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1005
aaacaggtct agaaaa                                                     16

<210> SEQ ID NO 1006
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1006
cacttgctgg cctgtc                                                     16

<210> SEQ ID NO 1007
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1007
ctccacggat ccttgg                                                     16

<210> SEQ ID NO 1008
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1008
ttcaaggcca gctcca                                                     16

<210> SEQ ID NO 1009
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1009
ataaactcca ggccta                                                     16

<210> SEQ ID NO 1010
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1010
cgtcgctgcg gaaacc                                                     16

<210> SEQ ID NO 1011
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1011
gtccacgccg gcggcg                                                      16

<210> SEQ ID NO 1012
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1012
caaggctagc accagc                                                      16

<210> SEQ ID NO 1013
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1013
gaaatctggg caggat                                                      16

<210> SEQ ID NO 1014
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1014
caccacagct agtgag                                                      16

<210> SEQ ID NO 1015
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1015
cactatttcc agaaca                                                      16

<210> SEQ ID NO 1016
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1016
aataatctca tgtcag                                                      16

<210> SEQ ID NO 1017
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1017
caaattatag cagcca                                                      16

<210> SEQ ID NO 1018
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1018
gatttattca gctcat                                                       16

<210> SEQ ID NO 1019
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1019
ccacagtacc tatgac                                                       16

<210> SEQ ID NO 1020
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1020
caaatgcgga ccaaaa                                                       16

<210> SEQ ID NO 1021
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1021
aggtatcccc ggcggg                                                       16

<210> SEQ ID NO 1022
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1022
atgcaggatc ttggtg                                                       16

<210> SEQ ID NO 1023
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1023
cgataagtgc tcaata                                                       16

<210> SEQ ID NO 1024
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1024
```

```
aaagaaggga cttcac                                              16

<210> SEQ ID NO 1025
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1025
acttagacta cgggtt                                              16

<210> SEQ ID NO 1026
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1026
tccttaaatg aatgtt                                              16

<210> SEQ ID NO 1027
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1027
cttgatcagg ctggga                                              16

<210> SEQ ID NO 1028
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1028
ggtaatccgc tccagg                                              16

<210> SEQ ID NO 1029
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1029
tcccattaaa ggatct                                              16

<210> SEQ ID NO 1030
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1030
acacatgacc gaccag                                              16

<210> SEQ ID NO 1031
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 1031
ctccagccaa gccctt                                                    16

<210> SEQ ID NO 1032
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1032
tctggataca ctgttg                                                    16

<210> SEQ ID NO 1033
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1033
ggtcaggagg ctgcaa                                                    16

<210> SEQ ID NO 1034
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1034
tgctcaggaa gcagcc                                                    16

<210> SEQ ID NO 1035
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1035
ccctaaggcc tccagt                                                    16

<210> SEQ ID NO 1036
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1036
ctgaacagca cctctg                                                    16

<210> SEQ ID NO 1037
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1037
ttagagacag gaagct                                                    16
```

<210> SEQ ID NO 1038
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1038
cttatagtta acacac                                                     16

<210> SEQ ID NO 1039
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1039
ctcctcgggc acattc                                                     16

<210> SEQ ID NO 1040
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1040
ccggccgctg accacc                                                     16

<210> SEQ ID NO 1041
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1041
ggcacccttg gccacg                                                     16

<210> SEQ ID NO 1042
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1042
gcccaagcca cctccc                                                     16

<210> SEQ ID NO 1043
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1043
aggaaagtct cagggc                                                     16

<210> SEQ ID NO 1044
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1044
agcccctgcc ccgtgc                                                    16

<210> SEQ ID NO 1045
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1045
ggcctaacgc agctct                                                    16

<210> SEQ ID NO 1046
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1046
aggcaccaag aggatg                                                    16

<210> SEQ ID NO 1047
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1047
gcggatttca gacttg                                                    16

<210> SEQ ID NO 1048
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1048
ccggaagttg ccggca                                                    16

<210> SEQ ID NO 1049
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1049
cgtgccacaa gaagcc                                                    16

<210> SEQ ID NO 1050
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1050
gcctttaaat tcggcc                                                    16

<210> SEQ ID NO 1051
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1051
gcaaagaggt ccacac                                                      16

<210> SEQ ID NO 1052
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1052
ggcactggag gtcccg                                                      16

<210> SEQ ID NO 1053
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1053
ctcaactcgg ccaggg                                                      16

<210> SEQ ID NO 1054
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1054
taggagagag gagggc                                                      16

<210> SEQ ID NO 1055
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1055
gcaaaacagc tgccaa                                                      16

<210> SEQ ID NO 1056
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1056
gcagcgggcg acggct                                                      16

<210> SEQ ID NO 1057
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1057
```
ctctcacacg agcatt 16

<210> SEQ ID NO 1058
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1058
agcaggcagc acctgg 16

<210> SEQ ID NO 1059
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1059
gcagtggaca cgggtc 16

<210> SEQ ID NO 1060
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1060
gtatggaact gcaagt 16

<210> SEQ ID NO 1061
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1061
attttaaagc aacggg 16

<210> SEQ ID NO 1062
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1062
aaacctaaaa tagtgg 16

<210> SEQ ID NO 1063
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1063
gggcagagga aagcca 16

<210> SEQ ID NO 1064
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1064
ttccatgctc cttgac                                                   16

<210> SEQ ID NO 1065
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1065
atacactcag gtttct                                                   16

<210> SEQ ID NO 1066
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1066
acccaggcgg ttctgc                                                   16

<210> SEQ ID NO 1067
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1067
gtcactggag ctcctg                                                   16

<210> SEQ ID NO 1068
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1068
aaaggcggaa gcatcc                                                   16

<210> SEQ ID NO 1069
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1069
gtgaaatgcc ccacag                                                   16

<210> SEQ ID NO 1070
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1070
gcacattggg agcagc                                                   16
```

<210> SEQ ID NO 1071
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1071
acggaacaag agctca                                                      16

<210> SEQ ID NO 1072
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1072
caacgatgtt tgtccc                                                      16

<210> SEQ ID NO 1073
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1073
gaaagctaag cctcca                                                      16

<210> SEQ ID NO 1074
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1074
tggcatagag cagagt                                                      16

<210> SEQ ID NO 1075
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1075
ctgcacactg ccgagt                                                      16

<210> SEQ ID NO 1076
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1076
tccaggtttc ttcctc                                                      16

<210> SEQ ID NO 1077
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 1077
gtgtgagctt ggcagg                                                   16

<210> SEQ ID NO 1078
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1078
cgtttctggc tcagtt                                                   16

<210> SEQ ID NO 1079
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1079
tgttacccgt aaaaat                                                   16

<210> SEQ ID NO 1080
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1080
taacggaaaa agttcc                                                   16

<210> SEQ ID NO 1081
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1081
tgctcaagga gggaca                                                   16

<210> SEQ ID NO 1082
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1082
caaaacaggt ctagaa                                                   16

<210> SEQ ID NO 1083
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1083
cttcaaggcc agctcc                                                   16
```

```
<210> SEQ ID NO 1084
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1084
acacttgctg gcctgt                                                      16

<210> SEQ ID NO 1085
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1085
ctgcaaccat gagcgc                                                      16

<210> SEQ ID NO 1086
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1086
ctagaggccg tgcgcg                                                      16

<210> SEQ ID NO 1087
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1087
gcaaggctag caccag                                                      16

<210> SEQ ID NO 1088
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1088
gaaactggga aatctg                                                      16

<210> SEQ ID NO 1089
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1089
gtcaagcacc acagct                                                      16

<210> SEQ ID NO 1090
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1090
cctcaagggc ttggtt                                              16

<210> SEQ ID NO 1091
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1091
aatctatgca gcaaaa                                              16

<210> SEQ ID NO 1092
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1092
aacaaattat agcagc                                              16

<210> SEQ ID NO 1093
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1093
gaccacagta cctatg                                              16

<210> SEQ ID NO 1094
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1094
accaaatgcg gaccaa                                              16

<210> SEQ ID NO 1095
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1095
ggcaacctcc acggat                                              16

<210> SEQ ID NO 1096
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1096
gaggtatccc cggcgg                                              16

<210> SEQ ID NO 1097
<211> LENGTH: 16
```

-continued

```
<212> TYPE: DNA
<213> ORGANISM: Artificial sequence
<220> FEATURE:
<223> OTHER INFORMATION: Synthetic oligonucleotide

<400> SEQUENCE: 1097
catgcaggat cttggt                                                         16

<210> SEQ ID NO 1098
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1098
tgcttggtac ccgata                                                         16

<210> SEQ ID NO 1099
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1099
cctaaagaag ggactt                                                         16

<210> SEQ ID NO 1100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1100
aggcattgac ttgtca                                                         16

<210> SEQ ID NO 1101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1101
tacctagcat ctgctg                                                         16

<210> SEQ ID NO 1102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1102
acagactagg agcctg                                                         16

<210> SEQ ID NO 1103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1103
```

```
ccgcccggta ccgtgg                                                          16
```

<210> SEQ ID NO 1104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1104

```
aggcatccca gacagg                                                          16
```

<210> SEQ ID NO 1105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1105

```
gcacacatga ccgacc                                                          16
```

<210> SEQ ID NO 1106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1106

```
ccccatgcca gcccaa                                                          16
```

<210> SEQ ID NO 1107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1107

```
attaatcttc tggata                                                          16
```

<210> SEQ ID NO 1108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1108

```
ggacagggtc aggagg                                                          16
```

<210> SEQ ID NO 1109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1109

```
ggatacaggt gctcag                                                          16
```

<210> SEQ ID NO 1110
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1110
acacacactg tctacc                                                     16

<210> SEQ ID NO 1111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1111
cctcaggtgg aatcag                                                     16

<210> SEQ ID NO 1112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1112
gaataacagt gatgtc                                                     16

<210> SEQ ID NO 1113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1113
accttatagt taacac                                                     16

<210> SEQ ID NO 1114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1114
tcctcctcgg gcacat                                                     16

<210> SEQ ID NO 1115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1115
cccggccgct gaccac                                                     16

<210> SEQ ID NO 1116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1116
tggcacccTT ggccac                                                     16
```

<210> SEQ ID NO 1117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1117
ggtcaaggct gaactc                                                    16

<210> SEQ ID NO 1118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1118
taggaaagtc tcaggg                                                    16

<210> SEQ ID NO 1119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1119
aggcaatagt gactgt                                                    16

<210> SEQ ID NO 1120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1120
ctggagactg gaggcc                                                    16

<210> SEQ ID NO 1121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1121
gaaagagagg caccaa                                                    16

<210> SEQ ID NO 1122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1122
tgcggatttc agactt                                                    16

<210> SEQ ID NO 1123
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1123
gaataaactc caggcc                                                   16

<210> SEQ ID NO 1124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1124
gtagaggcag gcatcg                                                   16

<210> SEQ ID NO 1125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1125
cagaagggtt cggcct                                                   16

<210> SEQ ID NO 1126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1126
ggctttgttt gcttga                                                   16

<210> SEQ ID NO 1127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1127
gggcaaagag gtccac                                                   16

<210> SEQ ID NO 1128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1128
catcaggcct acttca                                                   16

<210> SEQ ID NO 1129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1129
gagaagtgga tcagtc                                                   16

<210> SEQ ID NO 1130
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1130
tgcaaaaagg gcctgg                                              16

<210> SEQ ID NO 1131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1131
ctgcaaaaca gctgcc                                              16

<210> SEQ ID NO 1132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1132
gcgcagcggg cgacgg                                              16

<210> SEQ ID NO 1133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1133
atccagccag ctccac                                              16

<210> SEQ ID NO 1134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1134
tagcaggcag cacctg                                              16

<210> SEQ ID NO 1135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1135
ggcagtggac acgggt                                              16

<210> SEQ ID NO 1136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1136
```

```
ggcagaacca gagtat                                                    16

<210> SEQ ID NO 1137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1137
caatagttgc ctatac                                                    16

<210> SEQ ID NO 1138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1138
agacacaccc attggc                                                    16

<210> SEQ ID NO 1139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1139
ggccgggatt ccatgc                                                    16

<210> SEQ ID NO 1140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1140
acgcagcacc ccaccc                                                    16

<210> SEQ ID NO 1141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1141
aaggagagtt atacac                                                    16

<210> SEQ ID NO 1142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1142
ggacacaacc gtgtat                                                    16

<210> SEQ ID NO 1143
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 1143
acccatcctg ggatgg                                                   16

<210> SEQ ID NO 1144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1144
ggaaaggcgg aagcat                                                   16

<210> SEQ ID NO 1145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1145
ttgaatggtg aaatgc                                                   16

<210> SEQ ID NO 1146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1146
cggcacattg ggagca                                                   16

<210> SEQ ID NO 1147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1147
cacggaacaa gagctc                                                   16

<210> SEQ ID NO 1148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1148
ccccaacgat gtttgt                                                   16

<210> SEQ ID NO 1149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1149
cagaaagcta agcctc                                                   16
```

```
<210> SEQ ID NO 1150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1150
gcacagcctg gcatag                                                    16

<210> SEQ ID NO 1151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1151
actgcacact gccgag                                                    16

<210> SEQ ID NO 1152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1152
gttccaggtt tcttcc                                                    16

<210> SEQ ID NO 1153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1153
tgtgtgagct tggcag                                                    16

<210> SEQ ID NO 1154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1154
agccagccca atctgc                                                    16

<210> SEQ ID NO 1155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1155
cctcactgtt acccgt                                                    16

<210> SEQ ID NO 1156
<211> LENGTH: 16
<212> TYPE: DNA
<213> ORGANISM: Artificial sequence
<220> FEATURE:
```

```
<223> OTHER INFORMATION: Synthetic oligonucleotide

<400> SEQUENCE: 1156
gataacggaa aaagtt                                                   16

<210> SEQ ID NO 1157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1157
ataaatgtct gcttgc                                                   16

<210> SEQ ID NO 1158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1158
agcaaaacag gtctag                                                   16

<210> SEQ ID NO 1159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1159
acttcaaggc cagctc                                                   16

<210> SEQ ID NO 1160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1160
aactgaacgg cggcgc                                                   16

<210> SEQ ID NO 1161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1161
acctagaggc cgtgcg                                                   16

<210> SEQ ID NO 1162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1162
cgcaaggcta gcacca                                                   16
```

```
<210> SEQ ID NO 1163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1163
ggcgaggcag aaactg                                                    16

<210> SEQ ID NO 1164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1164
tcaaggataa gtgact                                                    16

<210> SEQ ID NO 1165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1165
agaaacatcc tcaagg                                                    16

<210> SEQ ID NO 1166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1166
taatctatgc agcaaa                                                    16

<210> SEQ ID NO 1167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1167
ccaaatttcc acatga                                                    16

<210> SEQ ID NO 1168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1168
aaggaatacc tgaagg                                                    16

<210> SEQ ID NO 1169
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1169
cctcagatac ctctgc                                                    16

<210> SEQ ID NO 1170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1170
gtatagtaga tgataa                                                    16

<210> SEQ ID NO 1171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1171
tgccaggcaa cctcca                                                    16

<210> SEQ ID NO 1172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1172
tgaggtatcc ccggcg                                                    16

<210> SEQ ID NO 1173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1173
acatgcagga tcttgg                                                    16

<210> SEQ ID NO 1174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1174
agccagtagt tactgt                                                    16

<210> SEQ ID NO 1175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1175
gaagatgtga catcca                                                    16

<210> SEQ ID NO 1176
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1176
gagcagactg atggaa                                                    16

<210> SEQ ID NO 1177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1177
gtggtaacag cctcct                                                    16

<210> SEQ ID NO 1178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1178
ggacagacta ggagcc                                                    16

<210> SEQ ID NO 1179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1179
attcatccgc ccggta                                                    16

<210> SEQ ID NO 1180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1180
aggtaggcag aggcat                                                    16

<210> SEQ ID NO 1181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1181
ggccgggtca gcacac                                                    16

<210> SEQ ID NO 1182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1182
```

| ggcccatgct tgtggc | 16 |

<210> SEQ ID NO 1183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1183

| aggaatggat taatct | 16 |

<210> SEQ ID NO 1184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1184

| tctaagtgca ggcggt | 16 |

<210> SEQ ID NO 1185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1185

| cagcaaggtg ggcaga | 16 |

<210> SEQ ID NO 1186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1186

| gcacagtccg aactgt | 16 |

<210> SEQ ID NO 1187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1187

| gcggaaatgg cctggc | 16 |

<210> SEQ ID NO 1188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1188

| ggagaataac agtgat | 16 |

<210> SEQ ID NO 1189
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1189
aaccttatag ttaaca                                                  16

<210> SEQ ID NO 1190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1190
gtcctcctcg ggcaca                                                  16

<210> SEQ ID NO 1191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1191
cacacttgct ggcctg                                                  16

<210> SEQ ID NO 1192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1192
tcccggccgc tgacca                                                  16

<210> SEQ ID NO 1193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1193
ctggcaccct tggcca                                                  16

<210> SEQ ID NO 1194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1194
agacatcacc ggattt                                                  16

<210> SEQ ID NO 1195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1195
ctgtaggaaa gtctca                                                  16
```

<210> SEQ ID NO 1196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1196
ggacacacaa tcacct					16

<210> SEQ ID NO 1197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1197
cagtaacagt tctaac					16

<210> SEQ ID NO 1198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1198
cttattatcc ctttcc					16

<210> SEQ ID NO 1199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1199
tcaaattctg caggaa					16

<210> SEQ ID NO 1200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1200
ccgaataaac tccagg					16

<210> SEQ ID NO 1201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1201
gagtagaggc aggcat					16

<210> SEQ ID NO 1202
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1202
ccaaagccag aagggt                                                    16

<210> SEQ ID NO 1203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1203
ttctaagtgc cacggg                                                    16

<210> SEQ ID NO 1204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1204
caatgatgtc ctcccc                                                    16

<210> SEQ ID NO 1205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1205
tcccgatcaa atgtcc                                                    16

<210> SEQ ID NO 1206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1206
gcagagaagt ggatca                                                    16

<210> SEQ ID NO 1207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1207
tgccaacctg caaaaa                                                    16

<210> SEQ ID NO 1208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1208
atacagtcct gcaaaa                                                    16

<210> SEQ ID NO 1209
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1209
agctcagcag ctcctc                                                       16

<210> SEQ ID NO 1210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1210
atccaggagg ccaaag                                                       16

<210> SEQ ID NO 1211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1211
gggtagcagg cagcac                                                       16

<210> SEQ ID NO 1212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1212
tggcagtgga cacggg                                                       16

<210> SEQ ID NO 1213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1213
ggagaagtaa ggtcac                                                       16

<210> SEQ ID NO 1214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1214
gtcaatagtt gcctat                                                       16

<210> SEQ ID NO 1215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1215
```

```
gttcaagggt aagccg                                                  16

<210> SEQ ID NO 1216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1216
tggcacaaac tgacac                                                  16

<210> SEQ ID NO 1217
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1217
ttaagagtgg actcct                                                  16

<210> SEQ ID NO 1218
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1218
ccaaagtgca gacggc                                                  16

<210> SEQ ID NO 1219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1219
ggccacggtc acctgc                                                  16

<210> SEQ ID NO 1220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1220
ccccagacac ccatcc                                                  16

<210> SEQ ID NO 1221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1221
ccggaaaggc ggaagc                                                  16

<210> SEQ ID NO 1222
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 1222
gcacagctcg acctgt                                                         16

<210> SEQ ID NO 1223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1223
ggacatcggc acattg                                                         16

<210> SEQ ID NO 1224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1224
gcacggaaca agagct                                                         16

<210> SEQ ID NO 1225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1225
tttcacactc accccc                                                         16

<210> SEQ ID NO 1226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1226
atccagaaag ctaagc                                                         16

<210> SEQ ID NO 1227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1227
tgctagcaca gcctgg                                                         16

<210> SEQ ID NO 1228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1228
cactgcacac tgccga                                                         16
```

<210> SEQ ID NO 1229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1229
ggttccaggt ttcttc                                                     16

<210> SEQ ID NO 1230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1230
ctgtgtgagc ttggca                                                     16

<210> SEQ ID NO 1231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1231
tcagagccag cccaat                                                     16

<210> SEQ ID NO 1232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1232
gagcttcctg gtctgt                                                     16

<210> SEQ ID NO 1233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1233
gtgataacgg aaaaag                                                     16

<210> SEQ ID NO 1234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1234
agataaatgt ctgctt                                                     16

<210> SEQ ID NO 1235
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1235
ttcaagttac aaaagc                                                    16

<210> SEQ ID NO 1236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1236
gcaacttcaa ggccag                                                    16

<210> SEQ ID NO 1237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1237
agccagtctc actgcc                                                    16

<210> SEQ ID NO 1238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1238
gctgacggtg cccatg                                                    16

<210> SEQ ID NO 1239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1239
gaacgcaagg ctagca                                                    16

<210> SEQ ID NO 1240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1240
ccaaatcgga acccac                                                    16

<210> SEQ ID NO 1241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1241
acagaacttt cccttc                                                    16

```
<210> SEQ ID NO 1242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1242
taaattcgat tcccac                                                       16

<210> SEQ ID NO 1243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1243
aggcagtaat gggcaa                                                       16

<210> SEQ ID NO 1244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1244
tccaacactg aggacc                                                       16

<210> SEQ ID NO 1245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1245
aaaggcaaca cttctt                                                       16

<210> SEQ ID NO 1246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1246
caatatttac tggttg                                                       16

<210> SEQ ID NO 1247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1247
cttacaaatt acaaca                                                       16

<210> SEQ ID NO 1248
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1248
tctgactgcg agaggt                                                      16

<210> SEQ ID NO 1249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1249
tggtgaggta tccccg                                                      16

<210> SEQ ID NO 1250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1250
aagacatgca ggatct                                                      16

<210> SEQ ID NO 1251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1251
gaccaatggg tttgat                                                      16

<210> SEQ ID NO 1252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1252
gagaataccc agtccc                                                      16

<210> SEQ ID NO 1253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1253
gctcaaggga aaggcc                                                      16

<210> SEQ ID NO 1254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1254
ggacaagagt gcatca                                                      16

<210> SEQ ID NO 1255
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1255
ggccttacct gatcaa                                                      16

<210> SEQ ID NO 1256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1256
ctagaaccct tcattc                                                      16

<210> SEQ ID NO 1257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1257
tctcacctgg ttggaa                                                      16

<210> SEQ ID NO 1258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1258
gttaagagtg cagggt                                                      16

<210> SEQ ID NO 1259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1259
ccgtaggtct tggcta                                                      16

<210> SEQ ID NO 1260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1260
agctgtacct gggttc                                                      16

<210> SEQ ID NO 1261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1261
```
cctagaggaa ccacta					16

<210> SEQ ID NO 1262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1262
acatgaattt caggca					16

<210> SEQ ID NO 1263
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1263
tctcagccag gccaaa					16

<210> SEQ ID NO 1264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1264
ccctattata gcctttt					16

<210> SEQ ID NO 1265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1265
ctccaccagg ctgcct					16

<210> SEQ ID NO 1266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1266
cccgtcctcc tcgggc					16

<210> SEQ ID NO 1267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1267
ccatcagacg gccgtg					16

<210> SEQ ID NO 1268
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1268
tgtcacactt gctggc                                                   16

<210> SEQ ID NO 1269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1269
ggcatcccgg ccgctg                                                   16

<210> SEQ ID NO 1270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1270
gcaggctgcg catgct                                                   16

<210> SEQ ID NO 1271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1271
tgcaagcaga agatag                                                   16

<210> SEQ ID NO 1272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1272
caggaactga cctgac                                                   16

<210> SEQ ID NO 1273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1273
tacagctgct agttat                                                   16

<210> SEQ ID NO 1274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1274
gtgcaggcca tggtct                                                   16
```

<210> SEQ ID NO 1275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1275
atatacgaac tcaggg                                                     16

<210> SEQ ID NO 1276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1276
ggccttaaga gaacag                                                     16

<210> SEQ ID NO 1277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1277
gaccagctgg cttttc                                                     16

<210> SEQ ID NO 1278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1278
cccaaagagt attggg                                                     16

<210> SEQ ID NO 1279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1279
aactattcgg tgtatc                                                     16

<210> SEQ ID NO 1280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1280
cccaactgtg atgacc                                                     16

<210> SEQ ID NO 1281
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1281
caaagcaggt gctgca                                                        16

<210> SEQ ID NO 1282
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1282
aggtaagaca gcctcc                                                        16

<210> SEQ ID NO 1283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1283
gatgacatct ttggca                                                        16

<210> SEQ ID NO 1284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1284
gaccatacag tcctgc                                                        16

<210> SEQ ID NO 1285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1285
gagaaactgg agcagc                                                        16

<210> SEQ ID NO 1286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1286
tagcagatcg ctgacc                                                        16

<210> SEQ ID NO 1287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1287
actcaagcac cctcat                                                        16

<210> SEQ ID NO 1288
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1288
catgctggcc tcagct                                                       16

<210> SEQ ID NO 1289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1289
tggtggcagt ggacac                                                       16

<210> SEQ ID NO 1290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1290
aatgaggcag gtaata                                                       16

<210> SEQ ID NO 1291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1291
cctcagggca ccatcc                                                       16

<210> SEQ ID NO 1292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1292
gggaaaacac catctt                                                       16

<210> SEQ ID NO 1293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1293
agcatctacc tggcaa                                                       16

<210> SEQ ID NO 1294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1294
```
gtgtacccag ggcaag                                                    16

<210> SEQ ID NO 1295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1295
aagcacatgt ctagcg                                                    16

<210> SEQ ID NO 1296
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1296
agtcagggtc cagccc                                                    16

<210> SEQ ID NO 1297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1297
cattttaaag ctcagc                                                    16

<210> SEQ ID NO 1298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1298
ctcaagggcc aggcca                                                    16

<210> SEQ ID NO 1299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1299
gcacccgagc acagct                                                    16

<210> SEQ ID NO 1300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1300
gcccacggac atcggc                                                    16

<210> SEQ ID NO 1301
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1301
ctggcacgga acaaga                                                        16

<210> SEQ ID NO 1302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1302
gatgagggcc atcagc                                                        16

<210> SEQ ID NO 1303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1303
ggctagatgc catcca                                                        16

<210> SEQ ID NO 1304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1304
ccgcaggcca cctttg                                                        16

<210> SEQ ID NO 1305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1305
agacagtgca tgcacc                                                        16

<210> SEQ ID NO 1306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1306
tctggttcca ggtttc                                                        16

<210> SEQ ID NO 1307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1307
ttcctgctgt gtgagc                                                        16
```

<210> SEQ ID NO 1308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1308
aagaagaggc ttggct                                                    16

<210> SEQ ID NO 1309
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1309
caccgagctt cctggt                                                    16

<210> SEQ ID NO 1310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1310
gtgaatcagg cctggg                                                    16

<210> SEQ ID NO 1311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1311
ggacagaccc aaaaga                                                    16

<210> SEQ ID NO 1312
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1312
tgctacaaaa cccaga                                                    16

<210> SEQ ID NO 1313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1313
cccgagccag tctcac                                                    16

<210> SEQ ID NO 1314
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 1314
cctggagctg acggtg                                                     16

<210> SEQ ID NO 1315
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1315
ggaacgcaag gctagc                                                     16

<210> SEQ ID NO 1316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1316
ttccaaacca aatcgg                                                     16

<210> SEQ ID NO 1317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1317
ggacaaaact gcaagt                                                     16

<210> SEQ ID NO 1318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1318
ttctaaattc gattcc                                                     16

<210> SEQ ID NO 1319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1319
ttagaaaggc agtaat                                                     16

<210> SEQ ID NO 1320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1320
caaggacggc accaag                                                     16
```

```
<210> SEQ ID NO 1321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1321
gaagggatga ctaagt                                                 16

<210> SEQ ID NO 1322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1322
aggaaaccgt ggacct                                                 16

<210> SEQ ID NO 1323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1323
cctacttaca aattac                                                 16

<210> SEQ ID NO 1324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1324
gggcagtgcg ctctga                                                 16

<210> SEQ ID NO 1325
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1325
ttggtgaggt atcccc                                                 16

<210> SEQ ID NO 1326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1326
gaagacatgc aggatc                                                 16

<210> SEQ ID NO 1327
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1327
ggcagaccaa tgggtt                                                16

<210> SEQ ID NO 1328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1328
taagatttga agcact                                                16

<210> SEQ ID NO 1329
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1329
ctgaactgta agctca                                                16

<210> SEQ ID NO 1330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1330
ggcactagca ggagtt                                                16

<210> SEQ ID NO 1331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1331
atggattcag ctcaga                                                16

<210> SEQ ID NO 1332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1332
tccaactaga accctt                                                16

<210> SEQ ID NO 1333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1333
cactgaagag gtctca                                                16

<210> SEQ ID NO 1334
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1334
aggaacctga agatca                                                     16

<210> SEQ ID NO 1335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1335
taataatgcc cccgta                                                     16

<210> SEQ ID NO 1336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1336
agttagccca ggtgag                                                     16

<210> SEQ ID NO 1337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1337
cgccacccta gaggaa                                                     16

<210> SEQ ID NO 1338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1338
agcaattcag tggctg                                                     16

<210> SEQ ID NO 1339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1339
ctccagcgca ggtctc                                                     16

<210> SEQ ID NO 1340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1340
```
gtgtaaaata aagccc                                                          16

<210> SEQ ID NO 1341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1341
ggagatacac ctccac                                                          16

<210> SEQ ID NO 1342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1342
tcccgtcctc ctcggg                                                          16

<210> SEQ ID NO 1343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1343
ggacagtgac agctgg                                                          16

<210> SEQ ID NO 1344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1344
ctgtcacact tgctgg                                                          16

<210> SEQ ID NO 1345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1345
cacgccggca tcccgg                                                          16

<210> SEQ ID NO 1346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1346
gcgcaggctg cgcatg                                                          16

<210> SEQ ID NO 1347
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1347
atgcaagtga gtgagt                                                    16

<210> SEQ ID NO 1348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1348
ggaaagaaca gcctcc                                                    16

<210> SEQ ID NO 1349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1349
gatacagaca cccacc                                                    16

<210> SEQ ID NO 1350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1350
taccataact ccccac                                                    16

<210> SEQ ID NO 1351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1351
atcaaactag ccaacc                                                    16

<210> SEQ ID NO 1352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1352
gaagacggag taaggc                                                    16

<210> SEQ ID NO 1353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1353
ggctggacca gctggc                                                    16
```

```
<210> SEQ ID NO 1354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1354
ggcccaaaga gtattg                                                     16

<210> SEQ ID NO 1355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1355
gaaactattc ggtgta                                                     16

<210> SEQ ID NO 1356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1356
ggcattggtg gcccca                                                     16

<210> SEQ ID NO 1357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1357
tgtgacacaa agcagg                                                     16

<210> SEQ ID NO 1358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1358
cgaaggtaag ccgcct                                                     16

<210> SEQ ID NO 1359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1359
cctcattgat gacatc                                                     16

<210> SEQ ID NO 1360
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1360
tgaccataca gtcctg                                                       16

<210> SEQ ID NO 1361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1361
gctcgccccg ccgctt                                                       16

<210> SEQ ID NO 1362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1362
ggctgagtcc agagta                                                       16

<210> SEQ ID NO 1363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1363
gaaatgggaa tctgct                                                       16

<210> SEQ ID NO 1364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1364
ccatgctggc ctcagc                                                       16

<210> SEQ ID NO 1365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1365
cagctataga gcggca                                                       16

<210> SEQ ID NO 1366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1366
gaacagctca gcctca                                                       16

<210> SEQ ID NO 1367
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1367
agccttagtt tctcag                                                         16

<210> SEQ ID NO 1368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1368
tcccagtggg agctgc                                                         16

<210> SEQ ID NO 1369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1369
ccacagcatc tacctg                                                         16

<210> SEQ ID NO 1370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1370
ccaggaagag cacctg                                                         16

<210> SEQ ID NO 1371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1371
agaaagcaca tgtcta                                                         16

<210> SEQ ID NO 1372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1372
agccagtcag ggtcca                                                         16

<210> SEQ ID NO 1373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1373
```

```
aaccatttta aagctc                                                    16

<210> SEQ ID NO 1374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1374
cactcaaggg ccaggc                                                    16

<210> SEQ ID NO 1375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1375
agcacccgag cacagc                                                    16

<210> SEQ ID NO 1376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1376
agtcattctg cccacg                                                    16

<210> SEQ ID NO 1377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1377
cctggcacgg aacaag                                                    16

<210> SEQ ID NO 1378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1378
gagatgaggg ccatca                                                    16

<210> SEQ ID NO 1379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1379
gcgcacctgt ctccag                                                    16

<210> SEQ ID NO 1380
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 1380
tcctaggtga tggctc                                                      16

<210> SEQ ID NO 1381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1381
tgagacagtg catgca                                                      16

<210> SEQ ID NO 1382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1382
ctctggttcc aggttt                                                      16

<210> SEQ ID NO 1383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1383
gttcctgctg tgtgag                                                      16

<210> SEQ ID NO 1384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1384
gtaagaagag gcttgg                                                      16

<210> SEQ ID NO 1385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1385
tcaccgagct tcctgg                                                      16

<210> SEQ ID NO 1386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1386
ggccagtgaa tcaggc                                                      16
```

```
<210> SEQ ID NO 1387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1387
agagaggaca gaccca                                                     16

<210> SEQ ID NO 1388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1388
aaatgctaca aaaccc                                                     16

<210> SEQ ID NO 1389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1389
ggcaacttca aggcca                                                     16

<210> SEQ ID NO 1390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1390
cgctgctgca acgacg                                                     16

<210> SEQ ID NO 1391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1391
accaggaccg cctgga                                                     16

<210> SEQ ID NO 1392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1392
cggaacgcaa ggctag                                                     16

<210> SEQ ID NO 1393
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 1393
gtcataaaga aattgc                                                   16

<210> SEQ ID NO 1394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1394
tggcagaatt ttcccc                                                   16

<210> SEQ ID NO 1395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1395
tttcattcta aattcg                                                   16

<210> SEQ ID NO 1396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1396
ctttacccaa agcctt                                                   16

<210> SEQ ID NO 1397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1397
catagcggga gaactt                                                   16

<210> SEQ ID NO 1398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1398
gcagaaggga tgacta                                                   16

<210> SEQ ID NO 1399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1399
agccaggaaa ccgtgg                                                   16

```
<210> SEQ ID NO 1400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1400
ccctacttac aaatta                                                    16

<210> SEQ ID NO 1401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1401
aggcggcggg cagtgc                                                    16

<210> SEQ ID NO 1402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1402
cttggtgagg tatccc                                                    16

<210> SEQ ID NO 1403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1403
ggaagacatg caggat                                                    16

<210> SEQ ID NO 1404
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1404
aggcagacca atgggt                                                    16

<210> SEQ ID NO 1405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1405
ctagaaggtg gtgcag                                                    16

<210> SEQ ID NO 1406
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1406
ccatagtcaa ctgtac                                                       16

<210> SEQ ID NO 1407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1407
agccaatggg aggcac                                                       16

<210> SEQ ID NO 1408
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1408
gggcaacttc aaggcc                                                       16

<210> SEQ ID NO 1409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1409
gggcagagca aatgga                                                       16

<210> SEQ ID NO 1410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1410
gttcacccca agctct                                                       16

<210> SEQ ID NO 1411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1411
ctccactgaa gaggtc                                                       16

<210> SEQ ID NO 1412
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1412
gatttaaccc tccaaa                                                       16

<210> SEQ ID NO 1413
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1413
gttaataatg ccccg                                                      16

<210> SEQ ID NO 1414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1414
gctgagttag cccagg                                                     16

<210> SEQ ID NO 1415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1415
aaacagtgct cgccac                                                     16

<210> SEQ ID NO 1416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1416
tacagagcaa ttcagt                                                     16

<210> SEQ ID NO 1417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1417
tgccaggcag gtccag                                                     16

<210> SEQ ID NO 1418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1418
caatatctaa caataa                                                     16

<210> SEQ ID NO 1419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1419
```
gtctaggaga tacacc 16

<210> SEQ ID NO 1420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1420
gtcccgtcct cctcgg 16

<210> SEQ ID NO 1421
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1421
aatcagcagg tggctg 16

<210> SEQ ID NO 1422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1422
actgtcacac ttgctg 16

<210> SEQ ID NO 1423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1423
gccacgccgg catccc 16

<210> SEQ ID NO 1424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1424
agcacgcgca ggctgc 16

<210> SEQ ID NO 1425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1425
ccacatctgc ctggcc 16

<210> SEQ ID NO 1426
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1426
tgccaggtca tgcaat                                                        16

<210> SEQ ID NO 1427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1427
gggatacaga caccca                                                        16

<210> SEQ ID NO 1428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1428
ccataccata actccc                                                        16

<210> SEQ ID NO 1429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1429
caattacacc agcaat                                                        16

<210> SEQ ID NO 1430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1430
ctgcgaaaat attttt                                                        16

<210> SEQ ID NO 1431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1431
ccacaggctg gaccag                                                        16

<210> SEQ ID NO 1432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1432
cctcaaccgc tcccat                                                        16
```

<210> SEQ ID NO 1433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1433
gagataggaa actatt                                                    16

<210> SEQ ID NO 1434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1434
ggtcaccggc tggtct                                                    16

<210> SEQ ID NO 1435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1435
tcccactctg tgacac                                                    16

<210> SEQ ID NO 1436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1436
acagacacta agctct                                                    16

<210> SEQ ID NO 1437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1437
ggcctcattg atgaca                                                    16

<210> SEQ ID NO 1438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1438
ctgaccatac agtcct                                                    16

<210> SEQ ID NO 1439
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1439
ctccatgcgc tcgccc                                                        16

<210> SEQ ID NO 1440
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1440
ctagagatgg ctgagt                                                        16

<210> SEQ ID NO 1441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1441
acggaaatgg gaatct                                                        16

<210> SEQ ID NO 1442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1442
gtccccatgc tggcct                                                        16

<210> SEQ ID NO 1443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1443
atacagagat gttaag                                                        16

<210> SEQ ID NO 1444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1444
tcttattcca ggctgg                                                        16

<210> SEQ ID NO 1445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1445
agctgaccag ctgtgt                                                        16

<210> SEQ ID NO 1446
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1446
tgccaaggtc ctccac                                                    16

<210> SEQ ID NO 1447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1447
caaaaacaga cccagc                                                    16

<210> SEQ ID NO 1448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1448
aaatagatgc tccagg                                                    16

<210> SEQ ID NO 1449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1449
cgaggaaaag aaagca                                                    16

<210> SEQ ID NO 1450
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1450
ctgcagccag tcaggg                                                    16

<210> SEQ ID NO 1451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1451
tcggaaccat tttaaa                                                    16

<210> SEQ ID NO 1452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1452
```
ccccactcaa gggcca 16

<210> SEQ ID NO 1453
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1453
cagcacccga gcacag 16

<210> SEQ ID NO 1454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1454
aaaagtcatt ctgccc 16

<210> SEQ ID NO 1455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1455
gcctggcacg gaacaa 16

<210> SEQ ID NO 1456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1456
ctggagatga gggcca 16

<210> SEQ ID NO 1457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1457
gcacagcctg tgacca 16

<210> SEQ ID NO 1458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1458
gccgagtcag tcctag 16

<210> SEQ ID NO 1459
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1459
gctgagacag tgcatg                                              16

<210> SEQ ID NO 1460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1460
cctctggttc caggtt                                              16

<210> SEQ ID NO 1461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1461
agttcctgct gtgtga                                              16

<210> SEQ ID NO 1462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1462
aagtaagaag aggctt                                              16

<210> SEQ ID NO 1463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1463
ctcaccgagc ttcctg                                              16

<210> SEQ ID NO 1464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1464
cgccaggcca gtgaat                                              16

<210> SEQ ID NO 1465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1465
acagagagga cagacc                                              16
```

<210> SEQ ID NO 1466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1466
agtcaccata ttaata                                                   16

<210> SEQ ID NO 1467
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1467
tgcaatgcca gccacg                                                   16

<210> SEQ ID NO 1468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1468
agccgctgct gcaacg                                                   16

<210> SEQ ID NO 1469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1469
gccaccagga ccgcct                                                   16

<210> SEQ ID NO 1470
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1470
cctcggaacg caaggc                                                   16

<210> SEQ ID NO 1471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1471
agcatgagtt ctgtgt                                                   16

<210> SEQ ID NO 1472
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1472
cagcacactc agacag                                                         16

<210> SEQ ID NO 1473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1473
aaaaggattg gtctaa                                                         16

<210> SEQ ID NO 1474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1474
ccctttaccc aaagcc                                                         16

<210> SEQ ID NO 1475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1475
aatcagcctt caaggg                                                         16

<210> SEQ ID NO 1476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1476
ggcagaaggg atgact                                                         16

<210> SEQ ID NO 1477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1477
tcgacaacag gttttc                                                         16

<210> SEQ ID NO 1478
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1478
tgacatggaa gaaacc                                                         16

```
<210> SEQ ID NO 1479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1479
gcaggcggcg ggcagt                                                    16

<210> SEQ ID NO 1480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1480
tcttggtgag gtatcc                                                    16

<210> SEQ ID NO 1481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1481
tggaagacat gcagga                                                    16

<210> SEQ ID NO 1482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1482
tgcattggca caagaa                                                    16

<210> SEQ ID NO 1483
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1483
agttagaggc caggaa                                                    16

<210> SEQ ID NO 1484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1484
tcccatagtc aactgt                                                    16

<210> SEQ ID NO 1485
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1485
ttgcaaagct tccagt                                                    16

<210> SEQ ID NO 1486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1486
atgtagtcga catggg                                                    16

<210> SEQ ID NO 1487
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1487
cgagaagtgg aaacca                                                    16

<210> SEQ ID NO 1488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1488
gtgaaagctg agttca                                                    16

<210> SEQ ID NO 1489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1489
gggtggtaat ttgtca                                                    16

<210> SEQ ID NO 1490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1490
aataactgat ttaacc                                                    16

<210> SEQ ID NO 1491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1491
gttcattcca ctgctt                                                    16

<210> SEQ ID NO 1492
<211> LENGTH: 16
```

<212> TYPE: DNA
<213> ORGANISM: Artificial sequence
<220> FEATURE:
<223> OTHER INFORMATION: Synthetic oligonucleotide

<400> SEQUENCE: 1492
caacgcacat cgagca                                                    16

<210> SEQ ID NO 1493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1493
accaaacagt gctcgc                                                    16

<210> SEQ ID NO 1494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1494
aataaggtct ggctca                                                    16

<210> SEQ ID NO 1495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1495
acagatgcca ggcagg                                                    16

<210> SEQ ID NO 1496
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1496
tcaatatcta acaata                                                    16

<210> SEQ ID NO 1497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1497
ctgtatgctg gtgtct                                                    16

<210> SEQ ID NO 1498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1498

```
ggtcccgtcc tcctcg                                                         16

<210> SEQ ID NO 1499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1499
catgagaaag accccc                                                         16

<210> SEQ ID NO 1500
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1500
tgactgtcac acttgc                                                         16

<210> SEQ ID NO 1501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1501
ggccacgccg gcatcc                                                         16

<210> SEQ ID NO 1502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1502
gttgagcacg cgcagg                                                         16

<210> SEQ ID NO 1503
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1503
ctccaccaca tctgcc                                                         16

<210> SEQ ID NO 1504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1504
cgtgccaggt catgca                                                         16

<210> SEQ ID NO 1505
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 1505
tgggatacag acaccc                                                       16

<210> SEQ ID NO 1506
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1506
taaaagactc catgcc                                                       16

<210> SEQ ID NO 1507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1507
gcaattacac cagcaa                                                       16

<210> SEQ ID NO 1508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1508
gcacagagtg atggtt                                                       16

<210> SEQ ID NO 1509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1509
ccccacaggc tggacc                                                       16

<210> SEQ ID NO 1510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1510
ctgcaccggg catgcg                                                       16

<210> SEQ ID NO 1511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1511
ccctaccata gccagg                                                       16
```

<210> SEQ ID NO 1512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1512
ccccagggtc accggc                                                  16

<210> SEQ ID NO 1513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1513
gcacacagac actaag                                                  16

<210> SEQ ID NO 1514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1514
aaccaggcct cattga                                                  16

<210> SEQ ID NO 1515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1515
gctgaccata cagtcc                                                  16

<210> SEQ ID NO 1516
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1516
ctatcctgta gcatca                                                  16

<210> SEQ ID NO 1517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1517
gacggaaatg ggaatc                                                  16

<210> SEQ ID NO 1518
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1518
ggcagaccag cttgcc                                                         16

<210> SEQ ID NO 1519
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1519
ggtccccatg ctggcc                                                         16

<210> SEQ ID NO 1520
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1520
tagcactcat catttc                                                         16

<210> SEQ ID NO 1521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1521
gacgagaatc aactct                                                         16

<210> SEQ ID NO 1522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1522
caccaggact cctgtg                                                         16

<210> SEQ ID NO 1523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1523
ggcttgtggg tgccaa                                                         16

<210> SEQ ID NO 1524
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1524
ctccaagtgg agtggg                                                         16

<210> SEQ ID NO 1525
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1525
actaaaatag atgctc                                                     16

<210> SEQ ID NO 1526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1526
tgccagagcc cgagga                                                     16

<210> SEQ ID NO 1527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1527
gggcactgca gccagt                                                     16

<210> SEQ ID NO 1528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1528
gacaagtcgg aaccat                                                     16

<210> SEQ ID NO 1529
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1529
ggcaaggagg ctgccc                                                     16

<210> SEQ ID NO 1530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1530
gcagcacccg agcaca                                                     16

<210> SEQ ID NO 1531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1531
```
taaaagtcat tctgcc                                                  16

<210> SEQ ID NO 1532
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1532
tgcctggcac ggaaca                                                  16

<210> SEQ ID NO 1533
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1533
agttagctgg agatga                                                  16

<210> SEQ ID NO 1534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1534
accaaggcac agcctg                                                  16

<210> SEQ ID NO 1535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1535
tgccgagtca gtccta                                                  16

<210> SEQ ID NO 1536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1536
gtggagcggg ttggct                                                  16

<210> SEQ ID NO 1537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1537
ccctctggtt ccaggt                                                  16

<210> SEQ ID NO 1538
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1538
tcagttcctg ctgtgt                                              16

<210> SEQ ID NO 1539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1539
gtgaagtaag aagagg                                              16

<210> SEQ ID NO 1540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1540
actcaccgag cttcct                                              16

<210> SEQ ID NO 1541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1541
ttagaagcat ctccgc                                              16

<210> SEQ ID NO 1542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1542
ggcaacagag aggaca                                              16

<210> SEQ ID NO 1543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1543
taaaaagtca ccatat                                              16

<210> SEQ ID NO 1544
<211> LENGTH: 27001
<212> TYPE: DNA
<213> ORGANISM: Macaca fascicularis

<400> SEQUENCE: 1544
cattgcaaat acaattccag ttacaggcaa caggaaggaa aaccacctct gtcagcaaac    60
aatgagctcc cactctgtgc tgcgatggtg gctcaatgcg gatagctctg accttacctc   120
```

```
atggagtcac tgtcaaccca ctggttgcac agtctttgtg ccctggctct ctggagtgag    180
gtctttgcaa acaaagtggg aaatgcagca actttggact ccagcaccta gattccgagc    240
aggtcatttc actcagaata tgctgtgcat ctgcaatgac ggatcataaa gccgcctttg    300
tttcttccca gtattgacag cccttccaga aagagcaagc ctcatggcat gccacatgta    360
caatctgagg ccaggagctc tctttcccct tttcatcctc ctgcctagta cacaataggt    420
gtttactgga tgcttgtcca gttgagttct tgaacatggt gtgtaaaagg aatctttgca    480
aattgaatct tctggaacgc tgagcttgtg cctaccatag aattctgaac gtacctatat    540
gacatctttg caaacttaaa acctgaatct ttgcagtata atcccttga aacgcatgga    600 ggctgggcat caaaagcaag cagtatcttc aaggaacagc tagtcggtaa ggtcagtgtg    660
cagggtgcat aaagagcaga ggccggcggg ggtccaagat aagtttagaa ggttgccagg    720
ttaaggtcgg tggaaagaat tcggtgggca gggaggagtc catagtagga ttgattcaga    780
agtctcactg gtcagcaggt gacaaggtgg acccaggaaa cactgaaaag gtgggctggg    840
cagaactcgg agtctggcat cccacgcagg gtgagaggcg ggagaggagg tgcctctaga    900
gcgccgaccc gccttccagc ccagttagaa tttgggagtt ttttcttccc tctgcacgta    960
atctgacgct gtttggggag ggcgaggccg aaacctgatc ctccagtccg ggggttccgt   1020
taatgtttaa tcagatagga tcgtccgatg gggctctggt ggcgtgatct gcggccccca   1080
ggcgtcaagc acccacaccc tagaaggttt ccgcagcggc gtcgaggcgc tcgtggttgc   1140
aggagggcgc cgccgctcag ttcagggtcc gagcctggag gagtgagcca ggcagtgaga   1200
ctgtctcagg cgggccggga cgtgtcgttg cagcggcggc tcccagctcc cagccaggat   1260
tccgcgcgcc ccttcgcgcg ccctgagcct gaactccagc tcctgcacag tcctccccac   1320
cgtaaggctc aaggcgccgc ccgcgtggac cgtgcacggc tctaggtct cctcatcagg   1380 acggcaacct ctcccctggc cctgatgggt accgtcagct ccaggcggtc ctggtggcct   1440
ctgccgctgc cactgctgct gctcctgctc ctgggtcccg ctggcgcccg tgcgcaggag   1500
gacgaggacg gcgactacga ggagctggtg ctagccttgc gttccgagga ggacggcctg   1560
gccgacgcac ccgagcacgg agccacagcc accttccacc gctgcgccaa ggtgcgggcg   1620
gaggggtggc aggcctgggg gaacccgcag ccgggacggt gcgatgctgt ttcctctcgg   1680
gtctcagttt cccccattt aagagaggaa gtggggtgca ggtctccgag ggctcttcgc   1740
ttggcacgat cttggggact gcaggcaagg cggcgtggga ggacgggtcg tggggagcgc   1800
ggtggagagc ggggacggcc ggcctttcgg ggacttgcgg gggcgtgcgg ctgcgctatt   1860
cagtgggaag gctcgcgggg ttgggagact gcgaggctga gggagggcgg gcagagcact   1920
gccagggtct cctgcccaga tttcagactt tccgcctcgc cgcggcacag gtgggtgaag   1980
aagtgaatgc ctggaaagca ctgggaacgc accagacaca gaggaagtgg gcttgccatt   2040
atagtgggtt ccgattcggt ttgggaaata tgggcagcgg aggatggagg gcctggagag   2100
aaggccctac ccgagacagg agcggggtgg gaaggactgc agatgctggg agcgcgaggc   2160 aatttctta cgacacagaa cttatgctgt agtattccat ctgtttcaat tgaagaaaag   2220
aaccagctga aggggcaggg gagaaggggc ggagttattc tcgaggccca ttggtgtcct   2280
ttaggactca ggcagggaag ggcccttggt gctctggagc cggaggtggc gcgcctggta   2340
ctgggacccc gcagttgagc ccggcgcctc agcccacctg gctgtctgcc gaccgaccga   2400
gggtgaggcg agtttgctca acgactctgc cagcatctgg ccctcaggct gtgggaagct   2460
```

```
tcttcccggg gcgggtcac tagtttttc taagtattat cagcccagga cttggctgag      2520
gttctgtgtc cccagcttg gagtcagatc tggggttgaa tgatggcttc ctctcactag      2580
ctgtggtgct tgacaagcca cttatccttg agcctccatt gcctagtctt taaaaaggaa      2640
gtgacaatcc tccctaaggg ctcagtggca gcagatgggg agatgaaggg aaagttctgt      2700
tgaccatgag tgacctcact catgcaagcc caggaggga tcacttgcag ttttgcccct      2760
gtctgcagcg tgacctgttg gtgacattgt ctttgctcca aactacagct cctggggcag      2820
aggggaaaat tctgccactc acagctgcct gccccatctg agtgttctgg gtggcaggat      2880
ggcaggtcct tactcagctc agtatagtcc tcttccttgt tccctgagcc tttgactttc      2940
tagagggatg ttgtggggtt gtggccagga taagaaaagg cacttcaagt taccactgct      3000
ccaaaacgac tgttctggaa atagtgagta ccccatcctg agaggtgagt aagcagaggc      3060
tgtatgacca cctgaaccaa gcccttgagg atgtttcttc tctggtggaa atttggaaca      3120
ggagcctcct cacgtttatt tattcattca ttcaatggat attctgtggg agtcgaattt      3180
agaatgaaaa tattttttgg caagcagaaa agaattttta gaccaatcct tttgttttag      3240
tcatgagaaa ctgaggctca gagagaggag gtcaccccag gtgcattaga actgggtttc      3300
cagaactcac attccactgc acagagtact ctcccaattc attcgatttt tatttagcgg      3360
aaggcatttt tagatgaatc tttgaagcat tagtaggagt tcagcgatga cgatgtcagg      3420
agaattttat tctaggatta ggaggtacca tgaacaaagg cacagagctg gaaaaccag       3480
aggtggagga taaggagcac atgtccacag ttcttttttct ttttttgaga tggagttttg      3540
ctcttgttgc ccaggctggg gtgcaatggt gcagtctcag ctcactgcaa cctccacctc      3600
ccaggttcaa gtgattctcc tgcctcagcc tcccaagaag ctgggattac aggcgcctgc      3660
caccacaccc ggctaatttt tgtatttta gtagagacgg ggtttcacca tgctggtcag      3720
gctggtcttg aactcctgac ctcctcagat ccactgattt gtccgccttg gtctcccaaa      3780
gtgctggaat tacagttgtg agccactgcg cccaggctcc acagttcttt atccaccttc      3840
tgaaatgtaa aatgttctga aaaccaaaag gttttctgt gatttatttg atggtagcat      3900
ctgacgtgaa ctgacatgag attattttta atctagttgt gtgaatatgt gtattcatgt      3960
attttgctgc atagattaca catgcagctc cagattcctc caagcaggct ctctgattgc      4020
ccactactgt ctttctaaaa tccaaacaag ttctgaggtt caaaaccgat ttggccctaa      4080
ggctttgggt aaaggggtg aactctgttc tactctgact ggagtccaag atgcgtatat      4140
acagagatgt gggtggtgag gctgcaaagg taggttgagg tagggccaa ggaggagcat      4200
ggagtttgga cttgatccat gaggctgtgg ggagccagtg aaggttcttg agcaggtgtg      4260
tctgcctgag agcagctgga gcagacgaga gctaaaacca aacaaatcac ctgcagatcg      4320
tggctgctat agtttgtccc ctccaaatct catgtggaaa tgtggtcccc ggtgttggaa      4380
gtgggggccta atgggaggtg tttgggtcgt ggggggaggaa ccccccatgaa aggcttggtg      4440
ccatccttgt gataatgact agattctccc tctatgattt cccttgaagg ctggttatta      4500
aaaagagctt ggtacctccc tctcttctct cttgcttctt ctcttgccat gtgatagatc      4560
tctgcacatg taggctcccc ttcaccttct gccatcaggg gaagcagctt aaggccctca      4620
ccagaagcag atgctggtgc catgcttctt ggagagcttg cagagccatg agctgaataa      4680
atccctttc cttataaatt acccaccttc aggtattcct ttatatagca acacaaaagg      4740
actaagacag tggccctgac tcttctctct ctttaagaag tgttgtcttt gctcacttag      4800
tcatcccttc cgcctgcatt tgtagagcat ctggatggga gatttctaca accgtcactc      4860
```

```
ttgaccttcc cagcaggcct gtgtcatacg tactatggtc tccacaatac agcggagata      4920
tctgaggccc agagaggttg agtgacttgc tcatggccac acaaccagta aatattagag      4980
ctggaattca ggtccacggt ttcctggctc caaagccatg agttttcccc tcagtttatt      5040
ctgattgggg caggggggag gaggtggcct ttgggcaggg ccgccacggg taaccaggcc      5100
catagagagc tggctgcagg tacagaggaa aacctcttgt cgagtgcggc ccatggttcc      5160 cattttgcc tgactggcac atttgaaagt gttatataac tatgtgaata ataatagttg       5220
gcctatatgc gttttttaat ttgcttttgg gtccgcattt ggtaacttct ttatcactta      5280
ctacactctg ttgtgcctct tttgttgtaa ttctaatttg taagtagggg tgagataaag      5340
tacacatagg gtttgctggg tttcttccac gtcatcatgt tcctccttgc acggggccag      5400
gatccgtgga ggctgcccgg cacctacgtg gtggtgctga aggaggagac ccaccgctcg      5460
cagtcagagc gcactgcccg ccgcctgcag gcccaagctg cccgccgggg atacctcacc      5520
aagatcctgc atgtcttcca tcaccttctt cctggcttcc tggtgaagat gagtggcgac      5580
ctgctggagc tggtgagcca ccctttctgg gaatggcact tcctgatagg gctgggccac      5640
tgcatataca ctgggactg tgctcagtag gcctattgct gaaaatcaga aggggacagc       5700
aagtatgtat tgagcactta ttgggtacca agcacagtaa ccactggctt tctgtatgga      5760
attcccttta agcctggcca tgccccagtg gtatgtccat cttcatttga aagttcagag      5820
gggaccacac agacagctag gggtaggacc tggatcaaac tcagtggtct gcctgccagc      5880
cattcttatg ccaatgcatc tgctaccat ggaaaccttt agggacaagg ccctgggatg       5940
ttcaatggag cctgagtcat tttataaaaa agcatgactc aagggtctac aatttctttg      6000
aggctgctgc tatcagagta aagacccac tttaggacag ggtggccctc ctccctcctg       6060
gatgtcacat ctttggtgga gaggcagaaa ggggactggg tattctcctc accctggccc      6120
taatgcttca aatcttaaaa aaaaaccttc ttgttttgc ttctgcccca ccttctagcc       6180
cacctctttt cctggcctgt cacttgatga gagcgtgtgt cattttcaca ctgattctcc      6240
acatggcagg gggtgctttt cagcctcctg cagacagtga ggcccagggt cttgcccaag      6300
gtcacacagc atgtaatggg cagggtcaga gtctggactt gggtctccta gctgcactgt      6360
actgctgctc cacgggttaa tcagctcagc atcccgtggc tgaacagcga cctcatacca      6420
aggcctgtgg gaccatgaca gggattgata gggtccctgc cttaggaacc cgtagtctaa      6480
gtagaggaga ctgacaagtc aatgccttcc atcagtctgc tcaacacaca tttaccaagc      6540
gcctactgtg tgctgcagag gcgaagatga cacagcccag gcctttccct cgagcttaca      6600
gttcagaagg agagactgat cagtgaccgc cagccagtac agctgactat gggacaatgt      6660
gctcagcagt ggggcgagac gaagaaggta cccgtatagc accagatgac aggcacaagc      6720
cccacaggcc agggcagctg ctcagaggag agtaggccaa gcagaagcca gcggaaagc      6780 tgcaggcatt tgccattgag acctgggctt caaactgggc atcctaccag cctgggtttg      6840
agtcccaccc agccccttat tagttgttta accctgggca aatgccttca cctctctgag      6900
cctcattccc ctatctgtaa accagttata ataatgggaa cattcattta aggactaaat     6960
gaggttgtga agcattcagc agatgctagg tatagaaact cgccaaagtg ggggcaggtt      7020
aagaagcctc tggggatacc aaggcatcca gggactagtt gtggcaggaa gctgttacca      7080
cttaggtctg aagggtaagg agagggaata gttttccctc tgcccaattg gagctggtgg      7140
catggaggag aggctgcccg tggggagtca cctgagagtt caccgctgcc atgcgcaggg      7200
```

```
agtcaggagg tagggaggga gtggggcaga tgcacagttt tttgttttg tttttgtttt      7260
tgagattctg ttgcccaggc tggagtgcag tggtgccatg tcagctcact gcaacctctg      7320
cctcccgggt tcaagcaatt ctcatgcctc agcctcctga gtagctggga ctacaggtgt      7380
gtgccaccat gcccagctaa ttttgtatt tttaatagag atggagtttc accatgttgg       7440
ccaggctggt ctcgaactct tgacctcagg tgatccccca cctcggcctc ccaaagtgct      7500
gggattacag gcatgagcca ccgcgcccag ctgcagatgc actcttgtcc ctctaactcc      7560
tgctggtgcc tcccattggc tgagcctaaa tggaggcttt gcaagggagc tggtgctgca      7620
gtttgcactg agcaggctgg agaaggctgg ggaatagact gggggacaaa ccgaattgcc      7680
agtgctgtta tgtcatgatt taggcatagt gtccagggcc tgagcttcac tccgtgtcca      7740
tcctgcccag agccttagca cagcctggct cccagacaag atgtcaagtc cagaatcctt      7800
cctaaaagga atcctttgtg ctaggccttg ttgcagggat atgggagtgc taggctccca      7860
gcctgatcaa tgagtgagaa aactcaggct cctagtctgt cctccggggc accaggaggg      7920
agtctgccgg gacaaggtgg gaggctgctg ggctgggata tggggacagg tgtgatcagg      7980
tgaggccagg ctgtggctgt gtttgctgct gtccagatgg cttaagcaga atcccccaac      8040
ctctctggct tctgcaggcc ctgaagttgc cccatgtcga ctacatcgag gaggactcct      8100
ctgtcttcgc ccagagcatc ccatggaacc tggagcgaat tactcctgca cggtaccggg      8160
cggatgaata ccagccccc agtaagaccc cccatctgtg cgctgcccct tcacacctga     8220
gctgaatcca tttgctctgc tctggccttg cctccctgcc agtggtttcc acttcttggg      8280
gggctttggg actcagcacc tccactgacc ccttttttc tgtcccatcc caacccctg      8340
cagccccac tgcctgcctt cctgtagctc cacaaatgca aaagtcttgc cttaaatgat      8400
cctcttttcc tccttgtctc ttgttttcct cttctctcca tttggaatgg cccagcaggc     8460
tgcacttacc ttagaaggag ggttcatctg atggtgactc tacctagggc ccctccccag     8520
gcctctataa ctcccagtgc cctgcagact ggaccagacc ccttaatggg acagacacaa     8580
cccggactgg gatgcccctg cctagcttcc tgttttgctg ctctccctgc tccagctct      8640
gtttggcttt ctggatctcc ctgcatggcc cactttgtgt cttccctcta ggcctttcct     8700
tccactgttc cctctgcctg gtgtggcctg actgtgggag ggagggagga ggagtagcca     8760
tggaaaacag tctgcattct agcagggcct tgcaggtggc aattccttgc aggtggcaat     8820
tcagtcaggg aagactctag atgcacctgg cctgaggaga ggatgaaggg ttctagttgg     8880
actgtgttaa gtttgaggtg cccatggtgt gaggtctgca gctcagtgca gagacaatgc     8940
aatgtggtgg gtccgtgcaa catggtgcca ggacgcagag cttggggtga actcagcttc     9000
cacccttac cggttctcgt ggggtcttgg gaagccactt cgttctatta gtcttgtctt      9060
tcttgtctgt aaaatgggca cataaccctg tccctgtcct tctcacaggt tgctgtgaga     9120
ctccagtgag ttgaagggtg tgcagatgct tttggaagtg aaaagttggg ggcttctgtg     9180
tgactttgca tactgtatga ccttgcatat gtctgagttc ctgccattgc aacagatcag     9240
agctggtggg caggaggtgg agatagggtt tgtgcggggg acatcctctg gcaagggtgg     9300
cagcagcaga agcgagggc ctggttggtc atgtgtgctg acctgacctg ggcagcctgt      9360
ggccagggag aggacagctc ctctgtagga ggagcctgtt cctttccaac caggtgggac     9420
ctcttctgtg gattcctgga gcccctgca ctccacattg gcgcctcagg gacctcccgg      9480
agcaggctaa tatcagagac tgagagggac actggcagag ggtcacagag gccccagtcc     9540
aggcagaaga ccaagaagat cttgcccctt aagttagttt cctagcactg ctgtgacaaa     9600
```

-continued

```
ctaccacccc cttgttggaa caaattgatt ctctgcagta ctggaggcca gaagcctgaa    9660
tcagtgttgg caggaccacg ttctccccgg gagctccagg gagaagcttc tcttgtctcc    9720
tctgtgtccc aacagcggca gcacacccat cccagcctct gtcttcacac agccttctct    9780
gtgtctctct cctcttcatt gtctcataag gacactcgtt gttggatttg gggccaactg    9840
gatcatccag gatgatctca tgtggagaac cgtaaccaca tctgcaagga cccttttccc    9900
aaataaggtc acagccacag gcggtgcggg ttaagatgtg agtgtaccct ttggcagcca    9960
ccattccctc ctctcccttg ggccagaagc agacgtgggg ccctttcctc cccataggat   10020
gcccatggat tgtcccctc cccacttccc ccgagtgtct gtgggaagtg gcaggaatgg   10080
caggcagggg tgtggaaccc cttctggagt cacatcaagg gcttggctgg aggatgtcct   10140
cctggagctg ttgcgctggc atggggcagg ctggctgggc ccagcagcag cctcttcatt   10200
catgggagg ccacaggcat gggccctgga gctggctgcc gccctcaaac ccagactctg   10260
cactcttaac tgtgtgaccc tgcacacatc actcaccctc tctgatcctc aggttcctag   10320
gttcctctgc aaaagcgagg gaatagtaag cctcgctctg gggggctgtt aggagggtta   10380
aatgagttat tgctatagca tgcatttctc tgtcaggtat tgagtgaggt gctgtgattt   10440
tagccctgca ttttctttt cttaccattc aacaataacg tcttgagcac ccactgtgtg   10500
ccaggcaccg tattaggtgc tggggataca aaggtgaatg aaatgacgt ggtctctttc   10560
cccaacagtg tatccagaag attaatccat tccttaaaca aatgctatcg acacaaatta   10620
gttccggata ggctgagagc tctgaaggag tgcaggcaac tgtgagcctg tgtatccggc   10680
agaaggatca ggaaaggctt cctggaggaa gcgctgttcc agccaagacc cacgggggca   10740
ttattaacca ggccaagggg acagtgtcca agcagaggaa tgaacatgga ctgaagctgt   10800
gaggcaggag ggagtgtagc ctgtacagaa gggactgagg ctggtgagac cagcagggcc   10860
tgggtgacct ccaggcaga tgtgaaagga agaactcggc cacagtctga gcttctcagg   10920
cgcatggcag ggctgcctgg tgagagctaa tgagctccct gctctggagg tatgcacgca   10980
ggactgggct cccaccctgcc agaggccgca gagctttctg taccaaccta gaggctggaa   11040
gaggccactc caaggcctct ttgcccctga gagtggtggc tttcttgag gccaccttgc   11100
cacactgtca cacggaacta gcagcctctg cctcacccag gggtttggag gatagaggg   11160
ggcctaggaa gggccccaga ggccctgtgt cctgtccgag ctgaaaccct ttccactgga   11220
aggaagccca aggatgttcc tgtggggct ttggcttgtg ctttccctcc agctgtagag   11280
gccatggtgg ggctgtgggc cctggtggg cgctccagcc ttacagcctc tctcctggca   11340
gtgtcttacc aagagctgcc ccttcgccag gcccgcctgc cctctgctgg ccatgcttgc   11400
agcctcctga ccctgtccca gcaggagagt gcgctggtgt cagcgggcag gaactgcctg   11460
tatttagaag ttgtggggct gcgctgggc cacacccag gcccagggat gtgacctcac   11520
agtggtcaca tcatcttgca gcggacccca agtacagctc ctggagcaga tggtggtccc   11580
aagcacaggt gggaccagaa aggattgtca cctgggctaa ctcagctgcg gcctcagttc   11640
cctcctcaca cacgacgagc agcatggact ggaatcctgc ccagcaggcc tttggcttga   11700
tgtgcgttgt gtggcttatg tccaggtggg gaagcagctt ctgtgctgtc ttctagatga   11760
gcctgtatcc cctgggctgt ctgccaatgt atccagttgt accgtcagcc tggaagctct   11820
gagggagaac cttgggctgc ttcctaagca cctgtatccc ctgtagccag ctcggggcct   11880
ctgctaggag cagaccgagc atggcctatg ggcctggcac catctggcct ctgcccacct   11940
```

```
tgctggcctt gtcatgtgtc tgcccctccg acattccata gcccagttca atatctagtg    12000
gttcctctag ggtgaccagc accctttggt ctccacatgt cttcaggtcg gagctcacag    12060
cgctctcaac tacccttcc cagtgcagca ccgggcacgt ggtagatgcc tactgatgag     12120
tgaaagctcc taacacactc ggagagcaag gactctgcct catcccgcag cctgggagga    12180
caggcagact gccgaggacc tgcccagcat gctacagaag taaccgaagt gcgcatgggc    12240
actgatcagt ggagcgtcct gctgagactg gaggccatag gcagggcga atagtgtctg     12300 tgcaggctgg ggactcacag ttcggactgg gcccagccct actgccacag tgggtgggtg    12360
ggaggacgta ggactgggag ctgaccttgc ctgaaattag tgtgggatct cagagcagcc    12420
actgaattgc tctgtagtgg gctaaatagt ggcccccaca gatacacaca cccagacaga    12480
gcctgtgagc cggaccttat ttggagaaaa ggtccttgta gatgtaatta agcatctcaa    12540
gatgacatca tctggattat gcggtgggct gtaagtccgg tgatgtgtct ttatgagcga    12600
aaggcggagg gagatttgag acacacagga ggggccactt ggagacagag gcagagattg    12660
gagaaatgtg accacaagcc agggagcatc agcagctacc agaagccgga agacgtgagg    12720
cagggttctc cctggagcct tcgttgctga gtctgggaat ttgttactga agccataaga    12780
agcgacgaca ctccctgagc ctcccgtact tgctcacctg tcctgagatg agaatctcta    12840
ctccgcagca tatttggagg atcactgccg gggacacaga ggtgctgttc agatagcact    12900
tcagaagact caggagaccc tggggcagga gcaggttgat tgacagccca gagggctacc    12960
atctggttcc acctgaggcc ctgcttctcc tggctgcagg ggttccaggg ccaggccatt    13020
tccgctggcg caggactctt ctagcagcaa cctgcctaag tcttcctttg cctggctga    13080 gagtttctga gacccgcact ggagcggagg tgcttccttc cttgcttccc ttcttcctcc    13140
cccccgtctc cgcccagtgg gctggacctg ccttgcatct gtgagctctc cctactttct    13200
cctacacccc aatctttgtc ctgcacaggc aactccctca gtgagtctct tgcagctttt    13260
accccagtgc cggcttcttg gagaatccaa actgatccaa ttaggtatag ggtaggctct    13320
cggtgactgt tttctctgag gccgtgactc gtgtgaggcg gaagcagccc ctgtgagccc    13380
ttctggtagc ttgtggagtg cagaatgctt ggacctggag tcaggaggcc cagacacaca    13440
tcctgtccga gctgcagctt cctgtctcta aaatgagccg accagcgcag gcggccagac    13500
atcactgtta ttcttttgagt cttttaaatca tgttgtcttt ctcgcagact cggtgagctg    13560
tgaaaagcta taatagggc tttattttac actatgatat tatttcttga acattcatat     13620
tattgttgga tattgatatt aatatgaagg agcaggatga cttgggtcct tcctggcagt    13680
agcattgcca gctgatggcc ttggacagtt atctgccccc tctaggcctc cctttccttg    13740
tctatgaaat atagaatagg atctagcgtg cgaggatttt tttggaggtt caatgagtga    13800
atatatttaa ggtgctttca ccagtgcctg ggatgtactc cacagtttct gtgtgttaac    13860
tacaaggttg acttcatgct cattccctcc tctcccacaa atgtcacctt ggaaagaagg    13920
aggcagcctg gtggaggtgt atctcctaga caccagcata cagagtgacc accgggaaat    13980
cgagggcagg gtcatggtca ccgacttcga gagtgtgccc gaggaggacg ggacccgctt    14040
ccacagacag gtaagcacgg ccctctggtg ggagggctgc ctctgcccat atccccatcc    14100
tggaggtggg tggagactcc cgtccaagag tgttgcagct gtactgctgg gctacagtcc    14160
ccagctgtca ctgtcccctc cctgccatca gttgtgggaa gggtgttcat ccatccagcc    14220
acttgctgat ttgttatggg gtgggggggt ctttcttatg tggtccttgt gttggctgag    14280
caggccagca agtgtgacag ccatggcacc cacctggcag gggtggtcag cggccgggat    14340
```

```
gccggcgtgg ccaagggcgc cggcctgcgt agcctgcgcg tgctcaactg ccaagggaag    14400
ggcacggtca gcggcaccct cataggtgag tgatggcccc agacagcgct ggtctctctc    14460
catctggacc tggcctggga agtggcttgg gctgggccca gggagagcta gtctcctaac    14520
caagaatgct gtggcagcct ctgccgcaga gccagagaac cagagtgcca aagctggcag    14580
ggtccccagt gaccacgagt gcagatgaag aaacccaggc cccaagaggg ttacgcaggt    14640
agcccaagga gtgcagactt gaccctgggt cagtgacctt ccacaattc cacactgctc     14700 cccttttcaa acctggtgac atctttgtgt cttttgtgat gttatcttca atgtggaggg    14760
actcgaggtg atctaagcaa acttcttcta tcttctgctt gcatacttct gagaccagag    14820
gactcactta cttgcatgac tggccctgca ggtcacactg gccaggcaga tgtggtggag    14880
gaactggcag aggactttt ctagactatg actctgttta gtccatctgg cggccccct      14940 gtgaagtccc gctgagaact aggactccgg gggcctgtgg acagagaaga gggagggtgc    15000
tctcccttac tgacttcctc ctgtggccac tgagcaaggc ctctgtacaa catgccctgg    15060
ggctggcctt gccatagctg ctgaacagtt gatgaaacca gtccagagag gggaggtgac    15120
tgcccagggt cacacagctc aagctgatga tgtcactggg aaaggtgcca gctctgggca    15180
gcagcttgac ttccactgca ggccccaggc cccagggtca aacactggct ctggagccag    15240
cggaagcagc ccatgggtcc gtttgaaagg ctgaggaggc ccaggagtct tccctgtgtc    15300
tgccctgaga cttcctaca gagtacaggt tttgatgttc agttttaaag gcaagaatca     15360
ataaccttcg gccccatcag gtgacccctt gtgcctgtcc cacccctta ttgactgacc      15420 tcggctcagt caggccagtt cctgaaggtc agtgtgtgga ggggaggctg ttctttccca    15480
gaaaggcctt ccccaggcct ggtgctctgg cctctggagg acttcctgga gaagtccctt    15540 cttggcatc ccagtcagtg tatgggaagc ccttactgca tgacctggca cggggcaggg     15600
gctcaacagt cactactgcc ttccttggcg ctgccatttc ctcctctgta agcaggtgat    15660
tgtgtgtcga gtctgagcac acagataagc acacagcagg tgcttaataa ctagcagctg    15720
caggctgggt gtggtggctc acgcctgtaa tcccagcact ttgggaggcc gaggtgggca    15780
gatcacctga ggttaggagt tcgagaccag cctggccaac atggtgaaac cccatctcta    15840
ctaaaaatac aaaaattagc caggcgtggt ggtgggtgcc tgtaattcca gctacttggg    15900
ggctgaggca ggagaatcac ttgaacccag gaggtggagg ttgcagtgag ccgagattgt    15960
gccactgcaa tccaacctgg gtgacacagc aagactccat ctcaaaaata aataaataaa    16020
tacataacca gcagctgtaa atgtggctgt tgttcttcac ctccacactc agtgccactc    16080
cgctcccttc ctccgtggtg tgagggtcct cactagctgt cttctaggag gagcatggct    16140
gtgagattcc agctccatcc ttggccacag ctcctggaga catctcagag accaggatct    16200
ggaaggctcc cacaccccat ttgacagggg agaaactgtc agttccaggt ccccttgcac    16260
atcagggcca gagctgagtt aggctcccag tctccaggcc actgggccag agctcacagg    16320
ctggcaaagg gttagaactg ttactggtgg ctgggtgtgg tggctcacac gtgtaatctt    16380
agcactttgg gaggctgagg ctggcagatc acgaggtcag gagatcgaga ccatcctggt    16440 gaaacccgt ctctactaaa actacaaaaa attagccagg tgtggtggcg ggggcctgta     16500
gttccagcta ctcaggaggc tgaggcagga gaatggcgtg aacccaggag gcggagcttg    16560
cagtgagtcg agatctcgcc actgcactcc agcctgggca agagagcgag actccgtctc    16620
aaaaaaaaaa aaaaaaaaa gagctgtcac tggtgacagt agcatgaggt agatcatggt      16680
```

```
ctacaccaaa atggggatg tagtgccact gaggccagag ggaaccacac cctcaaaggt    16740
ggggagttat ggtatggggg ggtcctgggc gtggagtctt ttaattcttc agacaatcct    16800
gggagcagct gtccctgttt catagagagt ggggtcacac agctggtgag tgggcagcca    16860
agactctgtt caagtttgtg tgggttcaac acttgtggcc acggtggagg ggcatctgag    16920
ccaggcctca gagagtggca gggagaagtt gggtggggca gggcgcccTt ctcattcctc    16980
tgaggctcat cctctcggtg cctccatttc ctggaaaggg ataataaggt tattgtgagg    17040
atcccctgag ttcatatatt cagacactta gagccaggca cacagaaggg ccggggtcgg    17100
ctagtttgat tgctgaggta attgctaata tcttccagtt tctattggtc aaggttccgc    17160
agagaagcag agccagtagg atgtatatat taagagtttc aaggaattgg ctcatgtgac    17220
cctgggggct ggcaagtctg aaatccacag ggcaggccag gcaattcctg cagaatttga    17280
tgttgcagta ttaagtccta aggcaggcct ggagtagaat tccttcttcc ctgggaggcc    17340
tcagtgtgtt ctctgcaggc cttcaactga ttagatgagg cccacccacg ttacggagag    17400
taacctgcct tactcagtct cctgatttaa atgttagtca catctaaaaa gtattttcgc    17460
agcagcattt ccactggctt ctgaccaaac atcaggtcac caagttgatc cccaaaatta    17520
accatcactc tgtgcctgta agggagggc tgggaatggg gaacagttct ccccagggg    17580 tgacctaggt ttgttcctcc caggcctgga gtttattcgg aaaagccagc tggtccagcc    17640 cgtgggcca ctggttgtgc tgctgcccct ggcgggtggg tacagccggg tcttcaacgc    17700
cgcctgccag cgcctggcga gggctggggt cgtgctggtc accgctgccg gcaacttccg    17760
ggacgatgcc tgcctctact ccccagcctc ggctcccgag gtaggtgctg aagctgctgc    17820
cccaagacgg ggagcgaagg gcaggcgggc ctcgtgggct tcttgcagca cgttcctgga    17880
ggctgaaccc ttctggcttt ggaaggagtc gtcagagccc cccgccatg cgggaggctg    17940 gggaggaatg gcctcgagcc tccatcatcc cagagtctga acagcagtga ccccgccacg    18000
cccccacgta gcgcgcccca cgaagccacg ccccacacc ccgtcctggc cactctccct    18060
cttgagggtc tcctggtagc cgccccctcc ccatctccct cccaggccc tgcgtcctct    18120 gcccaatagt cttagggccc gcccaatatt cttagggccc gcccaatagt cttaggcccT    18180
ccccactatc cagatccctc cgcagctgca tgactgacca cttgagcgag gctaatgtga    18240
atgggaacag ttgagggctc agacctcacc cgagggacat ccagagagtg tgccgcaggg    18300
ccgtgcagtg tggctgccgg gacacagaca cggagcctcg gccctgagga gctgggggc    18360 agtgaccgtc cctcctgtga ccaccactcc tccagtgtca ggtcactgcg ggtatctagg    18420
ggagagaatc ttgttccact tcaagtctgg aacttcaagt ctgtgtgtgt gcgcgcgcgc    18480
gttgtgggtg gggattgcgg agcagaagca tacctgacag cggtaaccca gatcctccct    18540
ggcctcggag gcttccctgg cagcccaatt taaaggcatc aagcaaacaa agcccaacac    18600
atctctgcct tgccctctca gtctcccccc gtggcactta gagccacctg atacaccgag    18660
tagtttccta tctccctcac tagaatgtaa actccacagg ggcattggga atgctgcctg    18720
gctatggtag ggacagaggg gagcaccagg gcggggcagg ggtgccagag ttctgcctgg    18780 ggagtcgat tttccttagg aggggacatt tgaatgggac ccaaacaggt gtatagcagt    18840
tgttcagccc agctggcaag gcctcagttt gcttctgcaa cccctctctt gggctccttt    18900
ctgtgccacc tacctcctca cctttccagg tcatcacagt tggggccacc aatgcccagg    18960
accagccggt gaccctgggg actttgggga ccaactttgg ccgctgtgtg gacctctttg    19020
ccccagggga ggacatcatt ggtgcctcca gcgactgcag cacctgcttt gtgtcacgga    19080
```

```
gtgggacatc gcaggctgct gcccacgtgg ctggtaagtc accacccac tgccttggcc    19140 accgtgatgc taacagccct ttggcggtca gggtctgtgc caggacctcc agtgccaggc    19200
tctgtgcagg gggaccagag atgagacagg cctgatggtg ccttcatgga cactcagtct    19260
gatgagggag acgagtgcac agtgggaaca cgaggttagg gctgtattag agggagccca    19320
gaggaggcac ctgcccagcc cgagggtcag agaaggcttc ttggacaagg gacatttgat    19380
ctggagcttg atggatgaat aggagtccac ctggccgata agacagcaac taccaaggct    19440
tagaggtgtg acggaaggct gtcttacctc actgtgtgag ggactgcagg cggcttacct    19500
tctagaagag agcttggtgt ctctggtgtg tgcacgtgtt tttgtgtgta tgtgtgtgcg    19560
tgtgtgcact ggcaggagtc ccctgctggg gcaggagggt caggccgtca ccatctttca    19620
ccattcaccc ctgtaccagg cattgcagcc atgatgctgt ctgccgagcc ggagctcact    19680
ctggccgagt tgaggcagag actgatccac ttctctgcca aagatgtcat caatgaggcc    19740
tggttccctg aggaccagcg ggtactgacc cccaacctgg tggccgccct gccccccagc    19800
acccacaggg caggtaagca ggacggcagg gtgggcgagg ccaggctggg gcttggggagg   19860 tctgtgtgac cttgacagtc tctcccctct cccttgtctg tgtaaggagg atgcaccac    19920 cttaaatagg attaaatgag aagggggctc tgaaagggct ttgcaatatt ttcataacat    19980
gtttttatag agacagttga gtatgttctt taagccctcc tctctcctac catgaactaa    20040 agattttttgt ggaggtcccc tcactcccag cacccctcc tcatcccagg cacttttttgc   20100 aggttggcag ctgttttgca ggactgtgtg gtcagcacac tcgggtccta cacgatggc    20160 cacagccgta gcccgctgcg cccaggatga ggagctgctg agctgctcca gtttctccag    20220
gagtgggaag cggcggggcg agcgcatcga ggtggctacc cctccttcgt gtgtgtgtgt    20280
gtgtgtgtgt gtgtgtgtgt gtgtgtgtgt gtgtgtgtga gtgctgggcc ctgagggacc    20340
cgcagcaagc ccctccatcc tcgacactcc agctcttctg taagcttaca gggctggcca    20400
gagcaggagt ggggcactcc tcatctcacg ctgctggggg ccgctggaga gagccacagt    20460
gagaaggatt tcctagaggc tgcaggacag tgctggatgg attttcaatg ggtgctggat    20520
gggtgtcagc gtgagggtca gggatctgct actctggact cagccatctc taggcccttc    20580
tcactcaggt gctccatggt tctgggagct gagaaatctc aaaccagcaa aaaaggggaa    20640
ttgatgttga tgctacaggg tagtgcacag atgccatctg gtcgcagcgt tttggtgaaa    20700
gggcagtgcc cagtcaggag agtgaggagg ggcaggcatt tctggcctgg gagatggtgt    20760
cttaatgctt gtgtgggagg cagagtgggt ggggtggagc ccgctgggtc cttgctttgg    20820
cctcttggat ttccctgtat ctccatttttg aaaccactct gtgtttggaa gaacttttga    20880
gtattcagag ctgcccattg gcagaacagt ctactttggg caggagcgag ctccttgtcc    20940
ccagaaggct aggggcaggg tctgactggc ccctggtagg gacactgacg agggtgcttg    21000
agttgatcct gtctagtccc tttctctgtt ttcaaagccc attctaaagc agattcctat    21060 ttctgtctttt gactctcagg cccaaggggg caagcgggtc tgccgggccc acaacgcttt    21120
tgggggtgag ggtgtctacg ccattgccag gtgctgcctg ctaccccagg tcaactgcag    21180
cgtccacaca gctccaccag ctgggccag catgggacc cgtgtccact gccatcagca    21240
gggccacgtc ctcacaggta ggaggctggg cctgccctgg ggtgaggaga gttcccttttc   21300 tccttatgca cccactgccc tcgaggcttg gtcctcatga gtgtgatcca tgagactgga    21360
acccgacttt ccattccata ctctggttct gtcacttcca tgcccttttga ccctgggcag    21420
```

```
gtgaccttac ttctcgtctc agcttcctcc tccataagag ggaaaaaggt atcacctgcc   21480
tcattgtgtt gcgaggagat agggcactgg cctggagcat ggcaggtgct ttgcctaagg   21540
tggtgcagtt caggagaggc agctccagag agaggacccc ggctggggct gaaaggaggg   21600
cagacctcgg tttgaatttc actctgccac tcgatagctc tgtgacctga gcaagttact   21660
taacgtctct gtatgaggaa atgatgggtg ctaagcactt agcttaatgc ttggacaata   21720
tagattctag ctatcgttac tattattgtc atcacctgtt gctttaaaat ccagtctctg   21780
gtataggcaa ctattgatag ctaccctgt gtcgaaaaca tgtccaggca ggtagcagga   21840
agtcacagat ggggactctt ggggcatcaa gggctggcgc cccaaggctg agctgttctg   21900
gttgggtgga gcgtgagagg tctgggaaga cagtggagct ccagcctgga ataagaggct   21960
cagagttgat tctcgtctga gcatgtccag gggagccact gagggtttgg gaacaggaag   22020
gtgagggtga gaacctaact ctgggcacag caggctggca tgtgggatgg atgttcagga   22080
aagatgagcg tagtcaggtg gctggtgccc ttgtccaggg gagaggctcc atccggtccg   22140
gggatcctgg cttggaggga agtccgccat gctgtaatca cactccccctt tggaagtgct   22200 cagccgatga actcacaggc acatgtcagt ttgaagtcat ggaatctgac tctatgaggc   22260
acacctcaaa gagccccatt ttgcagctaa gggaactgca ggctggacat gctgagtgac   22320
tgccctgagc ccttgcatct aggacataga gaatgctagt aaccacgacc ctaccatgtt   22380
cagagcacat gccaggctcc atgctggcgc ttcacacgtg tcatcttcac agtgtccctg   22440
tgagtaggtg cggtttctct ttccatctta caaatgagta aacagagcct cagtgtagct   22500
gagtaataac tattttcggt ttcttagcca atgcgtgtgt ctgactccta agcccatgga   22560
gggcatcccc aggtggtcca gacagacccc agcttaccgt tgaacttctg cctgctggct   22620
gcatggggag tttggggaa gtttgagcat ctcaggccat agagccctg cttcactgtc   22680 tccatctctg ggtggagaga tgatgttttt cctgagaaac taaggctcag gttgaatggc   22740
tctcccatgg gcacacagct ggtcaggagt ggagttgaga acacaggagt cctgatgctc   22800
aggccagcat ctcttatctt ctttgagttg tttctgggtt tcctagctcc tgcctcacac   22860
tttaaagaga gaaggtctga tggggatggg cactggagac ggagcattcc agcatttcac   22920
tatctgagct ggccttcctc tgacccaggc tgcagctccc actgggaggt ggaggacctt   22980
ggcacccaca agccgcctgt gctgaggcca cgaggtcagc ccaaccagtg tgtgggccac   23040
agggaggcca gcatccacgc ttcctgctgc catgccccag gtctggaatg caaagtcaag   23100
gagcatggaa tcccggcccc tcaggagcag gtgaggaggc ctgtgaggac gggtgggtgg   23160
ggtgccgtgg ggtggcgtga gtctctcctg tgcagctttt ctgggtcagt ttgtgccacc   23220
accataccgc catgcatcag ggtggcggtt tgccgggtag atgctgtggg cagcttccgc   23280
cattgtgtgg acagtgtgtg tatgtatctg tgtgtggctg ggtctgtttt tgcttttgtc   23340
cagatcagta aggtttgttg cctgagtacc ccactccact tggtgtagaa tgtgcataaa   23400
tttgccataa agaaatacaa tatgcatgca tttattgatt gatctatttt tttctaagat   23460
ggggtcttgc tatgttgtcc aggctggtct caaattcctg ggctcaagcg atcctctggc   23520
ctcagcctcc ccaaatgttg ggattacagg catgagccac tgcacctggc ctctctgatc   23580
tatttaacaa acctgctggg aggttctcag ggtcaggagc agcactgggc tgtgaggaca   23640
cagagctcac tcagccatga cccagagggg gtgcctgagc tgcatgccga aggttgttag   23700
catgaccagc aaggcaagaa aaggccctgc ggagattagc gaggcacgtg ccaagccctg   23760
gaatgtgaga gccaggcctt ctagaaacct gggtgtggac atgaccaaca gttgctctgg   23820
```

```
aactctcctt tttaaaagcc agtgggagct tcttcaaagg cagccctaag gagtccgctc   23880
ttaaatgaac tcagactcgg ttttaaaatg caagtctgtg ttgattctgg tctggatggt   23940
gcattcctcc atagcaaaag acagtgttgt tcttggatcc actttccctg ggtgcactga   24000
gggctgcgag gttccaggtg ctcttccggg cactggggag ggatacaggc tggacagaca   24060
tgttgttctc cctcctggag catctgtttt agtggggag gacagaaaac aaaccagtaa   24120
attacagagt actgaaaaga tgcgatggag aaaactatag caaggaaggg aatgggtgg    24180 gggagaagtc aggagaggtc ttgctgagaa ggtggaggaa atgggccatc aggcagggaa   24240
tgtgttccag gcagagcaaa ggccccgggg tgggatgcg cccggagta ccaggaaacc     24300 agaggtggga gtagttacga ggtgggggat gcctcagagg ggacagggcc aagtcaggtg   24360
agaccgaggg ccacagtcag gagtcagctg gggccacaca ggggtccagc ctaggggag    24420 tgcgatctgg cctggatctg aacctctcac tgtggcctag ctgctgagct gagaagagat   24480
gacaagggcc ttgggcagaa gcagggagac tggaggggag cggtgagggg tccaggcgtt   24540
ggggcggggc tcaggctgga gtctgaaggg agcctgcagg cctggtgggt ggacatggat   24600
gggagaaggg gaggacggca ccaaggctcg ggcccctgga cagatgcagt tgccattaag   24660
tgggatgggg caggctgtgg ggccgtcagt ttcagaagga agatgagttt ggcattggca   24720
tggtaggcat ctgtctgtcc ccgcgcccct caaaccaggc atgaagcagg agctcacgtg   24780
tttggtcatc gatggtgcag aaccgccggg gcgggaggtg cggggtggga gatatgtgtt   24840
tgtgtctcaa atgggctctg agccaggag ggctatctgc cccttggcct cacagcggga    24900
tgttggaggg agaaatgaag tgtaggtggg ggtcccgggc catgctggac tgtgctttct   24960
tctcctcggc tctggcaggt tatcgtggcc tgtgaggacg gctggaccct gaccggctgc   25020
agtgccctcc ctgggacctc ccatgtcctg ggggcctacg ctgtagacaa cacgtgtgtg   25080
gtcaggagcc gggacgtcag caccacaggc agcaccagca agaagccgt ggcagccgtt    25140 gccatctgct gccggagccg gcacctggtg caggcctccc aggagctcca gtgacagccc   25200
catcccagga tggtgcctgg gtagggtcag gggctgggc tgagctttaa aatggttcca    25260
acttgtccct ccctcagccc tccatggcct agcccgaggg gacggggatg cttccacctt   25320
cctggagctg ctggcctggc ccttgagtgg ggcaggctcc ttgcccagaa ctcactctgg   25380
atgccccctc ccctggtgga ggtgccagga agctccctcc ctcactgtgg ggcatttcac   25440
cattgaaaca ggttgagctg tgcttggtgc tgccagctgc tcccaacatg ccaacatctg   25500
tgggcagaac ggcttttatt gagctcttgt tcggtgccag gcattcagtc ctcacgtctc   25560
caccaaggag gcaggattct tcccatgggt aggggaggag gtggtagggg cagcagggac   25620
aagcatcgtc aggggcgag tgtgaaagat gctgatggcc ctcatctcca gctcactgtg    25680
gggaagcccc ttggggctcc cttgattagt ggaggctcag cttttttggat ggcatctagc  25740 cagaggctgg agatcaacgc gtccctggtg gtcatgggct gtgccttgtt ttcctgagtg   25800
acctttactc tgctctatgc caggctgtgc taacaacacc caagggtggc ctgcagggag   25860
ccgtcaccta gcactgactc tgcagtgtgc aatggtgcac gcaccgtctc agccaacccg   25920
ctccactacc cagcagacta cacatttgca cccctgcttt acaggggaag caacctggaa   25980
ccagaggagg catgcctgcc aagctcacac agcaggaact gagccagaaa cccagattgg   26040
gctgcctctg aagccaagcc tcttcttact ttaccccgca ggtaacagtg aggctgggaa   26100
ggggaacaca gaccaggaag ctcagtgagt gatggtggaa cgatgcctgc aggcacggaa   26160
```

| | |
|---|---|
| cttttcccgt atcatctagg cctgattcac tgtggcctga tggagatgct tctaagggat | 26220 |
| ggtgggagga gagggacaac tgtccctcct tgagcaccag ccccacccaa gcaagcagac | 26280 |
| atttatcttt tgggtctgtc ctctctgttg ccttttttaca gccagctttt ctagacctgt | 26340 |
| tttgcttttg taacttgaag atatttattc tgggttttgt agcattttta ttaatatagt | 26400 |
| gactttttaa aataaaaaca aactttgtcc tgacttttgc atagacttga ctgcctcggg | 26460 |
| tgatgccttg tttatactag gaactgggta agtttgttga gtaagccagg tacttgtatc | 26520 |
| ttgagtacaa gtattgggta agtactggtg atgtgaactt actccctgtg cctgtcctag | 26580 |
| gaatgaaatg aatgtcttcc tgcagctccc ctgatgaccc tggcagtcaa agtgcctcct | 26640 |
| ccttggtgac ggatgcccta catcctagat gctctgttgt cctaacctcc caatccctt | 26700 |
| ttcattcttt tctccccagt tcctggcaca gggcctggcc cagagtattt atggaataaa | 26760 |
| ttacagtgcc agatgcttct gtgatgagcc agtgctaagt ctatggctat ttttcatgat | 26820 |
| ttaaaattca gaacagtctc aggtcgggtg caatggctca cacctgtaat accagtactt | 26880 |
| tgggaggctg aggcttgcat gtaggagttc aagaccctgg gcaacacaaa cgtcatctct | 26940 |
| acaaaaaaaa ttttttttaat taggtaggtg tggtagcaca tgcctgtggt cccagatact | 27000 |
| c | 27001 |

<210> SEQ ID NO 1545
<211> LENGTH: 3891
<212> TYPE: DNA
<213> ORGANISM: Homo sapiens

<400> SEQUENCE: 1545

| | |
|---|---|
| ttatgagaga aaggcagagg gagatttgac acacacagga ggggccacgt ggagacagag | 60 |
| gtggagattg gagaaatgtg gccacaagcc agggaacacc agcagccacc agaagccgga | 120 |
| agacgtgagg cagggttctt cccagagcct tcgctgctga gtctgggaat tgttaccga | 180 |
| agccataaga agtgggtaca cgccctgagc ctcccacact tgctcacctg tcctgagatg | 240 |
| agaatctcta ctctgcagca tatttggagg atcactgcgg gggccacaga ggtgctgttc | 300 |
| agatggcact tcagaagact caggagaccc tggggcagga gcagtttgac tgacagccca | 360 |
| gagggctgcc ctctgattcc acctgaggcc ctgcttttcc tggctgcagg ggttccaggg | 420 |
| ccaggccatt tccgctggcg caggactctg ctagcagcaa cctgcctgaa gtcttccttt | 480 |
| ggcctggctg agagtttctg agacctgcgc tggagcggag gtgcttcctt ccttgcttcc | 540 |
| tttcttcctc tctcccttct ccatccagca ggctggacct gctggcatc tgtgagctct | 600 |
| ccctactttc tcctataccc taacctttgt cctgcatggg cgactccccc agtgagtctc | 660 |
| ttgcagcttt tacccagtg cctgcttctt ggagaatcca aactgatcca gttagggatg | 720 |
| ataaagtgta gggtaggtgc tcggtgactg ttttctctga ggttgtgact cgtgtgaggc | 780 |
| agaagcagtc cccgtgagcc ctcctggtat cttgtggagt ggagaacgct tggacctgga | 840 |
| gccaggaggc ccagacatac atcctgtccg agctgcagct tcctgtctct aaaatgagcc | 900 |
| ggccagcgca ggtggccaga catcactgtt attctccttt gagtctttaa atcttgttgt | 960 |
| cttctgca gactcggtga gctgtgaaag gctataatag gggctttatt ttacactttg | 1020 |
| atactatttt ttgaacattc atattattgt tagatattga tattcatatg aaggagcagg | 1080 |
| atgacttggg tccttcttgg cagtagcatt gccagctgat ggccttggac agttacctgc | 1140 |
| cctctctagg cctccctttc cttgtctatg aaatacatta tagaataggg tgtagtgtgt | 1200 |
| gaggattttt tggaggttaa acgagtgaat atatttaagg cgctttcacc agtggctggg | 1260 |

```
atgtgctctg tagtttctgt gtgttaacta taaggttgac tttatgctca ttccctcctc    1320
tcccacaaat gtcaccttgg aaagacggag gcagcctggt ggaggtgtat ctcctagaca    1380
ccagcataca gagtgaccac cgggaaatcg agggcagggt catggtcacc gacttcgaga    1440
atgtgcccga ggaggacggg acccgcttcc acagacaggc cagcaagtgt gacagtcatg    1500
gcacccacct ggcaggggtg gtcagcggcc gggatgccgg cgtggccaag ggtgccagca    1560
tgcgcagcct gcgcgtgctc aactgccaag ggaagggcac ggttagcggc accctcatag    1620
gcctggagtt tattcggaaa agccagctgg tccagcctgt ggggccactg gtggtgctgc    1680
tgccctggc gggtgggtac agccgcgtcc tcaacgccgc ctgccagcgc ctggcgaggg    1740
ctggggtcgt gctggtcacc gctgccggca acttccggga cgatgcctgc ctctactccc    1800
cagcctcagc tcccgagggg aggacatcat tggtgcctcc agcgactgca gcacctgctt    1860
tgtgtcacag agtgggacat cacaggctgc tgcccacgtg gctggcattg cagccatgat    1920
gctgtctgcc gagccggagc tcaccctggc cgagttgagg cagagactga tccacttctc    1980
tgccaaagat gtcatcaatg aggcctggtt ccctgaggac cagcgggtac tgaccccaa    2040
cctggtggcc gccctgcccc ccagcaccca tggggcaggt tggcagctgt tttgcaggac    2100
tgtgtggtca gcacactcgg ggcctacacg gatggccaca gccatcgccc gctgcgcccc    2160
agatgaggag ctgctgagct gctccagttt ctccaggagt gggaagcggc ggggcgagcg    2220
catggaggct gcagctccca ctgggaggtg gaggaccttg gcacccacaa gccgcctgtg    2280
ctgaggccac gaggtcagcc caaccagtgc gtgggccaca gggaggccag catccacgct    2340
tcctgctgcc atgccccagg tctggaatgc aaagtcaagg agcatggaat cccggcccct    2400
caggagcagg tgaccgtggc ctgcgaggag ggctggaccc tgactggctg cagtgccctc    2460
cctgggacct cccacgtcct gggggcctac gccgtagaca cacgtgtgt agtcaggagc    2520
cgggacgtca gcactacagg cagcaccagc gaagaggccg tgacagccgt tgccatctgc    2580
tgccggagcc ggcacctggc gcaggcctcc caggagctcc agtgacagcc ccatcccagg    2640
atgggtgtct ggggagggtc aagggctggg gctgagcttt aaaatggttc cgacttgtcc    2700
ctctctcagc cctccatggc ctggcacgag gggatgggga tgcttccgcc tttccggggc    2760
tgctggcctg gcccttgagt ggggcagcct ccttgcctgg aactcactca ctctgggtgc    2820
ctcctcccca ggtggaggtg ccaggaagct ccctccctca ctgtggggca tttcaccatt    2880
caaacaggtc gagctgtgct cgggtgctgc cagctgctcc caatgtgccg atgtccgtgg    2940
gcagaatgac ttttattgag ctcttgttcc gtgccaggca ttcaatcctc aggtctccac    3000
caaggaggca ggattcttcc catggatagg ggaggggcg gtagggctg cagggacaaa    3060
catcgttggg gggtgagtgt gaaaggtgct gatggccctc atctccagct aactgtggag    3120
aagcccctgg gggctccctg attaatggag gcttagcttt ctggatggca tctagccaga    3180
ggctggagac aggtgtgccc ctggtggtca caggctgtgc cttggtttcc tgagccacct    3240
ttactctgct ctatgccagg ctgtgctagc aacacccaaa ggtggcctgc ggggagccat    3300
cacctaggac tgactcggca gtgtgcagtg gtgcatgcac tgtctcagcc aacccgctcc    3360
actacccggc agggtacaca ttcgcacccc tacttcacag aggaagaaac ctggaaccag    3420
aggggggcgtg cctgccaagc tcacacagca ggaactgagc cagaaacgca gattgggctg    3480
gctctgaagc caagcctctt cttacttcac ccggctgggc tcctcatttt tacgggtaac    3540
agtgaggctg ggaaggggaa cacagaccag gaagctcggt gagtgatggc agaacgatgc    3600
```

-continued

| | |
|---|---|
| ctgcaggcat ggaactttt ccgttatcac ccaggcctga ttcactggcc tggcggagat | 3660 |
| gcttctaagg catggtcggg ggagagggcc aacaactgtc cctccttgag caccagcccc | 3720 |
| acccaagcaa gcagacattt atcttttggg tctgtcctct ctgttgcctt tttacagcca | 3780 |
| acttttctag acctgttttg cttttgtaac ttgaagatat ttattctggg ttttgtagca | 3840 |
| tttttattaa tatggtgact ttttaaaata aaaacaaaca aacgttgtcc t | 3891 |

<210> SEQ ID NO 1546
<211> LENGTH: 29001
<212> TYPE: DNA
<213> ORGANISM: Homo sapiens

<400> SEQUENCE: 1546

| | |
|---|---|
| acgttttaaa aaaacatttt tcatgtaaat ttaaaaaaat tgaacattca cacaaaaaga | 60 |
| tgccccctcc cttgcaaaaa agagtatgcc cgttcaaaat gttgaaatgt acactcacag | 120 |
| caatggtggc tgcagactcc aagtttctga ggttggagaa ggtagccagg gagcataaaa | 180 |
| gtgagttcta tctactcatt cagtctatga ggggaaggca atggctagaa aagcattttg | 240 |
| agggacagta aaagtggcat ttttagaggg aggaagcctt gaggatgctt gtggggtgaa | 300 |
| gggaaagaat aactcaggaa gaggcattta gggataagag gaggagagga gatagtggag | 360 |
| gtaggtgatc cctgcgcgga ggccagattggg gcaggggagt gtcagctgag tataagagga | 420 |
| tggtcccctc tgccctgaag gaggaaggca ggaggggaaa aggatgggtg ttgacccaga | 480 |
| aagcacttgt ggtggagggg aggccccaga agaggcttct gacttaccct gattgctggt | 540 |
| acctctcagg ggagctggct gcttatttgc tggccaggt gtgggggaac ccatttgaga | 600 |
| agagggagaa ggtgacacaa ttcctttggg caacttatgg gaggggtaat tggtgaggga | 660 |
| tgaaagccct gccaagtggc aggaggccca gctgggctg ccctcataa gagtgcagtg | 720 |
| gaggatatgg gatgagaagt gactgccct ctggttccat ctgtcgcaga gccagggtg | 780 |
| cttccttcct ccccccacctc cctcagaaca cacccactgc atgctggaca gcagcccct | 840 |
| tcctgggcct ggggacatcc atgtccctct gtgcacaggc ttcatcattc tctgggtgca | 900 |
| cggtaacgac cccggtaggt gagaggccaa ggtcccaaag gggagcagca gggaaagtta | 960 |
| gctcccatct attcttgctc caggggaggc ctttgatgag gaagctgcca aaagcacatt | 1020 |
| gcaaatacaa ttccaattac aggcaacagg aaggagaacc acctctgcca cctctgtcag | 1080 |
| caaaccatga gctcctactc tgtgctgcga tggcgggctc gatggggata actctgacct | 1140 |
| tacctcatgg agtcactgtc aacccactgg ttgcactgtc tttgtgcact ggctctctgg | 1200 |
| agtgaggtct ttgcaaacaa agtggaaaga gcatcaactt tggactccag cacctagatt | 1260 |
| cagagcaggc catttcactc ggaatctgct gtgcatctgc aagggaggat cataaattcg | 1320 |
| cctttgtttc ttcccagtat cgacagccct tccagaaaga gcaagcctca tgtcatgcca | 1380 |
| catgtacaat ctgaggccag gagctctctt tccccttttc atcctcctgc ctggtacaca | 1440 |
| ataggtgttt actggatgct tgtccagttg atttcttgaa catggtgtgt aaaaggaatc | 1500 |
| tttgcaaatt gaatcttctg gaaagctgag cttgtgccta ccatagaatt ctgaatgtac | 1560 |
| ctatatgacg tctttgcaaa cttaaaacct gaatctttgt agtataaatc ccttgaaatg | 1620 |
| catgtaggct ggacatcaaa agcaagcaat ctcttcaagg agcagctagt tggtaaggtc | 1680 |
| agtgtgcagg gtgcataaag ggcagaggcc ggaggggtc caggctaagt ttagaaggct | 1740 |
| gccaggttaa ggccagtgga aagaattcgg tgggcagcga ggagtccaca gtaggattga | 1800 |
| ttcagaagtc tcactggtca gcaggagaca aggtggaccc aggaaacact gaaaaggtgg | 1860 |

```
gcccggcaga acttggagtc tggcatccca cgcagggtga gaggcgggag aggaggagcc      1920
cctagggcgc cggcctgcct tccagcccag ttaggatttg ggagtttttt cttccctctg      1980
cgcgtaatct gacgctgttt ggggagggcg aggccgaaac ctgatcctcc agtccggggg      2040
ttccgttaat gtttaatcag ataggatcgt ccgatgggc tctggtggcg tgatctgcgc       2100
gccccaggcg tcaagcaccc acaccctaga aggtttccgc agcgacgtcg aggcgctcat      2160
ggttgcaggc gggcgccgcc gttcagttca gggtctgagc ctggaggagt gagccaggca      2220
gtgagactgg ctcgggcggg ccgggacgcg tcgttgcagc agcggctccc agctcccagc      2280
caggattccg cgcgcccctt cacgcgccct gctcctgaac ttcagctcct gcacagtcct      2340
ccccaccgca aggctcaagg cgccgccggc gtggaccgcg cacggcctct aggtctcctc      2400
gccaggacag caacctctcc cctggccctc atgggcaccg tcagctccag gcggtcctgg      2460
tggccgctgc cactgctgct gctgctgctg ctgctcctgg gtcccgcggg cgcccgtgcg      2520
caggaggacg aggacggcga ctacgaggag ctggtgctag ccttgcgttc cgaggaggac      2580
ggcctggccg aagcacccga gcacggaacc acagccacct tccaccgctg cgccaaggtg      2640
cgggtgtagg gatgggaggc cggggcgaac ccgcagccgg gacggtgcgg tgctgttccc     2700
tctcgggcct cagtttcccc ccatgtaaga gaggaagtgg agtgcaggtc gccgagggct      2760
cttcgcttgg cacgatcttg gggactgcag gcaaggcggc gggggaggac gggtagtggg      2820
gagcacggtg gagagcgggg acggccggct ctttggggac ttgctggggc gtgcggctgc      2880
gctattcagt gggaaggttc gcggggttgg gagacccgga ggccgaggaa gggcgagcag      2940
agcactgcca ggatatcctg cccagatttc ccagtttctg cctcgccgcg gcacaggtgg      3000
gtgaaggagt gaatgcctgg aacgtactgg gaactgcacc aggcacagag aaagcgggct      3060
tgccattata gtgggttccg atttggtttg gaaaacatgg gcagcggagg gtggagggcc      3120
tggagagaag gccctacccg agacaggggc ggggtgggaa ggacggcaga tgctgggagc      3180
acgaggcaat ttctttatga cacagaactc atgctctagt attccatctg tttcagccga      3240
agaaaagaac cagctgaagg ggcagggag aaggggcgga ggtattctcg aggcccattg       3300
gcgtccttta ggactcaggc agggaagggc ccttggtgct ctggagccgg aggtggtgcg      3360
cctggtactg ggaccccgga gctgagcccg gcgcctcagc ccacctggct gtctgccgac      3420
cgtgtgcggg gcgagtttgc tcaacaactc tgccagcttc tggccctcag gctgtgggaa      3480
gcttcttccc ggggcgagac cactagcttt ttctaagtat taccagccca ggacttggct      3540
gaggttctgt gtcccccagc ttggagtcag atgtggggtt gaatcttggc ttcctctcac      3600
tagctgtggt gcttgacaag tcacttatcc ttgagcctcc attgcctaat ctttaaaagg      3660
gaggtgacaa tcgtccctac ggctcagtgg cagcagatgg ggagatgaag ggaaagttct      3720
gttgaccatg agtgaactta caatgcaagc cccgggggga tcacttgcag ttttgtccct      3780
gtctgcagtg tgacctgttg gtgacattgt ctttgctcca aaccacagct cctggggcag      3840
agggaaaat tctgccactc acagctgcct gcccacgctt ctgtctgagt gtgctgggtg       3900
gcaggatggc aagtccttac tcagctcagt atagccctct tccttgttcc ctgagccttt      3960
gactttctcg agggatgttg tggggttgtg gccaggataa gaaagggcat ttcaagttac      4020
cactgctcca aaacaactgt tctggaaata gtgagtaccc catcctgaga ggtgagtaag      4080
cagaggctgt atgaccacct gaaccaagcc cttgaggatg tttcttctct ggtggaagtt      4140
tggaacagga gcctcctcaa gttcatttat tcattcattc aatggttatt ttgtgggaat      4200
```

```
cgaatttaga atgaaaatat tttttggcaa gcagaaaata attttttagac caatccttt     4260
cttttagtca tgagaaactg aggcccagag agaggaggtc accccaggtg cattagaact     4320
gggtttccag aactgacact ccactgcaca gagtactctc ccaattcatt caattttat      4380
ttagcggaag gcattttcag atgggtcttt gaagcattag taggagttca gcgatgatgg     4440
tgtcatgaga atttttattct aggattagga ggtaccatga acaaagatac agagctggga    4500
aaaccagagg tggaagataa ggagcacatg tccacagttc tttttctttt tttttgaga     4560
tggagtttcg ctcttgttgc ccaggctgga gtgcaatggt gcagtctcag ctcactgcaa    4620
catctgtctc ccgggttcaa gtggttctcc tgcctcagcc tcccaagaag ctgggattac     4680
aggtacctgc caccacgccc ggctaatttt tgtattttta gtagagaagg ggtttcacca    4740
cgttggccag gctagtcgca aactcctgac ctcctcagtg gatccgagga ggtgatcctc    4800
ccgcctcagc ctcccaaagt gctcgaatta caggtgtgag ccaccacgcc tggcctccac    4860
agttctttat ccaccgtctg aaatgtaaaa tgttacgaaa accaaaagtt ttttttgtga    4920
tttatttgat ggtagcacct gacgtgaact gacatgagat tatttttaat ttagttgtgt    4980
gaatatgcat attcatatat tttgctgcat agattacagt atgcagctcc agattcttcc    5040
aagcagactc tgattgccca ttactgcctt tctaaaatcc aaacaagttc tgaggttcaa    5100
aaccgttttg gccctaaggc tttgggtaaa ggggtggac tctgttctac tctgactgga      5160
gtccaagatg catatataca gagatatggg tgatggggct gcaaggtagg ttgaggtagg    5220
ggccaaggag gagcatggag tttggacttg attcatgagg ctgtggggag ccagtgaagg   5280
ttcttaagca ggtatgtctg cctgagagca gttggagcag acaagagcta aaaccaaac     5340
aaatcaccat agatagtggc tgctataatt tgtttgtccc ctccaaatct catgtggaaa    5400
tttggtcctc agtgttggaa gtggggccta atggaggtg tttgggtcat ggggaggaa       5460
cccctgtgaa aggcttggtg ccgtccttgt gataatgagt aagttctccc gctatgattt    5520
cccttgaagg ctgattatta aaagagcctt ggcacctccc tctcttctct cttgcttctt    5580
ctcttgccat gtgattgatc tctgcacatg taggctcccc ttcaccttct gccatcagtg    5640
aaagcagctt aaggccctca ccagaagcag atgctggtgc catgcttcct ggagagcttg    5700
cagaatcatg agctgaataa atcccttttc cttgtaaatt actcaccttc aggtattcct    5760
ttatatagca acacaaaagg actaagacag tggccttgac ttttctctct ctttaagaag    5820
tgttgccttt gctcacttag tcatcccttc tgcctgcatt tgtagagcat ctggatggga   5880
gatttatata accgtcactc ttgactttcc cagcaggcct atgtcatagg tactgtggtc    5940
tctacaatac agcagaggta tctgaggctc cgagaggttg agtgacttgc tcatggctgc    6000
acaaccagta aatattggag ctggaattca ggtccacggt ttcctggctc caaagcccat   6060
gatttttttcc ctcaatttat tctgactggg gcatggggga ggggtggcc tttgggcagg     6120
gccaccagga gcgaccaggc ccgtagagag ctgggtgcag gtacagagga aaacctgttg    6180
tcgagtgtgg cccgtagttc ccattttttgc ctgaatggca catttgaaag tgttatataa   6240
ccatgtgaat aataatagtt ggcctatatg agttctttaa tttgcttttt ggtccgcatt    6300
tggtaacttc tttatcatct actatactct gttgtgtctc ttttgttgta atttgtaagt    6360
aggggtgaga taaagtacac ctagggtttg ctgggtttct tccatgtcat catgttcctc    6420
cttgcatggg gccaggatcc gtggaggttg cctggcacct acgtggtggt gctgaaggag    6480
gagacccacc tctcgcagtc agagcgcact gcccgccgcc tgcaggccca ggctgcccgc    6540
cggggatacc tcaccaagat cctgcatgtc ttccatggcc ttcttcctgg cttcctggtg    6600
```

```
aagatgagtg gcgacctgct ggagctggtg agccacccti tttgggaatg gcacttcctg    6660
atagggctgg gccactgcat atacactggg gactgtgctt agtaggccca ttgctgaaaa    6720
tcagaagggg acagcaagta tgtattgagc acttatcggg taccaagcac agtaactact    6780
ggctttctgt atagaattcc ctttaagcct ggccatgccc cagtggtacg tctatcttca    6840
tttgaaagac gaggagactg aagttcagag gggaccacac agacagctag gggtagagcc    6900
tggatcaaac ccattggtct gcctgccagc cattcttgtg ccaatgcatc tgctgcctac    6960
ggaaacctgt agggacaagg ccctgggatg ttcagtggag cctgagtcat tttataaaaa    7020
agcatgactc tagggtccaa aattcctttg aagctgttgc tatccagagt gaagtccctt    7080
ctttaggaca gggtggccct cctccctcct ggatgtcaca tcttcggtgg aggggcagaa    7140
aggggactgg gtattctcct caccctggcc ctagtgcttc aaatcttaaa aaaacgtttt    7200
tatttgtgct tctgcaccac cttctagccc acctcgtttc ctggcctcta acttgatgag    7260
agcgtgtgtc attttcacac tgattctcca catggcaggc ggtgcttctt agcctcctgc    7320
agacagtgag gcccacggt cttgtccaag gtcacacagc gtgtaatggg cagggtcaga    7380
gtctggagtc tggacctggg tctcctagct gcactgcact gctgccccat gggttaatca    7440
gctcagcata ccgtggctga acagctacct cataccaagg cctgtggcgc catgacaggg    7500
attgacaggg tccctgcctt ggaaacccgt agtctaagta gaggagactg acaagtcaat    7560
gccttccatc agtctgctca acacacgttt accaagtgcc tactgtgtgc tgcagaggcg    7620
aagatgacac agctcaggcc tttcccttga gcttacagtt caggaggaga gactgaccag    7680
tgactgccag tacagttgac tatgggacaa tgtgctcagc cttggggaga gacgaagaag    7740
gtacccgtat agcaccagat gacaggcacg agccccacag gccagggcag ctgctcagag    7800
gagagtaggc caagcagaag gcaaacagaa ggctgcaggc atttgccatc gagagctgga    7860
cttcaaactg ggcatcatac cagcctgggt tcgagtcctg cccagcccct tattggctgt    7920
ctaaccctga gcaaatccct tcacctctct gagcctcatt cctctatctg taaaccagtt    7980
ataataattg gaacattcat ttaaggacta aatgaggtcg tgaagcattc agcagatgct    8040
aggtacggaa actcgctgaa gtgggggcag gttaagaagc ctctggggat acgaaggcat    8100
ccagggacta gttgtggcag gaggctgtta ccacttaggt ctgaagggta aggagaggga    8160
atagctttcc ctctgcccag ttggagccgg tggcatggag gagaggctgc ctgtggggaa    8220
tcacccgagg gttcaccgct gccatgcgca gggagtcagg aggtagggag ggagtggggc    8280
agatgcacac cattttttt ttttttttgag actctgttgc ccagactgga gtgcagtggt    8340
gccatatctg cacctctgcc tcccgggttc aagctcactg caacctctgc ctcccgggtt    8400
caagcgattc tcctgcctca gcctcccgag tagctgggac tacaggtgtg tgccaccatg    8460
cctggctaat ttttgtattt ttaatagaga tggggtttca ccatgttggc caggctggtc    8520
tcgaactctc gacctcaggt gatccccac ctcggcctcc caaagtgctg ggattacagg    8580
cgtgagtcac cgctcccagc tgctgatgca ctcttgtcct tctaactcct gctagtgcct    8640
cccattggct gagcccaact ggaagctttg caagggagct ggtgctgcag tttgcactga    8700
gcaggctgga gaaggctgga gaatagacta ggggacaaac cgaattgcca gtgctgttat    8760
gtcatgattt aggcatggag tccagggcct gagcttcact ccatgtccat cctgcccaga    8820
gccttggcac agcctggctc ccagacaaga tgtcaagttc agaatccttc ctaaaaggaa    8880
tcctctatgc cagaccgtgt tgcagggata tgggagtgct gggctcccag cctgatcaag    8940
```

```
gagcgagaaa actcaggctc ctagtctgtc ctccggggca ctagcaggga caaggtggga    9000
ggctgctggg ctgggatgtg gggacaggtt tgatcaggta aggccaggct gtggctgtgt    9060
ttgctgctgt ccaaatggct taagcagagt cccccggcct ctctggcttc tgcaggcctt    9120
gaagttgccc catgtcgact acatcgagga ggactcctct gtctttgccc agagcatccc    9180
gtggaacctg gagcggatta cccctccacg gtaccgggcg gatgaatacc agcccccgg    9240
taagacccc atctgtgccc tgccccaccc catctgagct gaatccattt gctctgccct    9300
ggcctggcct ccctgctggt ggtttccact tctcgggggg ctttgggact cagcacctcc    9360
actgacccct ttttttctgt cccatcccca tccctgcag ccccactgc ctgccttcct    9420
gttgccccac aaatgcaaaa gtcttgcctt aaatgatcct cttttccttc ttttctcttg    9480
ttttccttt ctcaccattt ggaatggccc agcaggctgc acttaccttg aaggagggt    9540
tcatctgatg gtgactctac ctagggcccc caggcctcta taactcccag tgccctgcag    9600
actggaccag atcctttaat gggatagaca caaccctgtc tgggatgcct ctgcctacct    9660
tcctgttttg ctgctccacc tgcctccagc tccgtttggc ttcctggggc tccctgcctg    9720
ggccactttg tgtcttccct ctaggccttt cttccactg ttccctctgc ctggtgtggc    9780
ctggctatgg aagggaggga ggaggagcgg ccatggaaaa cggtctgcat tctagcaggg    9840
acttgcaggt ggcaattcag tcggggaaga ctctagatgc acctggcctg aggagagaat    9900
gaagggttct agttggactg tgttaagttt gaggtgccca tggtgtgagg tctggagctc    9960
agcgcagaga tgatgcaatg tggtgggtcc atgcaacatg gtgccaggac gcagagcttg   10020
gggtgaactc agctttcacc ccttaccggt tctcgtggga tcttgggaag ccactttctt   10080
ctatgagctt tgtcgttctt gtctgtaaaa tgggcacata accctgtccc tgtccttctc   10140
acaggttgct gtgagactcc aatgagttga aggatgtgca gatgcttttg gaagtgaaaa   10200
gttgggggc tactgtgtga cttgcatac acccaaactg tgtgaccttg catatgtctg   10260
agttgctgcc attgcaacag atcagagctg gtgggctggg tgtggagaaa gggtttgtgt   10320
ggggacatc ctctggcaag ggtggcagca gcagaagtga ggggcctggt cggtcatgtg   10380
tgctgacccg gcctgggcag cctgtggcca gggagaggac agctcctctg taggaagagc   10440
ctgttccttt ccaaccaggt gagacctctt cagtggagcc ctggagcccc ctgtactcca   10500
catcagtgcc tcaggaccct cccggagcag gctaatatca gagaccaaga gggacactgg   10560
cagaggatca cagagacccc agtccaggca gggactgaga agatcttgcc ccctaagtta   10620
gtttcctagc actgctgtga caaattacca ccccctcggt tggaacaagt tgattctctg   10680
cagtcctgga ggccagaagc ctgaatcagt gtcggcagga ccactttctc ccgggggct   10740
ccagggagaa gcttctcttg cctcttccgt gtcccaacag cggcagcaca ccaatcccag   10800
cctctgtctt cacacagcct tctctgtgtc tctctcctct tcattgtctc ataaggacac   10860
ttgtcattgg atttagggcc cactggatcc tccaggatga tctcatgtgg ggaaccttaa   10920
ccacatctgc aaggacccct tttccaaata aggtcacagc cacaggttgt gggggttagg   10980
atgtgagtgt atctctttgg cagccactgt tccctcctct cccttgggcc agaagcagac   11040
gtggggcct tcttcccca taggatgccc atggattgcc ccccttcccg cttccccga    11100
gtgtctgtgg gaggtggcag gaatggcagg caggggtgtg gaacccttc tggagtcata   11160
tcaagggctt ggctggagga agtcctcctg gagctgttgg gctggcatgg ggcaggctgg   11220
ctgggcccag cagcagcttc ttcattcatg gggaggccac aagcatgggc cctagagctg   11280
gctgccgccc tcaaacccag accctgcact cttaactgtg tgaccttgca tacgtcactc   11340
```

| | | | | |
|---|---|---|---|---|
| accctctctg | atcttcaggt | tcctctgcaa | aagggaggta | atgataaccc tcactctggg | 11400 |
| gggctgtttg | gagggttaaa | tcagttattg | ctgtagcatg | catttctctg tcaggtattg | 11460 |
| agtgaggtgc | tgtgatttta | gccctgcatt | tttctttct | taccattcaa taataacgtt | 11520 |
| ttgagcaccc | actgtgcgcc | aggcaccata | ttaggtgctg | gggatacaaa tgtgaatgaa | 11580 |
| atgaatgtgg | tctcttcccc | caacagtgta | tccagaagat | taatccattc cttaaacaaa | 11640 |
| tgctacttga | cacagattag | ttctggatag | gctgagagct | ctgaaggagt gcaggcagct | 11700 |
| gcgagcctgt | gtatccagca | gaaggatcag | gaaaggattc | ctggaggaag cgctgttcta | 11760 |
| gccaagacct | acgggggcat | tattaaccag | gcaaagggga | cggtgtccaa gcagtggaat | 11820 |
| gaacgtggat | tgaagctgtg | aggcaggagg | gagtgtggcc | tgtgcagaag ggaccgaggc | 11880 |
| tggtgagacc | aggagggcct | gggtggcctc | caggtcagat | gtgaaaggaa gaacttggcc | 11940 |
| acagtctgag | cttctcaggc | gtatggcagg | gctgcctggt | gagagggaat gagctccctg | 12000 |
| ctctggaggt | atgcaagcag | gactgggctc | tcacctgcca | gaggccacag agctttccag | 12060 |
| aggctggaag | aggccactcc | aaggcctctt | tgcccctgag | agtggtggct cttcttgagg | 12120 |
| ccaccttgcc | acgctgtcac | agggaactag | cagcccctgc | ctcacccggg ggtttggaag | 12180 |
| atagagggag | gcctaggaag | ggccctgtgt | ctcatccgag | ctgggcccct ttccagcctc | 12240 |
| tcactggaag | gaagcccaag | gatgttcctg | tgggggcttt | taccaggccc acctgccctc | 12300 |
| tgctggccat | gcttgcagcc | tcctgaccct | gtcccagcag | gacagtgggc tggtgtgagc | 12360 |
| gggcaggaac | cgcctgcact | tagaaggtgt | ggggctgcct | ccccgagctt ccatctgccg | 12420 |
| ctggggccac | accccaggcc | cagggatggg | accccacagt | ggtcacatca tcttgcagca | 12480 |
| gaacccaggt | acagctcctg | gagcagatgg | tggtcccaag | cacgggtggg accagaaagg | 12540 |
| actctcacct | gggctaactc | agctgcagcc | tcagttccct | cctcacacac gacgaggaac | 12600 |
| atggactgga | agcctgccca | gcaggccttc | tgctcgatgt | gcgttgtgtg gcttacgtcc | 12660 |
| agggagggaa | gcagcctctg | tgctgtcttc | tagataagcc | tgtattcccc gggctgtctg | 12720 |
| ccaatgtatc | cagttgtccc | gtcagcctgg | aagctctgag | ggaaaacctt gggctgcttc | 12780 |
| ctgagcacct | gtatcccctg | cagccagccc | ggggcctctg | ctaggagcag actgagcatg | 12840 |
| gcttatgggc | ctggcaccat | ctggcctctg | cccaccttgc | tggccttgtc ttgtgtctgc | 12900 |
| cccttcgaca | ttccatagcc | cagctcaata | tctagtggtt | cctctagggt ggcgagcact | 12960 |
| gtttggtctc | cagatgtctt | caggtcggag | ctcacagcgc | tctcagccac cccttcccag | 13020 |
| tgtagcaccg | ggcacatggt | agatgcctat | tgatgagtga | aagctcctaa cacactcaga | 13080 |
| gagcaaggac | tccgcctcat | cccacagcct | gggaggagag | gcagactgcc aaggacctgc | 13140 |
| tcagcatgct | acagaagaaa | ccaaagtgcc | cacgggactg | atcagtggag cttcctgccg | 13200 |
| agactggagg | ccttagggca | gggtagacag | tgtgtgtgca | ggctggggac tcacagttcg | 13260 |
| gactgtgccc | agacctacta | gcatagtggg | tgggtgggag | gatgcgggac tggggccga | 13320 |
| ccttgcctga | aattcatgtg | ggatctcaga | gcagccactg | aattgctctg taggggcta | 13380 |
| aatagtggcc | cccacagata | cacacaccca | gacagagcct | gtgagccaga ccttatttgg | 13440 |
| agaaaaggtc | tttgtagatg | taattaagca | tctcaagatg | gcatcatctg gattatgcgg | 13500 |
| tgggctgtaa | gtcctgtgat | gtgtctttat | gagagaaagg | cagagggaga tttgacacac | 13560 |
| acaggagggg | ccacgtggag | acagaggtgg | agattggaga | aatgtggcca caagccaggg | 13620 |
| aacaccagca | gccaccagaa | gccggaagac | gtgaggcagg | gttcttccca gagccttcgc | 13680 |

-continued

```
tgctgagtct gggaatttgt gaccgaagcc ataagaagtg ggtacacgcc ctgagcctcc    13740
cacacttgct cacctgtcct gagatgagaa tctctactct gcagcatatt tggaggatca    13800 ctgcggggc cacagaggtg ctgttcagat ggcacttcag aagactcagg agaccctggg    13860
gcaggagcag tttgactgac agcccagagg gctgccctct gattccacct gaggccctgc    13920
ttttcctggc tgcaggggtt ccagggccag gccatttccg ctggcgcagg actctgctag    13980
cagcaacctg cctgaagtct tcctttggcc tggctgagag tttctgagac ctgcgctgga    14040
gcggaggtgc ttccttcctt gcttcctttc ttcctctctc ccttctccat ccagcaggct    14100
ggacctgcct ggcatctgtg agctctccct actttctcct ataccctaac ctttgtcctg    14160
catgggcgac tcccccagtg agtctcttgc agcttttacc ccagtgcctg cttcttggag    14220
aatccaaact gatccagtta gggatgataa agtgtagggt aggcgctcgg tgactgtttt    14280
ctctgaggtt gtgactcgtg tgaggcagaa gcagtcccg tgagccctcc tggtatcttg    14340
tggagtggag aacgcttgga cctggagcca ggaggcccag acatacatcc tgtccgagct    14400
gcagcttcct gtctctaaaa tgagccggcc agcgcaggtg gccagacatc actgttattc    14460
tcctttgagt cttaaatct tgttgtcttt cttgcagact cggtgagctg tgaaaggcta    14520 taatagggc tttattttac actttgatac tatttttga acattcatat tattgttaga    14580
tattgatatt catatgaagg agcaggatga cttgggtcct tcttggcagt agcattgcca    14640
gctgatggcc ttgacagtt acctgccctc tctaggcctc cctttccttg tctatgaaat    14700
acattataga ataggatgta gtgtgtgagg attttttgga ggttaaacga gtgaatatat    14760
ttaaggcgct ttcaccagtg cctgggatgt gctctgtagt ttctgtgtgt taactataag    14820 gttgactta tgctcattcc ctcctctccc acaaatgtcg ccttggaaag acggaggcag    14880
cctggtggag gtgtatctcc tagacaccag catacagagt gaccaccggg aaatcgaggg    14940
cagggtcatg gtcaccgact tcgagaatgt gcccgaggag gacgggaccc gcttccacag    15000
acaggtaagc acgccgtct gatgggaggg ctgcctctgc ccatatcccc atcctggagg    15060
tgggtgggga ctgccacccc agagcgttgc agctgtactc ctgggttgca cccccccag    15120 ctgtcactgt cccctccctg ccatcagttg tgggaagggc gttcatccat ccagccacct    15180
gctgatttgt tatagggtgg aggggggtc tttctcatgt ggtccttgtg ttcgtcgagc    15240
aggccagcaa gtgtgacagt catggcaccc acctggcagg ggtggtcagc ggccgggatg    15300
ccggcgtggc caagggtgcc agcatgcgca gcctgcgcgt gctcaactgc caagggaagg    15360
gcacggttag cggcaccctc ataggtaagt gatggcccca gacgctggtc tctctccatc    15420
tggacctggc ctgggaggtg gcttgggctg ggcccaggga gagctaatgt ctcctaacca    15480
agaatgctgt ggcagcctct gccgcagagc cagagaacca gagtgccaag gctggcaggg    15540
ttcccagtgg ccacgagtgc agatgaagaa acccaggccc caagagggtc atgcaggtag    15600
cccagggagt tcagccttga ccctgggtca atgacctttc cacagttcca cactgctccc    15660
cttttaaaat ccggtgatgt ctttatgtct tttgttatgt tatcttcaat gtggaggac    15720 tcgaggtgat ctaagcaaac tttttctatc ttctgcttgc atacctctga gaccagggga    15780
ctcactcact tgcatgactg ggccctgcag gtcacactgg ccaggcagat gtggtggagg    15840
aactggcaga ggactttttc tagactgtga ctacatttag tccacccagc ggccccccta    15900
tgaagtccag ttgagaacta ggactctggg ggccggtgga cagagaagag ggagggttct    15960
ctcccttact gacttccttc tgtggccaga cattgagcaa ggcctctgta cagcatgtcc    16020
tggggctggc cttgccgtag ctgctaaata gttgacgaaa ccagtccaga gaggggaggt    16080
```

```
gactgccagg gtcgcacagc tcaagctggg gaactcgctg ggaaaactgt cagctctggg   16140
cagcagcttg acttccactg taagcccag ccccccagggt caaacactgg ctctggtgct    16200
ggcagaggca gcccactagc ctgtttcaaa ggctgagaag gcccaggagt ctgccctgtg   16260
ctccaccagt tctgccctga actttccta cagagtacag gttttgatgt tcagttttaa     16320
aggcaagaat caataacctt ctgccccatc aggtgacccc ttgtgcctgt cccacccctt    16380
tattgactga cctcggctca gtcaggtcag ttcctgaagg tcagtgtgtg gaggggaggc   16440 tgttcttcc cagaaaggcc ttccccaggc ctggtgctct ggcctctgga ggacttcctg     16500
gagaagtccc ttctttgggg tcccagtcag tgtatgggaa gcccttattg catgacctgg   16560
cacggggcag gggctcaaca gtcactattg ccttccttgc cactgccatt tcctcctctg    16620
taagcaggta attgtgtgtc cagtctgagc acagagataa gcacacagca ggtgcttaat   16680
aactagcagc tgtaggctgg gcgcggtggc tcatgcctgt aatcccagca ctttgggagg   16740
ccgaggtggg cagatcacct gaggtcagga gttcgagacc agcctgttca acatggtgaa   16800
accccgtctc tactaaaaat acaaaaatta gccaggcatg gtggtgggtg tctgtatccc   16860
agctacttgg gaggctaagg caggagaatc gcttgaaccc aggaggtgga ggttgcagtg   16920
agctgagatc gtgccactgc aatccagcct gagtgataga gcgagattcc atctcaaaaa   16980
taaataagta aataactagc agctgtaaat gtggctgttg ttcttcacct ccacactcag    17040
tgccactcca ctccctccct ccgtggtgtg aggggcctca ctagctgtct cctaggagga   17100
gcatggctgt gagattccag ctccatcctt ggccacggct cctggagaca tcttagaggc   17160
caggatccag aaggctccca cacctcattt gacagtggag aagctgtcag ttccaggtcc   17220
ccttgcacat cagggccaga gctgcgttag gcctccagtc tccaggccac tgggccagag   17280
ctcacaggct ggcagagggt tagaactgtt actggtggct gggtgcagtg gctcacgcct    17340
gtaatcttag cactttggga gggcaaggcg ggaggatcat gaggtcagga catcgagacc   17400
atccttgcta acacggtgaa gccccgtctc tactaaaact acaaaaaatt agccgggcgt   17460
ggtggcaggc gcctgtagtc ccagctactc aggaggctga ggcaggagaa tggcgtgaac    17520
ccgggaggcg gagcttgcag tgagccgaga ttgcgccact gcactccagc ctgggcaata    17580
gagcgagact ccgtctggaa agaaaaaaaa aaaaagagc tgttactgtt gacagtagca    17640
tgaggtagac catggcctgc accaaaatgg gggagtggag tgccactgag gccagaagga   17700
accacaccct caagggtggg gagttatggt atgggggggtc ctaggcatgg agtctttaa    17760 ttctttagac aatcctggga gcaactgtcc ctgtttcaca gagggcgggg ccacacagct   17820
ggtgagtggg cagccaagac tctgttcaag tttgtgtggg tccaacactt gcggccacgg   17880
tggaggggca tctgagccag gcctcagaga gtggcggggg aagttgggtg gggaagtgtg   17940
cccttctcat tcctctgagg ctcatcctct tggtgcctct cttcatgga aagggataat     18000 aaggttattg tgaggatccc ctgagttcgt atattcagac gcttagacag agccaggcac   18060
agagaagggc ccggggttgg ctagtttgat tgctggtgta attgctaata tcttccagtt     18120
tgtattggtc aaggttctgc agagaagcag aaccagtagg atgtatatat taagagtttc   18180
aagctcatgt gaccgtgcgg gctggcaagt ctgaaatccg cagggcaggc caggcaggct   18240
ggcaattcct gcagaatttg atgttgcaat actgagtcct aaggcagtcc tggggcagaa   18300
ttccttcttc cctgggaggc ctcagtctgt tctcttaagg ccttcaactg attaaatgag    18360
gcctgcccaa gttatagaga gtaacctgcc ttactccgtc ttctgattta aatgttagtc   18420
```

```
acatctaaaa aatattttcg cagcagcatt tccactggct tttgaccaaa catcaggcca    18480
caaagttgat ccccaaaatt aaccatcact ctgtgcctgt aagggagggg ctgggaaagg    18540
ggagcaggtc tccccaaggg gtgaccttgg ctttgttcct cccaggcctg gagtttattc    18600
ggaaaagcca gctggtccag cctgtggggc cactggtggt gctgctgccc ctggcgggtg    18660
ggtacagccg cgtcctcaac gccgcctgcc agcgcctggc gagggctggg gtcgtgctgg    18720
tcaccgctgc cggcaacttc cgggacgatg cctgcctcta ctccccagcc tcagctcccg    18780
aggtaggtgc tggggctgct gccccaaggc gcgggtaggg ggcggagggc ggagggcgga    18840
gggagggcgg gcgggcaggc gggcttcttg tggcacgtgg gcttcttgtg gcacgttcct    18900
ggaggccgaa cccttctggc tttggaagga gtcgtcagag accccgcca tgcgggaggc     18960 tgggaggaa ggggctcgaa acctccatca tcgcagagtc tgaatagcag tggccccgcc     19020
atgcgcccac gtagcggcgc ctacgtagcc acgcccccac accccgtcct ggccactctc    19080
cctcctgaag gtcttctggt acccgccccc tccccatctc catcccagg ccctgcgtcc     19140 tctgcccaat actctttggg cctccctgtt gtccagctct ctccgcggct ccatgactga    19200
caacttgagc aaggctaatg tgaatgggag cggttgaggg ctcagacctc tcacccgagg    19260
aacatccaca gagtgtgccg catgcccggt gcagtgtggc tgcggggaca cagacacgga    19320
gcctcggccc tgaggagctg gggggcagtg accgtccctc ctctgaccca ccactcctcc    19380
agtgtcagga cactgcgggt atctagggga aggaatcttg ttccacttca agtctggaac    19440
ttcaagtctg tgtgtgtgcg tgcgcgcgcg cgcgttgggg gtgggggttg cagagcagat    19500
gcgtacctga cagcggtaac ctaggtcccc cctggcctat caaggcttcc ctggcggccg    19560
aatttaaagg catcaagcaa acaaagccca acacatctct gccttgtcct ctcagttttcc   19620 ccccgtggca cttagaacca cttgatacac cgaatagttt cctatctccc ccactaggat    19680
gtaaactcca caggggcatt gggaatgctg cctggctatg gtagggacag aggggagcac    19740
cagggcgggg cagggggtgcc agagttctgc ctgggcagtc agatttttcct taggagggga  19800 catttgagtg ggacccaaac aggtgtatag cagttgtcca gcccagctgg caaggcctga    19860
gtctgcctct gcaaccccctc tcttgggctc ctttctctgc cacccacctc ctcacctttc   19920
caggtcatca cagttggggc caccaatgcc caagaccagc cggtgacccct ggggactttg    19980 gggaccaact ttggccgctg tgtggacctc tttgccccag gggaggacat cattggtgcc   20040
tccagcgact gcagcacctg ctttgtgtca cagagtggga catcacaggc tgctgcccac   20100
gtggctggta agtcaccacc ccactgcctc ggccaccgtg atgctaacag ccccttttggc   20160 agtcagggtc tgtgccggga cctccagtgc caggctctgt gcaggggac cagagatgaa     20220 gtaggcctga tggtgccttc aaggacactc agtctgatga gggaggcgag tgcacagagg   20280
aaacacgagg tcagggctgt attagaggga gcccagagga ggcacctgcc cagcccgagg   20340
gtcagagaag gcatcttgga ggagggacat ttgatcggga gcttgatgga tgaataggag   20400
ttcacctggc cgataagaca gcaactacca aggcttagag gtgtgagagg aggctgtctt   20460
acctcactga gtaaggactg caggcggctt accttcgaga agagagctta gtgtctgtgt    20520
gcacgtgtgt ttgtgtgtat gtgtgtgcgt gtgtgcactg gcaggagtcc cctgctgggg   20580
caggagggcc gggccatcac catctttcac cattcacccc tgcaccaggc attgcagcca    20640
tgatgctgtc tgccgagccg gagctccacc tggccgagtt gaggcagaga ctgatccact   20700
tctctgccaa agatgtcatc aatgaggcct ggttccctga ggaccagcgg gtactgaccc   20760
ccaacctggt ggccgcccctg ccccccagca cccatggggc aggtaagcag gatggcaggg   20820
```

```
tgggcaagtc caggctgggg cttgggaggt ctgtgtgacc ttgacagtct ctcccttctc   20880
ccttgtctgt gtaaggagga tgacgccacc ttaaatagga ttaaatgaga atggggctct   20940
gaaagggctg tgcaatattt tcataacgtg tttttataga gacagttgag tatgttcttt   21000
aagccctcct ctctcctacc atgaactaaa gatttctgtg gaggtcccct cactcccagc   21060 acccctcct catcccaggc ccttttgca ggttggcagc tgttttgcag gactgtatgg    21120
tcagcacact cggggcctac acggatggcc acagccgtcg cccgctgcgc cccagatgag   21180
gagctgctga gctgctccag tttctccagg agtgggaagc ggcggggcga gcgcatggag   21240
gtgactgtac ccctccttcg tgtgtgtgtg tgtgtgtgtg tgtgtgtgtg tgtgtgtgtg   21300
tgtgtgtgtg tcagtgctgg gccctcaggg acccccagca agcccctcca tcctccagac   21360
tccagctctt ctgtaagctt acagggctgg ccagaccagg agtggggcac tcctcacttc   21420
acgcggctgg gggctgctgg agagagccac agcgggaagg gtttcctaga ggctgcagga   21480
cagtgctgga tggattttca atgctcacct gggtgtgagc gtgcggcagg gccgcgtgag   21540
ggtcagcgat ctgctactct ggactcagcc atctctaggc ccctctcact caggtgctcc   21600
atggttctgg gagctgagaa atctcaaacc agcaaaaaag tggaattgat gttgatgcta   21660
caggatagtg cacagatgcc atctggttgc agcattttgg tggaagggca gtgcccagct   21720
aggagagtga ggaggggcag gcatttctgg cttgaggaga tggggtctta atgctcgtgt   21780
gagaggcaga gtgggtggag tggagctggc tggatccttg ctttggcctc ctggatttct   21840
ctctatctcc attttgaaac cactctgtgt ttggaagaac ttttgagtat tcagagctgc   21900
ccactggcag aacagtcttc cttgggcagg agtgagctcc ttgtcccag aaggctgggt    21960 ctggctggcc cctggcaggg acactgatga gggtgcttga gttgatcctg tctagtccct   22020
ttctgtgttt tcaaagccca ttctaaagca gattcccatt tccgtctttg actctaaggc   22080 ccaaggggc aagctggtct gccgggccca caacgctttt gggggtgagg gtgtctacgc    22140
cattgccagg tgctgcctgc tacccaggc caactgcagc gtccacacag ctccaccagc    22200
tgaggccagc atgggaccc gtgtccactg ccaccaacag gccacgtcc tcacaggtag     22260 gaggctgggc ttgccctggg gtgaggaggg gtctctttct ccttatgcac ccactgcccg   22320
cgaggcttgg tcctcacaag tgtgatccat gagactcaag cctgacttgc agttccatac   22380
tctggttctg ccacttccat gccctttgag cctgggcagg tgaccttact tctcctcatc   22440
tcagcttcct cctccataag agggaaaaag gtattacctg cctcattgtg ttgcaaggag   22500
atgggcagca tctagggcac tggcctgag tatcgcaggt gctttgccta aggtggtgca    22560
gtccaggaga ggcagctcca gagagaggcc cccggctggg gctgaaagga gggcagacct   22620
cggtttgaat ttcaccctgc cgctctatag ctgtgtgact tgggcaaatt acttaacatc   22680
tctgtatgag gaaatgatga gtgctaagca cttagcttag tgccgggaca atataaattc   22740
tagctatcgt tactattgtt ttcatcaccc gttgctttaa aatccagcct ctggtatagg   22800
caactattga cgggctaccc tgtgtcgaaa acatgcccag gcaggtagca ggaagtcaca   22860
gatggggacc tcttggggca tcaagggatg gtgccctgag gctgagctgt tctggttggg   22920
tggagcatga gaggtctggg aagacagtgg gactccagcc tggaataaga ggctcagagt   22980
tgattctcgt ctgagcacgt ccaggggaac cactgagggt ttgggaacag gagagtgagg   23040
gtgagaacct ggttctgggc acagcaggct ggcatgtagg atggatgttc aggaaagatg   23100
agcatagtca ggtggctggt gcccttgtcc aggggagagg ctccgtcagg ttcaggggtc   23160
```

| | | | | | |
|---|---|---|---|---|---|
| ctggcttgga | gggaagtccg | ccatgctcta | atcacgctcc | cctttggaag | tgctcagccg | 23220 |
| atgagctcac | aggcacatgt | cagtttgaag | tcatggaatc | tgactccatg | aagcgcacct | 23280 |
| caaagagcac | cattttgcag | ctaagggaac | tgcaggctgg | acatgctgag | tggctgcccc | 23340 |
| gagcccttgc | agctaggaca | tagagaatgc | tagtaaccac | aaccctacca | tgttcagagc | 23400 |
| acatgccagg | ctccatgctg | gggcttcgca | cgtgtcatct | tcacagtgtc | cctgtgagta | 23460 |
| ggtgtggttt | ctcttccat | cttacaaatg | agtaaacaga | gcctcagtgt | agctaagtaa | 23520 |
| ccactatttt | aggtttctta | gccaatgggt | gtgtctgact | cctaagccca | tggagggcat | 23580 |
| tctgaggtgg | ttcagacaga | ccccggctta | cccttgaact | tctgcctgct | ggctgcatag | 23640 |
| ggaggggctg | gggggagttt | gagcatctca | ggccatagag | cccctgcctc | actgtctcca | 23700 |
| tctctgggtg | gaaagatggt | gttttccctg | agaaactaag | gctcagagag | gttgaatggc | 23760 |
| tctcccaagg | tcacacagct | ggtcagctgc | agagttgaga | acacaggagt | cctggtgctc | 23820 |
| aggccagcat | ctcttttttt | ctttgagttg | tttctaggtt | tcctagctct | tgcctcagac | 23880 |
| cttaaagaga | gagggtctga | tggggatggg | cactggagac | ggagcatccc | agcatttcac | 23940 |
| atctgagctg | gctttcctct | gccccaggct | gcagctccca | ctgggaggtg | gaggaccttg | 24000 |
| gcacccacaa | gccgcctgtg | ctgaggccac | gaggtcagcc | caaccagtgc | gtgggccaca | 24060 |
| gggaggccag | catccacgct | tcctgctgcc | atgccccagg | tctggaatgc | aaagtcaagg | 24120 |
| agcatggaat | cccggcccct | caggagcagg | tgaagaggcc | cgtgaggccg | ggtgggtggg | 24180 |
| gtgctgcgtg | tctctcctgc | acagcttttc | tgtgtcagtt | tgtgccacca | ccataccgcc | 24240 |
| atgcatcagg | gtggcggttt | gccaggtaga | tgctgtgggc | agcttccgcc | attgtgtgga | 24300 |
| cagcatgtat | atgtgtctct | gtgtggctgg | gtctgttttt | gcttttgtcc | agatcagtaa | 24360 |
| ggtttgctac | ctgggtaccc | cactccactt | ggagtagaat | gtgcataaat | atggcataaa | 24420 |
| gaaatgcaat | atgcatgcat | ttattgattg | atctattttt | ttctgagatg | gggtcttgct | 24480 |
| gtgttgccca | ggctggtctc | aaattcctgg | gctcaagcaa | tcctctggtc | tcagcctccc | 24540 |
| caagtgttgg | gattataggc | atgagccgct | gcacctggcc | tctctgatct | atttaacaaa | 24600 |
| cctgctggga | gggtctcagg | gtcaggagca | gcactgggct | ctgaggacac | agagctcact | 24660 |
| cagccgtgac | ccagagggg | tgcctgagct | gcatgctgaa | ggttgttagc | atgaccagca | 24720 |
| aggcaagaaa | aggccctgcc | gagattagca | aggcatgtgc | caagccctgg | aatgtgacag | 24780 |
| ccgggccttc | tagaaacctg | agtgtataac | tctccttaaa | agccagtagg | agctcctcaa | 24840 |
| aaggcagccc | taaggagtcc | actcttaaat | gaactcagag | tcagttttaa | aatgcaagtc | 24900 |
| tgtgttgatt | ctggtctgga | tggtgcattc | ctcgagagca | aaagacagtc | ttggtcttgg | 24960 |
| atccacttgc | cctgggtaca | ctgagggctg | ctaggttcca | ggtgctcttc | ctggcactgg | 25020 |
| ggagggatac | aggcccaaga | gacatgctgt | tctccctcct | ggagcatcta | ttttagtgga | 25080 |
| ggaagacaga | aaacaaacca | ttaatataga | gtactgaaaa | gatgcgatgg | agaaaactat | 25140 |
| agcaaggaag | ggaatggggt | gggagagagg | tcaggagagg | tctcgctgac | aaggtggacg | 25200 |
| aaacaggcca | tgaggcagag | aacatgttcc | aggcaaagca | aaggcccca | ggtggggatg | 25260 |
| tgcagggagt | accaggaaac | cagagaggtg | ggaatagtta | tgagatgggg | ggtgcctcag | 25320 |
| agggacagg | gccaagtcag | gtgagacctg | agggtcacag | tcagcagtga | gctggggcca | 25380 |
| tgcagggtc | tggcctcaga | ggagtgtggt | ctggcctgga | tctgaacctc | tcactgtggc | 25440 |
| ctagctgctg | agctgagaag | agatgacaag | gaccttgggc | agaagcaggg | agactggagg | 25500 |
| gaggcggtgg | agggtccagg | cgttggggcg | gggctcaggc | tggagtctga | agggagcctg | 25560 |

```
caggcctggt gggtggatgt gggtgggaga gggggaggat ggcaccaagg ctcgggcccc   25620
tggacagatg gagttgccat taagtgggat ggggcaggct atggggccat cagtttcaga   25680
gggatgagtt tggcactggc atggtaggca tctgtctatc tccacggccc tcaaaccagg   25740
catgaagcag gagctcacgt gtttggtcag ccatggtgca gaaccgcctg ggtgggaggt   25800
gcggggtggg agatacacgg ttgtgtccca aatgggctct gagccagcga gggccgtctg   25860
cactttggcc tcacagaagg atgtcggagg gagaaatgaa gtgtgggtgg gggtcccggg   25920
ccacgctaga catgtgcttt cttttcctcg ggctctggca ggtgaccgtg gcctgcgagg   25980
agggctggac cctgactggc tgcagtgccc tccctgggac ctcccacgtc ctgggggcct   26040
acgccgtaga caacacgtgt gtagtcagga gccgggacgt cagcactaca ggcagcacca   26100
gcgaaggggc cgtgacagcc gttgccatct gctgccggag ccggcacctg gcgcaggcct   26160
cccaggagct ccagtgacag ccccatccca ggatgggtgt ctggggaggg tcaagggctg   26220
gggctgagct ttaaaatggt tccgacttgt ccctctctca gccctccatg gcctggcacg   26280
aggggatggg gatgcttccg ccttttcggg gctgctggcc tggcccttga gtggggcagc   26340
ctccttgcct ggaactcact cactctgggt gcctcctccc caggtggagg tgccaggaag   26400
ctccctccct cactgtgggg catttcacca ttcaaacagg tcgagctgtg ctcgggtgct   26460
gccagctgct cccaatgtgc cgatgtccgt gggcagaatg acttttattg agctcttgtt   26520
ccgtgccagg cattcaatcc tcaggtctcc accaaggagg caggattctt cccatggata   26580
ggggaggggg cggtagggc tgcagggaca aacatcgttg gggggtgagt gtgaaaggtg   26640
ctgatggccc tcatctccag ctaactgtgg agaagcccct gggggctccc tgattaatgg   26700
aggcttagct ttctggatgg catctagcca gaggctggag acaggtgcgc ccctggtggt   26760
cacaggctgt gccttggttt cctgagccac ctttactctg ctctatgcca ggctgtgcta   26820
gcaacaccca aggtggcct gcggggagcc atcacctagg actgactcgg cagtgtgcag   26880
tggtgcatgc actgtctcag ccaacccgct ccactacccg gcagggtaca cattcgcacc   26940
cctacttcac agaggaagaa acctggaacc agagggggcg tgcctgccaa gctcacacag   27000
caggaactga gccagaaacg cagattgggc tggctctgaa gccaagcctc ttcttacttc   27060
acccggctgg gctcctcatt tttacgggta acagtgaggc tgggaagggg aacacagacc   27120
aggaagctcg gtgagtgatg gcagaacgat gcctgcaggc atggaacttt ttccgttatc   27180
acccaggcct gattcactgg cctggcggag atgcttctaa ggcatggtcg ggggagaggg   27240
ccaacaactg tccctccttg agcaccagcc ccacccaagc aagcagacat ttatcttttg   27300
ggtctgtcct ctctgttgcc tttttacagc caacttttct agacctgttt gcttttgta   27360 acttgaagat atttattctg ggttttgtag catttttatt aatatggtga ctttttaaaa   27420
taaaaacaaa caaacgttgt cctaactctt gcatagactt gactgcctag ggtgatgcct   27480
tgcttatact aggaactggg taagtttgtt gaatagttga gtaagccaag tatttgatga   27540
gtacttttat cttgagtaca agtattgggc aagtactggt gatgtgaact tactccttgt   27600
gcctatccta ggaatgaaat gaatgtcttc ctgcagctcc cctgaccacc ctgacagtca   27660
aagtgcctcc tccttggtga caggtgccct acagcactct agatgctctg ttgtcctgac   27720
ctcccaatgc ccttttcatt cttttctccc cagtacctgg cacacagcct ggcccgagta   27780
tttacggaat aagttacagt gccagatgct tctgtaatga gccagtgcta agtccatggc   27840 tttttttcatg atttaaaatt cagaacagtc tcagattggg tgcaatggct cacacctgta   27900
```

```
atctcagtac tttgggaggc tgaggcagga ggattgcttg tgtttaggaa ttcaagaccc    27960
tgggcaacag tgagacccg tctctataaa aaaatttaaa agattagcga ggtgtggtag    28020
cacatgcctg tggtcccggc tactcaggag gctgatatgg gaggcttgct tgagctggga    28080
ggctgagggt gcagtgagct gtaattacat catcactgca ctgcagcctg ggttacagag    28140
tgcataatga tcccattcaa tgtgggacct ccaggccctc cactctaagg ctggtgaata    28200
tagctgtctt aagcaagttc tctctctctc tagacagccc atgtcataag gaatctcagg    28260
caaaattcct cccagattac attttctgac aattcagtgt catatatgga aagcattcaa    28320
gagttgacag atggcaatgg cttgaacacc caactgtgtt atctctgccc gttggaacct    28380
aggcctgtgg tgcaacccta gactctctct ccttcccctc cacagaatca agtatcagct    28440
ggttagagat ccacccctg acagctctgt gatgttggaa caacttggtt cttgcagagg    28500
gttagcaggt ggtcaccagg gatcggggag gaagggtgt ggcttgcagg aaggcgaaaa    28560
tctggactag caaatagggga aggggaccca tgtgagcaac gctggccact aggaatgaga    28620
ctgagacctg tgggatctag caagaagccc agtgtgacca cgacacgat ctatgctggg    28680 gaccacttgg gagagccaaa agctttggtg gagatgaatg gagaccatca acctaagttc    28740
agcatcctcc tctaagcttt gcagatgaat cctgaaatgg tcagccctc cagagaaaag    28800 aacagcaaca ggctcagagg acccacagtc ccctttatta gtgtaaagta ctaagaggaa    28860
tcaacagcat ttagcaccag gcacaggctc gtgttccccc gcccactacg gctgtgttct    28920
gatatatgaa gaatggcggc aagactccaa ctctgttttt gaaaaattta ttttatactc    28980
ttagaagcta agaactttgc c                                              29001
```

<210> SEQ ID NO 1547
<211> LENGTH: 544
<212> TYPE: DNA
<213> ORGANISM: Homo sapiens

<400> SEQUENCE: 1547

```
aatctgacgc tgtttgggga gggcgaggcc gaaacctgat cctccagtcc gggggttccg     60
ttaatgttta atcagatagg atcgtccgat ggggctctgg tggcgtgatc tgcgcgcccc    120
aggcgtcaag cacccacacc ctagaaggtt tccgcagcga cgtcgaggcg ctcatggttg    180
caggcgggcg ccgccgttca gttcagggtc tgagcctgga ggagtgagcc aggcagtgag    240
actggctcgg gcgggccggg acgcgtcgtt gcagcagcgg ctcccagctc ccagccagga    300
ttccgcgcgc cccttcacgc gccctgctcc tgaacttcag ctcctgcaca gtcctcccca    360
ccgcaaggct caaggcgccg ccggcgtgga ccgcgcacgg cctctaggtc tcctcgccag    420
gacagcaacc tctcccctgg ccctcatggg caccgtcagc tccaggcggt cctggtggcc    480
gctgccactg ctgctgctgc tgctgctgct cctgggtccc gcgggcgccc gtgcgcagga    540
ggac                                                                544
```

<210> SEQ ID NO 1548
<211> LENGTH: 544
<212> TYPE: DNA
<213> ORGANISM: Homo sapiens
<220> FEATURE:
<221> NAME/KEY: misc_feature
<222> LOCATION: (371)..(371)
<223> OTHER INFORMATION: n is a, c, g, or t

<400> SEQUENCE: 1548

```
gagcacggtg gagagcgggg acggccggct ctttggggac ttgctggggc gtgcggctgc     60
```

```
gctattcagt gggaaggttc gcggggttgg gagacccgga ggccgaggaa gggcgagcag      120
agcactgcca ggatatcctg cccagatttc ccagtttctg cctcgccgcg gcacaggatc      180
cgtggaggtt gcctggcacc tacgtggtgg tgctgaagga ggagacccac ctctcgcagt      240
cagagcgcac tgcccgccgc ctgcaggccc aggctgcccg ccggggatac ctcaccaaga      300
tcctgcatgt cttccatggc cttcttcctg gcttcctggt gaagatgagt ggcgacctgc      360
tggagctggc ncttgaagtt gccccatgtc gactacatcg aggaggactc ctctgtcttt      420
gcccagagca tcccgtggaa cctggagcgg attacccctc cacggtaccg gcggatgaa      480 taccagcccc ccgacggagg cagcctggtg ggaggtgtat ctcctagaca ccagcataca      540
gagt                                                                   544

<210> SEQ ID NO 1549
<211> LENGTH: 580
<212> TYPE: DNA
<213> ORGANISM: Homo sapiens

<400> SEQUENCE: 1549
agtggggagc acggtggaga gcggggacgg ccggctcttt ggggacttgc tgggcgtgc       60 ggctgcgcta ttcagtggga aggttcgcgg ggttgggaga cccggaggcc gaggaagggc      120
gagcagagca ctgccaggat atcctgccca gatttcccag tttctgcctc gccgcggcac      180
agacggaggc agcctggtgg aggtgtatct cctagacacc agcatacaga gtgaccaccg      240
ggaaatcgag ggcagggtca tggtcaccga cttcgagaat gtgcccgagg aggacgggac      300
ccgcttccac agacaggcca gcaagtgtga cagtcatggc acccacctgg cagggtggt      360 cagcggccgg gatgccggcg tggccaaggg tgccagcatg cgcagcctgc gcgtgctcaa      420
ctgccaaggg aagggcacgg ttagcggcac cctcataggc ctggagtttta ttcggaaaag    480 ccagctggtc cagcctgtgg ggccactggt ggtgctgctg ccctggcgg gtgggtacag      540 ccgcgtcctc aacgccgcct gccagcgcct ggcgagggct                            580

<210> SEQ ID NO 1550
<211> LENGTH: 2976
<212> TYPE: DNA
<213> ORGANISM: Homo sapiens

<400> SEQUENCE: 1550
agtggggagc acggtggaga gcggggacgg ccggctcttt ggggacttgc tgggcgtgc       60 ggctgcgcta ttcagtggga aggttcgcgg ggttgggaga cccggaggcc gaggaagggc      120
gagcagagca ctgccaggat atcctgccca gatttcccag tttctgcctc gccgcggcac      180
agacggaggc agcctggtgg aggtgtatct cctagacacc agcatacaga gtgaccaccg      240
ggaaatcgag ggcagggtca tggtcaccga cttcgagaat gtgcccgagg aggacgggac      300
ccgcttccac agacaggcca gcaagtgtga cagtcatggc acccacctgg cagggtggt      360 cagcggccgg gatgccggcg tggccaaggg tgccagcatg cgcagcctgc gcgtgctcaa      420
ctgccaaggg aagggcacgg ttagcggcac cctcataggc ctggagtttta ttcggaaaag    480 ccagctggtc cagcctgtgg ggccactggt ggtgctgctg ccctggcgg gtgggtacag      540 ccgcgtcctc aacgccgcct gccagcgcct ggcgagggct ggggtcgtgc tggtcaccgc     600
tgccggcaac ttccgggacg atgcctgcct ctactcccca gcctcagctc ccagaggtcat   660 cacagttggg gccaccaatg cccaagacca gccggtgacc ctggggactt tggggaccaa    720
```

```
ctttggccgc tgtgtggacc tctttgcccc aggggaggac atcattggtg cctccagcga    780
ctgcagcacc tgctttgtgt cacagagtgg gacatcacag gctgctgccc acgtggctgg    840
cattgcagcc atgatgctgt ctgccgagcc ggagctcacc ctggccgagt tgaggcagag    900
actgatccac ttctctgcca aagatgtcat caatgaggcc tggttccctg aggaccagcg    960
ggttggcagc tgttttgcag gactgtatgg tcagcacact cggggcctac acggatggcc   1020
acagccgtcg cccgctgcgc cccagatgag gagctgctga gctgctccag tttctccagg   1080
agtgggaagc ggcggggcga gcgcatggag gcccaagggg gcaagctggt ctgccgggcc   1140
cacaacgctt ttgggggtga gggtgtctac gccattgcca ggtgctgcct gctaccccag   1200
gccaactgca gcgtccacac agctccacca gctgaggcca gcatggggac ccgtgtccac   1260
tgccaccaac agggccacgt cctcacaggc tgcagctccc actgggaggt ggaggacctt   1320
ggcacccaca agccgcctgt gctgaggcca cgaggtcagc ccaaccagtg cgtgggccac   1380
agggaggcca gcatccacgc ttcctgctgc catgccccag gtctggaatg caaagtcaag   1440
gagcatggaa tcccggcccc tcaggagcag gtgaccgtgg cctgcgagga gggctggacc   1500
ctgactggct gcagtgccct cctgggacc tcccacgtcc tgggggccta cgccgtagac   1560
aacacgtgtg tagtcaggag ccgggacgtc agcactacag gcagcaccag cgaaggggcc   1620
gtgacagccg ttgccatctg ctgccggagc cggcacctgg cgcaggcctc ccaggagctc   1680
cagtgacagc cccatcccag gatgggtgtc tggggagggt caaggctgg ggctgagctt   1740
taaaatggtt ccgacttgtc cctctctcag ccctccatgg cctggcacga ggggatgggg   1800
atgcttccgc ctttccgggg ctgctggcct ggcccttgag tggggcagcc tccttgcctg   1860
gaactcactc actctgggtg cctcctcccc aggtggaggt gccaggaagc tccctccctc   1920
actgtggggc atttcaccat tcaaacaggt cgagctgtgc tcgggtgctg ccagctgctc   1980
ccaatgtgcc gatgtccgtg ggcagaatga cttttattga gctcttgttc cgtgccaggc   2040
attcaatcct caggtctcca ccaaggagcc aggattcttc ccatggatag gggagggggc   2100
ggtaggggct gcagggacaa acatcgttgg ggggtgagtg tgaaaggtgc tgatggccct   2160
catctccagc taactgtgga gaagcccctg ggggctccct gattaatgga ggcttagctt   2220
tctggatggc atctagccag aggctggaga caggtgcgcc cctggtggtc acaggctgtg   2280
ccttggtttc ctgagccacc tttactctgc tctatgccag gctgtgctag caacacccaa   2340
aggtggcctg cggggagcca tcacctagga ctgactcggc agtgtgcagt ggtgcatgca   2400
ctgtctcagc caacccgctc cactacccgg cagggtacac attcgcaccc ctacttcaca   2460
gaggaagaaa cctggaacca gagggggcgt gcctgccaag ctcacacagc aggaactgag   2520
ccagaaacgc agattgggct ggctctgaag ccaagcctct tcttacttca cccggctggg   2580
ctcctcattt ttacgggtaa cagtgaggct gggaagggga acacagacca ggaagctcgg   2640
tgagtgatgg cagaacgatg cctgcaggca tggaactttt tccgttatca cccaggcctg   2700
attcactggc ctggcggaga tgcttctaag gcatggtcgg gggagagggc caacaactgt   2760
ccctccttga gcaccagccc cacccaagca agcagacatt tatcttttgg gtctgtcctc   2820
tctgttgcct ttttacagcc aacttttcta gacctgtttt gcttttgtaa cttgaagata   2880
tttattctgg gttttgtagc attttttatta atatggtgac ttttttaaaat aaaaacaaac   2940
aaacgttgtc ctaacaaaaa aaaaaaaaaa aaaaaa                             2976
```